(12) United States Patent
Franklin et al.

(10) Patent No.: US 10,006,034 B2
(45) Date of Patent: Jun. 26, 2018

(54) RECOMBINANT MICROALGAE INCLUDING KETO-ACYL ACP SYNTHASE

(71) Applicant: Corbion Biotech, Inc., South San Francisco, CA (US)

(72) Inventors: Scott Franklin, Woodside, CA (US); Aravind Somanchi, Redwood City, CA (US); Janice Wee, San Mateo, CA (US); George Rudenko, Mountain View, CA (US); Jeffrey L. Moseley, Redwood City, CA (US); Walt Rakitsky, San Diego, CA (US)

(73) Assignee: Corbion Biotech, Inc., South San Francisco, CA (US)

( * ) Notice: Subject to any disclaimer, the term of this patent is extended or adjusted under 35 U.S.C. 154(b) by 0 days. days.

(21) Appl. No.: 14/819,117

(22) Filed: Aug. 5, 2015

(65) Prior Publication Data
US 2016/0024538 A1 Jan. 28, 2016

Related U.S. Application Data

(63) Continuation of application No. 13/650,018, filed on Oct. 11, 2012, now Pat. No. 9,109,239, which is a continuation of application No. 13/118,369, filed on May 27, 2011, now abandoned.

(60) Provisional application No. 61/349,774, filed on May 28, 2010, provisional application No. 61/374,992, filed on Aug. 18, 2010, provisional application No. 61/414,393, filed on Nov. 16, 2010, provisional application No. 61/428,192, filed on Dec. 29, 2010.

(51) Int. Cl.

| | | |
|---|---|---|
| *C12N 15/79* | (2006.01) | |
| *C12N 9/16* | (2006.01) | |
| *C12P 7/64* | (2006.01) | |
| *C12N 15/82* | (2006.01) | |
| *A23D 7/00* | (2006.01) | |
| *A23D 9/00* | (2006.01) | |
| *C11B 1/00* | (2006.01) | |
| *C11C 3/00* | (2006.01) | |
| *C12N 9/02* | (2006.01) | |
| *C12N 9/26* | (2006.01) | |
| *C12N 9/40* | (2006.01) | |
| *C12N 15/67* | (2006.01) | |
| *A23K 20/158* | (2016.01) | |

(52) U.S. Cl.
CPC ............... *C12N 15/79* (2013.01); *A23D 7/00* (2013.01); *A23D 9/00* (2013.01); *A23K 20/158* (2016.05); *C11B 1/00* (2013.01); *C11C 3/00* (2013.01); *C12N 9/0071* (2013.01); *C12N 9/16* (2013.01); *C12N 9/2431* (2013.01); *C12N 9/2465* (2013.01); *C12N 15/8216* (2013.01); *C12P 7/64* (2013.01); *C12P 7/6445* (2013.01); *C12P 7/6463* (2013.01); *C12N 15/67* (2013.01); *C12Y 114/19001* (2013.01); *C12Y 301/02* (2013.01); *C12Y 301/02014* (2013.01); *C12Y 302/01022* (2013.01); *C12Y 302/01026* (2013.01); *Y02E 50/13* (2013.01); *Y02P 30/20* (2015.11); *Y02T 50/678* (2013.01)

(58) Field of Classification Search
None
See application file for complete search history.

(56) References Cited

U.S. PATENT DOCUMENTS

| | | |
|---|---|---|
| 2,235,056 A | 3/1941 | Walmesley |
| 2,383,602 A | 8/1945 | Gerald et al. |
| 2,967,700 A | 1/1961 | Lee et al. |
| 3,142,135 A | 7/1964 | Kathrein |
| 3,280,502 A | 10/1966 | Farrow et al. |
| 3,320,693 A | 5/1967 | Shirota et al. |
| 3,475,274 A | 10/1969 | Harned |
| 3,957,578 A | 5/1976 | Narita et al. |
| 3,962,466 A | 6/1976 | Nakabayashi |
| 3,983,008 A | 9/1976 | Shinozaki et al. |
| 4,005,062 A | 1/1977 | Schnell |
| 4,103,039 A | 7/1978 | Mandai et al. |
| 4,182,777 A | 1/1980 | Saunders |
| 4,273,790 A | 6/1981 | Bosco et al. |
| 4,341,038 A | 7/1982 | Bloch et al. |

(Continued)

FOREIGN PATENT DOCUMENTS

| | | |
|---|---|---|
| CN | 1251108 A | 4/2000 |
| CN | 1852986 A | 10/2006 |
| CN | 101037639 A | 9/2007 |
| CN | 101092353 A | 12/2007 |
| CN | 101108997 A | 1/2008 |
| CN | 101611125 A | 12/2009 |
| CN | 101765661 A | 6/2010 |
| CN | 101824440 A | 9/2010 |
| DE | 2756977 A1 | 6/1978 |
| EP | 0 562 504 B1 | 11/1995 |

(Continued)

OTHER PUBLICATIONS

"Soybean Oil Innovations, 3rd Edition," United Soybean Board, www.soyconnection.com, 8 pages, (2009). [Available from the Internet on Jan. 15, 2009: <URL: http://www.soyconnection.com/sites/default/files/soy-oil-solutions.pdf>].

(Continued)

*Primary Examiner* — Paul J Holland
(74) *Attorney, Agent, or Firm* — Weaver Austin Villeneuve & Sampson, LLP.

(57) ABSTRACT

Methods and compositions for the production of food compositions, oils, fuels, oleochemicals, and other compounds in recombinant microorganisms are provided, including oil-bearing microorganisms and methods of low cost cultivation of such microorganisms. Microalgal cells containing exogenous genes encoding, for example, a lipase, a sucrose transporter, a sucrose invertase, a fructokinase, a polysaccharide-degrading enzyme, a keto acyl-ACP synthase enzyme, a fatty acyl-ACP thioesterase, a fatty acyl-CoA/aldehyde reductase, a fatty acyl-CoA reductase, a fatty aldehyde reductase, a fatty aldehyde decarbonylase, and/or an acyl carrier protein are useful in manufacturing food compositions, and transportation fuels such as renewable diesel, biodiesel, and renewable jet fuel, as well as oleochemicals such as functional fluids, surfactants, soaps and lubricants.

34 Claims, 1 Drawing Sheet

(56) References Cited

U.S. PATENT DOCUMENTS

| | | |
|---|---|---|
| 4,373,434 A | 2/1983 | Alexander et al. |
| 4,390,561 A | 6/1983 | Blair et al. |
| 4,519,845 A | 5/1985 | Ou |
| 4,627,192 A | 12/1986 | Fick |
| 4,673,490 A | 6/1987 | Subramanian et al. |
| 4,755,467 A | 7/1988 | Scopes et al. |
| 4,901,635 A | 2/1990 | Williams |
| 4,992,605 A | 2/1991 | Craig et al. |
| 5,001,059 A | 3/1991 | Skatrud et al. |
| 5,091,116 A | 2/1992 | Krishnamurthy et al. |
| 5,130,242 A | 7/1992 | Barclay |
| 5,212,087 A | 5/1993 | Fournier et al. |
| 5,252,198 A | 10/1993 | Harrison et al. |
| 5,270,175 A | 12/1993 | Moll et al. |
| 5,270,177 A | 12/1993 | Ramos Lazcano et al. |
| 5,304,481 A | 4/1994 | Davies et al. |
| 5,330,913 A | 7/1994 | Nakayama |
| 5,338,673 A | 8/1994 | Thepenier et al. |
| 5,354,878 A | 10/1994 | Connemann et al. |
| 5,360,730 A | 11/1994 | Orndorff et al. |
| 5,391,724 A | 2/1995 | Kindl et al. |
| 5,395,455 A | 3/1995 | Scott et al. |
| 5,436,394 A | 7/1995 | Willmitzer et al. |
| 5,455,167 A | 10/1995 | Voelker et al. |
| 5,460,870 A | 10/1995 | Arthurs |
| 5,492,938 A | 2/1996 | Kyle et al. |
| 5,518,918 A | 5/1996 | Barclay et al. |
| 5,547,699 A | 8/1996 | Lizuka et al. |
| 5,563,058 A | 10/1996 | Davies et al. |
| 5,595,965 A | 1/1997 | Wiggins |
| 5,597,400 A | 1/1997 | Nonomura et al. |
| 5,680,812 A | 10/1997 | Linsgeseder |
| 5,685,218 A | 11/1997 | Kemper |
| 5,693,507 A | 12/1997 | Daniell et al. |
| 5,711,983 A | 1/1998 | Kyle et al. |
| 5,723,761 A | 3/1998 | Voelker et al. |
| 5,756,135 A | 5/1998 | Seeley |
| 5,826,500 A | 10/1998 | Kemper |
| 5,888,947 A | 3/1999 | Lambert et al. |
| 5,900,370 A | 5/1999 | Running |
| 5,910,630 A | 6/1999 | Davies et al. |
| 5,945,585 A | 8/1999 | Hitz et al. |
| 5,968,791 A | 10/1999 | Davies et al. |
| 6,139,897 A | 10/2000 | Goto et al. |
| 6,166,231 A | 12/2000 | Hoeksema |
| 6,255,505 B1 | 7/2001 | Bijl et al. |
| 6,338,866 B1 | 1/2002 | Criggall et al. |
| 6,344,231 B1 | 2/2002 | Nakajo et al. |
| 6,355,861 B1 | 3/2002 | Thomas |
| 6,372,460 B1 | 4/2002 | Gladue et al. |
| 6,410,281 B1 | 6/2002 | Barclay |
| 6,441,208 B2 | 8/2002 | Bijl et al. |
| 6,534,261 B1 | 3/2003 | Cox, III et al. |
| 6,620,427 B2 | 9/2003 | Lasekan et al. |
| 6,680,426 B2 | 1/2004 | Daniell et al. |
| 6,727,373 B2 | 4/2004 | Bijl et al. |
| 6,750,048 B2 | 6/2004 | Ruecker et al. |
| 6,762,345 B1 | 7/2004 | Cahoon et al. |
| 6,763,345 B1 | 7/2004 | Hempleman et al. |
| 6,867,308 B2 | 3/2005 | Bartok et al. |
| 7,053,267 B2 | 5/2006 | Knauf et al. |
| 7,063,957 B2 | 6/2006 | Chen |
| 7,081,567 B2 | 7/2006 | Xue et al. |
| 7,109,392 B1 | 9/2006 | Broglie et al. |
| 7,135,620 B2 | 11/2006 | Daniell et al. |
| 7,214,297 B2 | 5/2007 | Wang et al. |
| 7,268,276 B2 | 9/2007 | Ruezinsky et al. |
| 7,309,602 B2 | 12/2007 | David |
| 7,351,558 B2 | 4/2008 | Ruecker et al. |
| 7,468,267 B2 | 12/2008 | Monod et al. |
| 7,504,259 B2 | 3/2009 | Yadav et al. |
| 7,588,931 B2 | 9/2009 | Damude et al. |
| 7,622,570 B2 | 11/2009 | Oswald et al. |
| 7,652,156 B2 | 1/2010 | Hillion et al. |
| 7,662,598 B2 | 2/2010 | Ruecker et al. |
| 7,678,931 B2 | 3/2010 | Fichtali et al. |
| 7,781,193 B2 | 8/2010 | Ruecker et al. |
| 7,851,199 B2 | 12/2010 | Bailey et al. |
| 7,879,591 B2 | 2/2011 | Damude et al. |
| 7,883,882 B2 | 2/2011 | Franklin et al. |
| 7,914,832 B2 | 3/2011 | Uchino |
| 7,935,515 B2 | 5/2011 | Franklin et al. |
| 7,939,710 B1 | 5/2011 | Apt et al. |
| 8,003,365 B2 | 8/2011 | Yoshikuni et al. |
| 8,029,579 B2 | 10/2011 | Knuth et al. |
| 8,043,496 B1 | 10/2011 | Schuh et al. |
| 8,088,718 B2 | 1/2012 | Bicerano et al. |
| 8,119,583 B2 | 2/2012 | Day et al. |
| 8,163,675 B2 | 4/2012 | Navarrete et al. |
| 8,187,860 B2 | 5/2012 | Franklin et al. |
| 8,222,010 B2 | 7/2012 | Franklin et al. |
| 8,268,610 B2 | 9/2012 | Franklin et al. |
| 8,278,261 B2 | 10/2012 | Day et al. |
| 8,283,483 B2 | 10/2012 | Williams et al. |
| 8,435,767 B2 | 5/2013 | Franklin et al. |
| 8,450,083 B2 | 5/2013 | Day et al. |
| 8,476,059 B2 | 7/2013 | Trimbur et al. |
| 8,497,116 B2 | 7/2013 | Trimbur et al. |
| 8,512,999 B2 | 8/2013 | Trimbur et al. |
| 8,518,689 B2 | 8/2013 | Trimbur et al. |
| 8,530,207 B2 | 9/2013 | Watts et al. |
| 8,592,188 B2 | 11/2013 | Franklin et al. |
| 8,633,012 B2 | 1/2014 | Franklin et al. |
| 8,647,397 B2 | 2/2014 | Trimbur et al. |
| 8,674,180 B2 | 3/2014 | Franklin et al. |
| 8,697,402 B2 | 4/2014 | Trimbur et al. |
| 8,697,427 B2 | 4/2014 | Franklin et al. |
| 8,765,424 B2 | 7/2014 | Franklin et al. |
| 8,772,575 B2 | 7/2014 | Franklin et al. |
| 8,790,914 B2 | 7/2014 | Trimbur et al. |
| 8,802,422 B2 | 8/2014 | Trimbur et al. |
| 8,822,176 B2 | 9/2014 | Day et al. |
| 8,822,177 B2 | 9/2014 | Day et al. |
| 8,846,352 B2 | 9/2014 | Chua et al. |
| 8,846,375 B2 | 9/2014 | Franklin et al. |
| 8,852,885 B2 | 10/2014 | Franklin et al. |
| 8,889,401 B2 | 11/2014 | Trimbur et al. |
| 8,889,402 B2 | 11/2014 | Trimbur et al. |
| 8,945,908 B2 | 2/2015 | Franklin et al. |
| 8,951,777 B2 | 2/2015 | Franklin et al. |
| 9,062,294 B2 | 6/2015 | Franklin et al. |
| 9,066,527 B2 | 6/2015 | Franklin et al. |
| 9,068,213 B2 | 6/2015 | Franklin et al. |
| 9,102,973 B2 | 8/2015 | Franklin et al. |
| 9,109,239 B2 | 8/2015 | Franklin et al. |
| 9,200,307 B2 | 12/2015 | Franklin et al. |
| 9,249,436 B2 | 2/2016 | Franklin et al. |
| 9,249,441 B2 | 2/2016 | Franklin et al. |
| 9,255,282 B2 | 2/2016 | Franklin et al. |
| 9,279,136 B2 | 3/2016 | Franklin et al. |
| 9,353,389 B2 | 5/2016 | Franklin et al. |
| 9,388,435 B2 | 7/2016 | Franklin et al. |
| 9,434,909 B2 | 9/2016 | Trimbur et al. |
| 9,464,304 B2 | 10/2016 | Franklin et al. |
| 9,551,017 B2 | 1/2017 | Franklin et al. |
| 9,593,351 B2 | 3/2017 | Franklin et al. |
| 9,657,299 B2 | 5/2017 | Franklin et al. |
| 9,719,114 B2 | 8/2017 | Franklin et al. |
| 2002/0012979 A1 | 1/2002 | Berry et al. |
| 2002/0059661 A1 | 5/2002 | Dehesh |
| 2002/0122868 A1 | 9/2002 | Floeter et al. |
| 2002/0144455 A1 | 10/2002 | Bertrand et al. |
| 2002/0178467 A1 | 11/2002 | Dehesh |
| 2003/0054524 A1 | 3/2003 | Spener et al. |
| 2003/0079249 A1 | 4/2003 | Shanklin et al. |
| 2003/0082595 A1 | 5/2003 | Jiang et al. |
| 2003/0097686 A1 | 5/2003 | Knauf et al. |
| 2003/0145350 A1 | 7/2003 | Spener et al. |
| 2003/0211594 A1 | 11/2003 | Rosebrook |
| 2003/0229237 A1 | 12/2003 | Haas et al. |
| 2004/0053235 A1 | 3/2004 | Smirnoff et al. |
| 2004/0074760 A1 | 4/2004 | Portnoff et al. |
| 2004/0230085 A1 | 11/2004 | Jakkula et al. |
| 2004/0235123 A1 | 11/2004 | Liao et al. |

(56) References Cited

U.S. PATENT DOCUMENTS

| | | |
|---|---|---|
| 2004/0033557 A1 | 12/2004 | Scott et al. |
| 2005/0005333 A1 | 1/2005 | Ruezinsky et al. |
| 2005/0102716 A1 | 5/2005 | Venkatramesh et al. |
| 2005/0112735 A1 | 5/2005 | Zappi et al. |
| 2005/0153002 A1 | 7/2005 | Socia Rosales et al. |
| 2005/0170479 A1 | 8/2005 | Weaver et al. |
| 2005/0262588 A1 | 11/2005 | Dehesh et al. |
| 2005/0266537 A1 | 12/2005 | Chen |
| 2005/0272611 A1 | 12/2005 | Lord et al. |
| 2006/0048240 A1 | 3/2006 | Alexandrov et al. |
| 2006/0075522 A1 | 4/2006 | Cleveland et al. |
| 2006/0094088 A1 | 5/2006 | Picataggio et al. |
| 2006/0094089 A1 | 5/2006 | Barclay |
| 2006/0094090 A1 | 5/2006 | Damude et al. |
| 2006/0107346 A1 | 5/2006 | Schneeberger et al. |
| 2006/0122410 A1 | 6/2006 | Fichtali et al. |
| 2006/0130182 A1 | 6/2006 | Heim et al. |
| 2006/0153826 A1 | 7/2006 | Arnould et al. |
| 2006/0156436 A1 | 7/2006 | Nakamura et al. |
| 2006/0162006 A9 | 7/2006 | Sherman et al. |
| 2006/0199984 A1 | 9/2006 | Kuechler et al. |
| 2006/0225341 A1 | 10/2006 | Rohr et al. |
| 2006/0286205 A1 | 12/2006 | Fichtali et al. |
| 2007/0004016 A1 | 1/2007 | Picataggio et al. |
| 2007/0009988 A1 | 1/2007 | Monod et al. |
| 2007/0048848 A1 | 3/2007 | Sears |
| 2007/0099280 A1 | 5/2007 | Barclay |
| 2007/0118916 A1 | 5/2007 | Puzio et al. |
| 2007/0167396 A1 | 7/2007 | Dillon et al. |
| 2007/0218183 A1 | 9/2007 | Nakhasi et al. |
| 2007/0248531 A1 | 10/2007 | Debryun et al. |
| 2007/0254354 A1 | 11/2007 | Millis et al. |
| 2007/0261138 A1 | 11/2007 | Graham et al. |
| 2007/0275438 A1 | 11/2007 | David |
| 2008/0014620 A1 | 1/2008 | Op Den Camp et al. |
| 2008/0038804 A1 | 2/2008 | Du et al. |
| 2008/0040822 A1 | 2/2008 | Metz et al. |
| 2008/0107776 A1 | 5/2008 | Prakash et al. |
| 2008/0160593 A1 | 7/2008 | Oyler |
| 2008/0194029 A1 | 8/2008 | Hegemann et al. |
| 2008/0206379 A1 | 8/2008 | Fabritius et al. |
| 2008/0229451 A1 | 9/2008 | Cao et al. |
| 2008/0256666 A1 | 10/2008 | Zhu et al. |
| 2008/0283803 A1 | 11/2008 | Rapp et al. |
| 2009/0004715 A1 | 1/2009 | Trimbur et al. |
| 2009/0011480 A1 | 1/2009 | Trimbur et al. |
| 2009/0018300 A1 | 1/2009 | Bloom et al. |
| 2009/0035842 A1 | 2/2009 | Trimbur et al. |
| 2009/0047721 A1 | 2/2009 | Trimbur et al. |
| 2009/0061493 A1 | 3/2009 | Trimbur et al. |
| 2009/0064567 A1 | 3/2009 | Lippmeier et al. |
| 2009/0099260 A1 | 4/2009 | Namal Senanayake et al. |
| 2009/0117253 A1* | 5/2009 | Hong ............... C12N 9/0083 426/601 |
| 2009/0142322 A1 | 6/2009 | Ye |
| 2009/0145392 A1 | 6/2009 | Clark et al. |
| 2009/0148918 A1 | 6/2009 | Trimbur et al. |
| 2009/0176272 A1 | 7/2009 | Champagne et al. |
| 2009/0211150 A1 | 8/2009 | Wu et al. |
| 2009/0234146 A1 | 9/2009 | Cooney et al. |
| 2009/0271892 A1 | 10/2009 | Thomasset et al. |
| 2009/0274736 A1 | 11/2009 | Dillon et al. |
| 2009/0298143 A1 | 12/2009 | Roessler et al. |
| 2009/0298159 A1 | 12/2009 | Wu et al. |
| 2009/0305942 A1 | 12/2009 | Day et al. |
| 2009/0317878 A1 | 12/2009 | Champagne et al. |
| 2010/0010088 A1 | 1/2010 | Chilton et al. |
| 2010/0021912 A1 | 1/2010 | Farese et al. |
| 2010/0035320 A1 | 2/2010 | Blanchard et al. |
| 2010/0058651 A1 | 3/2010 | Knuth et al. |
| 2010/0093031 A1 | 4/2010 | Kobayashi et al. |
| 2010/0105955 A1 | 4/2010 | Alibhai et al. |
| 2010/0120643 A1 | 5/2010 | Brown et al. |
| 2010/0137647 A1 | 6/2010 | Bradin |
| 2010/0151112 A1 | 6/2010 | Franklin et al. |
| 2010/0151535 A1 | 6/2010 | Franklin et al. |
| 2010/0151538 A1 | 6/2010 | Franklin et al. |
| 2010/0151539 A1 | 6/2010 | Franklin et al. |
| 2010/0151567 A1 | 6/2010 | Franklin et al. |
| 2010/0154293 A1 | 6/2010 | Hom et al. |
| 2010/0170144 A1 | 7/2010 | Day et al. |
| 2010/0186117 A1 | 7/2010 | Fabijanski et al. |
| 2010/0196575 A1 | 8/2010 | Sanchez et al. |
| 2010/0239712 A1 | 9/2010 | Brooks et al. |
| 2010/0248322 A1 | 9/2010 | Pfeiffer et al. |
| 2010/0249260 A1 | 9/2010 | Casati et al. |
| 2010/0297292 A1 | 11/2010 | Brooks et al. |
| 2010/0297295 A1 | 11/2010 | Brooks et al. |
| 2010/0297296 A1 | 11/2010 | Brooks et al. |
| 2010/0297323 A1 | 11/2010 | Brooks et al. |
| 2010/0297325 A1 | 11/2010 | Brooks et al. |
| 2010/0297331 A1 | 11/2010 | Brooks et al. |
| 2010/0035309 A1 | 12/2010 | Havemen et al. |
| 2010/0303957 A1 | 12/2010 | Brooks et al. |
| 2010/0303961 A1 | 12/2010 | Brooks et al. |
| 2010/0303989 A1 | 12/2010 | Brooks et al. |
| 2010/0303990 A1 | 12/2010 | Brooks et al. |
| 2010/0323413 A1 | 12/2010 | Trimbur et al. |
| 2010/0323414 A1 | 12/2010 | Trimbur et al. |
| 2011/0014665 A1 | 1/2011 | Trimbur et al. |
| 2011/0015417 A1 | 1/2011 | Trimbur et al. |
| 2011/0047863 A1 | 3/2011 | Trimbur et al. |
| 2011/0065821 A1 | 3/2011 | Abraham et al. |
| 2011/0072714 A1 | 3/2011 | Gaertner et al. |
| 2011/0111470 A1 | 5/2011 | Berry et al. |
| 2011/0165634 A1 | 7/2011 | Franklin et al. |
| 2011/0190522 A1 | 8/2011 | Trimbur et al. |
| 2011/0203168 A1 | 8/2011 | Franklin et al. |
| 2011/0250658 A1 | 10/2011 | Franklin et al. |
| 2011/0252696 A1 | 10/2011 | Franklin et al. |
| 2011/0256268 A1 | 10/2011 | Franklin et al. |
| 2011/0256282 A1 | 10/2011 | Piechocki et al. |
| 2011/0284215 A1 | 11/2011 | Pfeiffer et al. |
| 2011/0293785 A1 | 12/2011 | Franklin et al. |
| 2011/0294174 A1 | 12/2011 | Franklin et al. |
| 2012/0009636 A1 | 1/2012 | Berry et al. |
| 2012/0021495 A1 | 1/2012 | Vanzin |
| 2012/0028319 A1 | 2/2012 | Trimbur et al. |
| 2012/0034662 A1 | 2/2012 | Hu et al. |
| 2012/0060242 A1 | 3/2012 | Senger et al. |
| 2012/0119862 A1 | 5/2012 | Franklin et al. |
| 2012/0122192 A1 | 5/2012 | Trimbur et al. |
| 2012/0128851 A1 | 5/2012 | Brooks et al. |
| 2012/0156717 A1 | 6/2012 | Allnutt et al. |
| 2012/0164701 A1 | 6/2012 | Trimbur et al. |
| 2012/0203018 A1 | 8/2012 | Franklin et al. |
| 2012/0277452 A1 | 11/2012 | Franklin et al. |
| 2012/0277453 A1 | 11/2012 | Franklin et al. |
| 2012/0283460 A1 | 11/2012 | Franklin et al. |
| 2012/0288930 A1 | 11/2012 | Trimbur et al. |
| 2012/0324784 A1 | 12/2012 | Franklin et al. |
| 2012/0329109 A1 | 12/2012 | Chua et al. |
| 2013/0004646 A1 | 1/2013 | Franklin et al. |
| 2013/0006006 A1 | 1/2013 | Day et al. |
| 2013/0031678 A1 | 1/2013 | Zheng et al. |
| 2013/0034887 A1 | 2/2013 | Franklin et al. |
| 2013/0078709 A1 | 3/2013 | Franklin et al. |
| 2013/0089916 A1 | 4/2013 | Franklin et al. |
| 2013/0096211 A1 | 4/2013 | Franklin et al. |
| 2013/0102039 A1 | 4/2013 | Franklin et al. |
| 2013/0116462 A1 | 5/2013 | Durrett et al. |
| 2013/0122180 A1 | 5/2013 | Brooks et al. |
| 2013/0165677 A1 | 6/2013 | Franklin et al. |
| 2013/0197247 A1 | 8/2013 | Franklin et al. |
| 2013/0273621 A1 | 10/2013 | Franklin et al. |
| 2013/0295268 A1 | 11/2013 | Day et al. |
| 2013/0296591 A1 | 11/2013 | Day et al. |
| 2013/0316410 A1 | 11/2013 | Franklin et al. |
| 2013/0323382 A1 | 12/2013 | Franklin et al. |
| 2013/0323823 A1 | 12/2013 | Franklin et al. |
| 2013/0330790 A1 | 12/2013 | Trimbur et al. |
| 2013/0331584 A1 | 12/2013 | Franklin et al. |
| 2013/0338385 A1 | 12/2013 | Franklin et al. |
| 2014/0170716 A1 | 6/2014 | Trimbur et al. |

(56) References Cited

U.S. PATENT DOCUMENTS

| | | |
|---|---|---|
| 2014/0256024 A1 | 9/2014 | Franklin et al. |
| 2014/0256600 A1 | 9/2014 | Dillon et al. |
| 2014/0305031 A1 | 10/2014 | Day et al. |
| 2014/0315267 A1 | 10/2014 | Franklin et al. |
| 2014/0336100 A1 | 11/2014 | Day et al. |
| 2014/0357746 A1 | 12/2014 | Ngantung et al. |
| 2014/0377847 A1 | 12/2014 | Franklin et al. |
| 2015/0073163 A1 | 3/2015 | Chua et al. |
| 2015/0125914 A1 | 5/2015 | Franklin et al. |
| 2015/0218604 A1 | 8/2015 | Franklin et al. |
| 2015/0275149 A1 | 10/2015 | Dummer et al. |
| 2015/0344917 A1 | 12/2015 | Franklin et al. |
| 2016/0010066 A1 | 1/2016 | Davis et al. |
| 2016/0032332 A1 | 2/2016 | Davis et al. |
| 2016/0186191 A1 | 6/2016 | Franklin et al. |
| 2016/0186219 A1 | 6/2016 | Franklin et al. |
| 2016/0194672 A1 | 7/2016 | Franklin et al. |
| 2016/0348119 A1 | 12/2016 | Franklin et al. |
| 2016/0376617 A1 | 12/2016 | Franklin et al. |
| 2017/0022436 A1 | 1/2017 | Trimbur et al. |
| 2017/0145450 A1 | 5/2017 | Franklin et al. |
| 2017/0314048 A1 | 11/2017 | Franklin et al. |

FOREIGN PATENT DOCUMENTS

| | | |
|---|---|---|
| EP | 1 178 118 A1 | 2/2002 |
| EP | 1 642 959 A1 | 4/2006 |
| EP | 1 681 337 A1 | 7/2006 |
| EP | 1 741 767 A1 | 1/2007 |
| EP | 1 947 189 A2 | 7/2008 |
| EP | 2 327 776 A1 | 6/2011 |
| EP | 2 152 849 B1 | 2/2013 |
| FR | 2924126 A1 | 5/2009 |
| GB | 824151 | 11/1959 |
| JP | 57-150379 | 9/1982 |
| JP | 06-253872 A | 9/1994 |
| JP | 07-008217 | 1/1995 |
| JP | 07-075557 | 3/1995 |
| JP | H09-511650 A | 11/1997 |
| JP | H10-46181 A | 2/1998 |
| JP | 2000-136199 | 5/2000 |
| JP | 2000-175696 A | 6/2000 |
| JP | 2002-125601 | 5/2002 |
| JP | 2002-523864 A | 7/2002 |
| JP | 2003-102467 A | 4/2003 |
| JP | 2003-325067 A | 11/2003 |
| JP | 2007-314549 A | 12/2007 |
| JP | 2008-081559 | 4/2008 |
| JP | 2008-514221 | 5/2008 |
| JP | 2008-148663 | 7/2008 |
| JP | 2008-178871 | 8/2008 |
| JP | 2010-528627 | 8/2010 |
| JP | 2015-500009 A | 1/2015 |
| JP | 6071904 | 2/2017 |
| KR | 10-2007-00085649 A | 8/2007 |
| WO | WO 91/018105 A1 | 11/1991 |
| WO | WO 92/11373 A1 | 7/1992 |
| WO | WO 93/06712 A1 | 4/1993 |
| WO | WO 94/10288 A2 | 5/1994 |
| WO | WO 95/13390 A2 | 5/1995 |
| WO | WO 95/27791 A1 | 10/1995 |
| WO | WO 95/31553 A1 | 11/1995 |
| WO | WO 97/40698 A1 | 11/1997 |
| WO | WO 98/32770 A1 | 7/1998 |
| WO | WO 99/37166 A1 | 7/1999 |
| WO | WO 99/64618 | 11/1999 |
| WO | WO 00/011682 A1 | 3/2000 |
| WO | WO 00/61740 A1 | 10/2000 |
| WO | WO 00/66750 A2 | 11/2000 |
| WO | WO 00/74471 A1 | 12/2000 |
| WO | WO 02/08403 A2 | 1/2002 |
| WO | WO 02/085293 A2 | 10/2002 |
| WO | WO 2004/016282 A1 | 2/2004 |
| WO | WO 04/101753 A2 | 11/2004 |
| WO | WO 2005/003310 A2 | 1/2005 |
| WO | WO 2005/035693 A2 | 4/2005 |
| WO | WO 2006/052807 A2 | 5/2006 |
| WO | WO 2006/055322 A2 | 5/2006 |
| WO | WO 2006/122299 A2 | 11/2006 |
| WO | WO 2007/027669 A1 | 3/2007 |
| WO | WO 2007/38566 A2 | 4/2007 |
| WO | WO 2007/106903 A2 | 9/2007 |
| WO | WO 2007/117511 A2 | 10/2007 |
| WO | WO 2007/121100 A2 | 10/2007 |
| WO | WO 2007/134294 A2 | 11/2007 |
| WO | WO 2007/141257 A2 | 12/2007 |
| WO | WO 2008/002643 A2 | 1/2008 |
| WO | WO 2008/011811 A1 | 1/2008 |
| WO | WO 2008/058664 A1 | 5/2008 |
| WO | WO 2008/060571 A2 | 5/2008 |
| WO | WO 2008/083352 A1 | 7/2008 |
| WO | WO 2008/130372 A2 | 10/2008 |
| WO | WO 2008/134836 A2 | 11/2008 |
| WO | WO 2008/151149 A2 | 12/2008 |
| WO | WO 2009/076559 A1 | 6/2009 |
| WO | WO 2009/105620 A1 | 8/2009 |
| WO | WO 2009/124070 A1 | 10/2009 |
| WO | WO 2009/126843 A2 | 10/2009 |
| WO | WO 2010/017346 A2 | 2/2010 |
| WO | WO 2010/019813 A2 | 2/2010 |
| WO | WO 2010/037209 A1 | 4/2010 |
| WO | WO 2010/045368 A2 | 4/2010 |
| WO | WO 2010/063031 A2 | 6/2010 |
| WO | WO 2010/063032 A2 | 6/2010 |
| WO | WO 2010/111698 A2 | 9/2010 |
| WO | WO 2010/120923 A1 | 10/2010 |
| WO | WO 2010/120939 A2 | 10/2010 |
| WO | WO 2011/026008 A1 | 3/2011 |
| WO | WO 2011/075716 A1 | 6/2011 |
| WO | WO 2011/090730 A1 | 7/2011 |
| WO | WO 2011/130573 A1 | 10/2011 |
| WO | WO 2011/130576 A1 | 10/2011 |
| WO | WO 2011/130578 A2 | 10/2011 |
| WO | WO 2011/150410 A2 | 12/2011 |
| WO | WO 2011/150411 A1 | 12/2011 |
| WO | WO 2012/061647 A2 | 5/2012 |
| WO | WO 2012/106560 A1 | 8/2012 |
| WO | WO 2012/154626 A1 | 11/2012 |
| WO | WO 2013/082186 A2 | 6/2013 |
| WO | WO 2013/096891 A1 | 6/2013 |
| WO | WO 2013/158938 | 10/2013 |
| WO | WO 2014/176515 A2 | 10/2014 |
| WO | WO 15/051319 A2 | 4/2015 |
| WO | WO 2016/007862 A2 | 1/2016 |
| WO | WO 2016/164495 A1 | 10/2016 |
| WO | WO 2017/058802 A1 | 4/2017 |

OTHER PUBLICATIONS

"Codex Standard for Named Vegetable Oils," Codex Alimentarius, Codex Stan 210-1999, pp. 1-16, (1999).

Abbadi et al., "Knockout of the regulatory site of 3-ketoacyl-ACP synthase III enhances short- and medium-chain acyl-ACP synthesis," The Plant Journal, 24(1):1-9, (2000).

Aggelis et al., "Enhancement of single cell oil production by Yarrowia lipolytica growing in the presence of Teucrium polium L. aqueous extract," Biotechnology Letters, 21:747-749, (1999).

Aguirre et al., "Engineering challenges in biodiesel production from microalgae," Critical Reviews in Biotechnology, 33(3): 293-308, (2013).

Altschul et al., "Basic local alignment search tool," J Mol Biol, 215(3):403-410, (1990).

Amaro et al., "Advances and perspectives in using microalgae to produce biodiesel," Applied Energy, 88:3402-3410, (2011).

Andersen, "Biology and Systematics of Heterokont and Haptophyte Algae," American Journal of Botany, 91(10):1508-1522, (2004).

Appel et al., "A multicopy vector system for genetic studies in Mucor circinelloides and other zygomycetes," Molecular Genetics and Genomics, 271(5):595-602, (2004).

Apt et al., "Stable nuclear transformation of the diatom Phaeodactylum tricornutum," Mol Gen Genet, 252(5):572-579, (1996).

(56) References Cited

OTHER PUBLICATIONS

Barnes et al., "Contribution of 5'- and 3'-untranslated regions of plastid mRNAs to the expression of Chlamydomonas reinhardtii chloroplast genes," Mol Genet Genomics, 274(6):625-636, (2005).
Beale et al., "Chlorophyll Synthesis in Chlorella: Regulation by Degree of Light Limitation of Growth," Plant Physiol., 47:230-235, (1971).
Bhunia et al., "Algal Biodiesel Production: Challenges and Opportunities," Bioenergy and Biofuel from Biowastes and Biomass, American Society of Civil Engineers, pp. 313-345, (2010).
Bigogno et al., "Biosynthesis of arachidonic acid in the oleaginous microalga Parietochloris incise (Cholorphyceae): Radiolabeling studies," Lipids 37(2):209-216 (2002); Abstract Only.
Bigogno et al., "Lipid and fatty acid composition of the green oleaginous alga *Parietochloris incisa*, the richest plant source of arachidonic acid," Pytochemistry, 60:497-503, (2002).
Blowers et al., "Studies on Chlamydomonas chloroplast transformation: foreign DNA can be stably maintained in the chromosome," Plant Cell, 1(1):123-132, (1989).
Bohacenko et al., "Detection of Olive Oils Authenticity by Determination of their Sterol Content using LC/GC," Czech J. Food Sci., 19(3):97-103, (2001).
Bonaventure et al., "Disruption of the Fats Gene in *Arabidopsis* Dethonstrates an Essential Role of Saturated Fatty Acids in Plant Growth," The Plant Cell 15:1020-1033, (2003).
Bordes et al., "A new recombinant protein expression system for high-throughput screening in the yeast *Yarrowia lipolytica*," Journal of Microbiological Methods, 70(3):493-502, (2007).
Bornscheuer et al. (ed), "Enzymes in Lipid Modification," Wiley-VCH Verlag Gmbh & Co. KGaA, 1st Edition, ISBN: 3-527-30176-3, Sections 1-11, 231 pages, (2000). (part 1 of 2 of book).
Bornscheuer et al. (ed), "Enzymes in Lipid Modification," Wiley-VCH Verlag Gmbh & Co. KGaA, 1st Edition, ISBN: 3-527-30176-3, Sections 12-18, 133 pages, (2000). (part 2 of 2 of book).
Borza et al., "Multiple Metabolic Roles for the Nonphotosynthetic Plastid of the Green Alga *Prototheca wickerhamii*," Eukaryotic Cell, 4(2):253-261, (2005).
Boutry et al., "Targeting of bacterial chloramphenicol acetyltransferase to mitochondria in transgenic plants," Nature, 328(6128):340-2, 1987.
Boynton et al., "Chloroplast Transformation in Chlamydomonas with High Velocity Microprojectiles," Science, 240(4858):1534-1538, (1998).
Broun et al., "A bifunctional oleate 12-hydroxylase: desaturase from Lesquerella fendleri," The Plant Journal, 13(2):201-210, (1998).
Broun et al., "Accumulation of Ricinoleic, Lesquerolic, and Densipolic Acids in Seeds of Transgenic *Arabidopsis* Plants That Express a Fatty Acyl Hydroxylase cDNA from Castor Bean," Plant Physiol., 113:933-942, (1997).
Broun et al., "Catalytic Plasticity of Fatty Acid Modification Enzymes Underlying Chemical Diversity of Plant Lipids," Science, 282:1315-1317, (1998). [Retrieved from the Internet Feb. 27 , 2007: URL: http://www.sciencemag.org>].
Brown et al., "The amino-acid and sugar composition of 16 species of micralgae used in mariculture," J. Exp. Mar. Biol. Ecol. 145:79-99 abstract (1991).
Burgal et al., "Metabolic engineering of hydroxy fatty acid production in plants: RcDGAT2 drives dramatic increases in ricinoleate levels in seed oil," Plant Biotechnol J., 6(8):819-831, (2008).
Cahoon et al., "A Determinant of Substrate Specificity Predicted from the Acyl-Acyl Carrier Protein Desaturase of Developing Cat's Claw Seed," Plant Physiol., 117:593-598, (1998).
Chang et al., "Deletion of the Δ12-oleic acid desaturase gene of a nonafiatoxigenic Aspergillus parasiticus field isolate affects conidiation and sclerotial development," Journal of Applied Microbiology, 97:1178-1184, (2004).
Chasan, "Engineering Fatty Acids—The Long and Short of It," Plant Cell, 7:235-237, (1995).

Chattopadhyay et al., "Effect of single amino acid mutations in the conserved GDNQ motif of L protein of Rinderpest virus on RNA synthesis in vitro and in vivo," Virus Research, 99:139-145, (2004).
Chen et al., "Recognition of prokaryotic transcription terminators by spinach chloroplast RNA polymerase," Nucleic Acids Research, 16(17):8411-8431, (1988).
Chen et al., "Effect of C/N ratio and aeration on the fatty acid composition of heterotrophic Chlorella sorokiniana," Journal of Applied Phycology, 3:203-209, (1991).
Chen et al., "Highly Effective Expression of Rabbit Neutrophil Peptide-1 Gene in Chlorella Ellipsoidea Cells," Current Genetics, 39:365-370, (2001).
Chen et al., "Structural classification and properties of ketoacyl synthases," Protein Science, 20(10):1659-1667, (2011).
Chica et al., "Semi-rational approaches to engineering enzyme activity: combining the benefits of directed evolution and rational design ," Current Opinion in Biotechnology, 16:378-384, (2005).
Chow et al., "Electrotranformation of Chlorella Vulgaris," Plant Cell Reports, 18:778-780, (1999).
Ciferri, "Thiamine-deficiency of Prototheca, a Yeast-like Achloric Alga," Nature, 178:1475-1476, (1956).
Co et al., "Matching the Functionality of Single-Cell Algal Oils with Different Molecular Compositions," J Am Oil Chem Soc, doi:10.1007/s11746-013-2405-y, 16 pages, (2014).
Cobley et al., "CpeR is an activator required for expression of the phycoerythrin operon (cpeBA) in the cyanobacterium Fremyella diplosiphon and is encoded in the phycoerythrin linker-polypeptide operon (cpeCDESTR)," Molecular Microbiology, 44(6):1517-153.
Cobley et al., Construction of Shuttle Plasmids Which Can Be Efficiently Mobilized From *Escherichia Coli* Into the Chromatically Adapting Cyanobacterium, Plasmid, 30:90-105, (1993).
Cohen et al., "The Heterotrophic Connection in a Photoautotrophic Chlorella Vulgaris Dominant in W Astew Ater Oxidation Ponds," War. Sci. Tech., 27(7-8):151-155, (1993).
Comai et al., "Chloroplast Transport of a Ribulose Biphosphate Carboxylase Small Subunit-5-Enolpyruvyl 3-Phosphoshikimate Synthase Chimeric Protein Requires Part of the Mature Small Subunit in Addition to the Transit Peptide," Journal of Biological Chemis.
Cordy et al., "Chlorellasis in a Lamb," Vet. Path., 10:171-176, (1973).
Courchesne et al., "Enhancement of Lipid Production Using Biochemical, Genetic and Transcription Factor Engineering Approaches," J Biotechnol. Epub, 141(1-2):31-41, (2009).
Covello et al., "Functional Expression of the Extraplastidial *Arabidopsis thaliana* Oleate Desaturase Gene (FAD2) in *Saccharomyces cerevisiae*'," Plant Physiol., 111:223-226, (1996).
Davies et al.,"Expression of the Arylsulfatase Gene from the Beta 2-Tubulin Promoter in Chlamydomonas reinhardtii," Nucleic Acids Research, 20(12):2959-2965, (1992).
Dawson et al., "Stable Transformation of Chlorella: Rescue of Nitrate Reductase-Deficient Mutants with the Nitrate Reductase Gene," Current Microbiology, 35:356-362, (1997).
Day, AL. et al., "Safety evaluation of a high-lipid algal biomass from Chlorella protorhecoides," Rego!. Toxicol. Pharmacol., doi:10.1016/j.yrtph.2009.06.014, 15 pages, (2009).
De Cock, "Structure development in confectionery products: importance of triacylglycerol composition," Master Thesis, Masters in Bioscience Engineering, Ghent University, 73 pages, (2011).
Debuchy et al., "The argininosuccinate lyase gene of Chlamydomonas reinhardtii: an important tool for nuclear transformation and for correlating the genetic and molecular maps of the ARG7 locus," EMBO J., 8(10):2803-2809, (1989).
Dehesh et al., "KAS IV: a 3-ketoacyl-ACP synthase from Cuphea sp. is a medium chain specific condensing enzyme," The Plant Journal, 15:383-390, (1998).
Dehesh et al., "Production of high levels of 8:0 and 10:0 fatty acids in transgenic canola by overexpression of Ch FatB2, a thioesterase cDNA from Cuphea hookeriana," The Plant Journal, 9(2):167-172, (1996).
Demirbas et al., "Importance of algae oil as a source of biodiesel," Energy Conversion and Management, 52:163-170, (2011).

(56) References Cited

OTHER PUBLICATIONS

Deshnium et al., "Transformation of Synechococcus with a gene for choline oxidase enhances tolerance to salt stress," Plant Mol Biol, 29(5):897-907, (1995).
Desmond et al., "Phylogenomics of Sterol Synthesis: Insights into the Origin, Evolution, and Diversity of a Key Eukaryotic Feature," Genome. Biol. Evol., 1:364-381, (2009).
Devos et al., "Practical Limits of Function Prediction," Proteins: Structure, Function, and Genetics, 41:98-107, (2000).
Dormann et al., "Cloning and Expression in *Escherichia coli* of a Novel Thioesterase from *Arabidopsis thaliana* Specific for Long-Chain Acyl-Acyl Carrier Proteins," Archives of Biochemistry and Biophysics, 316(1):612-618, (1995).
Dunahay et al., "Genetic Engineering of Microalgae for Fuel Production," Applied Biochemistry and Biotechnology, 34/35:331-339 (1992).
Dunahay et al., "Manipulation of Microalgal Lipid Production Using Genetic Engineering," Applied Biochemistry and Biotechnology, 57/58:223-231, (1996).
Eccleston et al., "Medium-chain Fatty Acid Biosynthesis and Utilization in Brassica Mapus Plants Expressing Lauroyl-Acyl Carrier Protein Thioesterase," Planta 198:46-53, (1996).
El-Fadaly et al., "Single Cell Oil Production by an Oleaginous Yeast Strain in a Low Cost Cultivation Medium," Research Journal of Microbiology, 4(8):301-313, (2009).
El-Sheekh, MM., "Stable Transformation of the Intact Cells of Chlorella Kessleri With High Velocity Microprotectiles," Biologic Plantarium 42(2): 209-216, (1999).
EPO Supplementary European Search Report and European Search Opinion for application EP 12782478.7 dated Oct. 22, 2014.
EPO Supplementary European Search Report and European Search Opinion for application EP08769988.0 dated Jul. 1, 2011.
EPO Supplementary European Search Report and European Search Opinion for application EP11158642.6 dated Jul. 1, 2011.
EPO Supplementary European Search Report and European Search Opinion for application EP12741997.6 dated Aug. 31, 2015.
EPO Supplementary European Search Report and European Search Opinion for application EP 09829850.8 dated May 16, 2014.
Erhan, "Vegetable Oils as Lubricants, Hydraulic Fluids, and Inks," Bailey's Industrial Oil and Fat Products, 6:259-278, (2005).
Evans et al., "A comparison of the oleaginous yeast, Candida curvata, grown on different carbon sources in continuous and batch culture," Lipids, 18(09):623-629, (1983).
Facciotti et al., "Improved stearate phenotype in transgenic canola expressing a modified acyl-acyl carrier protein thioesterase," Nat Biotechnol., 17(6):593-597, (1999).
Falciatore et al., "Transformation of Nonselectable Reporter Genes in Marine Diatoms," Marine Biotechnology; 1:239-251, (1999).
Fall et al., "Bioconversion of Xylan to Triglycerides by Oil-Rich Yeasts," Applied and Environmental Microbiology, 47(5):1130-1134, (1984).
Fernandez-Reiriz et al., "Biomass Production and Variation in the Biochemical Profile (Total Protein, Carbohydrates, RNA, Lipids and Fatty Acids) of Seven Species of Marine Microalgae," Aquaculture, 83:17-37, (1989).
Ferrentino, "Microalgal oil extraction and in situ transesterification," University of New Hampshire, Pub. No. MT 1447885, 8 pages, (2007).
Ferrentino, et al., "Microalgal Oil Extraction and In-situ Transesterification," AIChE Annual Mtg, San Francisco, CA, Nov. 11-13, 2006. Abstract.
Franklin et al., "Prospects for molecular farming in the green alga *Chlamydomonas reinhardtii*," Current Opinion in Plant Biology, 7:159-165, (2004).
Franzen et al., "Chloroplast transit peptides from the green alga *Chlamydomonas reinhardtii* share features with both mitochondrial and higher plant chloroplast presequences," FEBS Letters, 260(2):165-168, (1990).

Frenz et al., "Hydrocarbon recovery by extraction with a biocompatible solvent from free and immobilized cultures of Botryococcus braunli," Enzyme Microb Technol, 11(11):717-724, (1989).
Frohms et al., "Potassium ion channels of Chlorella viruses cause rapid depolarization of host cells during infection," J Virol, 80(5):2437-2444, (2006).
Fromm et al., "Expression of Genes Transferred into Monocot and Dicot Plant Cells by Electroporation," Proc Natl Acad Sci, 82:5824-5828, (1985).
Funes et al., "The typically mitochondrial DNA-encoded ATP6 subunit of the F1F0-ATPase is encoded by a nuclear gene in Chlamydomonas reinhardtii," J Biol Chem, 277(8):6051-6058, (2002).
Gabay et al., "Stigmasterol: a phytosterol with potential anti-osteoarthritic proteins," Osteoarthritis and Cartilage,18:106-116, (2010).
GenBank: Accession No. AAC49001.1, May 1995. [Retrieved from the Internet Oct. 14, 2014: <URL: http://www.ncbi.nlrrtnih.gov/protein/595955?sat=13&satkey=6522409>].
Gill et al., "Lipid Accumulation in an Oleaginous Yeast (Candida 107) Growing on Glucose in Single-Stage Continuous Culture," Applied and Environmental Microbiology, 33(02):231-239, (1977).
Gouveia et al., "Microalgae in Novel Food Products," Food Chemistry Research Developments, Chapter 2, Nova Science Publishers, Inc., ISBN 978-1-60456-262-0, 37 pages, (2008).
Graves et al., "Hyaluronan synthesis in virus PBCV-1-infected chlorella-like green algae," Virology, 257(1):15-23, (1999).
Grima et al., "Recovery of microalgal biomass and metabolites: process options and economics," Biotechnology Advances, 20:491-515, (2003).
Gruber et al., "*Escherichia coli*-Anacystis nidulans plasmid shuttle vectors containing the PL promoter from bacteriophage lambda," Current Microbiology, 22(1):15-19, (1991).
Guiry et al., "How Many Species of Algae are There?," J. Phycol., 48:1057-1063, (2012).
Gul et al., "Sterols and the Phytosterol Content in Oilseed Rape (*Brassica napus* L.)," Journal of Cell and Molecular Biology, 5:71-79 (2006).
Gunstone, "Enzymes as biocatalysts in the modification of natural lipids," Journal of the Science of Food and Agriculture, 79:1535-1549, (1999).
Guo et al., "Increase in nervonic acid content in transformed yeast and transgenic plants by introduction of a Lunaria annua L. 3-ketoacyl-CoA synthase (KCS) gene," Plant Mol. Biol., 69:565-575, (2009).
Guo-Zhong et al., "The Actin Gene Promoter-driven Bar as a Dominant Selectable Marker for Nuclear Transformation of Dunaliella Salina," Acta Genetica Sinica, 32(4): 424-433, (2005).
Guschina et al., "Lipids and lipid metabolism in eukaryotic algae," Progress in Lipid Research, 45:160-186, (2006).
Hall et al., "Expression of a foreign gene in Chlamydomonas reinhardtii," Gene, 124(1):75-81, (1993).
Hall et al., "Lipid Accumulation in an Oleaginous Yeast (Candida 107) Growing on Glucose Under Various Conditions in a One- and Two-Stage Continuous Culture," Applied and Environmental Microbiology, 33(3):577-584, (1977).
Hallmann et al., "Reporter Genes and Highly Regulated Promoters as Tools for Transformation Experiements in Volvox Carteri," Proc Natl Acad Sci U S A., 91(24):11562-11566, (1994).
Hanley-Bowdoin et al., "Chloroplast promoters," Trends in Biochemical Sciences, 12:67-70, (1987).
Hawkins et al., "Expression of Human Growth Hormone by the Eukaryotic Alga, Chlorella," Current Microbiology, 38:335-341, (1999).
Heifetz, "Genetic Engineering of the Chloroplast," Biochimie, 82:655-666, (2000).
Heise et al., "Factors Controlling Medium-Chain Fatty Acid Synthesis in Plastids From Cuphea Embryos," Prog. Lipid Res., 33(112):87-95, (1994).
Henderson et al., "Composition and Biosynthesis in the Marine Dinoflagellate Cryptheocodznzum Cohnii," Phytochem. 27(6):1679-1683 (1988).

(56) References Cited

OTHER PUBLICATIONS

Henikoff et al., "Amino Acid Substitution Matrices from Protein Blocks," Proc Natl Acad of Sci, 89(22):10915-10919, (1992).
Heredia et al., "Simultaneous utilization of glucose and xylose by Candida curvata D in continuous culture," Biotechnology Letters, 10(01):25-30, (1988).
Heredia-Arroyo et al., "Oil Accumulation via Heterotrophic/ Mixotrophic Chlorella protothecoides," Appl Biochem Biotechnol, 162:1978-1995, (2010).
Hillen et al., "Hydrocracking of the Oils of Botryococcus braunii to Transport Fuels," Biotechnology and Bioengineering, 24(1):193-205, (1982).
Hiramatsu et al., "Expression of a chitinase gene and lysis of the host cell wall during Chlorella virus CVK2 infection," Virology, 260(2):308-315, (1999).
Hu et al., "Microalgal Triacylglycerols as Feedstocks for Biofuel Production: Perspectives and Advances," The Plant Journal 54:621-639, (2008).
Huang et al., "Sterols as ecological indicators," Geochimica et Cosmochimica Acta, 43:739-745, (1979).
Huang et al., "Expression of Mercuric Reductase From Bacillus Megaterium MB1 in Eukaryotic Microalga Chlorella sp. DT: An Approach for Mercury Phytoremediation," Appl. Microbiol. Biotechnol., 72:197-205, (2006).
Huss et al., "Deoxyribonucleic acid reassociation in the taxonomy of the genus *Chlorella*," Arch Microbiol, 150:509-511, (1988).
Inoue et al., "Analysis of oil derived from liquefaction of Botryococcus Braunii," Biomass and Bioenergy, 6(4):269-274, (1994).
Itoh et al., "Sterol Compositoin of 19 Vegetable Oils," Journal of the American Oil Chmists' Society, 50:122-125, (1973).
Iturriaga et al. "Heterologous transformation of Mucor circinelloides with the Phycomyces blakesleeanus leu1 gene," Current Genetics, 21(3):215-223, (1992).
Jakobiak et al., "The Bacterial Paromomycin Resistance Gene, aphH, as a Dominant Selectable Marker in Volvox carteri," Protist, 55: 381-393, (2004).
Jarvis et al. "Transient Expression of Firefly Luciferase in Protoplasts of the Green Alga *Chlorella ellipsoidea*," Current Genet., 19: 317-322, (1991).
Jaworski et al., "Industrial oils from transgenic plants," Current Opinion in Plant Biology, 6:178-184, (2003).
Jha et al., "Cloning and functional expression of an acyl-ACP thioesterase FatB type from Diploknema (Madhuca) butyracea seeds in *Escherichia coli*," Plant Physiology and Biochemistry, 44:645-655, (2006).
Jiang et al., "The actin gene promoter-driven bar as a dominant selectable marker for nuclear transformation of Dunaliella salina," Yi Chuan Xue Bao, 32(4):424-433, (2005).
Jones et al., "Palmitoyl-Acyl Carrier Protein (ACP) Thioesterase and the Evolutionary Origin of Plant Acyl-ACP Thioesterases," Plant Cell, 7:359-371, (1995).
Kalscheuer et al., "Establishment of a Gene Transfer System for Rhodococcus Opacus PD630 Based on Electroporation and its Application for Recombinant Biosynthesis of Poly(3-hyroxyalkanoic acids)," Applied Microbiology and Biotechnology, 52(4):508-515, (1999).
Kamiya, "Effects of Blue Light and Ammonia on Nitrogen Metabolism in a Colorless Mutant of Chlorella," Plant Cell Physiol., 30(4):513-521, (1989).
Kamurthy et al., "Antinocieptive Activity of Stigmosterol-3-Glyceryl-2-Linoleiate, Campesterol and Daucosterol Isolated From Aerva Lanata Linn. Aerial Parts," Asian J Pharm Clin Res, 6(1):149-152, (2013).
Kang et al., "Genetic diversity in chlorella viruses flanking kcv, a gene that encodes a potassium ion channel protein," Virology, 326(1):150-159, (2004).
Kang et al., "The regulation activity of Chlorella virus gene 5' upstream sequence in *Escherichia coli* and eucaryotic alage," Institute of Microbiology, Chinese Academy of Sciences, Beijing, 16(4):443-6, (2000). Abstract only.
Karabulut et al., "Determination of changes in some physical and chemical properties of soybean oil during hydrogenation," Food Chemistry, 81:453-456, (2003).
Karlin et al., "Applications and statistics for multiple high-scoring segments in molecular sequences," Proc Natl Acad Sci, 90(12):5873-5877, (1993).
Katayama et al., "Alpha-Linolenate and Photosynethetic Activity in Chlorella Protothecoides," Plant Physiol., 42:308-313, (1967).
Kawasaki et al., "Characterization of Immediate Early Genes Expressed in Chlorovirus Infections," Nucleic Acids Symp Ser, 44:161-162, (2000).
Kawasaki et al., "Immediate Early Genes Expressed in Chlorovirus Infections," Virology, 318(1):214-223, (2004).
Kenyon, "Fatty Acid Composition of Unicellular Strains of Blue-Green Algae," J. Bacteriology 109(2):827-834 (1972).
Kim et al. "Stable Integraion and Functional Expression of Flounder Growth Hormone Gene in Tranformed Microalga, Chlorella Ellipsoidea," Mar. Biotechnol. 4:63-73 (2002).
Kimchi-Sarfaty et al., "A 'Silent' Polymorphism in the MDR1 Gene Changes Substrate Specificity," Science, 315:525-528, (2007). [Retrieved from the Internet Nov. 1, 2007: <URL: http://www.sciencemag.org>].
Kindle, "High-Frequency Nuclear Transformation of Chlamydomonas reinhardtii," Proc Natl Acad Sci, 87(3):1228-1232, (1990).
Kisselev, "Polypeptide Release Factors in Prokaryotes and Eukaryotes: Same Function, Different Structure," Structure, 10:8-9, (2002).
Klein et al., "High-velocity microprojectiles for delivering nucleic acids into living cells," Nature, 327:70-73, (1987).
Klosty et al., "Sterols of Algae. The Occurrence of Ergosterol in Chiorelia pyrarwidosa," J. Am. Chem. Soc., Notes, 74(6):1601-1601, (1952).
Knauf, "The application of genetic engineering to oilseed crops," Trends in Biotechnology, 5(2):40-47, (1987).
Knothe, "'Designer' Biodiesel: Optimizing Fatty Ester Composition to Improve Fuel Properties," Energy & Fuels, 22:1358-1364, (2008).
Knothe, "Analyzing Biodiesel: Standards and Other Methods," JAOCS, 83(10):823-833, (2006).
Kohler et al., "The green fluorescent protein as a marker to visualize plant mitochondria in vivo," Plant J, 11(3):613-621, (1997).
Koksharova, "Genetic Tools for Cyanobacteria," Appl Microbiol Biotechnol, 58(2):123-37, (2002).
Kong et al., "Microbial production of lipids by cofermentation of glucose and xylose with Lipomyces starkeyi 2#," Chinese Journal of Bioprocess Engineerng, 05(02):36, (2007). Abstract.
Krebbers et al., "The maize chloroplast genes for the beta and epsilon subunits of the photosynthetic coupling factor CF1 are fused," Nucleic Acids Res, 10(16): 4985-5002, (1982).
Kris-Etherton et al., "Monounsaturated Fatty Acids and Risk of Cardiovascular Disease," Circulation, 100:1253-1258, (1999).
Kuo et al., "Diversity of Oleic Acid, Ricinoleic Acid and Linoleic Acid Conversions Among Pseudomonas aeruginosa Strains," Current Microbiology, 49:261-266, (2004).
La Scala et al., "The effect of fatty acid composition on the acrylation kinetics of epoxidized triacyglycerols," Journal of the American Oil Chemists' Society, 79(1):59-63, (2002).
Lapidot et al., "Stable Chloroplast Transformation of the Unicellular Red Alga Porphyridium Species," Plant Physiol, 129:7-12, (2002).
Larson et al., "Acyl CoA profilesof transgenic plants that accumulate medium-chain fatty acids indicate inefficient storage lipid synthesis in developing oilseeds," The Plant Journal, 32(4):519-527, (2002).
Lawford et al., "Performance Testing of Zymomonas Mobilis Metabolically Engeineered for Confermation of Glucose, Xylose, and Arabinose," Appl Biochem Biotechnol., 98-100:429-48, (2002).

(56) References Cited

OTHER PUBLICATIONS

Leema et al., "Heterotrophic Production of Lutein and Biomass by Chlorella Vulgaris with Different Nitrogen Sources," Algae Biofuel, Studium Press (India) Pvt. Ltd., pp. 91-101, (2011).
Leon-Banares et al., "Transgenic microalgae as green cell-factories," Trends in Biotechnology, 22(1):45-52, (2004).
Levitan et al., "Dual targeting of the protein disulfide isomerase RB60 to the chloroplast and the endoplasmic reticulum," Proc Natl Acad Sci, 102(17):6225-6230, (2005).
Li et al., "Broad-spectrum oil-producing yeast carbon filter," China Biotechnology, 25(12):39-44 (2005), and machine translation.
Li et al., "High-density cultivation of oleaginous yeast Rhodosporidium toruloides Y4 in fed-batch culture," Enzyme and Microbial Technology, 41:312-317, (2007).
Lindley, "The impact of food processing antioxidants in vegetable oils, fruits, and vegetables," Trends in Food Science & Technology. 9:336-340, (1998).
List et al., "Melting properties of some structured lipids native to high stearic acid soybean oil," Grasas y Aceites, 55(Fasc. 2):135-137, (2004).
Lu et al., "Molecular cloning and stress-dependent expression of a gene encoding AI2-fatty acid desaturase in the Antarctic microalga Chlorella vulgaris NJ-7," Extremophiles, 13:875-884, (2009).
Lu, "Biosynthesis and Gene Engineering of Plant Fatty Acids," Chinese Bulletin of Botany, 17(6):481-491, (2000). Abstract only.
Lubitz, "The Protein Quality, Digestibility, and Composition of Algae, Chlorella 71105," J. Food Sci. 28(2):229-232 (1963).
Lumbreras et al., "Efficient Foreign Gene Expression in Chlamydomonas Reinhardtii Mediated by an Endogenous Intron," Plant Journal, 14(4):441-447, (1998).
Madzak et al., "Functional analysis of upstream regulating regions from Yarrowia lipolytica XPR2 promoter," Microbiology, 145:75-87, (1999).
Manuell et al., "Robust expression of a bioactive mammalian protein in Chlamydomonas chloroplast," Plant Biotech J, 5(3):402-412, (2007).
Maruyama et al., "Introduction of Foreign DNA Into Chlorella Saccharophila by Electroporation," Biotechnology Techniques, 8:821-826, (1994).
Mayer et al., "A Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Catalytic Residues," The Journal of Biological Chemistry, 280(5):3621-3627, (2005).
Mayer et al., "Identification of amino acid residues involved in substrate specificity of plant acyl-ACP thioesterases using a bioinformatics-guided approach," BMC Plant Biology, 7(1): 1-11, (2007).
Mayfield et al., "Expression and Assembly of a Fully Active Antibody in Algae," Proc Natl Acad Sci, 100(2):438-442, (2003).
Mayfield et al., "Stable nuclear transformation of Chlamydomonas reinhardtii by using a C. reinhardtii gene as the selectable marker," Proc. Natl. Acad. Sci. USA, Cell Biology, 87:2087-2091, (1990).
Meesters et al., "High-cell-density cultivation of the lipid accumulating yeast Cryptococcus curvatus using glycerol as a carbon source," Applied Microbiology and Biotechnology, 45:575-579, (1996).
Meguro et al., "Original Communication Solubilization of phytosterols in diacylglycerol versus triacylglycerol improves the serum cholesterol-lowering effect," European Journal of Clinical Nutrition, 55:513-517, (2001).
Mekhedov et al., "Toward a Functional Catalog of the Plant Genome. A Survey of Genes for Lipid Biosynthesis," Plant Physiology, 122:389-401, (2000).
Mendes et al., "Supercritical Carbon Dioxide Extraction of Compounds With Pharmaceutical Importance from Microalgae," Inorganica Chimica Acta, 356:328-334, (2003).
Meng et al., "Biodiesel production from oleaginous microorganisms," Renewable Energy, 34:1-5, (2009).
Metzger et al., "Botryococcus braunii: A Rich Source for Hydrocarbons and Related Ether Lipids," Applied Microbiology and Biotechnology, 66(5):486-496, (2005).
Miao et al., "High Yield Bio-Oil Production from Fast Pyrolysis by Metabolic Controlling of Chlorella Protothecoides," J. Biotech., 110:85-93, (2004).
Minowa et al., "Oil Production from Algal Cells of Dunaliella tertiolecta by Direct Thermochemical Liquefaction," Fuel, 74(12):1735-1738, (1995).
Mitra et al., "A Chlorella Virus Gene Promoter Functions as a Strong Promoter Both in Plants an Bacteria," Biochemical and Biophysical Research Communications, 204(1):189-194, (1994).
Mitra et al., "The Chlorella Virus Adenine Methyltransferase Gene Promoter is a Strong Promoter in Plants," Plant Molecular Biology, 26(1):85-93, (1994).
Moreno-Perez et al., "Reduced expression of FatA thioesterases in Arabidopsis affects the oil content and fatty acid composition of the seeds," Planta, 235:629-639, (2012).
Morris, "Effect of Growth Temperature on the Cryopreservation of Prototheca," Journal of General Microbiology, 94:395-399, (1976).
Mullet et al., "Multiple transcripts for higher plantrbcL andatpB genes and localization of the transcription initiation site of therbcL gene," Plant Molecular Biology, 4(1):39-54, (1985).
Murakami et al., "Lipid Composition of Commercial Bakers' Yeasts Having Different Freeze-tolerance in Frozen Dough," Biosci. Biotechnol. Biochem., 60(11)1874-1876, (1996).
Murakami et al., "Lipids and Fatty Acid Custipvsi lions of Chlorella," Nihon Yuka gakkai-shi, 46(4):423-427, (1997).
Nackley et al., "Human Catechol-O-Methyltransferase Haplotypes Modulate Protein Expression by Altering mRNA Secondary Structure," Science, 314:1930-1933, (2006).[Retrieved from the Internet Nov. 1, 2007: <URL: http://www.sciencemag.org>].
Nahm, "Quality Characteristics of West African Shea Butter (Vitellaria Paradoxa) and Approaches to Extend Shelf-Life," Master Thesis, Master of Science in Food Service, Rutgers, The State University of New Jersey, 133 pages, (2011).
Napier et al., "Tailoring plant lipid composition: designer oilseeds come of age," Current Opinion in Plant Biology, 13:330-337, (2010).
Nazaruddin et al., "The Effect of Enzymatic Alcoholysis on the Physicochemical Properties of Commercial Cocoa Butter Substitutes," Pakistan Journal of Nutrition, 10(8):718-723, (2011).
Needleman et al., "A general method applicable to the search for similarities in the amino acid sequence of two proteins," Journal of Molecular Biology, 48(3):443-453, (1970).
Nes et al., "Biosynthesis of Cholesterol and Other Sterols," Chem. Rev., 111:6423-6451, (2011).
Norton et al., "Identification of Ergosta-6(7),8(14),25(27)-trien-3β-ol and Ergosta-5(6),7(8),25(27)-trien-3β-ol, Two New Steroidal Trienes Synthesized by Prototheca wickerhamii," Lipids, 26: 247-249, (1991).
Onai et al., "Natural Tranformation of the Termophillic Cyanbacterium Thermosynechococcus Elongatus BP-1: A Simple and Efficicent Method for Gene Transfer," Mol Genet Genomics, 271(1):50-9, (2004).
Papanikolaou et al., "Single cell oil production by Yarrowia lipolytica growing on an industrial derivative of animal fat in batch cultures," Appl. Microbiol. Biotechnol., 58:308-312, (2002).
Papanikolaou et al., "Lipid production by Yarrowia lipolytica growing on industrial glycerol in a single-stage continuous culture," Bioresource Technology, 82:43-49, (2002).
Park et al., "Isolation and Characterization of Chlorella Virus From Fresh Water in Korea and Application in Chlorella Transformation System," Plant Pathol. J., 21(1):13-20, (2005).
Patil et al., "Fatty acid composition of 12 microalgae for possible use in aquaculture feed," Aquacult Int , 15:1-9, (2007).
Patterson et al., "Sterols of Chlorella. II. The Occurrence of an Unusual Sterol Mixture in Chlorella vulgaris," Plant Physiol., 42:1457-1459, (1967).
Patterson et al., "Sterols of Chlorella-III. Species Containing Ergosterol," Comp. Biochem. Physiol., 31:391-394, (1969).
PCT International Preliminary Report on Patentability (Chapter I) dated May 31, 2011 for application PCT/US09/066142.

(56) References Cited

OTHER PUBLICATIONS

PCT International Preliminary Report on Patentability (Chapter I) dated Aug. 13, 2012 for application PCT/US11/38463.
PCT International Preliminary Report on Patentability (Chapter I) dated Dec. 7, 2009 for application PCT/US08/65563.
PCT International Preliminary Report on Patentability for application PCT/US2011/059224 dated May 16, 2013.
PCT International Search Report and Written Opinion of the International Searching Authority for application PCT/US2013/037261 dated Aug. 23, 2013.
PCT International Search Report and Written Opinion of the International Searching Authority for application PCT/US2014/035476 dated Feb. 18, 2015.
PCT International Search Report and Written Opinion of the International Searching Authority for application PCT/US2014/059161 dated Jun. 1, 2015.
International Search Report and Written Opinion of the Internataional Searching Authority for application PCT/US2015/023181 dated Jul. 28, 2015.
PCT International Search Report for application PCT/US2011/032582 dated Aug. 9, 2011.
PCT International Search Report for application PCT/US2011/038463 dated Jan. 18, 2012.
PCT International Search Report for application PCT/US2011/059224 dated Jun. 27, 2012.
PCT International Search Report for application PCT/US2012/023696 dated May 23, 2012.
PCT International Search Report for application PCT/US2012/036690 dated Aug. 30, 2012.
PCT International Search Report dated Aug. 20, 2010 for application PCT/US2009/066142.
PCT International Search Report dated Nov. 5, 2010 for application PCT/US2009/066141.
PCT International Search Report dated Nov. 6, 2008 for application PCT/US2008/065563.
PCT Invitation to Pay Additional fees for application PCT/US2014/059161 dated Mar. 9, 2015.
PCT Invitation to Pay Additional Fees from the International Searching Authority for application PCT/US2014/035476 dated Dec. 1, 2014.
PCT Written Opinion of the International Search Authority of dated Aug. 20, 2010 for application PCT/US2009/066142.
PCT Written Opinion of the International Searching Authority for application PCT/US2011/032582 dated Aug. 9, 2011.
PCT Written Opinion of the International Searching Authority for application PCT/US2011/038463 dated Jan. 18, 2012.
PCT Written Opinion of the International Searching Authority for application PCT/US2012/023696 dated May 23, 2012.
PCT Written Opinion of the International Searching Authority for application PCT/US2012/036690 dated Aug. 30, 2012.
PCT Written Opinion of the International Searching Authority dated Nov. 5, 2010 for application PCT/US2009/066141.
PCT Written Opinion of the International Searching Authority dated Nov. 6, 2008 for application PCT/US2008/065563.
Pearson et al., "Improved tools for biological sequence comparison," Proc Natl Acad Sci, 85(8):2444-2448, (1988).
Petkov et al., "Which are fatty acids of the green alga *Chlorella*?," Biochemical Systematics and Ecology, 35:281-285, (2007).
Phippen et al., "Total seed oil and fatty acid methyl ester contents of Cuphea accessions," Industrial Crops and Products, 24:52-59, (2006).
Powell et al., "Algae Feeding in Humans," J. Nutrition, 75:7-12, (1961).
Pratoomyot et al., "Fatty acids composition of 10 microalgal species," Songklanakarin J. Sci. Technol., 27(6):1179-1187, (2005).
Proschold et al., "Portrait of a Species: *Chlamydomonas reinhardtii*," Genetics, 170(4)1601-1610, (2005).
Puglia et al., "In viva spectrophotometric evaluation of skin barrier recovery after topical application of soybean phytosterols," J. Cosmet. Sci., 59:217-224, (2008).

Qingyu et al., "Fine Cell Structure and Biochemical Compositions of Chlorella Protothecoides after Transferring from Autotrophic to Heterotrophic Metabolism," Journal of Nanjing University, Natural Sciences Edition, 29(4):622-630, (1993). Abstract.
Radakovits et al., "Genetic Engineering of Algae for Enhanced Biofuel Production," Eukaryotic Cell, 9(04): 486-501, (2010).
Radmer et al., "Commercial applications of algae: oppurtunities and constraints," Journal of Applied Phycology, 6:93-98, (1994).
Randolph-Anderson et al., "Further characterization of the respiratory deficient dum-1 mutation of Chlamydomonas reinhardtii and its use as a recipient for mitochondrial transformation," Mol Gen Genet, 236(2-3):235-244, (1993).
Ratledge, "Regulation of lipid accumulation in oleaginous microorganisms," Biochem Soc Trans., 30(Pt 6):1047-1050, (2002).
Rehm et al., "Heterologous expression of the acyl—acyl carrier protein thioesterase gene from the plant *Umbellularia californica* mediates polyhydroxyalkanoate biosynthesis in recombinant *Escherichia coli*," Appl Microbial Biotechnol, 55:205-209, (2001).
Rismani-Yazdi et al., "Transcriptome sequencing and annotation of the microalgae Dunaliella tertiolecta: Pathway description and gene discovery for production of next-generation biofuels," BMC Genomics, 12:148, 17 pages; doi:10.1186/1471-2164-12-148, (2011).
Roessler et al., "Genetic Engineering Approaches for Enhanced Production of Biodiesel Fuel from Microalgae," Enzymatic Conversion of Biomass for Fuels Production, Chapter 13, American Chemical Society, doi: 10.1021/bk-1994-0566.ch013, pp. 255-270, (1994).
Roscoe et al., "Mutations in the fatty acid elongation 1 gene are associated with a loss of beta-ketoacyl-CoA synthase activity in low erucic acid rapeseed," FEBS Letters, 492:107-111, (2001).
Rosenberg et al., "A Green Light for Engineered Algae: Redirecting Metabolism to Fuel a Biotechnology Revolution," Current Opinion in Biotechnology. Tissue, Cell and Pathyway Engineering, E-Pub 19:430-436, (2008).
Roy et al., "Production of Intracelluler Fat by the Yeast Lipomyces starkeyi," Indian Journal of Experimental Biology, 16(4):511-512, (1978).
Ruiz et al., "Lipids accumulation in Chlorella protothecoides through mixotrophic and heterotrophic cultures for biodiesel production," New Biotechnology, 255:S266-S266, (2009).
Running et al., "Extracellular production of L-ascorbic acid by Chlorella protothecoides, Prototheca species, and mutants of P. moriformis during aerobic culturing at low pH," Journal of Industrial Microbiology & Biotechnology, 29:93-98, (2002).
Saha et al., "Transformation in Aspergillus ochraceus," Current Microbiology, 30(2):83-86, (1995).
Sakuradani, "Studies of Metabolic Engineering of Useful Lipid-producing Microorganisms," NISR Research Grant, (2004).
Sanchez et al., "Mixotrophic culture of Chlorella pyrenoidosa with olive-mill wastewater as the nutrient medium," Journal of Applied Phycology, 13:443-449, (2001).
Sanford, "The biolistic process," Trends in Biotechnology, 6(12):299-302, (1988).
Sauna et al., "Silent Polymorphisms Speak: How They Affect Pharmacogenomics and the Treatment of Cancer," Cancer Res, 67(20):9609-9612 , (2007).
Sawayama et al., "Possibility of renewable energy production and CO2 mitigation by thermochemical liquefaction of microalgae," Biomass and Bioenergy, 17(1):33-39, (1999).
Schechter et al., "Relations between Structure and Function in Cytoplasmic Membrane Vesicles Isolated from an *Escherichia coli* Fatty-Acid Auxotroph," Eur. J. Biochem, 49 61-76, (1974).
Schomburg et al. (eds.), "Δ12-fatty-acid desaturase," Springer Handbook of Enzymes S8, Class 1 Oxidoreductases: EC 1, DOI 10.1007/978-3-642-36265-1_97, pp. 668-678, (2013).
Schreier et al., "The use of nuclear-encoded sequences to direct the light-regulated synthesis and transport of a foreign protein into plant chloroplasts," EMBO J, 4(1):25-32, (1985).
Schultz et al., "A common core of secondary structure of the internal transcribed spacer 2 (ITS2) throughout the Eukaryota," RNA, 11(4):361-364, (2005).

(56) References Cited

OTHER PUBLICATIONS

Schütt et al., "The role of acyl carrier protein isoforms from Cuphea lanceolate seeds in the denovo biosynthesis of medium-chain fatty acids," Publication, Planta, 205:263-268, (1998).

Schütt et al., "β-Ketoacyl-acyl carrier protein synthase IV: a key enzyme for regulation of medium-chain fatty acid synthesis in Cuphea lanceolate seeds," Planta, 215:847-854, (2002).

Seffernick et al., "Melamine Deaminase and Atrazine Chlorohydrolase: 98 Percent Identical but Functionally Different," Journal of Bacteriology, 183(8):2405-2410, (2001).

Sen et al., "Developments in Directed Evolution for Improving Enzyme Functions," Appl Biochem Biotechnol, 143:212-223, (2007).

Shao et al., "Cloning and expression of metallothionein mutant α-KKS-α in Anabaena sp. PCC 7120," Marine Pollution Bulletin, 45(1012):163-167, (2002).

Shi et al., "High-Yield Production of Lutein by the Green Microalga *Chlorella protothecoides* in Heterotrophic Fed-Batch Culture," Biotechnol. Prog., 18(4):723-727 (2002).

Shi et al., "Production and rapid extraction of lutein and the other lipid-soluble pigments from Chlorella protothecoides grown under heterotrophic and mixotrophic conditions," Nahrung, 43:109-113, (1999).

Skolnick et al., "From genes to protein structure and function: novel applications of computational approaches in the genomic era," Tibtech, 18: 34-39, (2000).

Smallwood et al., "Different Substitutions at Conserved Amino Acids in Domains II and III in the Sendai L RNA Polymerase Protein Inactivate Viral RNA Synthesis," Virology, 304:135-145, (2002).

Smith et al., "Comparison of Biosequences," Adv Appl Math, 2(4):482-489, (1981).

Smith et al., "Production of hydroxy fatty acids in the seeds of *Arabidopsis thaliana*," Biochemical Society Transactions, 28(6):947-950, (2000).

Sorger et al., "Triacylglycerol biosynthesis in yeast," Appl. Microbiol Biotechnol, 61:289-299, (2003).

Spolaore et al., "Commercial Applications of Microalgae," J. Biosci. Bioeng. 101(2):87-96 (2006).

Stemmer et al., "Single-Step Assembly of a Gene and Entire Plasmid from Large Numbers of Oligodeoxyribonucleotides," Gene, 164:49-53, (1995).

Sud et al., "Lipid Composition and Sensitivity of Prototheca wickerhamii to Membrane-Active Antimicrobial Agents," Antimicrobial Agents and Chemotherapy, 16:486-490, (1979).

Suda, et al., "Evidence for a novel Chlorella virus-encoded alginate lyase," FEMS Microbiology Letters, 180(1):45-53, (1999).

Suh et al., "What limits production of unusual monoenoic fatty acids in transgenic plants?," Planta, 215:584-595, (2002).

Sun et al., "Characterization of two chitinase genes and one chitosanase gene encoded by Chlorella virus PBCV-1," Virology, 263(2):376-387, (1999).

Sung et al., "The research on the Lipid content and composition of microalgae and their impact factors," Marine Science, 12(33)122-128, (2009). (Englsh translation of first two pages).

Swern et al. "Fractionation of tallow fatty acids:Preparation of purified oleic acid and an inedible olive oil substitute," Oil & Soap, 22(11):302-304 (1945).

Szabo et al., "Safety evaluation of a high lipid Whole Algalin Flour (WAF) from Chlorella protothecoides," Regulatory Toxicology and Pharmacology, 63:155-165, (2012).

Szabo et al., "Safety evaluation of Whole Algalin Protein (WAP) from Chlorella protothecoides," Food and Chemical Toxicology, 59:34-45, (2013).

Takaku et al., "Isolation of an Antitumor Compound from Agaricus blazei Murill and Its Mechanism of Action," J. Nutr., 131:1409-1413, (2001). [Retrieved from the Internet May 14, 2013: <URL: http://jn.nutrition.org>].

Takeno et al., "Establishment of an overall transformation system for an oil-producing filamentous fungus, Mortierella alpina 1S-4," Appl. Microbiol Biotechnol, 65:419-425, (2004).

Talbot et al., "Formulation and Production of Confectionery Fats," OFI Middle East 2007 Conference and Exhibition, 378 pages, (2007).

Talebi et al., "Genetic manipulation, a feasible tool to enhance unique characteristic of Chlarella vulgaris as a feedstock for biodiesel production," Mol Biol Rep, 40:4421-4428, (2013).

Tan et al., "Establishment of a Micro-Particle Bombardment Transformation System for Dunaliella Salina," J Microbiol.;43(4):361-365, (2005).

Tan et al., "Fatty acid production by heterotrophic Chlorella saccharophila," Hydrobiologia, 215:13-19, (1991).

Tang et al., "Insertion mutagenesis of Chlamydomonas reinhardtii by electroporation and heterologous DNA," Biochem Mol Biol Int, 36(5):1025-1035, (1995).

Tomasinsig et al., "The Cathelicidins—Structure, Function and Evolution," Current Protein and Peptide Science, 6: 23-34, (2005).

Tornabene et al., "Lipid composition of the nitrogen starved green alga *Neochloris oleoabundans*," Enzyme Microb. Technol., 5:435-440, (1983).

U.S. Appl. No. 12/131,766, Advisory Action dated Oct. 13, 2011.
U.S. Appl. No. 12/131,766, Non-Final Office Action dated Aug. 1, 2011.
U.S. Appl. No. 12/131,766, Non-Final Office Action dated Nov. 23, 2010.
U.S. Appl. No. 12/131,766, Non-Final Office Action dated Dec. 10, 2009.
U.S. Appl. No. 12/131,766, Requirement for Restriction/Election dated Aug. 5, 2009.
U.S. Appl. No. 12/131,766, Requirement for Restriction/Election dated Aug. 17, 2010.
U.S. Appl. No. 12/131,773, Advisory Action dated Jan. 27, 2014.
U.S. Appl. No. 12/131,773, Final Office Action dated Mar. 21, 2011.
U.S. Appl. No. 12/131,773, Final Office Action dated Oct. 15, 2013.
U.S. Appl. No. 12/131,773, Non-Final Office Action dated Jun. 5, 2013.
U.S. Appl. No. 12/131,773, Non-Final Office Action dated Jun. 25, 2010.
U.S. Appl. No. 12/131,773, Non-Final Office Action dated Dec. 15, 2009.
U.S. Appl. No. 12/131,773, Notice of Allowance and Examiner Initiated Interview Summary dated Apr. 1, 2014.
U.S. Appl. No. 12/131,773, Requirement for Restriction/Election dated Aug. 6, 2009.
U.S. Appl. No. 12/131,783, Final Office Action dated Jan. 12, 2012.
U.S. Appl. No. 12/131,783, Final Office Action dated Dec. 13, 2013.
U.S. Appl. No. 12/131,783, Non-Final Office Action dated Jun. 6, 2011.
U.S. Appl. No. 12/131,783, Non-Final Office Action dated Jul. 18, 2013.
U.S. Appl. No. 12/131,793, Notice of Allowance and Examiner Initiated Interview Summary dated Mar. 24, 2014.
U.S. Appl. No. 12/131,783, Requirement for Restriciton/Election mailed Apr. 19, 2011.
U.S. Appl. No. 12/131,793, Final Office Action dated Mar. 30, 2010.
U.S. Appl. No. 12/131,793, Non-Final Office Action dated Jun. 21, 2012.
U.S. Appl. No. 12/131,793, Non-Final Office Action dated Sep. 16, 2009.
U.S. Appl. No. 12/131,793, Non-Final Office Action dated Nov. 13, 2012.
U.S. Appl. No. 12/131,793, Notice of Allowance dated Apr. 3, 2013.
U.S. Appl. No. 12/131,793, Requirement for Restriction/Election dated Aug. 6, 2009.
U.S. Appl. No. 12/131,804, Final Office Action dated Feb. 2, 2011.
U.S. Appl. No. 12/131,804, Non-Final Office Action dated Oct. 26, 2012.
U.S. Appl. No. 12/131,804, Non-Final Office Action dated Mar. 3, 2010.
U.S. Appl. No. 12/131,804, Non-Final Office Action dated Jun. 7, 2012.

(56) References Cited

OTHER PUBLICATIONS

U.S. Appl. No. 12/131,804, Requirement for Restriction/Electiondated dated Sep. 17, 2009.
U.S. Appl. No. 12/131,804, Requirement for Restriction/Election dated Nov. 18, 2009.
U.S. Appl. No. 12/194,389, Final Office Action dated Jan. 5, 2011.
U.S. Appl. No. 12/194,389, Non-Final Office Action dated Feb. 4, 2010.
U.S. Appl. No. 12/194,389, Notice of Allowance dated Jan. 15, 2014.
U.S. Appl. No. 12/194,389, Requirement for Restriction/Election dated Oct. 5, 2010.
U.S. Appl. No. 12/194,389, Requirement for Restriction/Election dated Nov. 2, 2009.
U.S. Appl. No. 12/628,140, Final Office Action dated Mar. 15, 2013.
U.S. Appl. No. 12/628,140, Final Office Action dated May 22, 2014.
U.S. Appl. No. 12/628,140, Final Office Action dated Sep. 12, 2013.
U.S. Appl. No. 12/628,140, Final Office Action dated Oct. 8, 2014.
U.S. Appl. No. 12/628,140, Non-Final Office Action dated Jul. 17, 2015.
U.S. Appl. No. 12/628,140, Non-Final Office Action dated Oct. 30, 2012.
U.S. Appl. No. 12/628,144, Final Office Action dated Nov. 16, 2010.
U.S. Appl. No. 12/628,144, Final Office Action dated Dec. 5, 2011.
U.S. Appl. No. 12/628,144, Final Office Action dated Dec. 12, 2014.
U.S. Appl. No. 12/628,144, Non-Final Office Action dated May 16, 2014.
U.S. Appl. No. 12/628,144, Non-Final Office Action dated Jun. 7, 2011.
U.S. Appl. No. 12/628,144, Non-Final Office Action dated Jul. 8, 2010.
U.S. Appl. No. 12/628,144, Requirement for Restriction/Election and Examiner Initiated Interview Summary dated Oct. 7, 2014.
U.S. Appl. No. 12/628,147, Examiner Interview Summary Record dated Mar. 3, 2011.
U.S. Appl. No. 12/628,147, Final Office Action dated Jul. 12, 2012.
U.S. Appl. No. 12/628,147, Final Office Action dated Oct. 1, 2010.
U.S. Appl. No. 12/628,147, Non-Final Office Action dated May 25, 2010.
U.S. Appl. No. 12/628,147, Non-Final Office Action dated Oct. 25, 2011.
U.S. Appl. No. 12/628,147, Notice of Allowance and Examiner Initiated Interview Summary dated Aug. 7, 2012.
U.S. Appl. No. 12/628,149, Non-Final Office Action dated Jun. 25, 2010.
U.S. Appl. No. 12/628,149, Non-Final Office Action dated Sep. 16, 2010.
U.S. Appl. No. 12/628,149, Notice of Allowance dated Dec. 15, 2010.
U.S. Appl. No. 12/628,150, Non-Final Office Action dated Apr. 29, 2010.
U.S. Appl. No. 12/628,150, Non-Final Office Action dated Oct. 13, 2010.
U.S. Appl. No. 12/628,150, Notice of Allowance dated Mar. 21, 2011.
U.S. Appl. No. 12/772,163, Non-Final Office Action dated May 25, 2012.
U.S. Appl. No. 12/772,163, Non-Final Office Action dated Dec. 12, 2012.
U.S. Appl. No. 12/772,163, Notice of Allowance dated May 28, 2013.
U.S. Appl. No. 12/772,163, Requirement for Restriction/Election dated Jun. 24, 2011.
U.S. Appl. No. 12/772,164, Final Office Action dated May 24, 2012.
U.S. Appl. No. 12/772,164, Non-Final Office Action dated Oct. 12, 2011.
U.S. Appl. No. 12/772,164, Requirement for Restriction/Election dated Jul. 20, 2011.
U.S. Appl. No. 12/772,170, Final Office Action dated Feb. 21, 2012.
U.S. Appl. No. 12/772,170, Non-Final Office Action dated Sep. 13, 2011.
U.S. Appl. No. 12/772,170, Non-Final Office Action dated Dec. 17, 2013.
U.S. Appl. No. 12/772,170, Notice of Allowance and Examiner-Initiated Interview Summary dated Jul. 11, 2014.
U.S. Appl. No. 12/772,170, Requirement for Restriction/Election dated Jul. 13, 2011.
U.S. Appl. No. 12/772,173, Final Office Action dated May 7, 2012.
U.S. Appl. No. 12/772,173, Non-Final Office Action dated Dec. 16, 2011.
U.S. Appl. No. 12/772,173, Notice of Allowance dated Mar. 29, 2013.
U.S. Appl. No. 12/772,173, Notice of Allowance dated Jul. 10, 2013.
U.S. Appl. No, 12/772,173, Requirement for Restriction/Election dated Oct. 26, 2011.
U.S. Appl. No. 12/772,174, Non-Final Office Action dated Nov. 29, 2011.
U.S. Appl. No. 12/772,174, Requirement for Restriction/Election dated Aug. 10, 2011.
U.S. Appl. No. 12/960,388, Notice of Allowance dated May 28, 2013.
U.S. Appl. No. 12/960,388, Requirement for Restriction/Election mailed Apr. 1, 2013.
U.S. Appl. No. 12/981,409, Non-Final Office Action dated Jan. 6, 2012.
U.S. Appl. No. 12/981,409, Notice of Allowance dated May 29, 2012.
U.S. Appl. No. 12/981,409, Requirement for Restriction/Election dated Apr. 19, 2012.
U.S. Appl. No. 12/981,409, Requirement for Restriction/Election dated Oct. 28, 2011.
U.S. Appl. No. 13/029,061, Requirement for Restriction/Election dated Nov. 29, 2011.
U.S. Appl. No. 13/045,500, Non-Final Office Action dated Mar. 9, 2012.
U.S. Appl. No. 13/045,500, Non-Final Office Action dated Jun. 5, 2014.
U.S. Appl. No. 13/045,500, Final Office Action dated Sep. 26, 2012.
U.S. Appl. No. 13/073,757, Non-Final Office Action dated Aug. 15, 2011.
U.S. Appl. No. 13/073,757, Non-Final Office Action dated Dec. 29, 2011.
U.S. Appl. No. 13/073,757, Notice of Allowance dated Apr. 17, 2012.
U.S. Appl. No. 13/087,311, Final Office Action dated Dec. 16, 2013.
U.S. Appl. No. 13/087,311, Non-Final Office Action dated Apr. 23, 2013.
U.S. Appl. No. 13/087,311, Non-Final Office Action dated Jun. 24, 2014.
U.S. Appl. No. 13/118,365, Final Office Action dated Jul. 22, 2013.
U.S. Appl. No. 13/118,365, Non-Final Office Action dated Feb. 11, 2013.
U.S. Appl. No. 13/118,365, Requirement for Restriction/Election dated Oct. 11, 2012.
U.S. Appl. No. 13/273,179, Non-Final Office Action dated Jan. 28, 2014.
U.S. Appl. No. 13/273,179, Notice of Allowance dated Jul. 11, 2014.
U.S. Appl. No. 13/273,179, Requirement for Restriction/Election mailed Nov. 14, 2013.
U.S. Appl. No. 13/288,815, Final Office Action dated Oct. 22, 2014.
U.S. Appl. No. 13/288,815, Non-Final Office Action dated Jun. 18, 2014.
U.S. Appl. No. 13/288,815, Notice of Allowance dated Feb. 26, 2015.
U.S. Appl. No. 13/288,815, Requirement for Restriction/Election dated Jan. 30, 2014.
U.S. Appl. No. 13/365,253, Requirement for Restriction/Election dated Dec. 16, 2014.
U.S. Appl. No. 13/406,417, Non-Final Office Action dated Nov. 5, 2012.

(56) References Cited

OTHER PUBLICATIONS

U.S. Appl. No. 13/406,417, Requirement for Restriction/Election dated Apr. 30, 2012.
U.S. Appl. No. 13/464,948, Final Office Action dated Feb. 13, 2014.
U.S. Appl. No. 13/464,948, Non-Final Office Action dated Oct. 9, 2013.
U.S. Appl. No. 13/464,948, Notice of Allowance dated May 25, 2014.
U.S. Appl. No. 13/464,948, Requirement for Restriction/Election dated Aug. 21, 2013.
U.S. Appl. No. 13/479,194, Non-Final Office Action dated Mar. 26, 2014.
U.S. Appl. No. 13/479,200, Non-Final Office Action dated Apr. 10, 2013.
U.S. Appl. No. 13/479,200, Non-Final Office Action dated Sep. 9, 2013.
U.S. Appl. No. 13/479,200, Notice of Allowance dated Nov. 25, 2013.
U.S. Appl. No. 13/479,200,Requirement for Restriction/Election dated Jan. 15, 2013.
U.S. Appl. No. 13/527,480, Final Office Action dated Jan. 16, 2014.
U.S. Appl. No. 13/527,480, Non-Final Office Action dated Jun. 26, 2013.
U.S. Appl. No. 13/527,480, Requirement for Restriction/Election dated May 3, 2013.
U.S. Appl. No. 13/543,666, Non-Final Office Action dated Sep. 5, 2013.
U.S. Appl. No. 13/543,666, Notice of Allowance dated Feb. 10, 2014.
U.S. Appl. No. 13/543,666, Requirement for Restriction/Election dated Jan. 3, 2013.
U.S. Appl. No. 13/547,457, Final Office Action dated Mar. 20, 2014.
U.S. Appl. No. 13/547,457, Non-Final Office Action dated Jul. 8, 2013.
U.S. Appl. No. 13/547,457, Notice of Allowance and Examiner-Initiated Interview Summary dated May 29, 2014.
U.S. Appl. No. 13/550,412, Non-Final Office Action dated Oct. 29, 2012.
U.S. Appl. No. 13/550,412, Notice of Allowance dated Feb. 21, 2013.
U.S. Appl. No. 13/555,009, Notice of Allowance dated Jan. 9, 2015.
U.S. Appl. No. 13/555,009, Requirement for Restriction/Election dated Jun. 16, 2014.
U.S. Appl. No. 13/558,252, Final Office Action dated Jul. 9, 2013.
U.S. Appl. No. 13/558,252, Non-Final Office Action dated Jan. 18, 2013.
U.S. Appl. No. 13/558,252, Notice of Allowance dated Oct. 23, 2013.
U.S. Appl. No. 13/601,928, Non-Final Office Action dated Jan. 31, 2013.
U.S. Appl. No. 13/601,928, Notice of Allowance dated Feb. 26, 2013.
U.S. Appl. No. 13/621,722, Requirement for Restriction/Election dated Jan. 31, 2013.
U.S. Appl. No. 13/621,722, Final Office Action dated Oct. 25, 2013.
U.S. Appl. No. 13/621,722, Non-Final Office Action dated May 9, 2013.
U.S. Appl. No. 13/621,722, Notice of Allowance and Examiner Initiated Interview Summary dated Jan. 10, 2014.
U.S. Appl. No. 13/628,039, Non-Final Office Action dated Jun. 4, 2013.
U.S. Appl. No. 13/628,039, Notice of Allowance and Examiner-Initiated Interview Summary dated Feb. 20, 2014.
U.S. Appl. No. 13/628,039, Requirement for Restriction/Election dated Mar. 7, 2013.
U.S. Appl. No. 13/630,757, Non-Final Office Action dated Apr. 23, 2015.
U.S. Appl. No. 13/630,757, Non-Final Office Action dated Oct. 27, 2014.
U.S. Appl. No. 13/630,757, Requirement for Restriction/Election dated Jun. 12, 2014.
U.S. Appl. No. 13/650,018, Non-Final Office Action dated Dec. 23, 2013.
U.S. Appl. No. 13/650,018, Notice of Allowance dated Apr. 1, 2015.
U.S. Appl. No. 13/650,018, Notice of Allowance dated Apr. 10, 2015.
U.S. Appl. No. 13/650,018, Notice of Allowance dated Aug. 14, 2014.
U.S. Appl. No. 13/650,018, Requirement for Restriction/Election dated Aug. 22, 2013.
U.S. Appl. No. 13/650,024, Non-Final Office Action dated Jul. 2, 2013.
U.S. Appl. No. 13/650,024, Notice of Allowance dated Oct. 17, 2013.
U.S. Appl. No. 13/804,185, Non-Final Office Action dated Jun. 1, 2015.
U.S. Appl. No. 13/804,185, Requirement for Restriction/Election dated Mar. 16, 2015.
U.S. Appl. No. 13/849,330, Requirement for Restriction/Election dated Jan. 21, 2015.
U.S. Appl. No. 13/852,116, Final Office Action mailed Aug. 18, 2014.
U.S. Appl. No. 13/852,116, Non-Final Office Action dated Mar. 26, 2014.
U.S. Appl. No. 13/852,116, Notice of Allowance dated Nov. 7, 2014.
U.S. Appl. No. 13/865,974, Non-Final Office Action dated May 2, 2014.
U.S. Appl. No. 13/865,974, Notice of Allowance dated Oct. 22, 2014.
U.S. Appl. No. 13/865,974, Requirement for Requirement for Restriction/Election dated Jan. 29, 2014.
U.S. Appl. No. 13/889,214, Non-Final Office Action dated Sep. 18, 2013.
U.S. Appl. No. 13/889,214, Notice of Allowance dated Apr. 28, 2014.
U.S. Appl. No. 13/889,221, Non-Final Office Action dated Sep. 6, 2013.
U.S. Appl. No. 13/889,221, Notice of Allowance dated Apr. 24, 2014.
U.S. Appl. No. 13/941,342, Notice of Allowance dated Jul. 24, 2015.
U.S. Appl. No. 13/941,342, Requirement for Restriction/Election dated Apr. 13, 2015.
U.S. Appl. No. 13/941,346, Final Office Action dated Jun. 26, 2014.
U.S. Appl. No. 13/941,346, Non-Final Office Action dated Jan. 21, 2014.
U.S. Appl. No. 13/941,346, Non-Final Office Action dated Nov. 3, 2014.
U.S. Appl. No. 13/941,346, Notice of Allowance dated Feb. 23, 2015.
U.S. Appl. No. 13/941,353, Requirement for Restriction/Election dated Jan. 16, 2014.
U.S. Appl. No. 13/941,357, Final Office Action dated Nov. 6, 2014.
U.S. Appl. No. 13/941,357, Non-Final Office Action dated Jun. 3, 2014.
U.S. Appl. No. 13/941,357, Notice of Allowance dated Mar. 30, 2015.
U.S. Appl. No. 13/941,357, Requirement for Restriction/Election dated Jan. 7, 2014.
U.S. Appl. No. 14/184,288, Non-Final Office Action dated Sep. 11, 2015.
U.S. Appl. No. 14/148,288, Requirement for Restriction/Election dated Jun. 9, 2015
U.S. Appl. No. 14/184,288, Requirement for Restriction/Election dated Jun. 9, 2015.
U.S. Appl. No. 14/262,070, Non-Final Office Action dated Jul. 10, 2015.
U.S. Appl. No. 14/276,943, Requirement for Restriction/Election dated Jun. 4, 2015.
U.S. Appl. No. 14/285,354, Requirement for Restriction/Election dated Jul. 20, 2015.

(56) References Cited

OTHER PUBLICATIONS

U.S. Appl. No. 14/474,244, Final Office Action dated Jul. 30, 2015.
U.S. Appl. No. 14/474,244, Non-Final Office Action dated Apr. 24, 2015.
Ueno et al., "Optimization of heterotrophic culture conditions for n-alkane utilization and phylogenetic position based on the 18S rDNA sequence of a thermotolerant Prototheca zopfii strain," J Biosci Bioeng, 94(2):160-165, (2002). Abstract. [Retrieved from the Internet Dec. 1, 2014: <URL: http://www.ncbi.nlm.nih.gov/pubmed/16233286>].
Urano, et al., "Effect of Osmotic Stabilizers on Protoplast Generation of Chlorella eflipsoidea Yellow/White Color Mutants," Journal of Bioscience and Bioengineering, 90(5):567-569, (2000).
Van De Loo et al., "An oleate 12-hydroxylase from Ricinus communis L. is a fatty acyl desaturase homolog," Proc. Natl. Acad. Sci. USA, 92:6743-6747, (1995).
Van Etten et al., "Giant viruses infecting algae," Annu Rev Microbiol, 53:447-494, (1999).
Vazquez-Bermudez et al., "Carbon Supply and 2-Oxoglutarate Effects on Expression of Nitrate Reductase and Nitrogen-Regulated Genes in Synechococcus sp. strain FCC 7942," FEMS Microbiology Letters, 221(2)155-159, (2003).
Vazquez-Bermudez et al., "Uptake of 2-Oxoglutarate in Synechococcus Strains Transformed with the *Escherichia coli* kgtP Gene," Journal of Bacteriology, 182(1):211-215, (2000).
Voelker et al., "Alteration of the Specificity and Regulation of Fatty Acid Synthesis of *Escherichia coli* by Expression of a Plant Medium Chain Acyl-Acyl Carrier Protein Thioesterase," Journal of Bacteriology, 176(23):7320-7327, (1994).
Voelker et al., "Broad-Range and Binary-Range Acyl-Acyl-Carrier-Protein Thioesterases Suggest an Alternative Mechanism for Medium-Chain Production in Seeds," Plant Physiol., 114:669-677, (1997).
Voetz et al., "Three Different cDNAs Encoding Acyl Carrier Proteins from Cuphea lanceolata'," Plant Physiol., 106:785-786, (1994).
Volkman et al., "Sterols in microorganisms," Appl Microbial Biotechnol, 60:495-506, (2003).
Walker et al., "Characterization of the Dunaliella tertiolecta RbcS Genes and Their Promoter Activity in Chlamydomonas reinhardtii," Plant Cell Rep, 23(10-11):727-735, (2005).
Wang et al., "Rapid isolation and functional analysis of promoter sequences of the nitrate reductase gene from Chlorella elfipsoidea," J. Appl. Phycol., 16:11-16, (2004).
Warner et al., "Analysis of Tocopherols and Phytosterols in Vegetable Oils by HPLC with Evaporative Light-Scattering Detection," JAOCS, 67(11):827-831 (1990).
Westphal, et al., "Vipp1 Deletion Mutant of Synechocystis: A Connection Between Bacterial Phage Shock and Thylakoid Biogenesis," Proc Natl Acad Sci U S A., 98(7):4243-4248, (2001).
Whisstock et al., "Prediction of protein function from protein sequence and structure," Quarterly Reviews of Biophysics, 36(3):307-340, (2003).
Whittle et al., "Engineering $\Delta^9$-16:0-Acyl Carrier Protein (ACP) Desaturase Specificity Based on Combinatorial Saturation Mutagenesis and Logical Redesign of the Castor $\Delta^9$-18:0-ACP Desaturase," The Journal of Biological Chemistry, 276(24):21500-21505, (2001).
Wiberg et al., "The distribution of caprylate, caprate and laurate in lipids from developing and mature seeds of transgenic Brassica napus L.," Planta, 212:33-40, (2000).
Wirth et al., "Transforamtion of Various Species of Gram-Negitive Bacteria Belonging to 11 Difference Genera by Electroporation," Mol Gen Genet.; 216(1):175-177, (1989).
Wishart et al., "A Single Mutation Converts a Novel Phosphotyrosine Binding Domain into a Dual-specificity Phosphatase," The Journal of Biological Chemistry, 270(45):26782-26785, (1995).

Witkowski et al., "Conversion of a β-Ketoacyl Synthase to a Malonyl Decarboxylase by Replacement of the Active-Site Cysteine with Glutamine," Biochemistry, 38:11643-11650, (1999).
Wolk et al., "Construction of Shuttle Vectors Capable of Conjugative Transfer From *Escherichia Coli* to Nitrogen-Fixing Filamentous Cyanobacteria," Proc Natl Acad Sci U S A., 81(5):1561-1565, (1984).
Wong et al., "*Arabidopsis thaliana* small subunit leader and transit peptide enhance the expression of *Bacillus thuringiensis* proteins in transgenic plants," Plant Mol Biol, 20(1):81-93, (1992).
Wu et al., "A Comparative Study of Gases Generated from Simulant Thermal Degradation of Autotrophic and Heterotrophic Chlorella," Progress in Natural Science, 2(4):311-318, (1992).
Wu et al., "Comparative study on Liposoluble Compounds in Autotrophic and Heterotrophic Chlorella Protothecoides," Acta Botanica Sinica, 35(11):849-858, (1992).
Wu et al., "New Discoveries in Study on Hydrocarbons From Thermal Degradation of Heterotrophically Yellowing Algae," Science in China, 37(3):326-35, (1994).
Xiong et al., "High-density fermentation of microalga Chlorella protothecoides in bioreactor for microbio-diesel production," Appl. Microbiol. Biotechnol., 78:29-36, (2008).
Yamada et al., "Alternative expression of a chitosanase gene produces two different proteins in cells infected with Chlorella virus CVK2," Virology, 230(2):361-368, (1997).
Yamada et al., "Chlorella viruses," Adv Virus Res, 66:293-336, (2006).
Yu et al., "Modifications of the metabolic pathways of lipid and triacylglycerol production in microalgae," Microbial Cell Factories, 10:91, (2011). [Retrieved from the Internet Jul. 24, 2012: <URL: http://www.microbialcellfactories.com/content/10/1/91>].
Yuan et al., "Modification of the substrate specificity of an acyl-acyl carrier protein thioesterase by protein engineering," Proc. NatL Acad. Sci. USA, Biochemistry, 92:10639-10643, (1995).
Zaidul et al., "Supercritical carbon dioxide (SC—002) extraction and fractionation of palm kernel oil from palm kernel as cocoa butter replacers blend," Journal of Food Engineering, 73:210-216, (2006).
Zhang et al., "Matic enzyme: the controlling activity for lipid production? Overexpression of malic enzyme in Mucor circinelloides leads to a 2.5-fold increase in lipid accumulation," Microbiology, 153(7):2013-2025, (2007).
Zhao et al., "Medium optimization for lipid production through co-fermentation of glucose and xylose by the oleaginous yeast *Lipomyces starkeyi*," Eur. J. Lipid Sci. Technol., 110:405-412, (2008).
Zurawski et al., "Nucleotide sequence of the gene for the Mr 32,000 thylakoid membrane protein from Spinacia oleracea and Nicotiana debneyi predicts a totally conserved primary translation product of MR 38,950," Proc Natl Acad Sci, 79(24):7699-7703, (1982).
Blatti, Julian L. et al., "Engineering fatty acid biosynthesis in microalgae for sustainable biodiesel," Current Opinion in Chemical Biology, Jun. 2013, vol. 17, Issue 3, pp. 496-505.
U.S. Appl. No. 14/184,288, Notice of Allowance dated Feb. 3, 2016.
U.S. Appl. No. 15/173,335, Requirement for Restriction/Election dated Jul. 5, 2017.
U.S. Appl. No. 15/173,335, Non-Final Office Action dated Oct. 12, 2017.
U.S. Appl. No. 12/628,140, Final Office Action dated Feb. 2, 2016.
U.S. Appl. No. 12/628,140, Non-Final Office Action dated Nov. 21, 2016.
U.S. Appl. No. 12/628,144, Final Office Action dated Mar. 1, 2016.
U.S. Appl. No. 12/628,144, Notice of Allowance dated Jun. 13, 2016.
U.S. Appl. No. 14/285,354, Notice of Allowance dated Feb. 1, 2016.
U.S. Appl. No. 13/555,009, Non-Final Office Action dated Sep. 16, 2014.
U.S. Appl. No. 14/626,505, Requirement for Restriction/Election dated Apr. 26, 2016.
U.S. Appl. No. 14/626,505, Non-Final Office Action dated Jul. 19, 2016.
U.S. Appl. No. 13/118,365, Notice of Allowance dated Sep. 20, 2013.

(56) References Cited

OTHER PUBLICATIONS

U.S. Appl. No. 14/276,943, Notice of Allowance dated Sep. 22, 2015.
U.S. Appl. No. 14/975,016, Notice of Allowance dated Jan. 10, 2017.
U.S. Appl. No. 14/975,016, Notice of Allowance dated Jan. 31, 2017.
U.S. Appl. No. 14/975,016, Notice of Allowance dated Feb. 24, 2017.
U.S. Appl. No. 13/118,369, Requirement for Restriction/Election dated Dec. 13, 2012.
U.S. Appl. No. 13/118,369, Non-Final Office Action dated Mar. 28, 2013.
U.S. Appl. No. 13/118,369, Final Office Action dated Mar. 28, 2014.
U.S. Appl. No. 13/630,757, Notice of Allowance dated Oct. 23, 2015.
U.S. Appl. No. 13/630,757, Supplemental Notice of Allowance dated Dec. 3, 2015.
U.S. Appl. No. 13/630,757, Miscellaneous Communication dated Dec. 17, 2015.
U.S. Appl. No. 13/630,757, Notice of Allowance (Supplemental Notice of Allowability) dated Jan. 15, 2016.
U.S. Appl. No. 13/288,815, Requirement for Restriction/Election dated Feb. 11, 2014.
U.S. Appl. No. 14/730,671, Notice of Allowance dated Mar. 21, 2016.
U.S. Appl. No. 15/179,253, Requirement for Restriction/Election dated Sep. 28, 2017.
U.S. Appl. No. 13/365,253, Non-Final Office Action dated Mar. 25, 2015.
U.S. Appl. No. 13/365,253, Notice of Allowance dated Sep. 24, 2015.
U.S. Appl. No. 13/365,253, Notice of Allowance (Notice of Allowability) dated Nov. 6, 2015.
U.S. Appl. No. 14/974,983, Requirement for Restriction/Election dated Jul. 28, 2016.
U.S. Appl. No. 14/974,983, Non-Final Office Action dated Dec. 5, 2016.
U.S. Appl. No. 14/974,983, Final Office Action dated Jul. 19, 2017.
U.S. Appl. No. 14/974,983, Non-Final Office Action dated Oct. 26, 2017.
U.S. Appl. No. 13/804,185, Final Office Action dated Dec. 11, 2015.
U.S. Appl. No. 13/804,185, Non-Final Office Action dated Jul. 20, 2016.
U.S. Appl. No. 13/804,185, Notice of Allowance dated Jan. 27, 2017.
U.S. Appl. No. 13/941,353, Notice of Allowance dated May 21, 2014.
U.S. Appl. No. 14/474,244, Notice of Allowance dated Sep. 18, 2015.
U.S. Appl. No. 14/975,137, Notice of Allowance dated Sep. 6, 2016.
U.S. Appl. No. 15/369,557, Non-Final Office Action dated Jun. 23, 2017.
U.S. Appl. No. 15/369,557, Notice of Allowance dated Oct. 17, 2017.
U.S. Appl. No. 14/506,491, Requirement for Restriction/Election dated Jan. 19, 2017.
U.S. Appl. No. 14/506,491, Non-Final Office Action dated Jun. 1, 2017.
U.S. Appl. No. 14/506,491, Final Office Action dated Dec. 5, 2017.
U.S. Appl. No. 14/796,406, Requirement for Restriction/Election dated Oct. 5, 2016.
U.S. Appl. No. 14/796,406, Non-Final Office Action dated Jan. 25, 2017.
U.S. Appl. No. 14/796,406, Notice of Allowance dated Jun. 15, 2017.
U.S. Appl. No. 14/796,406, Notice of Allowance dated Oct. 3, 2017.
U.S. Appl. No. 15/092,538, Requirement for Restriction/Election dated Oct. 6, 2017.
U.S. Appl. No. 13/087,305, Non-Final Office Action dated Aug. 15, 2012.
U.S. Appl. No. 13/087,305, Final Office Action dated Mar. 18, 2013.
Australian Patent Examination Report No. 1 dated Jan. 23, 2013 issued in Application No. AU 2008259834.
Australian Patent Examination Report No. 1 dated May 4, 2015 issued in Application No. AU 2013251198.
Canadian Examination Report dated Nov. 30, 2015 issued in Application No. CA 2,689,724.
Chinese First Office Action dated Apr. 23, 2012 issued in Application No. CN 200880100976.9.
Chinese Second Office Action dated Jan. 21, 2013 issued in Application No. CN 200880100976.9.
Chinese Third Office Action dated May 28, 2013 issued in Application No. CN 200880100976.9.
Chinese Fourth Office Action dated Sep. 11, 2013 issued in Application No. CN 200880100976.9.
Chinese Fifth Office Action dated Jan. 23, 2014 issued in Application No. CN 200880100976.9.
Chinese First Office Action dated May 18, 2016 issued in Application No. CN 201410321130.5.
Colombian Opposition dated Sep. 5, 2011 [Brief Communication dated Sep. 5, 2011 re Application No. EP 06 075 479.3, D50-Declaration of Dr. Matthias Staufenbiel; D51-WO-A-2004/016282; D52-Sturchler-Pierrat et al. *Proc Natl. Acad. Sci.* USA, 94:13287-13292 (1997)].
Declaration of Dr. Matthias Staufenbiel, Opposition Document for European Patent No. EP-B-1679080 dated Aug. 2, 2011; Patentee: Janssen Alzheimer Immunotherapy; Opponent: Dr. Alexander Esslinger, 19 pp.
Colombian Office Action dated Jan. 28, 2013 issued in Application No. CO 09149183.
Colombian Office Action dated Jun. 13, 2013 issued in Application No. CO 09149183.
Colombian Office Action dated Sep. 25, 2013 issued in Application No. CO 09149183.
European Office Action dated Mar. 9, 2012 issued in Application No. EP 08 769 988.0.
Indonesian First Office Action dated Apr. 13, 2016 issued in Application No. W00200903371.
Indonesian Second Office Action dated Aug. 4, 2016 issued in Application No. W00200903371.
Indian Examination Report dated Oct. 4, 2016 issued in Application No. IN 8573/DELNP/2009.
Japanese Notice of Reason for Denial [no translation] dated May 24, 2016 issued in Application No. JP 2016-095504.
Korean Office Action dated Aug. 25, 2014 issued in Application No. KR 10-2009-7027618.
Mexican Office Action dated Oct. 13, 2011 issued in Application No. MX/a/2009/012850.
Mexican First Office Action dated Sep. 30, 2013 issued in Application No. MX/a/2012/000844.
Mexican Second Office Action dated Jan. 22, 2014 issued in Application No. MX/a/2012/000844.
Mexican Third Office Action dated Oct. 13, 2014 issued in Application No. MX/a/2012/000844.
Mexican Fourth Office Action dated Apr. 1, 2015 issued in Application No. MX/a/2012/000844.
Mexican Office Action dated Feb. 23, 2017 issued in Application No. MX/a/2015/008626.
Malaysian Examination and Search Report dated Dec. 31, 2013 issued in Application No. PI20095102.
Malaysian Examination and Adverse Report dated Dec. 31, 2014 issued in Application No. PI20095102.
Malaysian Examination and Clear Report dated Jul. 15, 2015 issued in Application No. PI20095102.
Malaysian Examination and Search Report dated May 15, 2017 issued in Application No. PI2014000965.
New Zealand First Examination Report dated Oct. 19, 2010 issued in Application No. NZ 581700.
New Zealand Examination Report dated Sep. 22, 2011 issued in Application No. NZ 581700.

(56) References Cited

OTHER PUBLICATIONS

New Zealand Examination Report dated Sep. 8, 2011 issued in Application No. NZ 595029.
New Zealand Examination Report dated Dec. 19, 2012 issued in Application No. NZ 595029.
Philippines Examination Report dated Apr. 7, 2014 issued in Application No. PH 1-2009-502294.
Philippines Examination Report dated Nov. 18, 2014 issued in Application No. PH 1-2009-502294.
Singapore Written Opinion and Search Report dated Apr. 29, 2011 issued in Application No. SG 200907978-1.
Thailand Office Action dated Feb. 22, 2011 issued in Application No. TH 0901005340.
Thailand Office Action dated Jul. 26, 2017 issued in Application No. TH 0901005340.
Australian Patent Examination Report No. 1 dated Dec. 9, 2014 issued in Application No. AU 2009319722.
Australian Patent Examination Report No. 1 dated Jul. 20, 2017 issued in Application No. AU 2016250460.
Canadian Examination Report dated Aug. 18, 2015 issued in Application No. CA 2,745,129.
Canadian Examination Report dated Nov. 16, 2017 issued in Application No. CA 2,745,129.
Canadian Examination Report dated Oct. 3, 2016 issued in Application No. CA 2,745,129.
Chinese First Office Action dated Apr. 26, 2013 issued in Application No. CN 200980155465.1.
Chinese Second Office Action dated Jan. 16, 2014 issued in Application No. CN 200980155465.1.
Chinese Third Office Action dated Aug. 28, 2014 issued in Application No. CN 200980155465.1.
Chinese Rejection Decision dated Mar. 24, 2015 issued in Application No. CN 200980155465.1.
Chinese Reexamination notification dated Nov. 10, 2016 issued in Application No. CN 200980155465.1.
Chinese Reexamination Decision dated Apr. 27, 2017 issued in Application No. CN 200980155465.1.
Chinese Fourth Office Action dated Sep. 25, 2017 issued in Application No. CN 200980155465.1.
Colombian Office Action dated Feb. 13, 2013 issued in Application No. CO 11.080.882.
Colombian Office Action dated Jun. 18, 2013 issued in Application No. CO 11.080.882.
Colombian Office Action dated Nov. 24, 2014 issued in Application No. CO 11.080.882.
Colombian Office Action dated Mar. 16, 2015 issued in Application No. CO 11.080.882.
Colombian Office Action dated Mar. 1, 2016 issued in Application No. CO 11.080.882.
European Extended Search Report dated Sep. 12, 2014 issued in Application No. EP 09 829 851.6.
European Office Action dated Jun. 25, 2015 issued in Application No. EP 09 829 851.6.
European Partial Search Report dated Sep. 12, 2016 issued in Application No. EP 16 16 6059.2.
European Extended Search Report dated Dec. 14, 2016 issued in Application No. EP 16 16 6059.2.
Indonesia Substantive Examination Report Stage 1 dated Aug. 5, 2015 issued in Application No. ID W-00 2011 02343.
Israel Office Action dated Sep. 30, 2013 issued in Application No. IL 213157.
Japanese Office Action dated May 27, 2014 issued in Application No. JP 2011-538719.
Japanese Final Office Action dated Feb. 24, 2015 issued in Application No. JP 2011-538719.
Japanese Pre-Appeal Examination Report dated Aug. 27, 2015 issued in Application No. JP 2011-538719.
Japanese Office Action dated Jul. 1, 2016 issued in Application No. JP 2011-538719.
Japanese Office Action dated Oct. 31, 2016 issued in Application No. JP 2011-538719.
Japanese Office Action [no translation] dated May 9, 2016 issued in Application No. JP 2015-126360.
Japanese Final Office Action [no translation] dated Nov. 24, 2016 issued in Application No. JP 2015-126360.
Korean Office Action dated Nov. 14, 2015 issued in Application No. KR 10-2011-7014923.
Korean Office Action dated Oct. 5, 2016 issued in Application No. KR 10-2011-7014923.
Malaysian Examination Report dated Mar. 31, 2016 issued in Application No. MY PI2011002435.
Mexican Office Action dated Sep. 14, 2012 issued in Application No. MX/a/2010/011065.
PCT International Search Report dated Nov. 5, 2010 issued in PCT/US2009/066141.
PCT International Preliminary Report on Patentability and Written Opinion dated Oct. 26, 2012 issued in PCT/US2009/066141.
Australian Patent Examination Report No. 1 dated Feb. 25, 2014 issued in Application No. AU 2009319721.
Australian Patent Examination Report No. 2 dated Oct. 29, 2015 issued in Application No. AU 2009319721.
Canadian Office Action dated Dec. 1, 2015 issued in Application No. CA 2,745,040.
Chinese First Office Action dated Dec. 23, 2013 issued in Application No. CN 200980155463.2.
Chinese Second Office Action dated Oct. 20, 2014 issued in Application No. CN 200980155463.2.
Colombian Office Action dated Mar. 21, 2013 issued in Application No. CO 11.080.835.
European Office Action dated Mar. 21, 2016 issued in Application No. EP 09 829 850.8.
European Extended Search Report dated May 16, 2016 issued in Application No. EP 09 829 850.8.
Indonesian Examination Report dated Feb. 22, 2017 issued in Application No. W-00201102342.
Israel Office Action dated Apr. 8, 2014 issued in Application No. IL 213154.
Israel Office Action dated Jun. 30, 2015 issued in Application No. IL 213154.
Israel Office Action dated Sep. 14, 2016 issued in Application No. IL 213154.
Indian Examination Report dated Sep. 1, 2017 issued in Application No. IN 4959/DELNP/2011.
Japanese Office Action dated May 13, 2014 issued in Application No. JP 2011-538718.
Japanese Office Action dated Jun. 1, 2015 issued in Application No. JP 2011-538718.
Japanese Office Action [no translation] dated Oct. 16, 2016 issued in Application No. JP 2014-227718.
Japanese Final Office Action [no translation] dated Jul. 13, 2016 issued in Application No. JP 2014-227718.
Korean Office Action dated Jan. 4, 2016 issued in Application No. KR 10-2011-7014925.
Korean Office Action dated Jul. 18, 2016 issued in Application No. KR 10-2011-7014925.
Korean Office Action dated Feb. 23, 2017 issued in Application No. KR 10-2011-7014925.
Mexican Office Action [no translation] dated Dec. 6, 2012 issued in Application No. MX/a/2011/005630.
Mexican Office Action [no translation] dated May 14, 2013 issued in Application No. MX/a/2011/005630.
Mexican Office Action [no translation] dated Dec. 9, 2013 issued in Application No. MX/a/2011/005630.
Malaysian Examination Report dated Mar. 15, 2017 issued in Application No. MY PI2011002435.
Australian Patent Examination Report No. 1 dated Jul. 21, 2016 issued in Application No. AU 2011257982.
Canadian Examination Report dated Feb. 23, 2017 issued in Application No. CA 2,801,057.
Chinese First Office Action dated May 29, 2014 issued in Application No. CN 201180036870.9.

(56) References Cited

OTHER PUBLICATIONS

Chinese Second Office Action dated Apr. 15, 2015 issued in Application No. CN 201180036870.9.
Chinese Third Office Action dated Nov. 4, 2015 issued in Application No. CN 201180036870.9.
Chinese Rejection Decision dated Apr. 14, 2016 issued in Application No. CN 201180036870.9.
Chinese Notification of Reexamination dated Jan. 26, 2017 issued in Application No. CN 201180036870.9.
European Extended Search Report dated Jun. 9, 2016 issued in Application No. EP 11 787 551.8.
European Office Action dated Jan. 25, 2017 issued in Application No. EP 11 787 551.8.
European Consultation by telephone dated May 29, 2017 issued in Application No. EP 11 787 551.8.
European Office Action dated Aug. 23, 2017 issued in Application No. EP 11 787 551.8.
Indonesian Office Action dated Sep. 21, 2017 issued in Application No. W00201205280.
Japanese Office Action dated Jul. 7, 2015 issued in Application No. JP 2013-512064.
Japanese Office Action dated Dec. 16, 2016 issued in Application No. JP 2016-001030.
Korean Office Action dated Nov. 29, 2017 issued in Application No. KR 10-2012-7034232.
Mexican Office Action dated Aug. 11, 2015 issued in Application No. MX/a/2012/013777.
Mexican Office Action dated Jan. 15, 2016 issued in Application No. MX/a/2012/013777.
Malaysian Examination Report dated Sep. 15, 2015 issued in Application No. MY PI 2012005117.
PCT International Search Report dated Nov. 3, 2011 issued in PCT/US2011/038464.
PCT Written Opinion of the International Searching Authority dated Nov. 3, 2011 issued in PCT/US2011/038464.
PCT International Preliminary Report on Patentability dated Jun. 28, 2012 issued in PCT/US2011/038464.
Australian Patent Examination Report No. 1 dated Feb. 26, 2015 issued in Application No. AU 2011257983.
Australian Examination Report No. 1 dated Feb. 1, 2017 issued in Application No. AU 2016202905.
Australian Examination Report No. 2 dated Aug. 28, 2017 issued in Application No. AU 2016202905.
Canadian Examination Report dated May 17, 2017 issued in Application No. CA 2,801,024.
Chinese First Office Action dated Oct. 29, 2013 issued in Application No. CN 201180036696.8.
Chinese Second Office Action dated Jun. 5, 2014 issued in Application No. CN 201180036696.8.
Chinese Rejection Decision dated Jan. 14, 2015 issued in Application No. CN 201180036696.8.
Chinese Re-examination Decision dated May 26, 2015 issued in Application No. CN 201180036696.8.
Chinese Third Office Action dated Jul. 31, 2015 issued in Application No. CN 201180036696.8.
Chinese Fourth Office Action dated Dec. 30, 2015 issued in Application No. CN 201180036696.8.
European Extended Search Report dated Feb. 19, 2016 issued in Application No. EP 11 787 552.6.
European Office Action dated Oct. 11, 2016 issued in Application No. EP 11 787 552.6.
Japanese Office Action dated Jul. 7, 2015 issued in Application No. JP 2013-512605.
Japanese Final Office Action dated Feb. 29, 2016 issued in Application No. JP 2013-512605.
Japanese Office Action [no translation] dated Jul. 8, 2016 issued in Application No. JP 2013-512605.
Japanese Office Action [no translation] dated Sep. 6, 2016 issued in Application No. JP 2015-199078.
Mexican Office Action dated Sep. 12, 2017 issued in Application No. MX/a/2012/013756.
Malaysian Examination Report dated Sep. 15, 2015 issued in Application No. MY PI 2012005120.
Australian Patent Examination Report No. 1 dated May 20, 2015 issued in Application No. AU 2011323288.
Australian Patent Examination Report No. 2 dated Mar. 23, 2016 issued in Application No. AU 2011323288.
Australian Patent Examination Report No. 1 dated Aug. 21, 2017 issued in Application No. AU 2016202999.
Canadian Office Action dated Aug. 8, 2017 issued in Application No. CA 2,816,125.
Chinese First Office Action dated Apr. 15, 2014 issued in Application No. CN 201180053258.2.
Chinese Second Office Action dated Feb. 2, 2015 issued in Application No. CN 201180053258.2.
Chinese Third Office Action dated Jul. 3, 2015 issued in Application No. CN 201180053258.2.
Chinese Fourth Office Action dated Dec. 16, 2015 issued in Application No. CN 201180053258.2.
Chinese Fifth Office Action dated Jun. 6, 2016 issued in Application No. CN 201180053258.2.
Chinese Sixth Office Action (Rejection Decision) dated Nov. 2, 2016 issued in Application No. CN 201180053258.2.
Chinese Notification of Reexamination dated Aug. 31, 2017 issued in Application No. CN 201180053258.2.
European Office Action dated Aug. 15, 2014 issued in Application No. EP 11 785 851.4.
European Office Action dated Apr. 11, 2017 issued in Application No. EP 11 785 851.4.
Japanese Office Action dated Oct. 21, 2015 issued in Application No. JP 2013-537836.
Japanese Office Action dated Feb. 12, 2016 issued in Application No. JP 2013-537836.
Japanese Office Action dated Apr. 3, 2017 issued in Application No. JP 2016-009933.
Mexican First Office Action dated Jul. 19, 2016 issued in Application No. MX/a/2013/004631.
Mexican Second Office Action dated Jan. 16, 2017 issued in Application No. MX/a/2013/004631.
Mexican Third Office Action dated May 10, 2017 issued in Application No. MX/a/2013/004631.
Mexican Fourth Office Action dated Jul. 18, 2017 issued in Application No. MX/a/2013/004631.
Malaysian Examination Report dated May 31, 2016 issued in Application No. MY PI2013001587.
Australian Patent Examination Report No. 1 dated Jul. 22, 2015 issued in Application No. AU 2012212079.
Canadian Examination Report dated Nov. 22, 2017 issued in Application No. CA 2,825,691.
Chinese First Office Action dated Apr. 7, 2015 issued in Application No. CN 201280007593.3.
Chinese Second Office Action dated Nov. 17, 2015 issued in Application No. CN 201280007593.3.
Chinese Third Office Action dated Apr. 26, 2016 issued in Application No. CN 201280007593.3.
Chinese Fourth Office Action dated Oct. 17, 2016 issued in Application No. CN 201280007593.3.
Chinese Rejection Decision dated May 26, 2017 issued in Application No. CN 201280007593.3.
European Partial Supplementary Search Report dated May 8, 2015 issued in Application No. EP 12 741 997.6.
European Office Action dated Feb. 6, 2017 issued in Application No. EP 12 741 997.6.
European Examination Report dated Oct. 10, 2017 issued in Application No. EP 12 741 997.6.
Japanese Office Action dated Jan. 25, 2016 issued in Application No. JP 2013-552645.
Japanese Office Action [no translation] dated Apr. 20, 2016 issued in Application No. JP 2016-145348.
Mexican First Office Action dated Nov. 6, 2015 issued in Application No. MX/a/2013/008651.

(56) References Cited

OTHER PUBLICATIONS

Mexican Second Office Action dated Mar. 23, 2016 issued in Application No. MX/a/2013/008651.
Mexican Third Office Action dated Jul. 15, 2016 issued in Application No. MX/a/2013/008651.
Mexican First Office Action dated Apr. 24, 2017 issued in Application No. MX/a/2016/015902.
Malaysia Office Action dated Sep. 30, 2016 issued in Application No. MY PI2013002880.
PCT International Preliminary Report on Patentability dated Oct. 30, 2014 issued in PCT/US2013/037261.
Australian Patent Examination Report No. 1 dated Apr. 20, 2016 issued in Application No. AU 2013249172.
Australian Examination Report No. 2 dated Jan. 25, 2017 issued in Application No. AU 2013249172.
Chinese First Office Action dated Jul. 7, 2016 issued in Application No. CN 201380031877.0.
Chinese Second Office Action dated Mar. 24, 2017 issued in Application No. CN 201380031877.0.
Chinese Rejection Decision dated Oct. 10, 2017 issued in Application No. CN 201380031877.0.
European Supplementary Search Report dated Jan. 25, 2016 issued in Application No. EP 13 778 920.2.
European Examination Report dated Mar. 6, 2017 issued in Application No. EP 13 778 920.2.
Japanese First Office Action dated Mar. 10, 2017 issued in Application No. JP 2015-507197.
Mexican First Office Action dated Jul. 27, 2017 issued in Application No. MX/a/2014/012552.
Singapore Search Report and Written Opinion dated Mar. 24, 2016 issued in Application No. SG 11201406711T.
PCT International Report on Patentability and Written Opinion of the International Searching Authority dated Apr. 5, 2016 issued in PCT/US2014/059161.
Singapore Search Report and Written Opinion dated Aug. 7, 2017 issued in Application No. SG 11201602638S.
PCT Invitation to Pay Additional Fees dated Nov. 20, 2015 issued in PCT/US2015/039951.
PCT International Search Report and Written Opinion of the International Searching Authority dated Jan. 29, 2016 issued in Application No. PCT/US2015/039951.
PCT International Preliminary Report on Patentability and Written Opinion dated Jan. 10, 2017 issued in PCT/US2015/039951.
PCT International Search Report and Written Opinion of the International Searching Authority dated Jan. 3, 2017 issued in PCT/US2016/053979.
PCT International Search Report and Written Opinion of the International Searching Authority dated Jul. 18, 2016 issued in PCT/US2016/026265.
PCT International Preliminary Report on Patentability and Written Opinion of the International Searching Authority dated Oct. 19, 2017 issued in PCT/US2016/026265.
GenBank Accession No. AAC49269.1 "FatB2 [Cuphea hookeriana]", (Apr. 30, 1996), 2pp.
Geneseq: Database Accession No. AED66345, CN1618976, May 25, 2005, Zhang et al., 11pp.
GenBank Accession No. M94159.1 "California Bay Tree thioesterase mRna, complete cds", (Apr. 27, 1993), 2pp.
GenBank: "Codon Usage Database file for Chlorella vulgaris," Jun. 2007. [Retrieved from the Internet Aug. 26, 2010: ,URL: http://www.kazusa.or.jp/coldo/cgi-bin/showcodon.cgi?species=3077] 2pp.
GenBank: U31813 "Cinnamomum camphora acyl-ACP thioesterase mRNA, complete cds," Jan. 31, 1996, 2pp.
Geneseq: Database Accession No. AXE01814, "Palmitic acid production-related gene, SEQ:20024," XP002750550, Oct. 14, 2010.
Geneseq: Database Accession No. ADJ49365, "Oil-associated gene related protein #865," XP002750551, Jun. 15, 2007.

UNIPROT Database publication; Borza et al., SubName: *Plastid acyl-[acyl-carrier protein] desaturase*, AC No. Q5IWZ3, Feb. 15, 2005, URL: http://www.genome.jp/dbget-bin/www_bget?uniprot:Q5IWZ3_PROWI, 1 page.
UNIPROT Accession No. P41758. Phosphoglycerate kinase, chloroplastic. Nov. 25, 2008. [Retrieved from the Internet Aug. 12, 2010:<http://www.uniprot.org/uniprot/P41758.txt?version=46>].
Alberto et al., (2006) "Crystal structure of inactivated Thermotoga maritima invertase in complex with the trisaccharide substrate raffinose," *Biochem. J.*, 395:457-462.
Alvarez et al., (2002) "Triacylglycerols in prokaryotic microorganisms," *Appl Microbiol Biotechnol*, 60(4):367-376.
Apt et al., (1996) "Stable nuclear transformation of the diatom Phaeodactylum tricornutum," *Mol Gen Genet*, 252(5):572-579.
Bergh et al., (1987) "Expression of the *Saccharomyces cerevisiae* glycoprotein invertase in mouse fibroblasts: Glycosylation, secretion, and enzymatic activity," *Proc. Natl. Acad. Sci. USA*, 84:3570-3574.
Blatti, Jillian L. et al., (Sep. 2012) "Manipulating Fatty Acid Biosynthesis in Microalgae for Biofuel through Protein-Protein Interactions," *PLoS ONE*, 7(9):e42949, 12pp.
Campbell et al., (1990) "Codon Usage in Higher Plants, Green Algae, and Cyanobacteria," *Plant Physiol.*, 92:1-11.
Carlson et al., (1983) "The Secreted Form of Invertase in *Saccharomyces cerevisiae* Is Synthesized from mRNA Encoding a Signal Sequence," *Molecular and Cellular Biology*, 3(3):439-447.
Chen et al., (1996) "High cell density culture of microalgae in heterotrophic growth," *Trends in Biotechnology*, 14(11):421-426.
Chi et al., (Apr. 2008) "Fatty Acid Biosynthesis in Eukaryotic Photosynthetic Microalgae: Identification of a Microsomal Delta 12 Desaturase in *Chlamydomonas reinhardtii*," *The Journal of Microbiology*, 46(2): 189-201.
Dehesh et al., (2001) "Overexpression of 3-Ketoacyl-Acyl-Carrier Protein Synthase IIIs in Plants Reduces the Rate of Lipid Synthesis," *Plant Physiology*, 125:1103-1114.
Ehneb et al., (1997) "Co-ordinated induction of mRNAs for extracellular invertase and a glucose transporter in Chenopodium rubrum by cytokinins," *The Plant Journal*, 11(3):539-548.
Elumalai et al., (2011) "Optimizatin of abiotic conditions suitable for the production of biodiesel from Chlorella vulgaris," *Indian J. Sci. Technol.*, 4(2):91-97.
Facciotti et al., (May 1998) "Molecular dissection of the plant acyl-acyl carrier protein thioesterases," *Fett/Lipid, Lipid-Weinheim*, 100(4-5), S.:167-172 [<URL:http://www.researchgate.net/publication/247961590>].
Garay et al., (2014) "Accumulation of High-Value lipids in Single-Cell Microorganisms: A Mechanistic Approach and Future Perspectives," *J. of Agric. and Food Chem.*, 62:2709-2727.
Gimpel et al., (Dec. 15, 2015) "In Metabolic Engineering of Eukaryotic Microalgae: Potential and Challenges Come with Great Diversity," *Metabolic Engineering of Eukaryotic Microalgae, Frontiers in Microbiology*, 6(Article 1376):14pp.
Hitz et al., "Cloning of a Higher-Plant Plastid Omega-6 Fatty Acid Desaturase cDNA and Its Expression in a Cyanobacterium," *Plant Physiology*, 105(2):635-641, (1994).
Hsieh et al., (2012) "Accumulation of Lipid Production in *Chlorella minutissima* by Triacylglycerol Biosynthesis-Related Genes Cloned from *Saccharomyces cerevisiae* and *Yarrowia lipolytica*," *The Journal of Microbiology*, 50(3):526-534.
Kessler et al., "Physiological and Biochemical Contributions to the Taxonomy of the Genus *Prototheca* III. Utilization of Organic Carbon and Nitrogen Compounds," *Arch Microbiol*, 132:103-106, (1982).
Khozin-Goldberg et al. (2011) "Unravelling algal lipid metabolism: Recent advances in gene identification," *Biochemie*, 93:91-100.
Kosa et al., (Feb. 2011) "Lipids from heterotrophic microbes: advances in metabolism research," *Trends in Biotechnology*, 29(2):53-61.
Leonard et al., (Mar. 1998) A *Cuphea* β-ketoacyl-ACP synthase shifts the synthesis of fatty acids toward shorter chains in *Arabidopsis* seeds expressing *Cuphea* FatB thioesterases, *The Plant Journal*, 13(5):621-628.
Matsuka et al., (1966) *Plant and Cell Physiol.*, 7:149-162.

(56) References Cited

OTHER PUBLICATIONS

Miao et al., (2006) "Biodiesel Production From Heterotrophic Microalgal Oil," *Biosource Technology*, 97(06): 841-846.

Otles et al., (2001) "Fatty Acid Composition of *Chlorella* and *Spirulina* Microalgae Species," *Journal of AOAC International*, 84(6):1708-1714.

Pidkowich et al., (Mar. 13, 2007) "Modulating seed β-ketoacyl-acyl carrier protein synthase II level converts the composition of a temperate seed oil to that of a palm-like tropical oil," *PNAS*, 104(11):4742-4747.

Sheehan et al. (1998) "A Look Back at the U.S. Department of Energy's Aquatic Species Program: Biodiesel from Algae," *NREL/TP*-580-24190.

Shen et al. (2010) "Heterotrophic Culture of *Chlorella protothecoides* in Various Nitrogen Sources for Lipid Production," *Appl Biochem Biotechnol*, 160:1674-1684.

Wang et al., (Jun. 1998) *Principle and Technology of Plant Genetic Engineering, Beijing: Science Press*, pp. 34-35 [19pp].

Xu et al., (2006) "High quality biodiesel production from a microalga *Chlorella protothecoides* by heterotrophic growth in fermenters," *Journal of Biotechnology*, 126:499-507.

U.S. Appl. No. 15/725,222, filed Oct. 4, 2017, Moseley et al.

\* cited by examiner

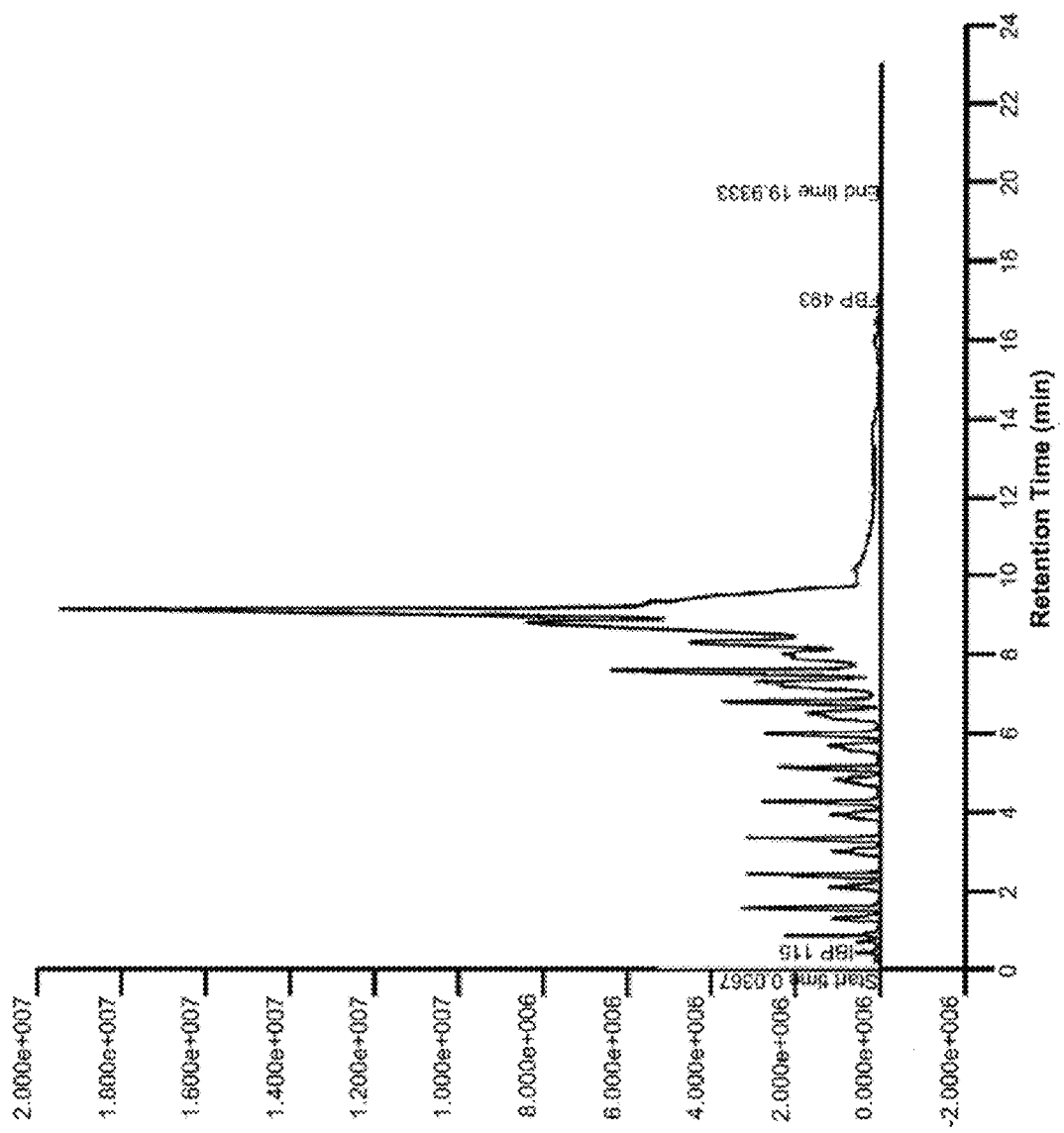

RECOMBINANT MICROALGAE INCLUDING KETO-ACYL ACP SYNTHASE

CROSS-REFERENCE TO RELATED APPLICATIONS

This application is a continuation of U.S. application Ser. No. 13/650,018, filed Oct. 11, 2012, which is a continuation of U.S. application Ser. No. 13/118,369, filed May 27, 2011, which claims the benefit under 35 U.S.C. 119(e) of U.S. Provisional Patent Application No. 61/349,774, filed May 28, 2010, U.S. Provisional Patent Application No. 61/374,992, filed Aug. 18, 2010, U.S. Provisional Patent Application No. 61/414,393, filed Nov. 16, 2010, and U.S. Provisional Patent Application No. 61/428,192, filed Dec. 29, 2010. Each of these applications is incorporated herein by reference in its entirety for all purposes.

REFERENCE TO A SEQUENCE LISTING

This application includes an electronic sequence listing in a file named "453749-Sequence.txt", created on Aug. 5, 2015 and containing 1,008,306 bytes, which is hereby incorporated by reference in its entirety for all purposes.

FIELD OF THE INVENTION

The present invention relates to the production of food compositions, oils, fuels, and oleochemicals made from microorganisms. In particular, the disclosure relates to oil-bearing microalgae, methods of cultivating them for the production of biomass and useful compounds, including lipids, fatty acid esters, fatty acids, aldehydes, alcohols, and alkanes, and methods and reagents for genetically altering them to improve production efficiency and alter the type and composition of the oils produced by them.

BACKGROUND OF THE INVENTION

As the human population continues to increase, there's a growing need for additional food sources, particularly food sources that are inexpensive to produce but nutritious. Moreover, the current reliance on meat as the staple of many diets, at least in the most developed countries, contributes significantly to the release of greenhouse gases, and there's a need for new foodstuffs that are equally tasty and nutritious yet less harmful to the environment to produce. There remains a need for methods to produce foodstuffs from microorganism, including algae, cheaply and efficiently, at large scale, particularly foodstuffs that are tasty and nutritious. The present invention meets these and other needs

SUMMARY OF THE INVENTION

The present invention provides oleaginous microbial cells, preferably microalgal cells, having distinct lipid profiles, and includes recombinant cells expressing exogenous genes encoding proteins such as fatty acyl-ACP thioesterases. The present invention also provides methods of making lipids and oil-based products, including fuels such as biodiesel, renewable diesel and jet fuel, from such cells.

In a first aspect, the present invention provides oleaginous microbial cells, preferably microalgal cells, having a lipid profile that is at least 1% or at least 5%, preferably at least 3%, C8:0. In some cases, the lipid profile is at least 10% or at least 15%, preferably at least 12%, C8:0. In some embodiments, the cell is a recombinant cell. In some cases, the recombinant cell comprises an exogenous gene encoding an acyl-ACP thioesterase protein that has hydrolysis activity towards fatty acyl-ACP substrates of chain length C8. In some embodiments, the exogenous gene encodes a *Cuphea palustris* acyl-ACP thioesterase. In some cases, the cell is a *Prototheca* cell. In some cases, the cell is of a microalgal genus or species selected from microalgae identified in Table 1.

In a second aspect, the present invention provides oleaginous microbial cells, preferably microalgal cells, having a lipid profile that is at least 4% C10:0. In some cases, the lipid profile is at least 20%, at least 25% or at least 30%, preferably at least 24%, C10:0. In some cases, the ratio of C10:0 to C12:0 is at least 6:1. In some embodiments, the cell is a recombinant cell. In some cases, the recombinant cell comprises an exogenous gene encoding an acyl-ACP thioesterase protein that has hydrolysis activity towards fatty acyl-ACP substrates of chain length C10. In some embodiments, the exogenous gene encodes an acyl-ACP thioesterase protein from a species selected from the group consisting of *Cuphea hookeriana* and *Ulmus americana*. In some cases, the cell is a *Prototheca* cell. In some embodiments, the cell is of a microalgal genus or species selected from microalgae identified in Table 1.

In a third aspect, the present invention provides oleaginous microbial cells, preferably microalgal cells, having a lipid profile that is at least 10% or at least 15%, preferably at least 13%, C12:0. In some cases, the lipid profile is at least 30%, at least 35% or at least 40%, preferably at least 34%, C12:0. In some cases, the ratio of C12 to C14 is at least 5:1. In some cases, the cell is a recombinant cell. In some embodiments, the recombinant cell comprises an exogenous gene encoding an acyl-ACP thioesterase protein that has hydrolysis activity towards fatty acyl-ACP substrates of chain length C12. In some cases, the recombinant cell comprises at least two exogenous genes encoding acyl-ACP thioesterase proteins from *Umbellularia californica* and *Cinnamomum camphora* that have hydrolysis activity towards fatty acyl-ACP substrates of chain length C12. In some embodiments, the cell is a *Prototheca* cell.

In a fourth aspect, the present invention provides oleaginous microbial cells, preferably microalgal cells, having a lipid profile that is at least 5% or at least 15%, preferably at least 10%, C14:0. In some cases, the lipid profile is at least 40%, at least 45%, or at least 50%, preferably at least 43%, C14:0. In some cases, the ratio of C14:0 to C12:0 is at least 7:1. In some cases, the cell is a recombinant cell. In some embodiments, the recombinant cell comprises an exogenous gene encoding an acyl-ACP thioesterase protein that has hydrolysis activity towards fatty acyl-ACP substrates of chain length C14. In some embodiments, the acyl-ACP thioesterase protein is from a species selected from the group consisting of *Cinnamomum camphora* and *Ulmus americana*. In some cases, the cell is a *Prototheca* cell. In some embodiments, the cell is of a microalgal genus or species selected from microalgae identified in Table 1.

In a fifth aspect, the present invention provides oleaginous microbial cells, preferably microalgal cells, having a lipid profile that is at least 10% or at least 20%, preferably at least 15%, C16:0. In some cases, the lipid profile is at least 30%, at least 35% or at least 40%, preferably at least 37%, C16:0. In some cases, the cell is a recombinant cell. In some embodiments, the recombinant cell comprises an exogenous gene encoding an acyl-ACP thioesterase protein that has hydrolysis activity towards fatty acyl-ACP substrates of chain length C16. In some embodiments, the recombinant cell comprises at least two exogenous genes encoding acyl- ACP thioesterase proteins from *Umbellularia californica* and *Cinnamomum camphora* that have hydrolysis activity towards fatty acyl-ACP substrates of chain length C16. In some cases, the cell is a *Prototheca* cell.

In a sixth aspect, the present invention provides oleaginous microbial cells, preferably microalgal cells, having a lipid profile that is at least 55% or at least 65%, preferably at least 60%, saturated fatty acids. In some cases the cells, have a lipid profile that is at least 80%, at least 85%, or at least 90%, preferably at least 86%, saturated fatty acids. In some cases, the cell is a recombinant cell. In some embodiments, the recombinant cell comprises an exogenous gene encoding an acyl-ACP thioesterase protein that has hydrolysis activity towards fatty acyl-ACP substrates of chain lengths C10-C16. In some embodiments, the cell comprises an exogenous gene encoding a ketoacyl synthase protein. In some cases, the cell is a *Prototheca* cell.

In a seventh aspect, the present invention provides oleaginous microbial cells, preferably microalgal cells, comprising a mutated endogenous desaturase gene, wherein the mutation renders the gene or desaturase inactive. In some cases, the cell has a lipid profile that is at least 40% or at least 50%, preferably at least 45%, saturated fatty acids. In some cases, the cell has a lipid profile that is at least 15%, at least 20% or at least 25%, preferably at least 19%, C18:0. In some embodiments, the cell comprises a mutated endogenous desaturase gene that results in at least a 2-fold increase in C18:0 fatty acid, as compared to a wild-type cell. In some cases, the microalgal cell has a lipid profile that is no more than 1% or no more than 5%, preferably no more than 2%, C18:2. In some embodiments, the microalgal cell has a lipid profile that is no more than 5% or no more than 10%, preferably no more than 7%, 18:1.

In some embodiments of the recombinant cells discussed herein, the cell comprises a mutated endogenous desaturase gene, wherein the mutation renders the gene or desaturase inactive.

In a eighth aspect, the present invention provides a method of making lipid. In one embodiment, the method comprises (a) cultivating a cell as discussed above until the cell is at least 15% or at least 25%, preferably at least 20%, lipid by dry weight, and (b) separating the lipid from water-soluble biomass components.

In a ninth aspect, the present invention provides another method of making lipid. In one embodiment, the method comprises (a) cultivating an oleaginous microbial, preferably a microalgae cell, containing exogenous genes encoding two distinct acyl-ACP thioesterases, wherein the lipid profile of the cell is distinct from (i) the profile of the cell without the exogenous genes and (ii) the profile of the cell with only one of the exogenous genes, and (b) separating the lipid from water-soluble biomass components. In some cases, at least one of the exogenous genes encodes a fatty acyl-ACP thioesterase selected from the group consisting of the thioesterases identified in Table 4.

In a tenth aspect, the present invention provides a method of making an oil-based product. In one embodiment, the method comprises (a) cultivating a cell as discussed above until the cell is at least 5% or at least 15%, preferably at least 10%, lipid by dry weight, (b) separating the lipid from water-soluble biomass components, and (c) subjecting the lipid to at least one chemical reaction selected from the group consisting of: saponification; metathesis; acid hydrolysis; alkaline hydrolysis; enzymatic hydrolysis; catalytic hydrolysis; hot-compressed water hydrolysis; a catalytic hydrolysis reaction wherein the lipid is split into glycerol and fatty acids; an amination reaction to produce fatty nitrogen compounds; an ozonolysis reaction to produce mono- and dibasic-acids; a triglyceride splitting reaction selected from the group consisting of enzymatic splitting and pressure splitting; a condensation reaction that follows a hydrolysis reaction; a hydroprocessing reaction; a hydroprocessing reaction and a deoxygenation reaction or a condensation reaction prior to or simultaneous with the hydroprocessing reaction; a gas removal reaction; a deoxygenation reaction selected from the group consisting of a hydrogenolysis reaction, hydrogenation, a consecutive hydrogenation-hydrogenolysis reaction, a consecutive hydrogenolysis-hydrogenation reaction, and a combined hydrogenation-hydrogenolysis reaction; a condensation reaction following a deoxygenation reaction; an esterification reaction; an interestification reaction; a transesterification reaction; a hydroxylation reaction; and a condensation reaction following a hydroxylation reaction, whereby an oil-based product is produced.

In some cases, the oil-based product is selected from soap or a fuel product. In some embodiments, the oil-based product is a fuel product selected from the group consisting biodiesel, renewable diesel, and jet fuel. In some cases, the fuel product is biodiesel with one or more of the following attributes: (i) 0.01-0.5 mcg/g, 0.025-0.3 mcg/g, preferably 0.05-0.244 mcg/g, total carotenoids; (ii) less than 0.01 mcg/g, less than 0.005 mcg/g, preferably less than 0.003 mcg/g, lycopene; (iii) less than 0.01 mcg/g, less than 0.005 mcg/g, preferably less than 0.003 mcg/g, beta carotene; (iv) 0.01-0.5 mcg/g, 0.025-0.3 mcg/g, preferably 0.045-0.268 mcg/g, chlorophyll A; (v) 1-500 mcg/g, 35-175 mcg/g, preferably 38.3-164 mcg/g, gamma tocopherol; (vi) less than 1%, less than 0.5%, preferably less than 0.25%, brassicasterol, campesterol, stignasterol, or beta-sitosterol; (vii) 100-500 mcg/g, 225-350 mcg/g, preferably 249.6-325.3 mcg/g, total tocotrienols; (viii) 0.001-0.1 mcg/g, 0.0025-0.05 mcg/g, preferably 0.003-0.039 mcg/g, lutein; or (ix) 10-500 mcg/g, 50-300 mcg/g, preferably 60.8-261.7 mcg/g, tocopherols. In some cases, the fuel product is renewable diesel that has a T10-T90 of at least 20° C., 40° C. or 60° C. In some cases, the fuel product is jet fuel that meets HRJ-5 and/or ASTM specification D1655.

In an eleventh aspect, the present invention provides a triglyceride oil comprising (a) a lipid profile of at least 3% C8:0, at least 4% C10:0, at least 13% C12:0, at least 10% C14:0, and/or at least 60% saturated fatty acids, and (b) one or more of the following attributes: (i) 0.01-0.5 mcg/g, 0.025-0.3 mcg/g, preferably 0.05-0.244 mcg/g, total carotenoids; (ii) less than 0.01 mcg/g, less than 0.005 mcg/g, preferably less than 0.003 mcg/g, lycopene; (iii) less than 0.01 mcg/g, less than 0.005 mcg/g, preferably less than 0.003 mcg/g, beta carotene; (iv) 0.01-0.5 mcg/g, 0.025-0.3 mcg/g, preferably 0.045-0.268 mcg/g, chlorophyll A; (v) 1-300 mcg/g, 35-175 mcg/g, preferably 38.3-164 mcg/g, gamma tocopherol; (vi) less than 1%, less than 0.5%, preferably less than 0.25%, brassicasterol, campesterol, stignasterol, or beta-sitosterol; (vii) 100-500 mcg/g, 225-350 mcg/g, preferably 249.6-325.3 mcg/g, total tocotrienols; (viii) 0.001-0.1 mcg/g, 0.0025-0.05 mcg/g, preferably 0.003-0.039 mcg/g, lutein; or (ix) 10-500 mcg/g, 50-300 mcg/g, preferably 60.8-261.7 mcg/g, tocopherols.

In a twelfth aspect, the present invention provides an isolated oil from microalgae that has a C8:C10 fatty acid ratio of at least 5:1. In a related aspect, the present invention provides an isolated oil from microalgae with at least 50% to 75%, preferably at least 60%, saturated fatty acids. In another related aspect, the present invention provides an isolated oil from microalgae that has a C16:14 fatty acid ratio of about 2:1. In still another related aspect, the present invention provides an isolated oil from microalgae that has a C12:C14 fatty acid ratio of at least 5:1. In some embodiments, the microalgae contains at least one exogenous gene. In some cases, the microalgae is of the genus *Prototheca*.

In a thirteenth aspect, the present invention provides a triglyceride oil comprising (a) a lipid profile of less than 5% or less than 2%, preferably less than 1%, <C12; between 1%-10%, preferably 2%-7%, C14:0; between 20%-35%, preferably 23%-30%, C16:0; between 5%-20%, preferably 7%-15%, C18:0; between 35-60%, preferably 40-55%, C18: 1; and between 1%-20%, preferably 2-15%, C18:2 fatty acids; and (b) one or more of the following attributes: (i) 0.01-0.5 mcg/g, 0.025-0.3 mcg/g, preferably 0.05-0.244 mcg/g, total carotenoids; (ii) less than 0.01 mcg/g, less than 0.005 mcg/g, preferably less than 0.003 mcg/g, lycopene; (iii) less than 0.01 mcg/g, less than 0.005 mcg/g, preferably less than 0.003 mcg/g, beta carotene; (iv) 0.01-0.5 mcg/g, 0.025-0.3 mcg/g, preferably 0.045-0.268 mcg/g, chlorophyll A; (v) 1-300 mcg/g, 35-175 mcg/g, preferably 38.3-164 mcg/g, gamma tocopherol; (vi) less than 1%, less than 0.5%, preferably less than 0.25%, brassicasterol, campesterol, stignasterol, or beta-sitosterol; (vii) 100-500 mcg/g, 225-350 mcg/g, preferably 249.6-325.3 mcg/g, total tocotrienols; (viii) 0.001-0.1 mcg/g, 0.0025-0.05 mcg/g, preferably 0.003-0.039 mcg/g, lutein; or (ix) 10-500 mcg/g, 50-300, preferably 60.8-261.7 mcg/g, tocopherols.

In some cases, the triglyceride oil is isolated from a microbe comprising one or more exogenous gene. In some embodiments, the one or more exogenous gene encodes a fatty acyl-ACP thioesterase. In some cases, the fatty acyl-ACP thioesterase has hydrolysis activity towards fatty acyl-ACP substrates of chain length C14. In some embodiments, the microbe further comprises a mutated endogenous desaturase gene, wherein the mutation renders the gene or desaturase inactive.

In a fourteenth aspect, the present invention provides a method of producing a triglyceride oil comprising a lipid profile of less than 5%, or less than 2%, preferably less than 1%, <C12; between 1%-10%, preferably 2%-7%, C14:0; between 20%-35%, preferably 23%-30%, C16:0; between 5%-20%, preferably 7%-15%, C18:0; between 35%-60%, preferably 40-55%, C18:1; and between 1%-20%, preferably 2-15%, C18:2 fatty acids, wherein the triglyceride oil is isolated from a microbe comprising one or more exogenous gene. In some cases, the triglyceride oil comprises a lipid profile of 1%-10%, preferably 3-5%, C14:0; 20%-30%, preferably 25%-27%, C16:0; 5%-20%, preferably 10-15%, C18:0; and 35%-50%, preferably 40-45%, C18:1. In some embodiments, the one or more exogenous gene encodes a fatty acyl-ACP thioesterase. In some cases, the fatty acyl-ACP thioesterase has hydrolysis activity towards fatty acyl-ACP substrates of chain length C14. In some cases, the microbe further comprises a mutated endogenous desaturase gene, wherein the mutation renders the gene or desaturase inactive. In some cases, the one or more exogenous gene is a sucrose invertase. In some embodiments, the mutated endogenous desaturase gene is a stearoyl-acyl carrier protein desaturase (SAD) (e.g., SEQ ID NOs: 199-200). In some embodiments, the mutated endogenous desaturase gene is a fatty acid desaturase (FAD).

In a fifteenth aspect, the present invention provides a oleaginous microbial cell, preferably a microalgal cell, comprising a triglyceride oil, wherein the fatty acid profile of the triglyceride oil is selected from the group consisting of at least about 1% C8:0, at least about 1% C10:0, at least about 1% C12:0, at least about 2% C14:0, at least about 30% C16:0, at least about 5% C18:0, at least about 60% C18:1, less than about 7% C18:2, and at least about 35% saturated fatty acids. In some cases, the oleaginous microbial cell comprises an exogenous gene, and optionally, an endogenous desaturase of the oleaginous microbial cell has been inactivated or mutated to have less enzymatic activity.

In some cases, the fatty acid profile of the triglyceride oil is similar to the fatty acid profile of a naturally occurring oil. In some cases, the naturally occurring oil is selected from the group consisting of cocoa butter, coconut oil, palm oil, palm kernel oil, shea butter, beef tallow and lard. In some cases, the fatty acid profile of the triglyceride oil comprises a profile selected from the group consisting of, the total combined amounts of C8:0 and C10:0 is at least about 10%, the total combined amount of C10:0, C12:0, and C14:0 is at least about 50%, the total combined amount of C16:0, C18:0 and C18:1 is at least about 60%, the total combined amount of C18:0, C18:1 and C18:2 is at least about 60%, the total combined amount of C14:0, C16:0, C18:0 and C18:1 is at least about 60%, and the total combined amount of C18:1 and C18:2 is less than about 30%. In some cases, the fatty acid profile of the triglyceride oil comprises a ratio of fatty acids selected from the group consisting of C8:0 to C10:0 ratio of at least about 5 to 1, C10:0 to C12:0 ratio of at least about 6 to 1, C12:0 to C14:0 ratio of at least about 5 to 1, C14:0 to C12:0 ratio of at least about 7:1, and C14:0 to C16:0 ratio of at least about 1 to 2.

In some cases, the endogenous desaturase is selected from the group consisting of stearoyl ACP desaturase and delta 12 fatty acid desaturase. In some cases, the exogenous gene is selected from the group consisting of a gene encoding an acyl-ACP thioesterase. In some cases, the exogenous gene encodes an acyl-ACP thioesterase selected from the group consisting of those identified in Table 4. In some cases, the oleaginous microbial cell further comprises a gene encoding a sucrose invertase.

In various embodiments, the oleaginous microbial cell is a cell of a microalgal genus or species selected from *Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora* sp., *Anabaena, Ankistrodesmus, Ankistrodesmus falcatus, Boekelovia hooglandii, Borodinella* sp., *Botryococcus braunii, Botryococcus sudeticus, Carteria, Chaetoceros gracilis, Chaetoceros muelleri, Chaetoceros muelleri subsalsum, Chaetoceros* sp., *Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora* (strain SAG 37.88), *Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella parva, Chlorella photophila, Chlorella pringsheimii, Chlorella protothecoides* (including any of UTEX strains 1806, 411, 264, 256, 255, 250, 249, 31, 29, 25, and CCAP strains 211/17 and 211/8d), *Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii,*

*Chlorella vulgaris, Chlorella vulgaris, Chlorella vulgaris f. tertia, Chlorella vulgaris* var. *autotrophica, Chlorella vulgaris* var. *viridis, Chlorella vulgaris* var. *vulgaris, Chlorella vulgaris* f. *tertia, Chlorella vulgaris* var. *vulgaris* f. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena, Franceia* sp., *Fragilaria crotonensis, Fragilaria* sp., *Gleocapsa* sp., *Gloeothamnion* sp., *Hymenomonas* sp., *Isochrysis aff galbana, Isochrysis galbana, Lepocinclis, Micractinium, Micractinium* (UTEX LB 2614), *Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Pascheria acidophila, Pavlova* sp., *Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pyramimonas* sp., *Pyrobotrys, Sarcinoid chrysophyte, Scenedesmus armatus, Spirogyra, Spirulina platensis, Stichococcus* sp., *Synechococcus* sp., *Tetraedron, Tetraselmis* sp., *Tetraselmis suecica, Thalassiosira weissflogii,* and *Viridiella fridericiana.*

In some cases, the oleaginous microbial cell is a cell of the genus *Prototheca*. In some cases, the oleaginous microbial cell is a cell of the genus *Prototheca moriformis*.

In some cases, the oleaginous microbial cell is an oleaginous yeast cell. In some cases, the oleaginous microbial cell is an oleaginous bacterial cell.

In some cases, the naturally occurring oil is cocoa butter and the exogenous gene comprises a *Carthamus tinctorus* thioesterase gene. In some cases, the naturally occurring oil is coconut oil. In some cases, the naturally occurring oil is palm oil and the exogenous gene comprises a *Elaeis guiniensis* thioesterase gene, a *Cuphea hookeriana* thioesterase gene, a combination of a *Cuphea hookeriana* KAS IV gene and a *Cuphea wrightii* FATB2 gene, or a construct designed to disrupt an endogenous KAS II gene. In some cases, the naturally occurring oil is palm kernel oil and the exogenous gene comprises a combination of a *Cuphea wrightii* FATB2 gene and a construct designed to disrupt an endogenous SAD2B gene. In some cases, the naturally occurring oil is shea butter. In some cases, the naturally occurring oil is beef tallow. In some cases, the naturally occurring oil is lard and the exogenous gene comprises a combination of *U. californica* thioesterase gene and a construct designed to disrupt an endogenous SAD2B gene, a combination of a *Garcinia mangostana* thioesterase gene and a construct designed to disrupt an endogenous SAD2B gene, a *Brassica napus* thioesterase gene, or a *Cuphea hookeriana* thioesterase gene.

In a sixteenth aspect, the present invention provides an oleaginous microbial triglyceride oil composition, wherein the fatty acid profile of the triglyceride oil is selected from the group consisting of at least about 1% C8:0, at least about 1% C10:0, at least about 1% C12:0, at least about 2% C14:0, at least about 30% C16:0, at least about 5% C18:0, at least about 60% C18:1, less than about 7% C18:2, and at least about 35% saturated fatty acids. In various embodiments, the triglyceride oil composition is produced by cultivating a population of oleaginous microbial cells or recombinant oleaginous microbial cells in a culture medium, wherein the oleaginous microbial cells are as described above, in particular those described above in connection with the fifteenth aspect of the invention.

In some cases, the oleaginous microbial triglyceride oil composition further comprises an attribute selected from the group consisting of: (i) less than 0.3 mcg/g total carotenoids; (ii) less than 0.005 mcg/g lycopene; (iii) less than 0.005 mcg/g beta carotene; (iv) less than 0.3 mcg/g chlorophyll A; (v) less than 175 mcg/g gamma tocopherol; (vi) less than 0.25% brassicasterol, campesterol, stignasterol, or beta-sitosterol; (vii) less than 350 mcg/g total tocotrienols; (viii) less than 0.05 mcg/g lutein; or (ix) less than 275 mcg/g tocopherols.

In a seventeenth aspect, the present invention provides a method of producing an oleaginous microbial triglyceride oil composition having a fatty acid profile selected from the group consisting of at least about 1% C8:0, at least about 1% C10:0, at least about 1% C12:0, at least about 2% C14:0, at least about 30% C16:0, at least about 5% C18:0, at least about 60% C18:1, less than about 7% C18:2, and at least about 35% saturated fatty acids, wherein the method comprises the steps of: (a) cultivating a population of oleaginous microbial cells in a culture medium until at least 10% of the dry cell weight of the oleaginous microbial cells is triglyceride oil; and (b) isolating the triglyceride oil composition from the oleaginous microbial cells. In various embodiments, the triglyceride oil composition is produced via cultivation of a population of oleaginous microbial cells or recombinant oleaginous microbial cells as described above, in particular those described above in connection with the fifteenth aspect of the invention.

In an eighteenth aspect, the present invention provides a method of making an oil-based product, wherein the method comprises the steps of: (a) subjecting the oleaginous microbial triglyceride oil composition, as described above in connection with the sixteenth aspect of the invention, to at least one chemical reaction selected from the group consisting of: saponification; metathesis; acid hydrolysis; alkaline hydrolysis; enzymatic hydrolysis; catalytic hydrolysis; hot-compressed water hydrolysis; a catalytic hydrolysis reaction wherein the lipid is split into glycerol and fatty acids; an amination reaction to produce fatty nitrogen compounds; an ozonolysis reaction to produce mono- and dibasic-acids; a triglyceride splitting reaction selected from the group consisting of enzymatic splitting and pressure splitting; a condensation reaction that follows a hydrolysis reaction; a hydroprocessing reaction; a hydroprocessing reaction and a deoxygenation reaction or a condensation reaction prior to or simultaneous with the hydroprocessing reaction; a gas removal reaction; a deoxygenation reaction selected from the group consisting of a hydrogenolysis reaction, hydrogenation, a consecutive hydrogenation-hydrogenolysis reaction, a consecutive hydrogenolysis-hydrogenation reaction, and a combined hydrogenation-hydrogenolysis reaction; a condensation reaction following a deoxygenation reaction; an esterification reaction; an interesterification reaction; a transesterification reaction; a hydroxylation reaction; and a condensation reaction following a hydroxylation reaction; and (b) isolating the product of the reaction from the other components.

In some cases, the oil-based product is selected from the group consisting of a soap, a fuel, a dielectric fluid, a hydraulic fluid, a plasticizer, a lubricant, a heat transfer fluid, and a metal working fluid. In some cases, the oil-based product is a fuel product selected from the group consisting of: (a) biodiesel; (b) renewable diesel; and (c) jet fuel.

In some cases, the fuel product is biodiesel with one or more of the following attributes: (i) less than 0.3 mcg/g total carotenoids; (ii) less than 0.005 mcg/g lycopene; (iii) less than 0.005 mcg/g beta carotene; (iv) less than 0.3 mcg/g chlorophyll A; (v) less than 175 mcg/g gamma tocopherol; (vi) less than 0.25% brassicasterol, campesterol, stignasterol, or beta-sitosterol; (vii) less than 350 mcg/g total tocotrienols; (viii) less than 0.05 mcg/g lutein; or (ix) less than 275 mcg/g tocopherols.

In some cases, the fuel product is renewable diesel that has a T10-T90 of at least 20° C., 40° C. or 60° C.

In some cases, the fuel product is jet fuel that meets HRJ-5 and/or ASTM specification D1655.

In another aspect, the oleaginous microbial cell of the invention is edible. The triglyceride oils of the invention are also edible. In some cases, the microbial strain is cultivated and processed under good manufacturing process (GMP) conditions. As a food or a food ingredient, the oleaginous microbial cell can be consumed whole. Alternatively, the microbial biomass is processed into a microbial flakes, powder or flour. Microbial flour is prepared by completely or partially lysing the cells in the form of a powder. When processed into microbial flour, the average particle size of lysed microbial biomass is between about 1 to 30 μm. The lysed microbial cells can agglomerate to form bigger particles of up to 1,000 μm. In one embodiment, the flour further comprises a flow agent, antioxidants and the like. The microbial cells and the microbial oils of the present invention can be consumed by itself. Alternatively, the microbial cells and the microbial oils of the present invention can be combined with at least one other ingredient. By way of example, the microbial cells and the microbial oils can be combined with edible ingredients, e.g., egg, egg products, milk, dairy products, meats, grains, other edible fats, natural sweetners, artificial sweetners, etc. The microbial cells and the microbial oils can also be combined with preservatives and other ingredients added to processed foods.

All of the processes described herein can be performed in accordance with GMP or equivalent regulations. In the United States, GMP regulations for manufacturing, packing, or holding human food are codified at 21 C.F.R. 110. These provisions, as well as ancillary provisions referenced therein, are hereby incorporated by reference in their entirety for all purposes. GMP conditions in the Unites States, and equivalent conditions in other jurisdictions, apply in determining whether a food is adulterated (the food has been manufactured under such conditions that it is unfit for food) or has been prepared, packed, or held under unsanitary conditions such that it may have become contaminated or otherwise may have been rendered injurious to health. GMP conditions can include adhering to regulations governing: disease control; cleanliness and training of personnel; maintenance and sanitary operation of buildings and facilities; provision of adequate sanitary facilities and accommodations; design, construction, maintenance, and cleanliness of equipment and utensils; provision of appropriate quality control procedures to ensure all reasonable precautions are taken in receiving, inspecting, transporting, segregating, preparing, manufacturing, packaging, and storing food products according to adequate sanitation principles to prevent contamination from any source; and storage and transportation of finished food under conditions that will protect food against physical, chemical, or undesirable microbial contamination, as well as against deterioration of the food and the container.

In some embodiments, the oleaginous microbial cells are algal cells of a species of the genus *Chlorella* or *Prototheca*. In one embodiment, the algae is *Chlorella protothecoides*. In another embodiment, the algae is *Prototheca moriformis*. In some cases, the biomass is derived from an algae that is a color mutant with reduced color pigmentation compared to the strain from which it was derived. Mutants with reduced color pigmentation are typically prepared using standard mutagenesis techniques. There are many fee-for-service laboratories that will generate mutants with reduced color pigmentation. In some embodiments, the microbial biomass is prepared by cultivating the microorganism heterotrophically and optionally in the absence of light.

In one embodiment, the microalgal strain is *Chlorella protothecoides* 33-55, deposited on Oct. 13, 2009 at the American Type Culture Collection under deposit designation PTA-10397. In one embodiment, the microalgal strain is *Chlorella protothecoides* 25-32, deposited on Oct. 13, 2009 at the American Type Culture Collection under deposit designation PTA-10396. In some cases, the microalgal strain providing the biomass has been grown and processed under good manufacturing process (GMP) conditions.

In another aspect, the present invention provides methods for preparing recombinant oleaginous microbial biomass suitable for use as a foodstuff. In these methods, the recombinant oleaginous microbes are fermented under heterotrophic conditions and so lack or have a significantly reduced amount of green pigment that characterizes other recombinant microalgal derived foodstuffs. In one embodiment, the recombinant oleaginous microbes lack or have significantly reduced amounts of any pigment. One aspect of the invention provides recombinant microalgae of the genus *Chlorella* and *Prototheckoides*. In some embodiments, the invention is a microalgae of the genus recombinant *Protothecoides*. Another embodiment provides recombinant *Protothecoides moriformis* for use in foods and food ingredients. In one embodiment, the fermentation conditions are manipulated to provide a biomass rich in lipid. In another embodiment, the fermentation conditions are manipulated to provide a biomass rich in protein. In all embodiments, the methods can be carried out cheaply and efficiently at large scale (biomass produced in 4500 L or larger fermentors).

In another aspect, the present invention provides recombinant oleaginous microbial biomass, preferably microalgal biomass, suitable for incorporation into human foodstuffs. In one embodiment, this recombinant microbial biomass is the concentrated biomass resulting directly from the biomass preparation methods of the present invention. In another embodiment, this biomass is in the form of dried flakes resulting from drying, e.g., drum drying, such biomass preparations. In this latter embodiment, an antioxidant can be added to the biomass prior to the drying step to extend the shelf-life of the biomass and any food product containing such biomass.

Yet another aspect of the invention provides methods for further processing the biomass into flakes or a homogenate.

In one embodiment, the dried flakes are rehydrated in deionized water to create a suspension. This suspension is then micronized with a high pressure homogenizer so that the average particle size is less than 20 μm, preferably 10 μm in size, creating a homogenate.

A further aspect of the present invention provides methods for processing the recombinant oleaginous microbial biomass, preferably microalgal biomass, into a food ingredient that is multifunctional in that it provides healthy oils to foods and provides structural benefits to foods such as baked goods. In one embodiment, the processing involves pneumatic drying (e.g., spray drying or flash drying) the biomass preparation to form a powder that contains a large percentage of intact recombinant cells. In another embodiment, the biomass is first micronized to disrupt the cells before pneumatic drying to form a flour that contains only a small percentage (or no) intact cells; in some embodiments a flow or dispersal agent is added prior to the drying step.

In yet another aspect, the present invention is directed to a method of producing an oil or oil-containing recombinant oleaginous microbial biomass suitable for human consumption. In some embodiments, the process involves extracting the lipid (triglyceride) from the biomass to form an oil. In one embodiment, the method comprises providing a microorganism, and culturing the microorganism in the presence of a feedstock that is not derived from a food composition suitable for human consumption, in which the microorganism converts at least some portion of the feedstock into triglyceride oil. In some cases, the triglyceride oil comprises at least 50%, 60%, 70%, 80% or 90% C18:1 lipid.

The present invention further provides foods that incorporate a recombinant microbial powder, recombinant microbial flour, and/or recombinant microbial oil. In one embodiment, the food is a baked good, dressing, sauce, or mayonnaise in which, relative to the same food produced using conventional recipes, all or a portion of the egg or butter has been replaced by a recombinant microbial flour rich in oil. In another embodiment, the food is a powdered egg product containing a recombinant microbial flour rich in oil. In another embodiment, the food is a liquid egg product containing a microbial flour rich in oil. In another embodiment, the food is a liquid milk product containing microbial protein, fiber, and oil. In another embodiment, the food is a meat product in which, relative to previously available meat products, a portion or all (a meat substitute) of the meat has been replaced by a recombinant microbial flour, recombinant microbial powder, or recombinant microbial flake rich in protein.

The invention also provides methods of inducing satiety by providing recombinant microbial foods or microbial food ingredients containing microbial fiber and optionally microbial protein and/or microbial oil.

These and other aspects and embodiments of the invention are described in the accompanying drawing, a brief description of which immediately follows, the detailed description of the invention below, and are exemplified in the examples below. Any or all of the features discussed above and throughout the application can be combined in various embodiments of the present invention.

BRIEF DESCRIPTION OF THE DRAWINGS

FIG. 1 shows a chromatogram of renewable diesel produced from *Prototheca* triglyceride oil.

DETAILED DESCRIPTION OF THE INVENTION

The present invention arises from the discovery that *Prototheca* and certain related microorganisms have unexpectedly advantageous properties for the production of oils, fuels, and other hydrocarbon or lipid compositions economically and in large quantities, as well as from the discovery of methods and reagents for genetically altering these microorganisms to improve these properties. The oils produced by these microorganisms can be used in the transportation fuel, oleochemical, and/or food and cosmetic industries, among other applications. Transesterification of lipids yields long-chain fatty acid esters useful as biodiesel. Other enzymatic and chemical processes can be tailored to yield fatty acids, aldehydes, alcohols, alkanes, and alkenes. In some applications, renewable diesel, jet fuel, or other hydrocarbon compounds are produced. The present invention also provides methods of cultivating microalgae for increased productivity and increased lipid yield, and/or for more cost-effective production of the compositions described herein.

This detailed description of the invention is divided into sections for the convenience of the reader. Section I provides definitions of terms used herein. Section II provides a description of culture conditions useful in the methods of the invention. Section III provides a description of genetic engineering methods and materials. Section IV provides a description of genetic engineering of microorganisms (e.g., *Prototheca*) to enable sucrose utilization. Section V provides a description of genetic engineering of microorganisms (e.g., *Prototheca*) to modify lipid biosynthesis. Section VI describes methods for making fuels and chemicals. Section VII describes methods for preparing recombinant microbial biomass. Section VIII describes methods for processing recombinant microbial biomass into finished food products. Section IX describes methods for combining recombinant microbial biomass or materials derived therefrom within other food ingredients. Section X discloses examples and embodiments of the invention. The detailed description of the invention is followed by examples that illustrate the various aspects and embodiments of the invention.

I. DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

"Active in microalgae" refers to a nucleic acid that is functional in microalgae. For example, a promoter that has been used to drive an antibiotic resistance gene to impart antibiotic resistance to a transgenic microalgae is active in microalgae.

"Acyl carrier protein" or "ACP" is a protein that binds a growing acyl chain during fatty acid synthesis as a thiol ester at the distal thiol of the 4'-phosphopantetheine moiety and comprises a component of the fatty acid synthase complex.

"Acyl-CoA molecule" or "acyl-CoA" is a molecule comprising an acyl moiety covalently attached to coenzyme A through a thiol ester linkage at the distal thiol of the 4'-phosphopantetheine moiety of coenzyme A.

"Area Percent" refers to the area of peaks observed using FAME GC/FID detection methods in which every fatty acid in the sample is converted into a fatty acid methyl ester (FAME) prior to detection. For example, a separate peak is observed for a fatty acid of 14 carbon atoms with no unsaturation (C14:0) compared to any other fatty acid such as C14:1. The peak area for each class of FAME is directly proportional to its percent composition in the mixture and is calculated based on the sum of all peaks present in the sample (i.e. [area under specific peak/total area of all measured peaks]×100). When referring to lipid profiles of oils and cells of the invention, "at least 4% C8-C14" means that at least 4% of the total fatty acids in the cell or in the extracted glycerolipid composition have a chain length that includes 8, 10, 12 or 14 carbon atoms.

"Axenic" is a culture of an organism free from contamination by other living organisms.

"Baked good" means a food item, typically found in a bakery, that is prepared by using an oven. Baked goods include, but are not limited to brownies, cookies, pies, cakes and pastries.

"Bread" means a food item that contains wheat flour, liquid, and a leavening agent. Breads are usually prepared by baking in an oven, although other methods of cooking are also acceptable. The leavening agent can be chemical or organic in nature. Typically, the organic leavening agent is yeast. In the case where the leavening agent is chemical in nature (such as baking powder and/or baking soda), these food products are referred to as "quick breads".

"Biodiesel" is a biologically produced fatty acid alkyl ester suitable for use as a fuel in a diesel engine.

"Biomass" is material produced by growth and/or propagation of cells. Biomass may contain cells and/or intracellular contents as well as extracellular material, includes, but is not limited to, compounds secreted by a cell.

"Bioreactor" is an enclosure or partial enclosure in which cells are cultured, optionally in suspension.

"Catalyst" is an agent, such as a molecule or macromolecular complex, capable of facilitating or promoting a chemical reaction of a reactant to a product without becoming a part of the product. A catalyst increases the rate of a reaction, after which, the catalyst may act on another reactant to form the product. A catalyst generally lowers the overall activation energy required for the reaction such that it proceeds more quickly or at a lower temperature. Thus, a reaction equilibrium may be more quickly attained. Examples of catalysts include enzymes, which are biological catalysts; heat, which is a non-biological catalyst; and metals used in fossil oil refining processes.

"Cellulosic material" is the product of digestion of cellulose, including glucose and xylose, and optionally additional compounds such as disaccharides, oligosaccharides, lignin, furfurals and other compounds. Nonlimiting examples of sources of cellulosic material include sugar cane bagasses, sugar beet pulp, corn stover, wood chips, sawdust and switchgrass.

"Co-culture", and variants thereof such as "co-cultivate" and "co-ferment", refer to the presence of two or more types of cells in the same bioreactor. The two or more types of cells may both be microorganisms, such as microalgae, or may be a microalgal cell cultured with a different cell type. The culture conditions may be those that foster growth and/or propagation of the two or more cell types or those that facilitate growth and/or proliferation of one, or a subset, of the two or more cells while maintaining cellular growth for the remainder.

"Cofactor" is any molecule, other than the substrate, required for an enzyme to carry out its enzymatic activity.

"Complementary DNA" or "cDNA" is a DNA copy of mRNA, usually obtained by reverse transcription of messenger RNA (mRNA) or amplification (e.g., via polymerase chain reaction ("PCR")).

"Conventional food product" means a composition intended for consumption, e.g., by a human, that lacks algal biomass or other algal components and includes ingredients ordinarily associated with the food product, particularly a vegetable oil, animal fat, and/or egg(s), together with other edible ingredients. Conventional food products include food products sold in shops and restaurants and those made in the home. Conventional food products are often made by following conventional recipes that specify inclusion of an oil or fat from a non-algal source and/or egg(s) together with other edible ingredient(s).

"Cooked product" means a food that has been heated, e.g., in an oven, for a period of time.

"Creamy salad dressing" means a salad dressing that is a stable dispersion with high viscosity and a slow pour-rate. Generally, creamy salad dressings are opaque.

"Cultivated", and variants thereof such as "cultured" and "fermented", refer to the intentional fostering of growth (increases in cell size, cellular contents, and/or cellular activity) and/or propagation (increases in cell numbers via mitosis) of one or more cells by use of selected and/or controlled conditions. The combination of both growth and propagation may be termed proliferation. Examples of selected and/or controlled conditions include the use of a defined medium (with known characteristics such as pH, ionic strength, and carbon source), specified temperature, oxygen tension, carbon dioxide levels, and growth in a bioreactor. Cultivate does not refer to the growth or propagation of microorganisms in nature or otherwise without human intervention; for example, natural growth of an organism that ultimately becomes fossilized to produce geological crude oil is not cultivation.

"Cytolysis" is the lysis of cells in a hypotonic environment. Cytolysis is caused by excessive osmosis, or movement of water, towards the inside of a cell (hyperhydration). The cell cannot withstand the osmotic pressure of the water inside, and so it explodes.

"Delipidated meal" and "delipidated microbial biomass" is microbial biomass after oil (including lipids) has been extracted or isolated from it, either through the use of mechanical (i.e., exerted by an expeller press) or solvent extraction or both. Delipidated meal has a reduced amount of oil/lipids as compared to before the extraction or isolation of oil/lipids from the microbial biomass but does contain some residual oil/lipid.

"Dietary fiber" means non-starch carbohydrates found in plants and other organisms containing cell walls, including microalgae. Dietary fiber can be soluble (dissolved in water) or insoluble (not able to be dissolved in water). Soluble and insoluble fiber makes up total dietary fiber.

"Digestible crude protein" is the portion of protein that is available or can be converted into free nitrogen (amino acids) after digesting with gastric enzymes. In vitro measurement of digestible crude protein is accomplished by using gastric enzymes such as pepsin and digesting a sample and measuring the free amino acid after digestion. In vivo measurement of digestible crude protein is accomplished by measuring the protein levels in a feed/food sample and feeding the sample to an animal and measuring the amount of nitrogen collected in the animal's feces.

"Dry weight" and "dry cell weight" mean weight determined in the relative absence of water. For example, reference to recombinant microalgal biomass as comprising a specified percentage of a particular component by dry weight means that the percentage is calculated based on the weight of the biomass after substantially all water has been removed.

"Edible ingredient" means any substance or composition which is fit to be eaten. "Edible ingredients" include, without limitation, grains, fruits, vegetables, proteins, herbs, spices, carbohydrates, and fats.

"Expression vector" or "expression construct" or "plasmid" or "recombinant DNA construct" refer to a nucleic acid that has been generated via human intervention, including by recombinant means or direct chemical synthesis, with a series of specified nucleic acid elements that permit transcription and/or translation of a particular nucleic acid in a host cell. The expression vector can be part of a plasmid, virus, or nucleic acid fragment. Typically, the expression vector includes a nucleic acid to be transcribed operably linked to a promoter.

"Exogenous gene" is a nucleic acid that codes for the expression of an RNA and/or protein that has been introduced ("transformed") into a cell. A transformed cell may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome or as an episomal molecule.

"Exogenously provided" refers to a molecule provided to the culture media of a cell culture.

"Expeller pressing" is a mechanical method for extracting oil from raw materials such as soybeans and rapeseed. An expeller press is a screw type machine, which presses material through a caged barrel-like cavity. Raw materials enter one side of the press and spent cake exits the other side while oil seeps out between the bars in the cage and is collected. The machine uses friction and continuous pressure from the screw drives to move and compress the raw material. The oil seeps through small openings that do not allow solids to pass through. As the raw material is pressed, friction typically causes it to heat up.

"Fat" means a lipid or mixture of lipids that is generally solid at ordinary room temperatures and pressures. "Fat" includes, without limitation, lard and butter.

"Fatty acyl-ACP thioesterase" is an enzyme that catalyzes the cleavage of a fatty acid from an acyl carrier protein (ACP) during lipid synthesis.

"Fatty acyl-CoA/aldehyde reductase" is an enzyme that catalyzes the reduction of an acyl-CoA molecule to a primary alcohol.

"Fatty acyl-CoA reductase" is an enzyme that catalyzes the reduction of an acyl-CoA molecule to an aldehyde.

"Fatty aldehyde decarbonylase" is an enzyme that catalyzes the conversion of a fatty aldehyde to an alkane.

"Fatty aldehyde reductase" is an enzyme that catalyzes the reduction of an aldehyde to a primary alcohol.

"Fiber" means non-starch carbohydrates in the form of polysaccharide. Fiber can be soluble in water or insoluble in water. Many microalgae produce both soluble and insoluble fiber, typically residing in the cell wall.

"Finished food product" and "finished food ingredient" mean a food composition that is ready for packaging, use, or consumption. For example, a "finished food product" may have been cooked or the ingredients comprising the "finished food product" may have been mixed or otherwise integrated with one another. A "finished food ingredient" is typically used in combination with other ingredients to form a food product.

"Fixed carbon source" is a molecule(s) containing carbon, typically an organic molecule, that is present at ambient temperature and pressure in solid or liquid form in a culture media that can be utilized by a microorganism cultured therein.

"Food", "food composition", "food product" and "foodstuff" mean any composition intended to be or expected to be ingested by humans as a source of nutrition and/or calories. Food compositions are composed primarily of carbohydrates, fats, water and/or proteins and make up substantially all of a person's daily caloric intake. A "food composition" can have a weight minimum that is at least ten times the weight of a typical tablet or capsule (typical tablet/capsule weight ranges are from less than or equal to 100 mg up to 1500 mg). A "food composition" is not encapsulated or in tablet form.

"Good manufacturing practice" and "GMP" mean those conditions established by regulations set forth at 21 C.F.R. 110 (for human food) and 111 (for dietary supplements), or comparable regulatory schemes established in locales outside the United States. The U.S. regulations are promulgated by the U.S. Food and Drug Administration under the authority of the Federal Food, Drug, and Cosmetic Act to regulate manufacturers, processors, and packagers of food products and dietary supplements for human consumption.

"Homogenate" means biomass that has been physically disrupted. Homogenization is a fluid mechanical process that involves the subdivision of particles into smaller and more uniform sizes, forming a dispersion that may be subjected to further processing. Homogenization is used in treatment of several foods and dairy products to improve stability, shelf-life, digestion, and taste.

"Hydrocarbon" is (a) a molecule containing only hydrogen and carbon atoms wherein the carbon atoms are covalently linked to form a linear, branched, cyclic, or partially cyclic backbone to which the hydrogen atoms are attached. The molecular structure of hydrocarbon compounds varies from the simplest, in the form of methane ($CH_4$), which is a constituent of natural gas, to the very heavy and very complex, such as some molecules such as asphaltenes found in crude oil, petroleum, and bitumens. Hydrocarbons may be in gaseous, liquid, or solid form, or any combination of these forms, and may have one or more double or triple bonds between adjacent carbon atoms in the backbone. Accordingly, the term includes linear, branched, cyclic, or partially cyclic alkanes, alkenes, lipids, and paraffin. Examples include propane, butane, pentane, hexane, octane, and squalene.

"Hydrogen:carbon ratio" is the ratio of hydrogen atoms to carbon atoms in a molecule on an atom-to-atom basis. The ratio may be used to refer to the number of carbon and hydrogen atoms in a hydrocarbon molecule. For example, the hydrocarbon with the highest ratio is methane $CH_4$ (4:1).

"Hydrophobic fraction" is the portion, or fraction, of a material that is more soluble in a hydrophobic phase in comparison to an aqueous phase. A hydrophobic fraction is substantially insoluble in water and usually non-polar.

"Increase lipid yield" refers to an increase in the productivity of a microbial culture by, for example, increasing dry weight of cells per liter of culture, increasing the percentage of cells that constitute lipid, or increasing the overall amount of lipid per liter of culture volume per unit time.

"Inducible promoter" is a promoter that mediates transcription of an operably linked gene in response to a particular stimulus. Examples of such promoters may be promoter sequences that are induced in conditions of changing pH or nitrogen levels.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"In situ" means "in place" or "in its original position".

"Limiting concentration of a nutrient" is a concentration of a compound in a culture that limits the propagation of a cultured organism. A "non-limiting concentration of a nutrient" is a concentration that supports maximal propagation during a given culture period. Thus, the number of cells produced during a given culture period is lower in the presence of a limiting concentration of a nutrient than when the nutrient is non-limiting. A nutrient is said to be "in excess" in a culture, when the nutrient is present at a concentration greater than that which supports maximal propagation.

"Lipase" is a water-soluble enzyme that catalyzes the hydrolysis of ester bonds in water-insoluble, lipid substrates. Lipases catalyze the hydrolysis of lipids into glycerols and fatty acids.

"Lipid modification enzyme" refers to an enzyme that alters the covalent structure of a lipid. Examples of lipid modification enzymes include a lipase, a fatty acyl-ACP thioesterase, a fatty acyl-CoA/aldehyde reductase, a fatty acyl-CoA reductase, a fatty aldehyde reductase, a desaturase, including a stearoyl acyl carrier protein desaturase (SAD) and a fatty acyl destaurase (FAD), and a fatty aldehyde decarbonylase.

"Lipid pathway enzyme" is any enzyme that plays a role in lipid metabolism, i.e., either lipid synthesis, modification, or degradation, and any proteins that chemically modify lipids, as well as carrier proteins.

"Lipids" are a class of molecules that are soluble in nonpolar solvents (such as ether and chloroform) and are relatively or completely insoluble in water. Lipid molecules have these properties, because they consist largely of long hydrocarbon tails which are hydrophobic in nature. Examples of lipids include fatty acids (saturated and unsaturated); glycerides or glycerolipids (such as monoglycerides, diglycerides, triglycerides or neutral fats, and phosphoglycerides or glycerophospholipids); nonglycerides (sphingolipids, sterol lipids including cholesterol and steroid hormones, prenol lipids including terpenoids, fatty alcohols, waxes, and polyketides); and complex lipid derivatives (sugar-linked lipids, or glycolipids, and protein-linked lipids). "Fats" are a subgroup of lipids called "triacylglycerides."

"Lysate" is a solution containing the contents of lysed cells.

"Lysis" is the breakage of the plasma membrane and optionally the cell wall of a biological organism sufficient to release at least some intracellular content, often by mechanical, viral or osmotic mechanisms that compromise its integrity.

"Lysing" is disrupting the cellular membrane and optionally the cell wall of a biological organism or cell sufficient to release at least some intracellular content.

"Microalgae" is a eukaryotic microbial organism that contains a chloroplast or plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, *Volvox*, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca*.

"Microbial biomass," "Microalgal biomass," "algal biomass," and "biomass" mean a material produced by growth and/or propagation of microbial or microalgal cells. Biomass may contain cells and/or intracellular contents as well as extracellular material. Extracellular material includes, but is not limited to, compounds secreted by a cell.

"Micronized" means biomass that has been homogenized under high pressure (or an equivalent process) so that at least 50% of the particle size is no more 10 μm in their longest dimension. Typically, at least 50% to 90% or more of such particles are less than 5 μm in their longest dimension. In any case, the average particle size of micronized biomass is smaller than the intact recombinant microalgal cell.

"Microorganism" and "microbe" are microscopic unicellular organisms.

"Naturally co-expressed" with reference to two proteins or genes means that the proteins or their genes are co-expressed naturally in a tissue or organism from which they are derived, e.g., because the genes encoding the two proteins are under the control of a common regulatory sequence or because they are expressed in response to the same stimulus.

"Oil" means any triacylglyceride, produced by organisms, including microalgae, other plants, and/or animals. "Oil," as distinguished from "fat", refers, unless otherwise indicated, to lipids that are generally liquid at ordinary room temperatures and pressures. For example, "oil" includes vegetable or seed oils derived from plants, including without limitation, an oil derived from soy, rapeseed, canola, palm, palm kernel, coconut, corn, olive, sunflower, cotton seed, *cuphea*, peanut, *camelina sativa*, mustard seed, cashew nut, oats, lupine, kenaf, *calendula*, hemp, coffee, linseed, hazelnut, *euphorbia*, pumpkin seed, coriander, *camellia*, sesame, safflower, rice, tung oil tree, cocoa, copra, pium poppy, castor beans, pecan, jojoba, *jatropha, macadamia*, Brazil nuts, and avocado, as well as combinations thereof.

"Osmotic shock" is the rupture of cells in a solution following a sudden reduction in osmotic pressure. Osmotic shock is sometimes induced to release cellular components of such cells into a solution.

"Pasteurization" means a process of heating which is intended to slow microbial growth in food products. Typically pasteurization is performed at a high temperature (but below boiling) for a short amount of time. As described herein, pasteurization can not only reduce the number of undesired microbes in food products, but can also inactivate certain enzymes present in the food product.

"Polysaccharide-degrading enzyme" is any enzyme capable of catalyzing the hydrolysis, or saccharification, of any polysaccharide. For example, cellulases catalyze the hydrolysis of cellulose.

"Polysaccharides" or "glycans" are carbohydrates made up of monosaccharides joined together by glycosidic linkages. Cellulose is a polysaccharide that makes up certain plant cell walls. Cellulose can be depolymerized by enzymes to yield monosaccharides such as xylose and glucose, as well as larger disaccharides and oligosaccharides.

"Port" means an opening in a bioreactor that allows influx or efflux of materials such as gases, liquids, and cells; a port is usually connected to tubing.

"Predominantly encapsulated" means that more than 50% and typically more than 75% to 90% of a referenced component, e.g., algal oil, is sequestered in a referenced container, which can include, e.g., a recombinant microalgal cell.

"Predominantly intact cells" and "predominantly intact biomass" mean a population of cells that comprise more than 50, and often more than 75, 90, and 98% intact cells. "Intact", in this context, means that the physical continuity of the cellular membrane and/or cell wall enclosing the intracellular components of the cell has not been disrupted in any manner that would release the intracellular components of the cell to an extent that exceeds the permeability of the cellular membrane in culture.

"Predominantly lysed" means a population of cells in which more than 50%, and typically more than 75 to 90%, of the cells have been disrupted such that the intracellular components of the cell are no longer completely enclosed within the cell membrane.

"Proliferation" means a combination of both growth and propagation.

"Promoter" is a nucleic acid control sequence that directs transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

"Propagation" means an increase in cell number via mitosis or other cell division.

"Proximate analysis" means analysis of foodstuffs for fat, nitrogen/protein, crude fiber (cellulose and lignin as main components), moisture and ash. Soluble carbohydrate (total dietary fiber and free sugars) can be calculated by subtracting the total of the known values of the proximate analysis from 100 (carbohydrate by difference).

"Recombinant" is a cell, nucleic acid, protein or vector, that has been modified due to the introduction of an exogenous nucleic acid or the alteration of a native nucleic acid. Thus, e.g., recombinant cells express genes that are not found within the native (non-recombinant) form of the cell or express native genes differently than those genes are expressed by a non-recombinant cell. A "recombinant nucleic acid" is a nucleic acid originally formed in vitro, in general, by the manipulation of nucleic acid, e.g., using polymerases and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

"Recombinant microbial oil," "Recombinant microalgal oil" and "algal oil" mean any of the lipid components produced by recombinant microbial or microalgal cells or algal cells, respectively, including triacylglycerols.

"Renewable diesel" is a mixture of alkanes (such as C10:0, C12:0, C14:0, C16:0 and C18:0) produced through hydrogenation and deoxygenation of lipids.

"Saccharification" is a process of converting biomass, usually cellulosic or lignocellulosic biomass, into monomeric sugars, such as glucose and xylose. "Saccharified" or "depolymerized" cellulosic material or biomass refers to cellulosic material or biomass that has been converted into monomeric sugars through saccharification.

The term "similar," when used in the context of a comparison to a naturally occurring oil, without further qualification, means that the oil being compared to the naturally occurring oil contains about +/−15%, or +/−10% of the top two triglycerides of the naturally occurring oil. For example, Shea butter (the oil of *B. Parkii*) contains 41.2-56.8% C18:0 and 34.0-46.9% C18:1 as the two most common triglyceride components (see Table 5). A "similar" oil that is within +/−10% would contain from about 37% to about 62% C18:0 and from 31% to about 52% C18:1 as the two most common triglyceride components. When used in this context, the term "similar" includes +/−9%, +/−8%, +/−7%, +/−6%, +/−5%, +/−4%, +/−3%, +/−2%, or +/−1%, and can further represent a comparison to the top three or top four triglycerides of the naturally occurring oil, or two out of the top three triglycerides, or three out of the top four triglycerides.

"Sonication" is a process of disrupting biological materials, such as a cell, by use of sound wave energy.

"Species of furfural" is 2-furancarboxaldehyde or a derivative that retains the same basic structural characteristics.

"Stover" is the dried stalks and leaves of a crop remaining after a grain has been harvested.

"Sucrose utilization gene" is a gene that, when expressed, aids the ability of a cell to utilize sucrose as an energy source. Proteins encoded by a sucrose utilization gene are referred to herein as "sucrose utilization enzymes" and include sucrose transporters, sucrose invertases, and hexokinases such as glucokinases and fructokinases.

"Suitable for human consumption" means a composition can be consumed by humans as dietary intake without ill health effects and can provide significant caloric intake due to uptake of digested material in the gastrointestinal tract.

"Uncooked product" means a composition that has not been subjected to heating but may include one or more components previously subjected to heating.

"V/V" or "v/v", in reference to proportions by volume, means the ratio of the volume of one substance in a composition to the volume of the composition. For example, reference to a composition that comprises 5% v/v recombinant microalgal oil means that 5% of the composition's volume is composed of recombinant microalgal oil (e.g., such a composition having a volume of 100 mm$^3$ would contain 5 mm$^3$ of recombinant microalgal oil), and the remainder of the volume of the composition (e.g., 95 mm$^3$ in the example) is composed of other ingredients.

"W/W" or "w/w", in reference to proportions by weight, means the ratio of the weight of one substance in a composition to the weight of the composition. For example, reference to a composition that comprises 5% w/w recombinant microalgal biomass means that 5% of the composition's weight is composed of recombinant microalgal biomass (e.g., such a composition having a weight of 100 mg would contain 5 mg of recombinant microalgal biomass) and the remainder of the weight of the composition (e.g., 95 mg in the example) is composed of other ingredients.

II. CULTIVATION

The present invention generally relates to cultivation of microorganisms (e.g., microalgae, oleaginous yeast, fungi, and bacteria), particularly recombinant microalgal strains, including *Prototheca* strains, for the production of lipid. For the convenience of the reader, this section is subdivided into subsections. Subsection 1 describes *Prototheca* species and strains and how to identify new *Prototheca* species and strains and related microalgae by genomic DNA comparison, as well as other microorganisms. Subsection 2 describes bioreactors useful for cultivation. Subsection 3 describes media for cultivation. Subsection 4 describes oil production in accordance with illustrative cultivation methods of the invention. These descriptions are also more generally applicable to other microorganisms.

1. *Prototheca* Species and Strains and Other Microorganisms

*Prototheca* is a remarkable microorganism for use in the production of lipid, because it can produce high levels of lipid, particularly lipid suitable for fuel production. The lipid produced by *Prototheca* has hydrocarbon chains of shorter chain length and a higher degree of saturation than that produced by other microalgae. Moreover, *Prototheca* lipid is generally free of pigment (low to undetectable levels of chlorophyll and certain carotenoids) and in any event contains much less pigment than lipid from other microalgae. Moreover, recombinant *Prototheca* cells provided by the invention can be used to produce lipid in greater yield and efficiency, and with reduced cost, relative to the production of lipid from other microorganisms. Illustrative *Prototheca* strains for use in the methods of the invention include In addition, this microalgae grows heterotrophically and can be genetically engineered as *Prototheca wickerhamii, Prototheca stagnora* (including UTEX 327), *Prototheca portoricensis, Prototheca moriformis* (including UTEX strains 1441, 1435), and *Prototheca zopfii*. Species of the genus *Prototheca* are obligate heterotrophs.

Species of *Prototheca* for use in the invention can be identified by amplification of certain target regions of the genome. For example, identification of a specific *Prototheca* species or strain can be achieved through amplification and sequencing of nuclear and/or chloroplast DNA using primers and methodology using any region of the genome, for example using the methods described in Wu et al., *Bot. Bull. Acad. Sin.* (2001) 42:115-121 Identification of *Chlorella* spp. isolates using ribosomal DNA sequences. Well established methods of phylogenetic analysis, such as amplification and sequencing of ribosomal internal transcribed spacer (ITS1 and ITS2 rDNA), 23S rRNA, 18S rRNA, and other conserved genomic regions can be used by those skilled in the art to identify species of not only *Prototheca*, but other hydrocarbon and lipid producing organisms with similar lipid profiles and production capability. For examples of methods of identification and classification of algae also see for example *Genetics*, 2005 August; 170(4):1601-10 and *RNA*, 2005 April; 11(4):361-4.

Thus, genomic DNA comparison can be used to identify suitable species of microalgae to be used in the present invention. Regions of conserved genomic DNA, such as but not limited to DNA encoding for 23S rRNA, can be amplified from microalgal species and compared to consensus sequences in order to screen for microalgal species that are taxonomically related to the preferred microalgae used in the present invention. Examples of such DNA sequence comparison for species within the *Prototheca* genus are shown below. Genomic DNA comparison can also be useful to identify microalgal species that have been misidentified in a strain collection. Often a strain collection will identify species of microalgae based on phenotypic and morphological characteristics. The use of these characteristics may lead to miscategorization of the species or the genus of a microalgae. The use of genomic DNA comparison can be a better method of categorizing microalgae species based on their phylogenetic relationship.

Microalgae for use in the present invention typically have genomic DNA sequences encoding for 23S rRNA that have at least 99%, least 95%, at least 90%, or at least 85% nucleotide identity to at least one of the sequences listed in SEQ ID NOs: 11-19.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (at the web address www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Other considerations affecting the selection of microorganisms for use in the invention include, in addition to production of suitable lipids or hydrocarbons for production of oils, fuels, and oleochemicals: (1) high lipid content as a percentage of cell weight; (2) ease of growth; (3) ease of genetic engineering; and (4) ease of biomass processing. In particular embodiments, the wild-type or genetically engineered microorganism yields cells that are at least 40%, at least 45%, at least 50%, at least 55%, at least 60%, at least 65%, or at least 70% or more lipid. Preferred organisms grow heterotrophically (on sugars in the absence of light).

Examples of algae that can be used to practice the present invention include, but are not limited to the following algae listed in Table 1.

TABLE 1

Examples of algae.

*Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora* sp., *Anabaena, Ankistrodesmus, Ankistrodesmus falcatus, Boekelovia hooglandii, Borodinella* sp., *Botryococcus braunii, Botryococcus sudeticus, Carteria, Chaetoceros gracilis, Chaetoceros muelleri, Chaetoceros muelleri subsalsum, Chaetoceros* sp. , *Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora* (strain SAG 37.88), *Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella parva, Chlorella photophila, Chlorella pringsheimii, Chlorella protothecoides* (including any of UTEX strains 1806, 411, 264, 256, 255, 250, 249, 31, 29, 25, and CCAP strains 211/17 and 211/8d), *Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris, Chlorella vulgaris f. tertia, Chlorella vulgaris* var. *autotrophica, Chlorella vulgaris* var. *viridis, Chlorella vulgaris* var. *vulgaris, Chlorella vulgaris* var. *vulgaris f. tertia, Chlorella vulgaris* var. *vulgaris f. viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena, Franceia* sp., *Fragilaria crotonensis, Fragilaria* sp., *Gleocapsa* sp., *Gloeothamnion* sp., *Hymenomonas* sp., *Isochrysis aff. galbana, Isochrysis galbana, Lepocinclis, Micractinium, Micractinium* (UTEX LB 2614), *Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Pascheria acidophila, Pavlova* sp., *Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pyramimonas* sp., *Pyrobotrys, Sarcinoid chrysophyte, Scenedesmus armatus, Spirogyra, Spirulina platensis, Stichococcus* sp., *Synechococcus* sp., *Tetraedron, Tetraselmis* sp., *Tetraselmis suecica, Thalassiosira weissflogii*, and *Viridiella fridericiana*

Examples of oleaginous yeast that can be used to practice the present invention include, but are not limited to the following oleaginous yeast listed in Table 26.

TABLE 26

Examples of oleaginous yeast.

*Cryptococcus curvatus, Cryptococcus terricolus, Candida* sp., *Lipomyces starkeyi, Lipomyces lipofer, Endomycopsis vernalis, Rhodotorula glutinis, Rhodotorula gracilis,* and *Yarrowia lipolytica*

Examples of other fungi that can be used to practice the present invention include, but are not limited to the following fungi listed in Table 27.

TABLE 27

Examples of fungi.

*Mortierella, Mortierrla vinacea, Mortierella alpine, Pythium debaryanum, Mucor circinelloides, Aspergillus ochraceus, Aspergillus terreus, Pennicillium iilacinum, Hensenulo, Chaetomium, Cladosporium, Malbranchea, Rhizopus,* and *Pythium*

In some embodiments of the present invention, the microorganism is a bacterium. Examples of expression of exogenous genes in bacteria, such as *E. coli*, are well known; see for example *Molecular Cloning: A Laboratory Manual*, Sambrook et al. (3d edition, 2001, Cold Spring Harbor Press).

2. Bioreactor

Microorganisms are cultured both for purposes of conducting genetic manipulations and for production of hydrocarbons (e.g., lipids, fatty acids, aldehydes, alcohols, and alkanes). The former type of culture is conducted on a small scale and initially, at least, under conditions in which the starting microorganism can grow. Culture for purposes of hydrocarbon production is usually conducted on a large scale (e.g., 10,000 L, 40,000 L, 100,000 L or larger bioreactors) in a bioreactor. Microalgae, including *Prototheca* species are typically cultured in the methods of the invention in liquid media within a bioreactor. Typically, the bioreactor does not allow light to enter.

The bioreactor or fermentor is used to culture oleaginous microbial cells, preferably microalgal cells through the various phases of their physiological cycle. Bioreactors offer many advantages for use in heterotrophic growth and propagation methods. To produce biomass for use in food, microalgae are preferably fermented in large quantities in liquid, such as in suspension cultures as an example. Bioreactors such as steel fermentors can accommodate very large culture volumes (40,000 liter and greater capacity bioreactors are used in various embodiments of the invention). Bioreactors also typically allow for the control of culture conditions such as temperature, pH, oxygen tension, and carbon dioxide levels. For example, bioreactors are typically configurable, for example, using ports attached to tubing, to allow gaseous components, like oxygen or nitrogen, to be bubbled through a liquid culture. Other culture parameters, such as the pH of the culture media, the identity and concentration of trace elements, and other media constituents can also be more readily manipulated using a bioreactor.

Bioreactors can be configured to flow culture media though the bioreactor throughout the time period during which the microalgae reproduce and increase in number. In some embodiments, for example, media can be infused into the bioreactor after inoculation but before the cells reach a desired density. In other instances, a bioreactor is filled with culture media at the beginning of a culture, and no more culture media is infused after the culture is inoculated. In other words, the microalgal biomass is cultured in an aqueous medium for a period of time during which the microalgae reproduce and increase in number; however, quantities of aqueous culture medium are not flowed through the bioreactor throughout the time period. Thus in some embodiments, aqueous culture medium is not flowed through the bioreactor after inoculation.

Bioreactors equipped with devices such as spinning blades and impellers, rocking mechanisms, stir bars, means for pressurized gas infusion can be used to subject microalgal cultures to mixing. Mixing may be continuous or intermittent. For example, in some embodiments, a turbulent flow regime of gas entry and media entry is not maintained for reproduction of microalgae until a desired increase in number of said microalgae has been achieved.

Bioreactor ports can be used to introduce, or extract, gases, solids, semisolids, and liquids, into the bioreactor chamber containing the microalgae. While many bioreactors have more than one port (for example, one for media entry, and another for sampling), it is not necessary that only one substance enter or leave a port. For example, a port can be used to flow culture media into the bioreactor and later used for sampling, gas entry, gas exit, or other purposes. Preferably, a sampling port can be used repeatedly without altering compromising the axenic nature of the culture. A sampling port can be configured with a valve or other device that allows the flow of sample to be stopped and started or to provide a means of continuous sampling. Bioreactors typically have at least one port that allows inoculation of a culture, and such a port can also be used for other purposes such as media or gas entry.

Bioreactors ports allow the gas content of the culture of microalgae to be manipulated. To illustrate, part of the volume of a bioreactor can be gas rather than liquid, and the gas inlets of the bioreactor to allow pumping of gases into the bioreactor. Gases that can be beneficially pumped into a bioreactor include air, air/$CO_2$ mixtures, noble gases, such as argon, and other gases. Bioreactors are typically equipped to enable the user to control the rate of entry of a gas into the bioreactor. As noted above, increasing gas flow into a bioreactor can be used to increase mixing of the culture.

Increased gas flow affects the turbidity of the culture as well. Turbulence can be achieved by placing a gas entry port below the level of the aqueous culture media so that gas entering the bioreactor bubbles to the surface of the culture. One or more gas exit ports allow gas to escape, thereby preventing pressure buildup in the bioreactor. Preferably a gas exit port leads to a "one-way" valve that prevents contaminating microorganisms from entering the bioreactor.

3. Media

Microalgal culture media typically contains components such as a fixed nitrogen source, a fixed carbon source, trace elements, optionally a buffer for pH maintenance, and phosphate (typically provided as a phosphate salt). Other components can include salts such as sodium chloride, particularly for seawater microalgae. Nitrogen sources include organic and inorganic nitrogen sources, including, for example, without limitation, molecular nitrogen, nitrate, nitrate salts, ammonia (pure or in salt form, such as, $(NH_4)_2SO_4$ and $NH_4OH$), protein, soybean meal, cornsteep liquor, and yeast extract. Examples of trace elements include zinc, boron, cobalt, copper, manganese, and molybdenum in, for example, the respective forms of $ZnCl_2$, $H_3BO_3$, $CoCl_2.6H_2O$, $CuCl_2.2H_2O$, $MnCl_2. 4H_2O$ and $(NH_4)_6Mo_7O_{24}. 4H_2O$.

Microorganisms useful in accordance with the methods of the present invention are found in various locations and environments throughout the world. As a consequence of their isolation from other species and their resulting evolutionary divergence, the particular growth medium for optimal growth and generation of lipid and/or hydrocarbon constituents can be difficult to predict. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, and instructions for the preparation of particular media that is suitable for a wide variety of strains of microorganisms can be found, for example, online at www.utex.org, a site maintained by the University of Texas at Austin, 1 University Station A6700, Austin, Tex., 78712-0183, for its culture collection of algae (UTEX). For example, various fresh water and salt water media include those described in PCT Pub. No. 2008/151149, incorporated herein by reference.

In a particular example, Proteose Medium is suitable for axenic cultures, and a 1 L volume of the medium (pH ~6.8) can be prepared by addition of 1 g of proteose peptone to 1 liter of Bristol Medium. Bristol medium comprises 2.94 mM $NaNO_3$, 0.17 mM $CaCl_2.2H_2O$, 0.3 mM $MgSO_4.7H_2O$, 0.43 mM, 1.29 mM $KH_2PO_4$, and 1.43 mM NaCl in an aqueous solution. For 1.5% agar medium, 15 g of agar can be added to 1 L of the solution. The solution is covered and autoclaved, and then stored at a refrigerated temperature prior to use. Another example is the *Prototheca* isolation medium (PIM), which comprises 10 g/L potassium hydrogen phthalate (KHP), 0.9 g/L sodium hydroxide, 0.1 g/L magnesium sulfate, 0.2 g/L potassium hydrogen phosphate, 0.3 g/L ammonium chloride, 10 g/L glucose 0.001 g/L thiamine hydrochloride, 20 g/L agar, 0.25 g/L 5-fluorocytosine, at a pH in the range of 5.0 to 5.2 (see Pore, 1973, App. Microbiology, 26: 648-649). Other suitable media for use with the methods of the invention can be readily identified by consulting the URL identified above, or by consulting other organizations that maintain cultures of microorganisms, such as SAG, CCAP, or CCALA. SAG refers to the Culture Collection of Algae at the University of Göttingen (Göttingen, Germany), CCAP refers to the culture collection of algae and protozoa managed by the Scottish Association for Marine Science (Scotland, United Kingdom), and CCALA refers to the culture collection of algal laboratory at the Institute of Botany (Třeboň, Czech Republic). Additionally, U.S. Pat. No. 5,900,370 describes media formulations and conditions suitable for heterotrophic fermentation of *Prototheca* species.

For oil production, selection of a fixed carbon source is important, as the cost of the fixed carbon source must be sufficiently low to make oil production economical. Thus, while suitable carbon sources include, for example, acetate, floridoside, fructose, galactose, glucuronic acid, glucose, glycerol, lactose, mannose, N-acetylglucosamine, rhamnose, sucrose, and/or xylose, selection of feedstocks containing those compounds is an important aspect of the methods of the invention. Suitable feedstocks useful in accordance with the methods of the invention include, for example, black liquor, corn starch, depolymerized cellulosic material, milk whey, molasses, potato, sorghum, sucrose, sugar beet, sugar cane, rice, and wheat. Carbon sources can also be provided as a mixture, such as a mixture of sucrose and depolymerized sugar beet pulp. The one or more carbon source(s) can be supplied at a concentration of at least about 50 µM, at least about 100 µM, at least about 500 µM, at least about 5 mM, at least about 50 mM, and at least about 500 mM, of one or more exogenously provided fixed carbon source(s). Carbon sources of particular interest for purposes of the present invention include cellulose (in a depolymerized form), glycerol, sucrose, and sorghum, each of which is discussed in more detail below.

In accordance with the present invention, microorganisms can be cultured using depolymerized cellulosic biomass as a feedstock. Cellulosic biomass (e.g., stover, such as corn stover) is inexpensive and readily available; however, attempts to use this material as a feedstock for yeast have failed. In particular, such feedstocks have been found to be inhibitory to yeast growth, and yeast cannot use the 5-carbon sugars produced from cellulosic materials (e.g., xylose from hemicellulose). By contrast, microalgae can grow on processed cellulosic material. Cellulosic materials generally include about 40-60% cellulose; about 20-40% hemicellulose; and 10-30% lignin.

Suitable cellulosic materials include residues from herbaceous and woody energy crops, as well as agricultural crops, i.e., the plant parts, primarily stalks and leaves, not removed from the fields with the primary food or fiber product. Examples include agricultural wastes such as sugarcane bagasse, rice hulls, corn fiber (including stalks, leaves, husks, and cobs), wheat straw, rice straw, sugar beet pulp, citrus pulp, citrus peels; forestry wastes such as hardwood and softwood thinnings, and hardwood and softwood residues from timber operations; wood wastes such as saw mill wastes (wood chips, sawdust) and pulp mill waste; urban wastes such as paper fractions of municipal solid waste, urban wood waste and urban green waste such as municipal grass clippings; and wood construction waste. Additional cellulosics include dedicated cellulosic crops such as switchgrass, hybrid poplar wood, and *miscanthus*, fiber cane, and fiber sorghum. Five-carbon sugars that are produced from such materials include xylose.

Cellulosic materials are treated to increase the efficiency with which the microbe can utilize the sugar(s) contained within the materials. The invention provides novel methods for the treatment of cellulosic materials after acid explosion so that the materials are suitable for use in a heterotrophic culture of microbes (e.g., microalgae and oleaginous yeast). As discussed above, lignocellulosic biomass is comprised of various fractions, including cellulose, a crystalline polymer of beta 1,4 linked glucose (a six-carbon sugar), hemicellulose, a more loosely associated polymer predominantly comprised of xylose (a five-carbon sugar) and to a lesser extent mannose, galactose, arabinose, lignin, a complex aromatic polymer comprised of sinapyl alcohol and its derivatives, and pectins, which are linear chains of an alpha 1,4 linked polygalacturonic acid. Because of the polymeric structure of cellulose and hemicellulose, the sugars (e.g., monomeric glucose and xylose) in them are not in a form that can be efficiently used (metabolized) by many microbes. For such microbes, further processing of the cellulosic biomass to generate the monomeric sugars that make up the polymers can be very helpful to ensuring that the cellulosic materials are efficiently utilized as a feedstock (carbon source).

Celluose or cellulosic biomass is subjected to a process, termed "explosion", in which the biomass is treated with dilute sulfuric (or other) acid at elevated temperature and pressure. This process conditions the biomass such that it can be efficiently subjected to enzymatic hydrolysis of the cellulosic and hemicellulosic fractions into glucose and xylose monomers. The resulting monomeric sugars are termed cellulosic sugars. Cellulosic sugars can subsequently be utilized by microorganisms to produce a variety of metabolites (e.g., lipid). The acid explosion step results in a partial hydrolysis of the hemicellulose fraction to constitutent monosaccharides. These sugars can be completely liberated from the biomass with further treatment. In some embodiments, the further treatment is a hydrothermal treatment that includes washing the exploded material with hot water, which removes contaminants such as salts. This step is not necessary for cellulosic ethanol fermentations due to the more dilute sugar concentrations used in such processes. In other embodiments, the further treatment is additional acid treatment. In still other embodiments, the further treatment is enzymatic hydrolysis of the exploded material. These treatments can also be used in any combination. The type of treatment can affect the type of sugars liberated (e.g., five carbon sugars versus six carbon sugars) and the stage at which they are liberated in the process. As a consequence, different streams of sugars, whether they are predominantly five-carbon or six-carbon, can be created. These enriched five-carbon or six-carbon streams can thus be directed to specific microorganisms with different carbon utilization cabilities.

The methods of the present invention typically involve fermentation to higher cell densities than what is achieved in ethanol fermentation. Because of the higher densities of the cultures for heterotrophic cellulosic oil production, the fixed carbon source (e.g., the cellulosic derived sugar stream(s)) is preferably in a concentrated form. The glucose level of the depolymerized cellulosic material is preferably at least 300 g/liter, at least 400 g/liter, at least 500 g/liter or at least 600 g/liter prior to the cultivation step, which is optionally a fed batch cultivation in which the material is fed to the cells over time as the cells grow and accumulate lipid. Cellulosic sugar streams are not used at or near this concentration range in the production of cellulosic ethanol. Thus, in order to generate and sustain the very high cell densities during the production of lignocellulosic oil, the carbon feedstock(s) must be delivered into the heterotrophic cultures in a highly concentrated form. However, any component in the feedstream that is not a substrate for, and is not metabolized by, the oleaginous microorganism will accumulate in the bioreactor, which can lead to problems if the component is toxic or inhibitory to production of the desired end product. While ligin and lignin-derived by-products, carbohydrate-derived byproducts such as furfurals and hydroxymethyl furfurals and salts derived from the generation of the cellulosic materials (both in the explosion process and the subsequent neutralization process), and even non-metabolized pentose/hexose sugars can present problems in ethanolic fermentations, these effects are amplified significantly in a process in which their concentration in the initial feedstock is high. To achieve sugar concentrations in the 300 g/L range (or higher) for six-carbon sugars that may be used in large scale production of lignocellulosic oil described in the present invention, the concentration of these toxic materials can be 20 times higher than the concentrations typically present in ethanolic fermentations of cellulosic biomass.

The explosion process treatment of the cellulosic material utilizes significant amounts of sulfuric acid, heat and pressure, thereby liberating by-products of carbohydrates, namely furfurals and hydroxymethyl furfurals. Furfurals and hydroxymethyl furfurals are produced during hydrolysis of hemicellulose through dehydration of xylose into furfural and water. In some embodiments of the present invention, these by-products (e.g., furfurals and hydroxymethyl furfurals) are removed from the saccharified lignocellulosic material prior to introduction into the bioreactor. In certain embodiments of the present invention, the process for removal of the by-products of carbohydrates is hydrothermal treatment of the exploded cellulosic materials. In addition, the present invention provides methods in which strains capable of tolerating compounds such as furfurals or hydroxymethyl furfurals are used for lignocellulosic oil production. In another embodiment, the present invention also provides methods and microorganisms that are not only capable of tolerating furfurals in the fermentation media, but are actually able to metabolize these by-products during the production of lignocellulosic oil.

The explosion process also generates significant levels of salts. For example, typical conditions for explosion can result in conductivites in excess of 5 mS/cm when the exploded cellulosic biomass is resuspended at a ratio of 10:1 water:solids (dry weight). In certain embodiments of the present invention, the diluted exploded biomass is subjected to enzymatic saccharification, and the resulting supernatant is concentrated up to 25 fold for use in the bioreactor. The salt level (as measured by conductivity) in the concentrated sugar stream(s) can be unacceptably high (up to 1.5 M $Na^+$ equivalents). Additional salts are generated upon neutralization of the exploded materials for the subsequent enzymatic saccharification process as well. The present invention provides methods for removing these salts so that the resulting concentrated cellulosic sugar stream(s) can be used in heterotrophic processes for producing lignocellulosic oil. In some embodiments, the method of removing these salts is deionization with resins, such as, but not limited to, DOWEX Marathon MR3. In certain embodiments, the deionization with resin step occurs before sugar concentration or pH adjustment and hydrothermal treatment of biomass prior to saccharification, or any combination of the preceding; in other embodiments, the step is conducted after one or more of these processes. In other embodiments, the explosion process itself is changed so as to avoid the generation of salts at unacceptably high levels. For example, a suitable alternative to sulfuric acid (or other acid) explosion of the cellulosic biomass is mechanical pulping to render the cellulosic biomass receptive to enzymatic hydrolysis (saccharification). In still other embodiments, native strains of microorganisms resistant to high levels of salts or genetically engineered strains with resistance to high levels of salts are used.

A preferred embodiment for the process of preparing of exploded cellulosic biomass for use in heterotrophic lignocellulosic oil production using oleaginous microbes. A first step comprises adjusting the pH of the resuspended exploded cellulosic biomass to the range of 5.0-5.3 followed by washing the cellulosic biomass three times. This washing step can be accomplished by a variety of means including the use of desalting and ion exchange resins, reverse omosis, hydrothermal treatment (as described above), or just repeated re-suspension and centrifugation in deionized water. This wash step results in a cellulosic stream whose conductivity is between 100-300 μS/cm and the removal of significant amounts of furfurals and hydroxymethyl furfurals. Decants from this wash step can be saved to concentrate five-carbon sugars liberated from the hemicellulose fraction. A second step comprises enzymatic saccharification of the washed cellulosic biomass. In a preferred embodiment, Accellerase (Genencor) is used. A third step comprises the recovery of sugars via centrifugation or decanting and rinsing of the saccharified biomass. The resulting biomass (solids) is an energy dense, lignin rich component that can be used as fuel or sent to waste. The recovered sugar stream in the centrifugation/decanting and rinse process is collected. A fourth step comprises microfiltration to remove contaminating solids with recovery of the permeate. A fifth step comprises a concentration step which can be accomplished using a vacuum evaporator. This step can optionally include the addition of antifoam agents such as P'2000 (Sigma/Fluka), which is sometimes necessary due to the protein content of the resulting sugar feedstock.

In another embodiment of the methods of the invention, the carbon source is glycerol, including acidulated and non-acidulated glycerol byproduct from biodiesel transesterification. In one embodiment, the carbon source includes glycerol and at least one other carbon source. In some cases, all of the glycerol and the at least one other fixed carbon source are provided to the microorganism at the beginning of the fermentation. In some cases, the glycerol and the at least one other fixed carbon source are provided to the microorganism simultaneously at a predetermined ratio. In some cases, the glycerol and the at least one other fixed carbon source are fed to the microbes at a predetermined rate over the course of fermentation.

Some microalgae undergo cell division faster in the presence of glycerol than in the presence of glucose (see PCT Pub. No. 2008/151149). In these instances, two-stage growth processes in which cells are first fed glycerol to rapidly increase cell density, and are then fed glucose to accumulate lipids can improve the efficiency with which lipids are produced. The use of the glycerol byproduct of the transesterification process provides significant economic advantages when put back into the production process. Other feeding methods are provided as well, such as mixtures of glycerol and glucose. Feeding such mixtures also captures the same economic benefits. In addition, the invention provides methods of feeding alternative sugars to microalgae such as sucrose in various combinations with glycerol.

In another embodiment of the methods of the invention, the carbon source is invert sugar. Invert sugar is produced by splitting the sucrose into its monosaccharide components, fructose and glucose. Production of invert sugar can be achieved through several methods that are known in the art. One such method is heating an aqueous solution of sucrose. Often, catalysts are employed in order to accelerate the conversion of sucrose into invert sugar. These catalysts can be biological, for example enzymes such as invertases and sucrases can be added to the sucrose to accelerate the hydrolysis reaction to produce invert sugar. Acid is an example of non-biological catalyst, when paired with heat, can accelerate the hydrolysis reaction. Once the invert sugar is made, it is less prone to crystallization compared to sucrose and thus, provides advantages for storage and in fed batch fermentation, which in the case of heterotrophic cultivation of microbes, including microalgae, there is a need for concentrated carbon source. In one embodiment, the carbon source is invert sugar, preferably in a concentrated form, preferably at least 800 g/liter, at least 900 g/liter, at least 1000 g/liter or at least 1100 g/liter prior to the cultivation step, which is optionally a fed batch cultivation. The invert sugar, preferably in a concentrated form, is fed to the cells over time as the cells grow and accumulate lipid.

In another embodiment of the methods of the invention, the carbon source is sucrose, including a complex feedstock containing sucrose, such as thick cane juice from sugar cane processing. Because of the higher densities of the cultures for heterotrophic oil production, the fixed carbon source (e.g., sucrose, glucose, etc.) is preferably in a concentrated form, preferably at least 500 g/liter, at least 600 g/liter, at least 700 g/liter or at least 800 g/liter of the fixed carbon source prior to the cultivation step, which is optionally a fed batch cultivation in which the material is fed to the cells over time as the cells grow and accumulate lipid. In the some cases, the carbon source is sucrose in the form of thick cane juice, preferably in a concentrated form, preferably at least 60% solids or about 770 g/liter sugar, at least 70% solids or about 925 g/liter sugar, or at least 80% solids or about 1125 g/liter sugar prior to the cultivation step, which is optionally a fed batch cultivation. The concentrated thick cane juice is fed to the cells over time as the cells grow and accumulate lipid.

In one embodiment, the culture medium further includes at least one sucrose utilization enzyme. In some cases, the culture medium includes a sucrose invertase. In one embodiment, the sucrose invertase enzyme is a secretable sucrose invertase enzyme encoded by an exogenous sucrose invertase gene expressed by the population of microorganisms. Thus, in some cases, as described in more detail in Section IV, below, the microalgae has been genetically engineered to express a sucrose utilization enzyme, such as a sucrose transporter, a sucrose invertase, a hexokinase, a glucokinase, or a fructokinase.

Complex feedstocks containing sucrose include waste molasses from sugar cane processing; the use of this low-value waste product of sugar cane processing can provide significant cost savings in the production of hydrocarbons and other oils. Another complex feedstock containing sucrose that is useful in the methods of the invention is sorghum, including sorghum syrup and pure sorghum. Sorghum syrup is produced from the juice of sweet sorghum cane. Its sugar profile consists of mainly glucose (dextrose), fructose and sucrose.

4. Oil Production

For the production of oil in accordance with the methods of the invention, it is preferable to culture cells in the dark, as is the case, for example, when using extremely large (40,000 liter and higher) fermentors that do not allow light to strike the culture. *Prototheca* species are grown and propagated for the production of oil in a medium containing a fixed carbon source and in the absence of light; such growth is known as heterotrophic growth.

As an example, an inoculum of lipid-producing oleaginous microbial cells, preferably microalgal cells are introduced into the medium; there is a lag period (lag phase) before the cells begin to propagate. Following the lag period, the propagation rate increases steadily and enters the log, or exponential, phase. The exponential phase is in turn followed by a slowing of propagation due to decreases in nutrients such as nitrogen, increases in toxic substances, and quorum sensing mechanisms. After this slowing, propagation stops, and the cells enter a stationary phase or steady growth state, depending on the particular environment provided to the cells. For obtaining lipid rich biomass, the culture is typically harvested well after then end of the exponential phase, which may be terminated early by allowing nitrogen or another key nutrient (other than carbon) to become depleted, forcing the cells to convert the carbon sources, present in excess, to lipid. Culture condition parameters can be manipulated to optimize total oil production, the combination of lipid species produced, and/or production of a specific oil.

As discussed above, a bioreactor or fermentor is used to allow cells to undergo the various phases of their growth cycle. As an example, an inoculum of lipid-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells. Lipid production by cells disclosed herein can occur during the log phase or thereafter, including the stationary phase wherein nutrients are supplied, or still available, to allow the continuation of lipid production in the absence of cell division.

Preferably, microorganisms grown using conditions described herein and known in the art comprise at least about 20% by weight of lipid, preferably at least about 40% by weight, more preferably at least about 50% by weight, and most preferably at least about 60% by weight. Process conditions can be adjusted to increase the yield of lipids suitable for a particular use and/or to reduce production cost. For example, in certain embodiments, a microalgae is cultured in the presence of a limiting concentration of one or more nutrients, such as, for example, nitrogen, phosphorous, or sulfur, while providing an excess of fixed carbon energy such as glucose. Nitrogen limitation tends to increase microbial lipid yield over microbial lipid yield in a culture in which nitrogen is provided in excess. In particular embodiments, the increase in lipid yield is at least about: 10%, 50%, 100%, 200%, or 500%. The microbe can be cultured in the presence of a limiting amount of a nutrient for a portion of the total culture period or for the entire period. In particular embodiments, the nutrient concentration is cycled between a limiting concentration and a non-limiting concentration at least twice during the total culture period. Lipid content of cells can be increased by continuing the culture for increased periods of time while providing an excess of carbon, but limiting or no nitrogen.

In another embodiment, lipid yield is increased by culturing a lipid-producing microbe (e.g., microalgae) in the presence of one or more cofactor(s) for a lipid pathway enzyme (e.g., a fatty acid synthetic enzyme). Generally, the concentration of the cofactor(s) is sufficient to increase microbial lipid (e.g., fatty acid) yield over microbial lipid yield in the absence of the cofactor(s). In a particular embodiment, the cofactor(s) are provided to the culture by including in the culture a microbe (e.g., microalgae) containing an exogenous gene encoding the cofactor(s). Alternatively, cofactor(s) may be provided to a culture by including a microbe (e.g., microalgae) containing an exogenous gene that encodes a protein that participates in the synthesis of the cofactor. In certain embodiments, suitable cofactors include any vitamin required by a lipid pathway enzyme, such as, for example: biotin, pantothenate. Genes encoding cofactors suitable for use in the invention or that participate in the synthesis of such cofactors are well known and can be introduced into microbes (e.g., microalgae), using constructs and techniques such as those described above.

The specific examples of bioreactors, culture conditions, and heterotrophic growth and propagation methods described herein can be combined in any suitable manner to improve efficiencies of microbial growth and lipid and/or protein production.

Microalgal biomass with a high percentage of oil/lipid accumulation by dry weight has been generated using different methods of culture, which are known in the art (see PCT Pub. No. 2008/151149). Microalgal biomass generated by the culture methods described herein and useful in accordance with the present invention comprises at least 10% microalgal oil by dry weight. In some embodiments, the microalgal biomass comprises at least 25%, at least 50%, at least 55%, or at least 60% microalgal oil by dry weight. In some embodiments, the microalgal biomass contains from 10-90% microalgal oil, from 25-75% microalgal oil, from 40-75% microalgal oil, or from 50-70% microalgal oil by dry weight.

The microalgal oil of the biomass described herein, or extracted from the biomass for use in the methods and compositions of the present invention can comprise glycerolipids with one or more distinct fatty acid ester side chains. Glycerolipids are comprised of a glycerol molecule esterified to one, two or three fatty acid molecules, which can be of varying lengths and have varying degrees of saturation. The length and saturation characteristics of the fatty acid molecules (and the microalgal oils) can be manipulated to modify the properties or proportions of the fatty acid molecules in the microalgal oils of the present invention via culture conditions or via lipid pathway engineering, as described in more detail in Section IV, below. Thus, specific blends of algal oil can be prepared either within a single species of algae by mixing together the biomass or algal oil from two or more species of microalgae, or by blending algal oil of the invention with oils from other sources such as soy, rapeseed, canola, palm, palm kernel, coconut, corn, waste vegetable, Chinese tallow, olive, sunflower, cottonseed, chicken fat, beef tallow, porcine tallow, microalgae, macroalgae, microbes, *Cuphea*, flax, peanut, choice white grease, lard, *Camelina sativa*, mustard seed, cashew nut, oats, lupine, kenaf, *calendula*, help, coffee, linseed (flax), hazelnut, *euphorbia*, pumpkin seed, coriander, *camellia*, sesame, safflower, rice, tung tree, cocoa, copra, pium poppy, castor beans, pecan, jojoba, *macadamia*, Brazil nuts, avocado, petroleum, or a distillate fraction of any of the preceding oils.

The oil composition, i.e., the properties and proportions of the fatty acid constituents of the glycerolipids, can also be manipulated by combining biomass or oil from at least two distinct species of microalgae. In some embodiments, at least two of the distinct species of microalgae have different glycerolipid profiles. The distinct species of microalgae can be cultured together or separately as described herein, preferably under heterotrophic conditions, to generate the respective oils. Different species of microalgae can contain different percentages of distinct fatty acid constituents in the cell's glycerolipids.

Generally, *Prototheca* strains have very little or no fatty acids with the chain length C8-C14. For example, *Prototheca moriformis* (UTEX 1435), *Prototheca krugani* (UTEX 329), *Prototheca stagnora* (UTEX 1442) and *Prototheca zopfii* (UTEX 1438) contains no (or undetectable amounts) C8 fatty acids, between 0-0.01% C10 fatty acids, between 0.03-2.1% C12 fatty acids and between 1.0-1.7% C14 fatty acids.

In some cases, the *Prototheca* strains containing a transgene encoding a fatty acyl-ACP thioesterase that has activity towards fatty acyl-ACP substrate of chain lengths C8 or C8-10 has at least 1%, at least 1.5%, at least 2%, at least 3%, at least 4%, at least 5%, at least 10%, at least 12%, or at least 15% or more, fatty acids of chain length C8. In other instances, the *Prototheca* strains containing a transgene encoding a fatty acyl ACP thioesterase that has activity towards fatty acyl-ACP substrate of chain lengths C10 has at least at least 1%, at least 5%, at least 10%, at least 15%, at least 20%, at least 24%, or at least 25% or more, fatty acids of chain length C10. In other instances, the *Prototheca* strains containing a transgene encoding a fatty acyl-ACP thioesterase that has activity towards fatty acyl-ACP substrate of chain length C12 has at least 1%, at least 5%, at least 10%, at least 15%, at least 20%, at least 25%, at least 30%, at least 34%, at least 35% or at least 40% or more, fatty acids of the chain length C12. In other cases, the *Prototheca* strains containing a transgene encoding a fatty acyl-ACP thioesterase that has activity towards fatty acyl-ACP substrate of chain length C14 has at least 1%, at least 2%, at least 3%, at least 4%, at least 5%, at least 6%, at least 7%, at least 10%, at least 15%, at least 30%, at least 43%, or at least 45% or more, fatty acids of the chain length C14.

In non-limiting examples, the *Prototheca* strains containing a transgene encoding a fatty acyl-ACP thioesterase that has activity towards fatty acyl-ACP substrate of chain length C8 has between 1%-25%, or between 1%-15%, preferably 1.8-12.29%, fatty acids of chain length C8. In other non-limiting examples, *Prototheca* strains containing a transgene encoding a fatty acyl-ACP thioesterase that has activity towards fatty acyl-ACP substrate of chain length C10 has between 1%-50%, or between 1%-25%, preferably 1.91-23.97% fatty acids of chain length C10. In other non-limiting examples, *Prototheca* strains containing a transgene encoding a fatty acyl-ACP thioesterase that has activity towards fatty acyl-ACP substrate of chain length C12 has between 5%-50%, or between 10%-40, preferably 13.55-34.01%, fatty acids of the chain length C12. In other non-limiting examples, *Prototheca* strains containing a transgene encoding a fatty acyl-ACP thioesterase that has activity towards fatty acyl-ACP substrate of chain length C14 has between 1%-60%, or between 2%-45%, preferably 2.59-43.27%, fatty acids of the chain length C14. In other non-limiting examples, *Prototheca* strains containing a transgene encoding a fatty acyl-ACP thioesterase that has broad specificity towards fatty acyl-ACP substrates of varying carbon chain length has up to 30%, up to 35%, or preferably up to 39.45% fatty acids of the chain length C16. In some cases, the *Prototheca* strains containing a transgene encoding a fatty acyl-ACP thioesterase that has activity towards fatty acyl-ACP substrate of chain lengths between C8 and C14 have between 1%-75%, or between 2%-60%, preferably 2.69-57.98%, medium chain (C8-C14) fatty acids. In some cases, the *Prototheca* strains containing a transgene encoding a fatty acyl-ACP thioesterase that has activity towards fatty acyl-ACP substrates of chain lengths between C12 and C14 have at least 30%, at least 40%, or at least 49% C12-C14 fatty acids. In some instances, keeping the transgenic *Prototheca* strains under constant and high selective pressure to retain exogenous genes is advantageous due to the increase in the desired fatty acid of a specific chain length. High levels of exogenous gene retention can also be achieved by inserting exogenous genes into the nuclear chromosomes of the cells using homologous recombination vectors and methods disclosed herein. Recombinant cells containing exogenous genes integrated into nuclear chromosomes are an object of the invention.

Microalgal oil can also include other constituents produced by the microalgae, or incorporated into the microalgal oil from the culture medium. These other constituents can be present in varying amount depending on the culture conditions used to culture the microalgae, the species of microalgae, the extraction method used to recover microalgal oil from the biomass and other factors that may affect microalgal oil composition. Non-limiting examples of such constituents include carotenoids, present from 0.01-0.5 mcg/g, 0.025-0.3 mcg/g, preferably 0.05 to 0.244 micrograms/gram, of oil; chlorophyll A present from 0.01-0.5 mcg/g, 0.025-0.3 mcg/g, preferably 0.045 to 0.268 micrograms/gram, of oil; total chlorophyll of less than 0.1 mcg/g, less than 0.05 mcg/g, preferably less than 0.025 micrograms/gram, of oil; gamma tocopherol present from 1-300 mcg/g, 35-175 mcg/g, preferably 38.3-164 micrograms/gram, of oil; total tocopherols present from 10-500 mcg/g, 50-300 mcg/g, preferably 60.8 to 261.7 microgram/gram, of oil; less than 1%, less than 0.5%, preferably less than 0.25% brassicasterol, campesterol, stigmasterol, or betasitosterol; total tocotrienols less than 400 mcg/g, preferably less than 300 micrograms/gram, of oil; or total tocotrienols present from 100-500 mcg/g, 225-350 mcg/g, preferably 249.6 to 325.3 micrograms/gram, of oil.

The other constituents can include, without limitation, phospholipids, tocopherols, tocotrienols, carotenoids (e.g., alpha-carotene, beta-carotene, lycopene, etc.), xanthophylls (e.g., lutein, zeaxanthin, alpha-cryptoxanthin and beta-crytoxanthin), and various organic or inorganic compounds. In some cases, the oil extracted from *Prototheca* species comprises between 0.001-0.01 mcg/g, 0.0025-0.05 mcg/g, preferably 0.003 to 0.039 microgram lutein/gram, of oil, less than 0.01 mcg/g, less than 0.005 mcg/g, preferably less than 0.003 micrograms lycopene/gram, of oil; and less than 0.01 mcg/g, less than 0.005 mcg/g, preferably less than 0.003 microgram beta carotene/gram, of oil.

In some embodiments, the present invention provides an oleaginous microbial cell comprising a triglyceride oil, wherein the fatty acid profile of the triglyceride oil is selected from the group consisting of: at least about 1%, at least about 2%, at least about 5%, at least about 7%, at least about 10%, or at least about 15%, C8:0; at least about 1%, at least about 5%, at least about 15%, at least about 20%, at least about 25%, or at least about 30%, C10:0; at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, C12:0; at least about 2%, at least about 5%, at least about 10%, at least about 15%, at least about 20%, at least about 25%, at least about 30%, at least about 35%, at least about 40%, at least about 45%, or at least about 50%, C14:0; at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, C16:0; at least about 5%, at least about 10%, at least about 15%, at least about 20%, at least about 25%, at least about 30%, at least about 35%, at least about 40%, at least about 45%, or at least about 50%, C18:0; at least about 60%, at least about 65%, at least about 70%, at least about 75%, at least about 80%, at least about 85%, or at least about 90%, C18:1; less than about 7%, less than about 5%, less than about 3%, less than about 1%, or about 0%, C18:2; and at least about 35%, at least about 40%, at least about 45%, at least about 50%, at least about 55%, at least about 60%, at least about 65%, at least about 70%, at least about 75%, at least about 80%, at least about 85%, or at least about 90%, saturated fatty acids.

In some embodiments, the oleaginous microbial cell comprises triglyceride oil comprising a fatty acid profile selected from the group consisting of: total combined amounts of C8:0 and C10:0 of at least about 10%, at least about 20%, at least about 30%, at least about 40%, at least about 50%, at least about 60%, at least about 70%, at least about 80%, at least about 90%, or about 100%; total combined amounts of C10:0, C12:0, and C14:0 of at least about 50%, at least about 60%, at least about 70%, at least about 80%, at least about 90%, or about 100%; total combined amounts of C16:0, C18:0 and C18:1 of at least about 60%, at least about 70%, at least about 80%, at least about 90%, or about 100%; total combined amounts of C18:0, C18:1 and C18:2 of at least about 60%, at least about 70%, at least about 80%, at least about 90%, or about 100%; total combined amounts of C14:0, C16:0, C18:0 and C18:1 of at least about 60%, at least about 70 s %, at least about 80%, at least about 90%, or about 100%; and total combined amounts of C18:1 and C18:2 of less than about 30%, less than about 25%, less than about 20%, less than about 15%, less than about 10%, less than about 5%, or about 0%, In some embodiments, the oleaginous microbial cell comprises triglyceride oil having a fatty acid profile comprising a ratio of fatty acids selected from the group consisting of: a C8:0 to C10:0 ratio of at least about 5 to 1, at least 6 to 1, at least 7 to 1, at least 8 to 1, at least 9 to 1, or at least 10 to 1; a C10:0 to C12:0 ratio of at least about 6 to 1, at least 7 to 1, at least 8 to 1, at least 9 to 1, or at least 10 to 1; a C12:0 to C14:0 ratio of at least about 5 to 1, at least 6 to 1, at least 7 to 1, at least 8 to 1, at least 9 to 1, or at least 10 to 1; a C14:0 to C12:0 ratio of at least 7 to 1, at least 8 to 1, at least 9 to 1, or at least 10 to 1; and a C14:0 to C16:0 ratio of at least 1 to 2, at least 1 to 3, at least 1 to 4, at least 1 to 5, at least 1 to 6, at least 1 to 7, at least 1 to 8, at least 1 to 9, or at least 1 to 10.

In some embodiments, the present invention provides an oleaginous microbial triglyceride oil composition, wherein the fatty acid profile of the triglyceride oil is selected from the group consisting of: at least about 1%, at least about 2%, at least about 5%, at least about 7%, at least about 10%, or at least about 15%, C8:0; at least about 1%, at least about 5%, at least about 15%, at least about 20%, at least about 25%, or at least about 30% C10:0; at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, C12:0; at least about 2%, at least about 5%, at least about 10%, at least about 15%, at least about 20%, at least about 25%, at least about 30%, at least about 35%, at least about 40%, at least about 45%, or at least about 50%, C14:0; at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, C16:0; at least about 5%, at least about 10%, at least about 15%, at least about 20%, at least about 25%, at least about 30%, at least about 35%, at least about 40%, at least about 45%, or at least about 50%, C18:0; at least about 60%, at least about 65%, at least about 70%, at least about 75%, at least about 80%, at least about 85%, or at least about 90%, C18:1; less than about 7%, less than about 5%, less than about 3%, less than about 1%, or about 0%, C18:2; and at least about 35%, at least about 40%, at least about 45%, at least about 50%, at least about 55%, at least about 60%, at least about 65%, at least about 70%, at least about 75%, at least about 80%, at least about 85%, or at least about 90%, saturated fatty acids.

In some embodiments, the oleaginous microbial triglyceride oil composition comprises triglyceride oil comprising a fatty acid profile in which: the total combined amount of C10:0, C12:0 and C14:0 is at least about 50%, at least bout 60%, at least about 70%, at least about 80%, at least about 90%, or about 100%; the total combined amount of C16:0, C18:0 and C18:1 is at least about 60%, at least about 70%, at least about 80%, at least about 90%, or about 100%; the total combined amount of C18:0, C18:1 and C18:2 is at least about 60%, at least about 70%, at least about 80%, at least about 90%, or about 100%; the total combined amount of C14:0, C16:0, C18:0 and C18:1 is at least about 60%, at least about 70%, at least about 80%, at least about 90%, or about 100%; the total combined amounts of C8:0 and C10:0 is less than about 50%, less than about 45%, less than about 40%, less than about 35%, less than about 30%, less than about 25%, less than about 20%, less than about 15%, less than about 10%, less than about 5%, or about 0%.

In some embodiments, the oleaginous microbial triglyceride oil composition comprises triglyceride oil having a fatty acid profile comprising a ratio of fatty acids selected from the group consisting of: a C8:0 to C10:0 ratio of at least about 5 to 1, at least about 6 to 1, at least about 7 to 1, at least about 8 to 1, at least about 9 to 1, or at least about 10 to 1; a C10:0 to C12:0 ratio of at least about 6 to 1, at least about 7 to 1, at least about 8 to 1, at least about 9 to 1, or at least about 10 to 1; a C12:0 to C14:0 ratio of at least about 5 to 1, at least about 6 to 1, at least about 7 to 1, at least about 8 to 1, at least about 9 to 1, or at least about 10 to 1; a C14:0 to C12:0 ratio of at least about 7 to 1, at least about 8 to 1, at least about 9 to 1, or at least about 10 to 1; a C14:0 to C16:0 ratio of at least about 1 to 2, at least about 1 to 3, at least about 1 to 4, at least about 1 to 5, at least about 1 to 6, at least about 1 to 7, at least about 1 to 8, at least about 1 to 9, or at least about 1 to 10.

In some embodiments, the present invention provides a method of producing an oleaginous microbial triglyceride oil composition having a fatty acid profile selected from the group consisting of: at least about 1%, at least about 2%, at least about 5%, at least about 7%, at least about 10%, or at least about 15%, C8:0; at least about 1%, at least about 5%, at least about 10%, at least about 15%, at least about 20%, at least about 25%, or at least about 30%, C10:0; at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, C12:0; at least about 2%, at least about 5%, at least about 10%, at least about 15%, at least about 20%, at least about 25%, at least about 30%, at least about 35%, at least about 40%, at least about 45%, or at least about 50%, C14:0; at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, C16:0; at least about 5%, at least about 10%, at least about 15%, at least about 20%, at least about 25%, at least about 30%, at least about 35%, at least about 40%, at least about 45%, or at least about 50% C18:0; at least about 60%, at least about 65%, at least about 70%, at least about 75%, at least about 80%, at least about 85%, or at least about 90%, C18:1; less than about 7%, less than about 5%, less than about 3%, less than about 1%, or about 0%, C18:2; and at least about 35%, at least about 40%, at least about 45%, at least about 50%, at least about 55%, at least about 60%, at least about 65%, at least about 70%, at least about 75%, at least about 80%, at least about 85%, or at least about 90%, saturated fatty acids, wherein the method comprises the steps of: (a)

cultivating a population of oleaginous microbial cells in a culture medium until at least 10% of the dry cell weight of the oleaginous microbial cells is triglyceride oil; and (b) isolating the triglyceride oil composition from the oleaginous microbial cells.

In some embodiments, the method of producing oleaginous microbial triglyceride oil compositions yields triglyceride oils comprising a fatty acid profile in which: the total combined amount of C10:0, C12:0 and C14:0 is at least about 50%, at least about 60%, at least about 70%, at least about 80%, at least about 90%, or about 100%; the total combined amount of C16:0, C18:0 and C18:1 is at least about 60%, at least about 70%, at least about 80%, at least about 90%, or about 100%; the total combined amount of C18:0, C18:1 and C18:2 is at least about 60%, at least about 70%, at least about 80%, at least about 90%, or about 100%; the total combined amount of C14:0, C16:0, C18:0 and C18:1 is at least about 60%, at least about 70%, at least about 80%, at least about 90%, or about 100%; the total combined amount of C8:0 and C10:0 is less than about 50%, less than about 45%, less than about 40%, less than about 35%, less than about 30%, less than about 25%, less than about 20%, less than about 15%, less than about 10%, less than about 5%, or about 0%.

In some embodiments, the method of producing oleaginous microbial triglyceride oil compositions yields triglyceride oils having a fatty acid profile comprising a ratio of triglyceride oils selected from the group consisting of: a C8:0 to C10:0 ratio of at least about 5 to 1, at least about 6 to 1, at least about 7 to 1, at least about 8 to 1, at least about 9 to 1, or at least about 10 to 1; a C10:0 to C12:0 ratio of at least about 6 to 1, at least about 7 to 1, at least about 8 to 1, at least about 9 to 1, or at least about 10 to 1; a C12:0 to C14:0 ratio of at least about 5 to 1, at least about 6 to 1, at least about 7 to 1, at least about 8 to 1, at least about 9 to 1, or at least about 10 to 1; a C14:0 to C12:0 ratio of at least about 7 to 1, at least about 8 to 1, at least about 9 to 1, or at least about 10 to 1; and a C14:0 to C16:0 ratio of at least about 1 to 2, at least about 1 to 3, at least about 1 to 4, at least about 1 to 5, at least about 1 to 6, at least about 1 to 7, at least about 1 to 8, at least about 1 to 9, or at least about 1 to 10.

III. GENETIC ENGINEERING METHODS AND MATERIALS

The present invention provides methods and materials for genetically modifying microorganisms, including *Prototheca* cells and recombinant host cells, useful in the methods of the present invention, including but not limited to recombinant *Prototheca moriformis, Prototheca zopfii, Prototheca krugani,* and *Prototheca stagnora* host cells. The description of these methods and materials is divided into subsections for the convenience of the reader. In subsection 1, transformation methods are described. In subsection 2, genetic engineering methods using homologous recombination are described. In subsection 3, expression vectors and components are described.

In certain embodiments of the present invention it is desirable to genetically modify a microorganism to enhance lipid production, modify the properties or proportions of components generated by the microorganism, or to improve or provide de novo growth characteristics on a variety of feedstock materials. *Chlorella,* particularly *Chlorella protothecoides, Chlorella minutissima, Chlorella sorokiniana, Chlorella ellipsoidea, Chlorella* sp., and *Chlorella emersonii* are preferred microorganisms for use in the genetic engineering methods described herein, although other *Chlorella* species as well as other varieties of microorganisms can be used.

Promoters, cDNAs, and 3'UTRs, as well as other elements of the vectors, can be generated through cloning techniques using fragments isolated from native sources (see for example Molecular Cloning: A Laboratory Manual, Sambrook et al. (3d edition, 2001, Cold Spring Harbor Press; and U.S. Pat. No. 4,683,202). Alternatively, elements can be generated synthetically using known methods (see for example Gene. 1995 Oct. 16; 164(1):49-53).

1. Engineering Methods—Transformation

Cells can be transformed by any suitable technique including, e.g., biolistics, electroporation (see Maruyama et al. (2004), Biotechnology Techniques 8:821-826), glass bead transformation and silicon carbide whisker transformation. Another method that can be used involves forming protoplasts and using $CaCl_2$ and polyethylene glycol (PEG) to introduce recombinant DNA into microalgal cells (see Kim et al. (2002), *Mar. Biotechnol.* 4:63-73, which reports the use of this method for the transformation of *Chorella ellipsoidea*). Co-transformation of microalgae can be used to introduce two distinct vector molecules into a cell simultaneously (see for example Protist 2004 December; 155(4): 381-93).

Biolistic methods (see, for example, Sanford, Trends In Biotech. (1988) 6:299 302, U.S. Pat. No. 4,945,050; electroporation (Fromm et al., Proc. Nat'l. Acad. Sci. (USA) (1985) 82:5824 5828); use of a laser beam, microinjection or any other method capable of introducing DNA into a microalgae can also be used for transformation of a *Prototheca* cell.

Any convenient technique for introducing a transgene into a microorganism, such as *Chorella,* can be employed in the present invention. Dawson et al. (1997) (supra) described the use of micro-projectile bombardment to introduce the nitrate reductase (NR) gene from *Chlorella vulgaris* into NR-deficient *Chlorella sorokiniana* mutants, resulting in stable transformants. Briefly, 0.4 micron tungsten beads were coated with plasmid; $3\times10^7$ *C. sorokiniana* cells were spread in the center third of a non-selective agar plate and bombarded with the PDS-1000/He Biolistic Particle Delivery® system (Bio-Rad).

A preferred method for introducing a transgene into a microorganism, such as *Chlorella,* is the method described by Kim et al. (2002), *Mar. Biotechnol.* 4:63-73. Kim reports the transformation of *Chorella ellipsoidea* protoplasts using $CaCl_2$ and polyethylene glycol (PEG). In particular, protoplasts were prepared by growing *C. ellipsoidea* cells to a density of $1-2\times10^8$/Ml. Cells were recovered and washed by centrifugation for 5 minutes at 1600 g and resuspended in 5 Ml of phosphate buffer (Ph 6.0) containing 0.6 M sorbitol, 0.6 M mannitol, 4% (weight/volume) cellulose (Calbiochem), 2% (weight/volume) macerase (Calbiochem), and 50 units pectinase (Sigma). The cell suspension was incubated at 25° C. for 16 hours in the dark with gentle shaking. The resultant protoplasts were recovered by centrifugation at 400 g for 5 minutes. The pellet was gently resuspended in 5 Ml of f/2 medium containing 0.6 M sorbitol and 0.6 M mannitol and centrifuged at 400 g for 5 minutes. This pellet was resuspended in 1 Ml of 0.6 M sorbitol/mannitol solution containing 50 mM $CaCl_2$. Then, 5 mg of transgene DNA was added, along with 25 µg calf thymus DNA (Sigma), to $10^7$-$10^8$ protoplasts in 0.4 Ml. After 15 minutes at room temperature, 200 µL of PNC (40% polyethylene glycol 4000, 0.8 M NaCl, 50 Mm $CaCl_2$) was added and mixed gently for 30 minutes at room temperature. After this, 0.6 Ml of f/2 medium supplemented with 0.6 M sorbitol/mannitol solution, 1% yeast extract and 1% glucose was added, and the transformed cells were incubated at 25° C. for 12 hours in the dark for cell wall regeneration. A similar method was used by Huang et al. (2007) (supra) to introduce a transgene encoding mercuric reductase into *Chlorella* sp. DT.

Electorporation has also been employed to transform microorganisms, such as *Chorella*. As reported by Maruyama et al. (2004), Biotechnology Techniques 8:821-826 (incorporated by reference herein in its entirety), this technique was used to introduce a transgene into protoplasts of *Chlorella saccharophila* c-211-1a prepared from the cells in the stationary phase. Transient expression of the introduced plasmid was observed under a field strength of between 600 and 900 V/cm, and a pulse duration of around 400 ms, where high membrane permeability to 70-kDa FITC-dextran was ascertained.

Examples of expression of transgenes in microorganisms, such as *Chlorella*, can be found in the literature (see for example Current Microbiology Vol. 35 (1997), pp. 356-362; Sheng Wu Gong Cheng Xue Bao. 2000 July; 16(4):443-6; Current Microbiology Vol. 38 (1999), pp. 335-341; Appl Microbiol Biotechnol (2006) 72: 197-205; Marine Biotechnology 4, 63-73, 2002; Current Genetics 39:5, 365-370 (2001); Plant Cell Reports 18:9, 778-780, (1999); Biologia Plantarium 42(2): 209-216, (1999); Plant Pathol. J 21(1): 13-20, (2005)). Also see Examples herein.

Examples of expression of transgenes in oleaginous yeast (e.g., *Yarrowia lipolytica*) can be found in the literature (see, for example, Bordes et al., J Microbiol Methods, June 27 (2007)). Examples of expression of transgenes in fungi (e.g., *Mortierella* alpine, *Mucor circinelloides*, and *Aspergillus ochraceus*) can also be found in the literature (see, for example, Microbiology, July; 153(Pt. 7):2013-25 (2007); Mol Genet Genomics, June; 271(5):595-602 (2004); Curr Genet, March; 21(3):215-23 (1992); Current Microbiology, 30(2):83-86 (1995); Sakuradani, NISR Research Grant, "Studies of Metabolic Engineering of Useful Lipid-producing Microorganisms" (2004); and PCT/JP2004/012021). Examples of expression of exogenous genes in bacteria such as *E. coli* are well known; see for example Molecular Cloning: A Laboratory Manual, Sambrook et al. (3d edition, 2001, Cold Spring Harbor Press.

Vectors for transformation of microorganisms in accordance with the present invention can be prepared by known techniques familiar to those skilled in the art. The nucleotide sequence of the construct used for transformation of multiple *Chlorella* species corresponds to SEQ ID NO: 8. In one embodiment, an exemplary vector design for expression of a lipase gene in a microorganism such as a microalgae contains a gene encoding a lipase in operable linkage with a promoter active in microalgae. Alternatively, if the vector does not contain a promoter in operable linkage with the gene of interest, the gene can be transformed into the cells such that it becomes operably linked to an endogenous promoter at the point of vector integration. The promoterless method of transformation has been proven to work in microalgae (see for example Plant Journal 14:4, (1998), pp. 441-447). The vector can also contain a second gene that encodes a protein that, e.g., imparts resistance to an antibiotic or herbicide, i.e., a selectable marker. Optionally, one or both gene(s) is/are followed by a 3' untranslated sequence containing a polyadenylation signal. Expression cassettes encoding the two genes can be physically linked in the vector or on separate vectors. Co-transformation of microalgae can also be used, in which distinct vector molecules are simultaneously used to transform cells (see for example Protist 2004 December; 155(4):381-93). The transformed cells can be optionally selected based upon the ability to grow in the presence of the antibiotic or other selectable marker under conditions in which cells lacking the resistance cassette would not grow.

2. Engineering Methods—Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding genomic homologous sequences. The mechanistic steps of this process, in most cases, include: (1) pairing of homologous DNA segments; (2) introduction of double-stranded breaks into the donor DNA molecule; (3) invasion of the template DNA molecule by the free donor DNA ends followed by DNA synthesis; and (4) resolution of double-strand break repair events that result in final recombination products.

The ability to carry out homologous recombination in a host organism has many practical implications for what can be carried out at the molecular genetic level and is useful in the generation of an oleaginous microbe that can produced tailored oils. By its very nature homologous recombination is a precise gene targeting event, hence, most transgenic lines generated with the same targeting sequence will be essentially identical in terms of phenotype, necessitating the screening of far fewer transformation events. Homologous recombination also targets gene insertion events into the host chromosome, resulting in excellent genetic stability, even in the absence of genetic selection. Because different chromosomal loci will likely impact gene expression, even from heterologous promoters/UTRs, homologous recombination can be a method of querying loci in an unfamiliar genome environment and to assess the impact of these environments on gene expression.

Particularly useful genetic engineering applications using homologous recombination is to co-opt specific host regulatory elements such as promoters/UTRs to drive heterologous gene expression in a highly specific fashion. For example, ablation or knockout of desaturase genes/gene families with a heterologous gene encoding a selective marker might be expected to increase overall percentage of saturated fatty acids produced in the host cell. Example 11 describes the homologous recombination targeting constructs and a working example of such desaturase gene ablations or knockouts generated in *Prototheca moriformis*.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, and thus affecting the desired change in metabolism of the host cell. Homologous recombination provides a powerful means to manipulate the ghost genome resulting in gene targeting, gene conversion, gene deletion, gene duplication, gene inversion and exchanging gene expression regulatory elements such as promoters, enhancers and 3'UTRs.

Homologous recombination can be achieve by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

For purposes of non-limiting illustration, regions of donor DNA sequences that are useful for homologous recombination include the KE858 region of DNA in *Prototheca moriformis*. KE858 is a 1.3 kb, genomic fragment that encompasses part of the coding region for a protein that shares homology with the transfer RNA (tRNA) family of proteins. Southern blots have shown that the KE858 sequence is present in a single copy in the *Prototheca moriformis* (UTEX 1435) genome. This region and Examples of using this region for homologous recombination targeting has been described in PCT Application No. PCT/US2009/66142. Another region of donor DNA that is useful is portions of the 6S rRNA genomic sequence. The use of this sequence in homologous recombination in *Prototheca morifomis* are described below in the Examples.

3. Vectors and Vector Components

Vectors for transformation of microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell. To aid the reader, this subsection is divided into subsections. Subsection A describes control sequences typically contained on vectors as well as novel control sequences provided by the present invention. Subsection B describes genes typically contained in vectors as well as novel codon optimization methods and genes prepared using them provided by the invention.

A. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location in or outside the cell.

Thus, an exemplary vector design for expression of an exogenous gene in a microalgae contains a coding sequence for a desired gene product (for example, a selectable marker, a lipid pathway modification enzyme, or a sucrose utilization enzyme) in operable linkage with a promoter active in microalgae. Alternatively, if the vector does not contain a promoter in operable linkage with the coding sequence of interest, the coding sequence can be transformed into the cells such that it becomes operably linked to an endogenous promoter at the point of vector integration. The promoterless method of transformation has been proven to work in microalgae (see for example Plant Journal 14:4, (1998), pp. 441-447).

Many promoters are active in microalgae, including promoters that are endogenous to the algae being transformed, as well as promoters that are not endogenous to the algae being transformed (i.e., promoters from other algae, promoters from higher plants, and promoters from plant viruses or algae viruses). Illustrative exogenous and/or endogenous promoters that are active in microalgae (as well as antibiotic resistance genes functional in microalgae) are described in PCT Pub. No. 2008/151149 and references cited therein).

The promoter used to express an exogenous gene can be the promoter naturally linked to that gene or can be a heterologous gene. Some promoters are active in more than one species of microalgae. Other promoters are species-specific. Illustrative promoters include promoters such as β-tubulin from *Chlamydomonas reinhardtii*, used in the Examples below, and viral promoters, such as cauliflower mosaic virus (CMV) and *chlorella* virus, which have been shown to be active in multiple species of microalgae (see for example Plant Cell Rep. 2005 March; 23(10-11):727-35; J Microbiol. 2005 August; 43(4):361-5; Mar Biotechnol (NY). 2002 January; 4(1):63-73). Another promoter that is suitable for use for expression of exogenous genes in *Prototheca* is the *Chlorella sorokiniana* glutamate dehydrogenase promoter/5'UTR. Optionally, at least 10, 20, 30, 40, 50, or 60 nucleotides or more of these sequences containing a promoter are used. Illustrative promoters useful for expression of exogenous genes in *Prototheca* are listed in the sequence listing of this application, such as the promoter of the *Chlorella* HUP1 gene (SEQ ID NO:1) and the *Chlorella ellipsoidea* nitrate reductase promoter (SEQ ID NO:2). *Chlorella* virus promoters can also be used to express genes in *Prototheca*, such as SEQ ID NOs: 1-7 of U.S. Pat. No. 6,395,965. Additional promoters active in *Prototheca* can be found, for example, in Biochem Biophys Res Commun. 1994 Oct. 14; 204(1):187-94; Plant Mol Biol. 1994 October; 26(1):85-93; Virology. 2004 Aug. 15; 326(1):150-9; and Virology. 2004 Jan. 5; 318(1):214-23. Other useful promoters are described in detail in the Examples below.

A promoter can generally be characterized as either constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule (e.g, glucose, as in SEQ ID NO:1), temperature (heat or cold), lack of nitrogen in culture media, etc. Suitable promoters can activate transcription of an essentially silent gene or upregulate, preferably substantially, transcription of an operably linked gene that is transcribed at a low level. Examples below describe additional inducible promoters that are useful in *Prototheca* cells.

Inclusion of termination region control sequence is optional, and if employed, then the choice is be primarily one of convenience, as the termination region is relatively interchangeable. The termination region may be native to the transcriptional initiation region (the promoter), may be native to the DNA sequence of interest, or may be obtainable from another source. See, for example, Chen and Orozco, Nucleic Acids Res. (1988) 16:8411.

The present invention also provides control sequences and recombinant genes and vectors containing them that provide for the compartmentalized expression of a gene of interest. Organelles for targeting are chloroplasts, plastids, mitochondria, and endoplasmic reticulum. In addition, the present invention provides control sequences and recombinant genes and vectors containing them that provide for the secretion of a protein outside the cell.

Proteins expressed in the nuclear genome of *Prototheca* can be targeted to the plastid using plastid targeting signals. Plastid targeting sequences endogenous to *Chlorella* are known, such as genes in the *Chlorella* nuclear genome that encode proteins that are targeted to the plastid; see for example GenBank Accession numbers AY646197 and AF499684, and in one embodiment, such control sequences are used in the vectors of the present invention to target expression of a protein to a *Prototheca* plastid.

The Examples below describe the use of algal plastid targeting sequences to target heterologous proteins to the correct compartment in the host cell. cDNA libraries were made using *Prototheca moriformis* and *Chlorella protothecodies* cells and are described in PCT Application No. PCT/US2009/066142.

In another embodiment of the present invention, the expression of a polypeptide in *Prototheca* is targeted to the endoplasmic reticulum. The inclusion of an appropriate retention or sorting signal in an expression vector ensure that proteins are retained in the endoplasmic reticulum (ER) and do not go downstream into Golgi. For example, the IMPACTVECTOR1.3 vector, from Wageningen UR-Plant Research International, includes the well known KDEL retention or sorting signal. With this vector, ER retention has a practical advantage in that it has been reported to improve expression levels 5-fold or more. The main reason for this appears to be that the ER contains lower concentrations and/or different proteases responsible for post-translational degradation of expressed proteins than are present in the cytoplasm. ER retention signals functional in green microalgae are known. For example, see Proc Natl Acad Sci USA. 2005 Apr. 26; 102(17):6225-30.

In another embodiment of the present invention, a polypeptide is targeted for secretion outside the cell into the culture media. See Hawkins et al., Current Microbiology Vol. 38 (1999), pp. 335-341 for examples of secretion signals active in *Chlorella* that can be used, in accordance with the methods of the invention, in *Prototheca*.

Many promoters are active in microalgae, including promoters that are endogenous to the algae being transformed, as well as promoters that are not endogenous to the algae being transformed (i.e., promoters from other algae, promoters from higher plants, and promoters from plant viruses or algae viruses). Exogenous and/or endogenous promoters that are active in microalgae, and antibiotic resistance genes functional in microalgae are described by e.g., Curr Microbiol. 1997 December; 35(6):356-62 (*Chlorella vulgaris*); Mar Biotechnol (NY). 2002 January; 4(1):63-73 (*Chlorella ellipsoidea*); Mol Gen Genet. 1996 Oct. 16; 252(5):572-9 (*Phaeodactylum tricornutum*); Plant Mol Biol. 1996 April; 31(1):1-12 (*Volvox carteri*); Proc Natl Acad Sci USA. 1994 Nov. 22; 91(24):11562-6 (*Volvox carteri*); Falciatore A, Casotti R, Leblanc C, Abrescia C, Bowler C, PMID: 10383998, 1999 May; 1(3):239-251 (Laboratory of Molecular Plant Biology, Stazione Zoologica, Villa Comunale, I-80121 Naples, Italy) (*Phaeodactylum tricornutum* and *Thalassiosira weissflogii*); Plant Physiol. 2002 May; 129(1): 7-12. (*Porphyridium* sp.); Proc Natl Acad Sci USA. 2003 Jan. 21; 100(2):438-42. (*Chlamydomonas reinhardtii*); Proc Natl Acad Sci USA. 1990 February; 87(3):1228-32. (*Chlamydomonas reinhardtii*); Nucleic Acids Res. 1992 Jun. 25; 20(12):2959-65; Mar Biotechnol (NY). 2002 January; 4(1): 63-73 (*Chlorella*); Biochem Mol Biol Int. 1995 August; 36(5):1025-35 (*Chlamydomonas reinhardtii*); J Microbiol. 2005 August; 43(4):361-5 (*Dunaliella*); Yi Chuan Xue Bao. 2005 April; 32(4):424-33 (*Dunaliella*); Mar Biotechnol (NY). 1999 May; 1(3):239-251. (*Thalassiosira* and *Phaedactylum*); Koksharova, Appl Microbiol Biotechnol 2002 February; 58(2):123-37 (various species); Mol Genet Genomics. 2004 February; 271(1):50-9 (*Thermosynechococcus elongates*); J. Bacteriol. (2000), 182, 211-215; FEMS Microbiol Lett. 2003 Apr. 25; 221(2):155-9; Plant Physiol. 1994 June; 105(2):635-41; Plant Mol Biol. 1995 December; 29(5):897-907 (*Synechococcus* PCC 7942); Mar Pollut Bull. 2002; 45(1-12):163-7 (*Anabaena* PCC 7120); Proc Natl Acad Sci USA. 1984 March; 81(5):1561-5 (*Anabaena* (various strains)); Proc Natl Acad Sci USA. 2001 Mar. 27; 98(7):4243-8 (*Synechocystis*); Wirth, Mol Gen Genet 1989 March; 216(1):175-7 (various species); Mol Microbiol, 2002 June; 44(6):1517-31 and Plasmid, 1993 September; 30(2):90-105 (*Fremyella diplosiphon*); Hall et al. (1993) Gene 124: 75-81 (*Chlamydomonas reinhardtii*); Gruber et al. (1991). Current Micro. 22: 15-20; Jarvis et al. (1991) Current Genet. 19: 317-322 (*Chlorella*); for additional promoters see also table 1 from U.S. Pat. No. 6,027,900).

The promoter used to express an exogenous gene can be the promoter naturally linked to that gene or can be a heterologous gene. Some promoters are active in more than one species of microalgae. Other promoters are species-specific. Preferred promoters include promoters such as RBCS2 from *Chlamydomonas reinhardtii* and viral promoters, such as cauliflower mosaic virus (CMV) and *chlorella* virus, which have been shown to be active in multiple species of microalgae (see for example Plant Cell Rep. 2005 March; 23(10-11):727-35; J Microbiol. 2005 August; 43(4): 361-5; Mar Biotechnol (NY). 2002 January; 4(1):63-73). In other embodiments, the *Botryococcus* malate dehydrogenase promoter, such a nucleic acid comprising any part of SEQ ID NO: 150, or the *Chlamydomonas reinhardtii* RBCS2 promoter (SEQ ID NO: 151) can be used. Optionally, at least 10, 20, 30, 40, 50, or 60 nucleotides or more of these sequences containing a promoter are used. Preferred promoters endogenous to species of the genus *Chlorella* are SEQ ID NO:1 and SEQ ID NO:2.

Preferred promoters useful for expression of exogenous genes in *Chlorella* are listed in the sequence listing of this application, such as the promoter of the *Chlorella* HUP1 gene (SEQ ID NO:1) and the *Chlorella ellipsoidea* nitrate reductase promoter (SEQ ID NO:2). *Chlorella* virus promoters can also be used to express genes in *Chlorella*, such as SEQ ID NOs: 1-7 of U.S. Pat. No. 6,395,965. Additional promoters active in *Chlorella* can be found, for example, in Biochem Biophys Res Commun. 1994 Oct. 14; 204(1):187-94; Plant Mol Biol. 1994 October; 26(1):85-93; Virology. 2004 Aug. 15; 326(1):150-9; and Virology. 2004 Jan. 5; 318(1):214-23.

B. Genes and Codon Optimization

Typically, a gene includes a promoter, coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated, in which case, the vector typically includes an origin of replication, which is capable of providing for replication of the heterologous vector DNA.

A common gene present on a vector is a gene that codes for a protein, the expression of which allows the recombinant cell containing the protein to be differentiated from cells that do not express the protein. Such a gene, and its corresponding gene product, is called a selectable marker. Any of a wide variety of selectable markers can be employed in a transgene construct useful for transforming Prototheca. Examples of suitable selectable markers include the G418 resistance gene, the nitrate reductase gene (see Dawson et al. (1997), Current Microbiology 35:356-362), the hygromycin phosphotransferase gene (HPT; see Kim et al. (2002), Mar. Biotechnol. 4:63-73), the neomycin phosphotransferase gene, the ble gene, which confers resistance to phleomycin (Huang et al. (2007), Appl. Microbiol. Biotechnol. 72:197-205), and the aminoglycoside-3'-O-phosphotransferase (SEQ ID NO: 194), which confers resistance to kanamycin. Methods of determining sensitivity of microalgae to antibiotics are well known. For example, Mol Gen Genet. 1996 Oct. 16; 252(5):572-9.

Other selectable markers that are not antibiotic-based can also be employed in a transgene construct useful for transforming microalgae in general, including Prototheca species. Genes that confers the ability to utilize certain carbon sources that were previously unable to be utilized by the microalgae can also be used as a selectable marker. By way of illustration, Prototheca moriformis strains typically grow poorly, if at all, on sucrose. Using a construct containing a sucrose invertase gene can confer the ability of positive transformants to grow on sucrose as a carbon substrate. Additional details on using sucrose utilization as a selectable marker along with other selectable markers are discussed in Section IV below.

For purposes of the present invention, the expression vector used to prepare a recombinant host cell of the invention will include at least two, and often three, genes, if one of the genes is a selectable marker. For example, a genetically engineered Prototheca of the invention can be made by transformation with vectors of the invention that comprise, in addition to a selectable marker, one or more exogenous genes, such as, for example, sucrose invertase gene or acyl ACP-thioesterase gene. One or both genes can be expressed using an inducible promoter, which allows the relative timing of expression of these genes to be controlled to enhance the lipid yield and conversion to fatty acid esters. Expression of the two or more exogenous genes may be under control of the same inducible promoter or under control of different inducible (or constitutive) promoters. In the latter situation, expression of a first exogenous gene can be induced for a first period of time (during which expression of a second exogenous gene may or may not be induced) and expression of a second exogenous gene can be induced for a second period of time (during which expression of a first exogenous gene may or may not be induced).

In other embodiments, the two or more exogenous genes (in addition to any selectable marker) are: a fatty acyl-ACP thioesterase and a fatty acyl-CoA/aldehyde reductase, the combined action of which yields an alcohol product. Further provided are other combinations of exogenous genes, including without limitation, a fatty acyl-ACP thioesterase and a fatty acyl-CoA reductase to generate aldehydes. In one embodiment, the vector provides for the combination of a fatty acyl-ACP thioesterase, a fatty acyl-CoA reductase, and a fatty aldehyde decarbonylase to generate alkanes. In each of these embodiments, one or more of the exogenous genes can be expressed using an inducible promoter.

Other illustrative vectors of the invention that express two or more exogenous genes include those encoding both a sucrose transporter and a sucrose invertase enzyme and those encoding both a selectable marker and a secreted sucrose invertase. The recombinant Prototheca transformed with either type of vector produce lipids at lower manufacturing cost due to the engineered ability to use sugar cane (and sugar cane-derived sugars) as a carbon source. Insertion of the two exogenous genes described above can be combined with the disruption of polysaccharide biosynthesis through directed and/or random mutagenesis, which steers ever greater carbon flux into lipid production. Individually and in combination, trophic conversion, engineering to alter lipid production and treatment with exogenous enzymes alter the lipid composition produced by a microorganism. The alteration can be a change in the amount of lipids produced, the amount of one or more hydrocarbon species produced relative to other lipids, and/or the types of lipid species produced in the microorganism. For example, microalgae can be engineered to produce a higher amount and/or percentage of TAGs.

For optimal expression of a recombinant protein, it is beneficial to employ coding sequences that produce mRNA with codons preferentially used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the heterologous mRNA resulting in ribosomal stalling and termination and possible instability of the transgenic mRNA.

The present invention provides codon-optimized nucleic acids useful for the successful expression of recombinant proteins in Prototheca. Codon usage in Prototheca species was analyzed by studying cDNA sequences isolated from Prototheca moriformis. This analysis represents the interrogation over 24,000 codons and resulted in Table 2 below.

TABLE 2

Preferred codon usage in Prototheca strains.

| Ala | GCG | 345 (0.36) |
|---|---|---|
|  | GCA | 66 (0.07) |
|  | GCT | 101 (0.11) |
|  | GCC | 442 (0.46) |
| Cys | TGT | 12 (0.10) |
|  | TGC | 105 (0.90) |
| Asp | GAT | 43 (0.12) |
|  | GAC | 316 (0.88) |
| Glu | GAG | 377 (0.96) |
|  | GAA | 14 (0.04) |
| Phe | TTT | 89 (0.29) |
|  | TTC | 216 (0.71) |

TABLE 2-continued

Preferred codon usage in Prototheca strains.

| | | | |
|---|---|---|---|
| Gly | GGG | 92 | (0.12) |
| | GGA | 56 | (0.07) |
| | GGT | 76 | (0.10) |
| | GGC | 559 | (0.71) |
| His | CAT | 42 | (0.21) |
| | CAC | 154 | (0.79) |
| Ile | ATA | 4 | (0.01) |
| | ATT | 30 | (0.08) |
| | ATC | 338 | (0.91) |
| Lys | AAG | 284 | (0.98) |
| | AAA | 7 | (0.02) |
| Leu | TTG | 26 | (0.04) |
| | TTA | 3 | (0.00) |
| | CTG | 447 | (0.61) |
| | CTA | 20 | (0.03) |
| | CTT | 45 | (0.06) |
| | CTC | 190 | (0.26) |
| Met | ATG | 191 | (1.00) |
| Asn | AAT | 8 | (0.04) |
| | AAC | 201 | (0.96) |
| Pro | CCG | 161 | (0.29) |
| | CCA | 49 | (0.09) |
| | CCT | 71 | (0.13) |
| | CCC | 267 | (0.49) |
| Gln | CAG | 226 | (0.82) |
| | CAA | 48 | (0.18) |
| Arg | AGG | 33 | (0.06) |
| | AGA | 14 | (0.02) |
| | CGG | 102 | (0.18) |
| | CGA | 49 | (0.08) |
| | CGT | 51 | (0.09) |
| | CGC | 331 | (0.57) |
| Ser | AGT | 16 | (0.03) |
| | AGC | 123 | (0.22) |
| | TCG | 152 | (0.28) |
| | TCA | 31 | (0.06) |
| | TCT | 55 | (0.10) |
| | TCC | 173 | (0.31) |
| Thr | ACG | 184 | (0.38) |
| | ACA | 24 | (0.05) |
| | ACT | 21 | (0.05) |
| | ACC | 249 | (0.52) |
| Val | GTG | 308 | (0.50) |
| | GTA | 9 | (0.01) |
| | GTT | 35 | (0.06) |
| | GTC | 262 | (0.43) |
| Trp | TGG | 107 | (1.00) |
| Tyr | TAT | 10 | (0.05) |
| | TAC | 180 | (0.95) |
| Stop | TGA/TAG/TAA | | |

In other embodiments, the gene in the recombinant vector has been codon-optimized with reference to a microalgal strain other than a Prototheca strain. For example, methods of recoding genes for expression in microalgae are described in U.S. Pat. No. 7,135,290. Additional information for codon optimization is available, e.g., at the codon usage database of GenBank.

Other non-limiting examples of codon usage in Chlorella pyrenoidosa, Dunaliella salina, and Chlorella protothecoides are shown in Tables 28, 29, and 30, respectively.

TABLE 28

Codon usage in Chlorella pyrenoidosa.

| | | | |
|---|---|---|---|
| Phe | UUU | 39 | (0.82) |
| | UUC | 56 | (1.18) |
| Leu | UUA | 10 | (0.20) |
| | UUG | 46 | (0.91) |
| Tyr | UAU | 15 | (0.59) |
| | UAC | 36 | (1.41) |
| ter | UAA | 9 | (0.00) |
| ter | UAG | 15 | (0.00) |
| Leu | CUU | 49 | (0.97) |
| | CUC | 73 | (1.45) |
| | CUA | 22 | (0.44) |
| | CUG | 103 | (2.04) |
| His | CAU | 50 | (0.88) |
| | CAC | 3 | (1.12) |
| Gln | CAA | 59 | (0.84) |
| | CAG | 2 | (1.16) |
| Ile | AUU | 24 | (0.69) |
| | AUC | 61 | (1.76) |
| | AUA | 19 | (0.55) |
| Met | AUG | 42 | (1.00) |
| Asn | AAU | 26 | (0.75) |
| | AAC | 3 | (1.25) |
| Lys | AAA | 32 | (0.54) |
| | AAG | 86 | (1.46) |
| Val | GUU | 36 | (0.75) |
| | GUC | 54 | (1.13) |
| | GUA | 30 | (0.63) |
| | GUG | 71 | (1.49) |
| Asp | GAU | 60 | (0.95) |
| | GAC | 66 | (1.05) |
| Glu | GAA | 41 | (0.68) |
| | GAG | 80 | (1.32) |
| Ser | UCU | 50 | (1.04) |
| | UCC | 60 | (1.25) |
| | UCA | 6 | (0.96) |
| | UCG | 43 | (0.89) |
| Cys | UGU | 46 | (0.77) |
| | UGC | 73 | (1.23) |
| ter | UGA | 43 | (0.00) |
| Trp | UGG | 69 | (1.00) |
| Pro | CCU | 80 | (0.98) |
| | CCC | 88 | (1.08) |
| | CCA | 93 | (1.14) |
| | CCG | 65 | (0.80) |
| Arg | CGU | 39 | (0.76) |
| | CGC | 63 | (1.23) |
| | CGA | 46 | (0.90) |
| | CGG | 47 | (0.92) |

TABLE 28-continued

Codon usage in *Chlorella pyrenoidosa*.

| | | | |
|---|---|---|---|
| Thr | ACU | 32 | (0.67) |
| | ACC | 76 | (1.60) |
| | ACA | 41 | (0.86) |
| | ACG | 41 | (0.86) |
| Ser | AGU | 23 | (0.48) |
| | AGC | 67 | (1.39) |
| Arg | AGA | 51 | (1.00) |
| | AGG | 61 | (1.19) |
| Ala | GCU | 57 | (0.79) |
| | GCC | 97 | (1.34) |
| | GCA | 89 | (1.23) |
| | GCG | 47 | (0.65) |
| Gly | GGU | 35 | (0.60) |
| | GGC | 78 | (1.33) |
| | GGA | 54 | (0.92) |
| | GGG | 67 | (1.15) |

TABLE 29

Preferred codon usage in *Dunaliella salina*.

TTC (Phe)
TGG (Trp)
CTG (Leu)
AAC (Asn)
GCC (Ala)
GAG (Glu)
TAC (Tyr)
CCC (Pro)
CAG (Gln)
AGC (Ser)
GAC (Asp)
TGC (Cys)
CAC (His)
ATC (Ile)
ATG (Met)
GGC (Gly)
TAA (Stop)
CGC (Arg)
ACC (Thr)
AAG (Lys)
GTG (Val)

TABLE 30

Preferred codon usage in *Chlorella protothecoides*.

TTC (Phe)
TGG (Trp)

TABLE 30-continued

Preferred codon usage in *Chlorella protothecoides*.

CTG (Leu)
GAC (Asp)
GCC (Ala)
GAG (Glu)
TAC (Tyr)
CCC (Pro)
CAG (Gln)
TCC (Ser)
AAC (Asn)
TGC (Cys)
CAC (His)
ATC (Ile)
ATG (Met)
GGC (Gly)
TGA (Stop)
CGC (Arg)
ACC (Thr)
AAG (Lys)
GTG (Val)

C. Inducible Expression

The present invention also provides for the use of an inducible promoter to express a gene of interest. In particular, the use of an inducible promoter to express a lipase gene permits production of the lipase after growth of the microorganism when conditions have been adjusted, if necessary, to enhance transesterification, for example, after disruption of the cells, reduction of the water content of the reaction mixture, and/or addition sufficient alcohol to drive conversion of TAGs to fatty acid esters.

Inducible promoters useful in the invention include those that mediate transcription of an operably linked gene in response to a stimulus, such as an exogenously provided small molecule (e.g, glucose, as in SEQ ID NO:1), temperature (heat or cold), light, etc. Suitable promoters can activate transcription of an essentially silent gene or upregulate, preferably substantially, transcription of an operably linked gene that is transcribed at a low level. In the latter case, the level of transcription of the lipase preferably does not significantly interfere with the growth of the microorganism in which it is expressed.

Expression of transgenes in *Chlorella* can be performed inducibly through promoters such as the promoter that drives the *Chlorella* hexose transporter gene (SEQ ID NO:1). This promoter is strongly activated by the presence of glucose in the culture media.

D. Expression of Two or More Exogenous Genes

Further, a genetically engineered microorganism, such as a microalgae, may comprise and express two or more exogenous genes, such as, for example, a lipase and a lytic gene, e.g., one encoding a polysaccharide-degrading enzyme. One or both genes can be expressed using an inducible promoter, which allows the relative timing of expression of these genes to be controlled to enhance the lipid yield and conversion to fatty acid esters. Expression of the two or more exogenous genes may be under control of the same inducible promoter or under control of a different inducible promoters. In the latter situation, expression of a first exogenous gene can be induced for a first period of time (during which expression of a second exogenous gene may or may not be induced) and expression of a second exogenous gene can be induced for a second period of time (during which expression of a first exogenous gene may or may not be induced). Provided herein are vectors and methods for engineering lipid-producing microbes to metabolize sucrose, which is an advantageous trait because it allows the engineered cells to convert sugar cane feedstocks into lipids.

Also provided herein are genetically engineered strains of microbes (e.g., microalgae, oleaginous yeast, bacteria, or fungi) that express two or more exogenous genes, such as, for example, a fatty acyl-ACP thioesterase and a fatty acyl-CoA/aldehyde reductase, the combined action of which yields an alcohol product. Further provided are other combinations of exogenous genes, including without limitation, a fatty acyl-ACP thioesterase and a fatty acyl-CoA reductase to generate aldehydes. In addition, this application provides for the combination of a fatty acyl-ACP thioesterase, a fatty acyl-CoA reductase, and a fatty aldehyde decarbonylase to generate alkanes. One or more of the exogenous genes can be expressed using an inducible promoter.

Examples of further modifications suitable for use in the present invention are include genetically engineering strains of microalgae to express two or more exogenous genes, one encoding a transporter of a fixed carbon source (such as sucrose) and a second encoding a sucrose invertase enzyme. The resulting fermentable organisms produce hydrocarbons at lower manufacturing cost than what has been obtainable by previously known methods of biological hydrocarbon production. Insertion of the two exogenous genes described above can be combined with the disruption of polysaccharide biosynthesis through directed and/or random mutagenesis, which steers ever greater carbon flux into hydrocarbon production. Individually and in combination, trophic conversion, engineering to alter hydrocarbon production and treatment with exogenous enzymes alter the hydrocarbon composition produced by a microorganism. The alteration can be a change in the amount of hydrocarbons produced, the amount of one or more hydrocarbon species produced relative to other hydrocarbons, and/or the types of hydrocarbon species produced in the microorganism. For example, microalgae can be engineered to produce a higher amount and/or percentage of TAGs.

E. Compartmentalized Expression

The present invention also provides for compartmentalized expression of a gene of interest. In particular, it can be advantageous, in particular embodiments, to target expression of the lipase to one or more cellular compartments, where it is sequestered from the majority of cellular lipids until initiation of the transesterification reaction. Preferred organelles for targeting are chloroplasts, mitochondria, and endoplasmic reticulum.

(1) Expression in Chloroplasts

In one embodiment of the present invention, the expression of a polypeptide in a microorganism is targeted to chloroplasts. Methods for targeting expression of a heterologous gene to the chloroplast are known and can be employed in the present invention. Methods for targeting foreign gene products into chloroplasts are described in Shrier et al., EMBO J. (1985) 4:25 32. See also Tomai et al. Gen. Biol. Chem. (1988) 263:15104 15109 and U.S. Pat. No. 4,940,835 for the use of transit peptides for translocating nuclear gene products into the chloroplast. Methods for directing the transport of proteins to the chloroplast are also reviewed in Kenauf TIBTECH (1987) 5:40 47. Chloroplast targeting sequences endogenous to *Chlorella* are known, such as genes in the *Chlorella* nuclear genome that encode proteins that are targeted to the chloroplast; see for example GenBank Accession numbers AY646197 and AF499684.

Wageningen UR-Plant Research International sells an IMPACTVECTOR1.4 vector, which uses the secretion signal of the *Chrysanthemum morifolium* small subunit protein to deliver a heterologous protein into the chloroplast stroma (cytoplasmic) environment, shuttling across a double membrane system. The protein is fused to the first 11 amino acids of the mature rubisco protein in order to allow proper processing of the signal peptide (Wong et al., Plant Molecular Biology 20: 81-93 (1992)). The signal peptide contains a natural intron from the RbcS gene.

In another approach, the chloroplast genome is genetically engineered to express the heterologous protein. Stable transformation of chloroplasts of *Chlamydomonas reinhardtii* (a green alga) using bombardment of recipient cells with high-velocity tungsten microprojectiles coated with foreign DNA has been described. See, for example, Boynton et al., Science (1988) 240: 1534 1538; Blowers et al. Plant Cell (1989) 1:123 132 and Debuchy et al., EMBO J. (1989) 8: 2803 2809. The transformation technique, using tungsten microprojectiles, is described by Klein et al., Nature (London) (1987) 7:70 73. Other methods of chloroplast transformation for both plants and microalgae are known. See for example U.S. Pat. Nos. 5,693,507; 6,680,426; and Plant Physiol. 2002 May; 129(1):7-12; and Plant Biotechnol J. 2007 May; 5(3):402-12.

As described in U.S. Pat. No. 6,320,101 (issued Nov. 20, 2001 to Kaplan et al.; which is incorporated herein by reference), cells can be chemically treated so as to reduce the number of chloroplasts per cell to about one. Then, the heterologous nucleic acid can be introduced into the cells via particle bombardment with the aim of introducing at least one heterologous nucleic acid molecule into the chloroplasts. The heterologous nucleic acid is selected such that it is integratable into the chloroplast's genome via homologous recombination which is readily effected by enzymes inherent to the chloroplast. To this end, the heterologous nucleic acid includes, in addition to a gene of interest, at least one nucleic acid sequence that is derived from the chloroplast's genome. In addition, the heterologous nucleic acid typically includes a selectable marker. Further details relating to this technique are found in U.S. Pat. Nos. 4,945,050 and 5,693,507 which are incorporated herein by reference. A polypeptide can thus be produced by the protein expression system of the chloroplast.

U.S. Pat. No. 7,135,620 (issued Nov. 14, 2006 to Daniell et al.; incorporated herein by reference) describes chloroplast expression vectors and related methods. Expression cassettes are DNA constructs including a coding sequence and appropriate control sequences to provide for proper expression of the coding sequence in the chloroplast. Typical expression cassettes include the following components: the 5' untranslated region from a microorganism gene or chloroplast gene such as psbA which will provide for transcription and translation of a DNA sequence encoding a polypeptide of interest in the chloroplast; a DNA sequence encoding a polypeptide of interest; and a translational and transcriptional termination region, such as a 3' inverted repeat region of a chloroplast gene that can stabilize RNA of introduced genes, thereby enhancing foreign gene expression. The cassette can optionally include an antibiotic resistance gene.

Typically, the expression cassette is flanked by convenient restriction sites for insertion into an appropriate genome. The expression cassette can be flanked by DNA sequences from chloroplast DNA to facilitate stable integration of the expression cassette into the chloroplast genome, particularly by homologous recombination. Alternatively, the expression cassette may remain unintegrated, in which case, the expression cassette typically includes a chloroplast origin of replication, which is capable of providing for replication of the heterologous DNA in the chloroplast.

The expression cassette generally includes a promoter region from a gene capable of expression in the chloroplast. The promoter region may include promoters obtainable from chloroplast genes, such as the psbA gene from spinach or pea, or the rbcL and atpB promoter region from maize and Rma promoters. Examples of promoters are described in Hanley-Bowdoin and Chua, TIBS (1987) 12:67 70; Mullet et al., Plant Molec Biol. (1985) 4: 39 54; Hanley-Bowdoin (1986) PhD. Dissertation, the Rockefeller University; Krebbers et al., Nucleic Acids Res. (1982) 10: 4985 5002; Zurawaki et al., Nucleic Acids Res. (1981) 9:3251 3270; and Zurawski et al., Proc. Nat'l Acad Sci. U.S.A. (1982) 79: 7699 7703. Other promoters can be identified and the relative strength of promoters so identified evaluated, by placing a promoter of interest 5' to a promoterless marker gene and observing its effectiveness relative to transcription obtained from, for example, the promoter from the psbA gene, a relatively strong chloroplast promoter. The efficiency of heterologous gene expression additionally can be enhanced by any of a variety of techniques. These include the use of multiple promoters inserted in tandem 5' to the heterologous gene, for example a double psbA promoter, the addition of enhancer sequences and the like.

Numerous promoters active in the *Chlorella* chloroplast can be used for expression of exogenous genes in the *Chlorella* chloroplast, such as those found in GenBank accession number NC_001865 (*Chlorella vulgaris* chloroplast, complete genome), Where it is desired to provide for inducible expression of the heterologous gene, an inducible promoter and/or a 5' untranslated region containing sequences which provide for regulation at the level of transcription and/or translation (at the 3' end) may be included in the expression cassette. For example, the 5' untranslated region can be from a gene wherein expression is regulatable by light. Similarly, 3' inverted repeat regions could be used to stabilize RNA of heterologous genes. Inducible genes may be identified by enhanced expression in response to a particular stimulus of interest and low or absent expression in the absence of the stimulus. For example, a light-inducible gene can be identified where enhanced expression occurs during irradiation with light, while substantially reduced expression or no expression occurs in low or no light. Light regulated promoters from green microalgae are known (see for example Mol Genet Genomics. 2005 December; 274(6):625-36).

The termination region which is employed will be primarily one of convenience, since the termination region appears to be relatively interchangeable among chloroplasts and bacteria. The termination region may be native to the transcriptional initiation region, may be native to the DNA sequence of interest, or may be obtainable from another source. See, for example, Chen and Orozco, Nucleic Acids Res. (1988) 16:8411.

The expression cassettes may be transformed into a plant cell of interest by any of a number of methods. These methods include, for example, biolistic methods (See, for example, Sanford, Trends In Biotech. (1988) 6:299 302, U.S. Pat. No. 4,945,050; electroporation (Fromm et al., Proc. Nat'l. Acad. Sci. (USA) (1985) 82:5824 5828); use of a laser beam, microinjection or any other method capable of introducing DNA into a chloroplast.

Additional descriptions of chloroplast expression vectors suitable for use in microorganisms such as microalgae are found in U.S. Pat. No. 7,081,567 (issued Jul. 25, 2006 to Xue et al.); U.S. Pat. No. 6,680,426 (issued Jan. 20, 2004 to Daniell et al.); and U.S. Pat. No. 5,693,507 (issued Dec. 2, 1997 to Daniell et al.).

Proteins expressed in the nuclear genome of *Chlorella* can be targeted to the chloroplast using chloroplast targeting signals. Chloroplast targeting sequences endogenous to *Chlorella* are known, such as genes in the *Chlorella* nuclear genome that encode proteins that are targeted to the chloroplast; see for example GenBank Accession numbers AY646197 and AF499684. Proteins can also be expressed in the *Chlorella* chloroplast by insertion of genes directly into the chloroplast genome. Chloroplast transformation typically occurs through homologous recombination, and can be performed if chloroplast genome sequences are known for creation of targeting vectors (see for example the complete genome sequence of a *Chlorella* chloroplast; Genbank accession number NC_001865). See previous sections herein for details of chloroplast transformation.

(2) Expression in Mitochondria

In another embodiment of the present invention, the expression of a polypeptide in a microorganism is targeted to mitochondria. Methods for targeting foreign gene products into mitochnodria (Boutry et al. Nature (London) (1987) 328:340 342) have been described, including in green microalgae (see for example Mol Gen Genet. 1993 January; 236(2-3):235-44).

For example, an expression vector encoding a suitable secretion signal can target a heterologus protein to the mitochondrion. The IMPACTVECTOR1.5 vector, from Wageningen UR-Plant Research International, uses the yeast CoxIV secretion signal, which was shown to deliver proteins in the mitochondrial matrix. The protein is fused to the first 4 amino acids of the yeast CoxIV protein in order to allow proper processing of the signal peptide (Kohler et al. Plant J 11: 613-621 (1997)). Other mitochondrial targeting sequences are known, including those functional in green microalgae. For example, see FEBS Lett. 1990 Jan. 29; 260(2):165-8; and J Biol Chem. 2002 Feb. 22; 277(8):6051-8.

Proteins expressed in the nuclear genome of *Chlorella* can be targeted to the mitochondria using mitochondrial targeting signals. See previous sections herein for details of mitochondrial protein targeting and transformation.

(3) Expression in Endoplasmic Reticulum

In another embodiment of the present invention, the expression of a polypeptide in a microorganism is targeted to the endoplasmic reticulum. The inclusion of an appropriate retention or sorting signal in an expression vector ensure that proteins are retained in the endoplasmic reticulum (ER) and do not go downstream into Golgi. For example, the IMPACTVECTOR1.3 vector, from Wageningen UR-Plant Research International, includes the well known KDEL retention or sorting signal. With this vector, ER retention has a practical advantage in that it has been reported to improve expression levels 5-fold or more. The main reason for this appears to be that the ER contains lower concentrations and/or different proteases responsible for post-translational degradation of expressed proteins than are present in the cytoplasm. ER retention signals functional in green microalgae are known. For example, see Proc Natl Acad Sci USA. 2005 Apr. 26; 102(17):6225-30.

While the methods and materials of the invention allow for the introduction of any exogenous gene into a microorganism, for example *Prototheca*, genes relating to sucrose utilization and lipid pathway modification are of particular interest, as discussed in the following sections.

IV. SELECTABLE MARKERS

1. Sucrose Utilization

In embodiment, the recombinant *Prototheca* cell of the invention further contains one or more exogenous sucrose utilization genes. In various embodiments, the one or more genes encode one or more proteins selected from the group consisting of a fructokinase, a glucokinase, a hexokinase, a sucrose invertase, a sucrose transporter. For example, expression of a sucrose transporter and a sucrose invertase allows *Prototheca* to transport sucrose into the cell from the culture media and hydrolyze sucrose to yield glucose and fructose. Optionally, a fructokinase can be expressed as well in instances where endogenous hexokinase activity is insufficient for maximum phosphorylation of fructose. Examples of suitable sucrose transporters are Genbank accession numbers CAD91334, CAB92307, and CAA53390. Examples of suitable fructokinases are Genbank accession numbers P26984, P26420 and CAA43322.

In one embodiment, the present invention provides a *Prototheca* host cell that secretes a sucrose invertase. Secretion of a sucrose invertase obviates the need for expression of a transporter that can transport sucrose into the cell. This is because a secreted invertase catalyzes the conversion of a molecule of sucrose into a molecule of glucose and a molecule of fructose, both of which can be transported and utilized by microbes provided by the invention. For example, expression of a sucrose invertase (such as SEQ ID NO:3) with a secretion signal (such as that of SEQ ID NO: 4 (from yeast), SEQ ID NO: 5 (from higher plants), SEQ ID NO: 6 (eukaryotic consensus secretion signal), and SEQ ID NO: 7 (combination of signal sequence from higher plants and eukaryotic consensus) generates invertase activity outside the cell. Expression of such a protein, as enabled by the genetic engineering methodology disclosed herein, allows cells already capable of utilizing extracellular glucose as an energy source to utilize sucrose as an extracellular energy source.

*Prototheca* species expressing an invertase in media containing sucrose are a preferred microalgal species for the production of oil. The expression and extracellular targeting of this fully active protein allows the resulting host cells to grow on sucrose, whereas their non-transformed counterparts cannot. Thus, the present invention provides *Prototheca* recombinant cells with a codon-optimized invertase gene, including but not limited to the yeast invertase gene, integrated into their genome such that the invertase gene is expressed as assessed by invertase activity and sucrose hydrolysis. The present invention also provides invertase genes useful as selectable markers in *Prototheca* recombinant cells, as such cells are able to grow on sucrose, while their non-transformed counterparts cannot; and methods for selecting recombinant host cells using an invertase as a powerful, selectable marker for algal molecular genetics.

The successful expression of a sucrose invertase in *Prototheca* also illustrates another aspect of the present invention in that it demonstrates that heterologous (recombinant) proteins can be expressed in the algal cell and successfully transit outside of the cell and into the culture medium in a fully active and functional form. Thus, the present invention provides methods and reagents for expressing a wide and diverse array of heterologous proteins in microalgae and secreting them outside of the host cell. Such proteins include, for example, industrial enzymes such as, for example, lipases, proteases, cellulases, pectinases, amylases (e.g., SEQ ID NO: 190-191), esterases, oxidoreductases, transferases, lactases, isomerases, and invertases, as well as therapeutic proteins such as, for example, growth factors, cytokines, full length antibodies comprising two light and two heavy chains, Fabs, scFvs (single chain variable fragment), camellid-type antibodies, antibody fragments, antibody fragment-fusions, antibody-receptor fusions, insulin, interferons, and insulin-like growth factors.

The successful expression of a sucrose invertase in *Prototheca* also illustrates another aspect of the present invention in that it provides methods and reagents for the use of fungal transit peptides in algae to direct secretion of proteins in *Prototheca*; and methods and reagents for determining if a peptide can function, and the ability of it to function, as a transit peptide in *Prototheca* cells. The methods and reagents of the invention can be used as a tool and platform to identify other transit peptides that can successfully traffic proteins outside of a cell, and that the yeast invertase has great utility in these methods. As demonstrated in this example, removal of the endogenous yeast invertase transit peptide and its replacement by other transit peptides, either endogenous to the host algae or from other sources (eukaryotic, prokaryotic and viral), can identify whether any peptide of interest can function as a transit peptide in guiding protein egress from the cell.

Examples of suitable sucrose invertases include those identified by Genbank accession numbers CAB95010, NP_012104 and CAA06839. Non-limiting examples of suitable invertases are listed below in Table 3 Amino acid sequences for each listed invertase are included in the Sequence Listing below. In some cases, the exogenous sucrose utilization gene suitable for use in the methods and vectors of the invention encodes a sucrose invertase that has at least 40, 50, 60, 75, or 90% or higher amino acid identity with a sucrose invertase selected from Table 3.

TABLE 3

| | Sucrose invertases. | | |
|---|---|---|---|
| Description | Organism | GenBank Accession No. | SEQ ID NO: |
| Invertase | *Chicorium intybus* | Y11124 | SEQ ID NO: 20 |
| Invertase | *Schizosaccharomyces pombe* | AB011433 | SEQ ID NO: 21 |

TABLE 3-continued

Sucrose invertases.

| Description | Organism | GenBank Accession No. | SEQ ID NO: |
|---|---|---|---|
| beta-fructofuranosidase (invertase) | Pichia anomala | X80640 | SEQ ID NO: 22 |
| Invertase | Debaryomyces occidentalis | X17604 | SEQ ID NO: 23 |
| Invertase | Oryza sativa | AF019113 | SEQ ID NO: 24 |
| Invertase | Allium cepa | AJ006067 | SEQ ID NO: 25 |
| Invertase | Beta vulgaris subsp. Vulgaris | AJ278531 | SEQ ID NO: 26 |
| beta-fructofuranosidase (invertase) | Bifidobacterium breve UCC2003 | AAT28190 | SEQ ID NO: 27 |
| Invertase | Saccharomyces cerevisiae | NP_012104 | SEQ ID NO: 8 (nucleotide) SEQ ID NO: 28 (amino acid) |
| Invertase A | Zymomonas mobilis | AAO38865 | SEQ ID NO: 29 |
| Invertase | Arabadopsis thaliana | NP_566464 | SEQ ID NO: 188 |

The secretion of an invertase to the culture medium by Prototheca enable the cells to grow as well on waste molasses from sugar cane processing as they do on pure reagent-grade glucose; the use of this low-value waste product of sugar cane processing can provide significant cost savings in the production of lipids and other oils. Thus, the present invention provides a microbial culture containing a population of Prototheca microorganisms, and a culture medium comprising (i) sucrose and (ii) a sucrose invertase enzyme. In various embodiments the sucrose in the culture comes from sorghum, sugar beet, sugar cane, molasses, or depolymerized cellulosic material (which may optionally contain lignin). In another aspect, the methods and reagents of the invention significantly increase the number and type of feedstocks that can be utilized by recombinant Prototheca. While the microbes exemplified here are altered such that they can utilize sucrose, the methods and reagents of the invention can be applied so that feedstocks such as cellulosics are utilizable by an engineered host microbe of the invention with the ability to secrete cellulases, pectinases, isomerases, or the like, such that the breakdown products of the enzymatic reactions are no longer just simply tolerated but rather utilized as a carbon source by the host. An example of this is described below and in the Examples of microbes engineered to express a secretable α-galactosidase, conferring the ability to hydrolyze α-galactosyl bonds in oligosaccharides such as those contained in raffinose and stachyose which are two oligosaccharides found in agricultural waste streams.

2. Alpha-Galactosidase Expression

While the expression of a sucrose invertase, as described above, confers the ability for Prototheca cells to more efficiently utilize sucrose as a carbon source (via the enzyme hydrolyzing the α-linkage between fructose and glucose molecules in the disaccharide sucrose), the expression of other enzymes that hydrolyze other types of α-linkages in oligosaccharides can confer the ability for Prototheca cells to utilize other carbon sources. The expression of these enzymes (and the resulting ability to utilize carbon sources that Prototheca and other microalgal cells ordinarily would not be able to) can be used as a selectable marker for these transgenic Prototheca cells by allowing for the selection of positive clones that are able to grow on these carbon sources.

In an embodiment, the recombinant Prototheca cell of the invention further contains one or more exogenous genes encoding polysaccharide-degrading enzymes. In various embodiments, the one or more genes encoding a polysaccharide-degrading enzyme is a gene encoding a secreted α-galactosidase. The expression of an exogenous secreted α-galactosidase in a Prototheca cell confers the ability of such transformed strains to grow on sugars (carbon sources) containing D-galactosyl linkages, such as α-linkages between galactose and glucose monosaccharide units. Prototheca strains expressing an exogenous, secreted α-galactosidase will be able to utilize disaccharides such as melibiose (disaccharide composed of α-D-galactose-glucose).

Sugars such as raffinose (a trisaccharide comprised of α-linked galactose-glucose-fructose) and stachyose (a tetrasaccharide composed to two α-linked D-galactose units, followed by α-linked glucose and fructose) are present in significant proportions in agricultural waste streams such as beet pulp (raffinose) and soybean meal (stachyose). Such agricultural residues represent a significant untapped carbon source for the conversion into oil by microbes (including Prototheca) capable of utilizing them.

Prototheca strains are unable to utilize oligosaccharides such as raffinose and stachyose in any significant quantity or at all. In the case of raffinose and stachyose, although transgenic strains expressing a sucrose invertase (as described above) have the ability to hydrolyze the α-linkage between fructose and glucose in α-galactosyl derivatives of sucrose, but the remainder of the oligosaccharide remains unutilized, as sucrose invertase will not cleave the remaining α-linkages in such sugars and the resulting disaccharides are not utilizable. In another embodiment, the recombinant Prototheca cell of the invention comprises both an exogenous gene encoding a sucrose invertase and an exogenous gene encoding an α-galactosidase. Thus, strains expressing both a sucrose invertase and an α-galactosidase will be capable of fully hydrolyzing oligosaccharides such as raffinose and stachyose, enabling the consumption of the component monomers. In addition, α-galactosidase encoding genes may be used as a selectable marker for transformation. Clones containing the exogenous α-galactosidase gene will have the ability to grow on melibiose. Examples of suitable α-galactosidase genes for use in Prototheca strains include the MEL1 gene from Saccharomyces carlbergensis, the Ag/C gene from Aspergillus niger. Interestingly, not all α-galactosidase genes are functional in Prototheca species, even if the genes are optimized according to the preferred codon usage in Prototheca strains. The Examples below demonstrates the ability of transgenic Pro-

*totheca* cells to grow on melibiose when transformed with codon-optimized MEL1 gene from *S. carlbergensis* and the AglC gene from *A. niger*, but not an α-galactosidase encoding gene from the higher plant, *Cyamopsis tetragonobola* (Guar bean).

3. Thiamine Auxotrophy Complementation

*Prototheca* strains including *Prototheca moriformis* are known to be thiamine auxotrophic (See, for example, Ciferri, O. (1956) Nature, v. 178, pp. 1475-1476), meaning that these strains require thiamine in the nutrient media for growth Thiamine auxotrophy can be the result of mutations or lack of expression of enzymes in the thiamine biosynthetic pathway. Complemented transgenic strains expressing the missing enzyme(s) in the thiamine biosynthetic pathway can then be grown without added thiamine, thus reducing the cost of the nutrient media as well as rendering the resulting microalgal biomass more desirable from an animal nutrition perspective. Complementation with a thiamine biosynthetic pathway enzyme can also be used as a selectable marker as the transgenic gene confers the ability to grow on plates/media that does not contain thiamine.

In an embodiment, the recombinant *Prototheca* cell of the invention further contains one or more exogenous genes encoding thiamine biosynthetic pathway enzyme. In another embodiment, the recombinant *Prototheca* cell of the invention comprises an exogenous gene encoding hydroxymethylpyrimidine phosphate synthases (e.g., SEQ ID NO: 192) from algal, plant or cyanobacterial sources. In still other embodiments, the hydroxymethylpyrimidine phosphate synthase is encoded by a THIC gene. In still other embodiments, the THIC gene is the *Coccomyxa* C-169 THIC, *Arabidopsis thaliana* THIC, the *Synechocystis* sp. PCC 6803 THIC, or the *Salmonella enterica* subsp. *enterica* serovar *Typhimurium* str.THIC (SEQ ID NO: 193). The Examples below details the engineering of *Prototheca moriformis* UTEX 1435 with restored thiamine prototrophy.

4. Other Selectable Markers

Any of a wide variety of selectable markers can be employed in a transgene construct useful for transforming microorganisms, such as *Chlorella*. Examples of suitable selectable markers include the nitrate reductase gene, the hygromycin phosphotransferase gene (HPT), the neomycin phosphotransferase gene, and the ble gene, which confers resistance to phleomycin. Methods of determining sensitivity of microalgae to antibiotics are well known. For example, Mol Gen Genet. 1996 Oct. 16; 252(5):572-9.

More specifically, Dawson et al. (1997), Current Microbiology 35:356-362 (incorporated by reference herein in its entirety), described the use of the nitrate reductase (NR) gene from *Chlorella vulgaris* as a selectable marker for NR-deficient *Chlorella sorokiniana* mutants. Kim et al. (2002), Mar. Biotechnol. 4:63-73 (incorporated by reference herein in its entirety), disclosed the use of the HPT gene as a selectable marker for transforming *Chorella ellipsoidea*. Huang et al. (2007), Appl. Microbiol. Biotechnol. 72:197-205 (incorporated by reference herein in its entirety), reported on the use of Sh ble as a selectable marker for *Chlorella* sp. DT.

V. LIPID PATHWAY ENGINEERING

In addition to altering the ability of microorganisms (e.g., microalgae, oleaginous yeast, fungi, or bacteria), such as *Prototheca* to utilize feedstocks such as sucrose-containing feedstocks, the present invention also provides recombinant microorganisms (e.g., *Prototheca*) that have been modified to alter the properties and/or proportions of lipids produced. The pathway can further, or alternatively, be modified to alter the properties and/or proportions of various lipid molecules produced through enzymatic processing of lipids and intermediates in the fatty acid pathway. In various embodiments, the recombinant microorganisms (e.g., *Prototheca* cells) of the invention have, relative to their untransformed counterparts, optimized lipid yield per unit volume and/or per unit time, carbon chain length (e.g., for renewable diesel production or for industrial chemicals applications requiring lipid feedstock), reduced number of double or triple bonds, optionally to zero, and increasing the hydrogen:carbon ratio of a particular species of lipid or of a population of distinct lipid. In addition, microorganisms that produce desirable hydrocarbons can be engineered to produce such components in higher quantities, or with greater specificity.

In the case of microalgae, some wild-type cells already have good growth characteristics but do not produce the desired types or quantities of lipids. Examples include, without limitation, *Pyrobotrys, Phormidium, Agmenellum, Carteria, Lepocinclis, Pyrobotrys, Nitzschia, Lepocinclis, Anabaena, Euglena, Spirogyra, Chlorococcum, Tetraedron, Oscillatoria, Phagus,* and *Chlorogonium*, which have the desirable growth characteristic of growing in municipal sewage or wastewater. Such cells, as well as species of *Chlorella, Prototheca* and other microbes, can be engineered to have improved lipid production characteristics. Desired characteristics include optimizing lipid yield per unit volume and/or per unit time, carbon chain length (e.g., for biodiesel production or for industrial applications requiring hydrocarbon feedstock), reducing the number of double or triple bonds, optionally to zero, removing or eliminating rings and cyclic structures, and increasing the hydrogen:carbon ratio of a particular species of lipid or of a population of distinct lipid. In addition, microalgae that produce appropriate hydrocarbons can also be engineered to have even more desirable hydrocarbon outputs. Examples of such microalgae include species of the genus *Chlorella* and the genus *Prototheca*.

In particular embodiments, one or more key enzymes that control branch points in metabolism to fatty acid synthesis have been up-regulated or down-regulated to improve lipid production. Up-regulation can be achieved, for example, by transforming cells with expression constructs in which a gene encoding the enzyme of interest is expressed, e.g., using a strong promoter and/or enhancer elements that increase transcription. Such constructs can include a selectable marker such that the transformants can be subjected to selection, which can result in amplification of the construct and an increase in the expression level of the encoded enzyme. Examples of enzymes suitable for up-regulation according to the methods of the invention include pyruvate dehydrogenase, which plays a role in converting pyruvate to acetyl-CoA (examples, some from microalgae, include Genbank accession numbers NP_415392; AAA53047; Q1XDM1; and CAF05587). Up-regulation of pyruvate dehydrogenase can increase production of acetyl-CoA, and thereby increase fatty acid synthesis. Acetyl-CoA carboxylase catalyzes the initial step in fatty acid synthesis. Accordingly, this enzyme can be up-regulated to increase production of fatty acids (examples, some from microalgae, include Genbank accession numbers BAA94752; AAA75528; AAA81471; YP_537052; YP_536879; NP_045833; and BAA57908). Fatty acid production can also be increased by up-regulation of acyl carrier protein (ACP), which carries the growing acyl chains during fatty acid synthesis (examples, some from microalgae, include Genbank accession numbers A0T0F8; P51280; NP_849041; YP_874433).

Glycerol-3-phosphate acyltransferase catalyzes the rate-limiting step of fatty acid synthesis. Up-regulation of this enzyme can increase fatty acid production (examples, some from microalgae, include Genbank accession numbers AAA74319; AAA33122; AAA37647; P44857; and ABO94442).

Up- and/or down-regulation of genes can be applied to global regulators controlling the expression of the genes of the fatty acid biosynthetic pathways. Accordingly, one or more global regulators of fatty acid synthesis can be up- or down-regulated, as appropriate, to inhibit or enhance, respectively, the expression of a plurality of fatty acid synthetic genes and, ultimately, to increase lipid production. Examples include sterol regulatory element binding proteins (SREBPs), such as SREBP-1a and SREBP-1c (for examples see Genbank accession numbers NP_035610 and Q9WTN3).

The present invention also provides recombinant microorganisms (e.g., *Prototheca* cells) that have been modified to contain one or more exogenous genes encoding lipid modification enzymes such as, for example, fatty acyl-ACP thioesterases (e.g., *C. callophylla* (SEQ ID NO: 145 and SEQ ID NO: 146; see also Table 4), fatty acyl-CoA/aldehyde reductases (see Table 6), fatty acyl-CoA reductases (see Table 7), fatty aldehyde decarbonylase (see Table 8), fatty aldehyde reductases, desaturases (such as stearoyl-ACP desaturases (e.g., a codon optimized *R. communis* SAD, SEQ ID NO: 147 and SEQ ID NO: 148) and fatty acyl desaturases and squalene synthases (see GenBank Accession number AF205791). In some embodiments, genes encoding a fatty acyl-ACP thioesterase and a naturally co-expressed acyl carrier protein are transformed into a *Prototheca* cell, optionally with one or more genes encoding other lipid modification enzymes. In other embodiments, the ACP and the fatty acyl-ACP thioesterase may have an affinity for one another that imparts an advantage when the two are used together in the microbes and methods of the present invention, irrespective of whether they are or are not naturally co-expressed in a particular tissue or organism. Thus, the present invention contemplates both naturally co-expressed pairs of these enzymes as well as those that share an affinity for interacting with one another to facilitate cleavage of a length-specific carbon chain from the ACP.

In still other embodiments, an exogenous gene encoding a desaturase is transformed into the microorganism (e.g., a *Prototheca* cell) in conjunction with one or more genes encoding other lipid modification enzymes to provide modifications with respect to lipid saturation. In other embodiments, an endogenous desaturase gene is overexpressed (e.g., through the introduction of additional copies off the gene) in the microorganism (e.g., a *Prototheca* cell). Stearoyl-ACP desaturase (see, e.g., GenBank Accession numbers AAF15308; ABM45911; and AAY86086), for example, catalyzes the conversion of stearoyl-ACP to oleoyl-ACP. Up-regulation of this gene can increase the proportion of monounsaturated fatty acids produced by a cell; whereas down-regulation can reduce the proportion of monounsaturates. For illustrative purposes, stearoyl-ACP desaturases (SAD) are responsible for the synthesis of C18:1 fatty acids from C18:0 precursors. Another family of desaturases are the fatty acyl desaturases (FAD), including delta 12 fatty acid desaturases (Δ12 FAD). These desaturases also provide modifications with respect to lipid saturation. For illustrative purposes, delta 12 fatty acid desaturases are responsible for the synthesis of C18:2 fatty acids from C18:1 precursors. Similarly, the expression of one or more glycerolipid desaturases can be controlled to alter the ratio of unsaturated to saturated fatty acids such as ω-6 fatty acid desaturase, ω-3 fatty acid desaturase, or ω-6-oleate desaturase. In some embodiments, the desaturase can be selected with reference to a desired carbon chain length, such that the desaturase is capable of making location specific modifications within a specified carbon-length substrate, or substrates having a carbon-length within a specified range. In another embodiment, if the desired fatty acid profile is an increase in monounsaturates (such as C16:1 and/or C18:1) overexpression of a SAD or expression of a heterologous SAD can be coupled with the silencing or inactivation (e.g., through mutation, RNAi, knockout of an endogenous desaturase gene, etc.) of a fatty acyl desaturase (FAD).

In other embodiments, the microorganism (e.g., *Prototheca* cell) has been modified to have a mutated endogenous desaturase gene, wherein the mutation renders the gene or desaturase enzyme inactive. In some cases, the mutated endogenous desaturase gene is a fatty acid desaturase (FAD). In other cases, the mutated endogenous desaturase gene is a stearoyl Acyl carrier protein desaturase (SAD). Example 11 below describes the targeted ablation or knock-out of stearoyl-ACP desaturases and delta 12 fatty acid desaturases.

In some cases, it may be advantageous to pair one or more of the genetic engineering techniques in order to achieve a transgenic cell that produces the desired lipid profile. In one embodiment, a microorganism (e.g., a *Prototheca* cell) comprises a mutated endogenous desaturase gene and one or more exogenous gene. In non-limiting examples, a *Prototheca* cell with a mutated endogenous desaturase gene can also express an exogenous fatty acyl-ACP thioesterase gene and/or a sucrose invertase gene. Example 11 below describes a transgenic *Prototheca* cell containing a targeted ablation or knockout of an endogenous SAD and also expresses a *Cinnamomum camphora* C14-preferring thioesterase and a sucrose invertase. In this case, the transgenic *Prototheca* cell produces a lipid profile that closely approximates the lipid profile found in tallow. Tallow is typically derived from rendered beef or mutton fat, is solid at room temperature and is utilized in a variety of applications in the food, cosmetics, and chemicals industries. The fatty acid profile of tallow is: 4% C14:0; 26% C16:0; 3% C16:1; 14% C18:0; 41% C18:1; 3% C18:2; and 1% C18:3. As is shown in Example 11 below, clones of transgenic *Prototheca* cells with a targeted ablation or knockout of an endogenous SAD and expressing a *C. camphora* C14-preferring thioesterase have lipid profiles of: less than 1% C12 and shorter carbon chain length fatty acids; 2.74% to 6.13% C14:0; 23.07% to 25.69% C16:0; 7.02% to 11.08% C18:0; 42.03% to 51.21% C18:1; and 9.37% to 13.45% C18:2 (expressed in area percent). In some cases, the transgenic *Prototheca* cells have lipid profiles of: 3-5% C14:0; 25-27% C16:0; 10-15% C18:0; and 40-45% C18:1.

Thus, in particular embodiments, microbes of the present invention are genetically engineered to express one or more exogenous genes selected from an acyl-ACP thioesterase, an acyl-CoA/aldehyde reductase, a fatty acyl-CoA reductase, a fatty aldehyde reductase, a fatty aldehyde decarbonylase, or a naturally co-expressed acyl carrier protein. Suitable expression methods are described above with respect to the expression of a lipase gene, including, among other methods, inducible expression and compartmentalized expression. A fatty acyl-ACP thioesterase cleaves a fatty acid from an acyl carrier protein (ACP) during lipid synthesis. Through further enzymatic processing, the cleaved fatty acid is then combined with a coenzyme to yield an acyl-CoA molecule. This acyl-CoA is the substrate for the enzymatic activity of a fatty acyl-CoA reductase to yield an aldehyde, as well as for a fatty acyl-CoA/aldehyde reductase to yield an alcohol. The aldehyde produced by the action of the fatty acyl-CoA reductase identified above is the substrate for further enzymatic activity by either a fatty aldehyde reductase to yield an alcohol, or a fatty aldehyde decarbonylase to yield an alkane or alkene.

In some embodiments, fatty acids, glycerolipids, or the corresponding primary alcohols, aldehydes, alkanes or alkenes, generated by the methods described herein, contain 8, 10, 12, or 14 carbon atoms. Preferred fatty acids for the production of diesel, biodiesel, renewable diesel, or jet fuel, or the corresponding primary alcohols, aldehydes, alkanes and alkenes, for industrial applications contain 8 to 14 carbon atoms. In certain embodiments, the above fatty acids, as well as the other corresponding hydrocarbon molecules, are saturated (with no carbon-carbon double or triple bonds); mono unsaturated (single double bond); poly unsaturated (two or more double bonds); are linear (not cyclic) or branched. For fuel production, greater saturation is preferred.

The enzymes described directly above have a preferential specificity for hydrolysis of a substrate containing a specific number of carbon atoms. For example, a fatty acyl-ACP thioesterase may have a preference for cleaving a fatty acid having 12 carbon atoms from the ACP. In some embodiments, the ACP and the length-specific thioesterase may have an affinity for one another that makes them particularly useful as a combination (e.g., the exogenous ACP and thioesterase genes may be naturally co-expressed in a particular tissue or organism from which they are derived). Therefore, in various embodiments, the recombinant *Prototheca* cell of the invention can contain an exogenous gene that encodes a protein with specificity for catalyzing an enzymatic activity (e.g., cleavage of a fatty acid from an ACP, reduction of an acyl-CoA to an aldehyde or an alcohol, or conversion of an aldehyde to an alkane) with regard to the number of carbon atoms contained in the substrate. The enzymatic specificity can, in various embodiments, be for a substrate having from 8 to 34 carbon atoms, preferably from 8 to 18 carbon atoms, and more preferably from 8 to 14 carbon atoms. A preferred specificity is for a substrate having fewer, i.e., 12, rather than more, i.e., 18, carbon atoms.

Other fatty acyl-ACP thioesterases suitable for use with the microbes and methods of the invention include, without limitation, those listed in Table 4.

TABLE 4

Fatty acyl-ACP thioesterases and GenBank accession numbers.

*Umbellularia californica* fatty acyl-ACP thioesterase (GenBank #AAC49001) (SEQ ID NO: 203)
*Cinnamomum camphora* fatty acyl-ACP thioesterase (GenBank #Q39473)
*Umbellularia californica* fatty acyl-ACP thioesterase (GenBank #Q41635)
*Myristica fragrans* fatty acyl-ACP thioesterase (GenBank #AAB71729) (SEQ ID NO: 224)
*Myristica fragrans* fatty acyl-ACP thioesterase (GenBank #AAB71730) (SEQ ID NO: 222)
*Elaeis guineensis* fatty acyl-ACP thioesterase (GenBank #ABD83939) (SEQ ID NO: 204)
*Elaeis guineensis* fatty acyl-ACP thioesterase (GenBank #AAD42220)
*Populus tomentosa* fatty acyl-ACP thioesterase (GenBank #ABC47311) (SEQ ID NO: 207)
*Arabidopsis thaliana* fatty acyl-ACP thioesterase (GenBank #NP_172327) (SEQ ID NO: 208)
*Arabidopsis thaliana* fatty acyl-ACP thioesterase (GenBank #CAA85387) (SEQ ID NO: 209)
*Arabidopsis thaliana* fatty acyl-ACP thioesterase (GenBank #CAA85388) (SEQ ID NO: 210)
*Gossypium hirsutum* fatty acyl-ACP thioesterase (GenBank #Q9SQI3) (SEQ ID NO: 211)
*Cuphea lanceolata* fatty acyl-ACP thioesterase (GenBank #CAA54060) (SEQ ID NO: 212)
*Cuphea hookeriana* fatty acyl-ACP thioesterase (GenBank #AAC72882) (SEQ ID NO: 202)
*Cuphea calophylla* subsp. *mesostemon* fatty acyl-ACP thioesterase (GenBank #ABB71581) (SEQ ID NO: 213)
*Cuphea lanceolata* fatty acyl-ACP thioesterase (GenBank #CAC19933)
*Elaeis guineensis* fatty acyl-ACP thioesterase (GenBank #AAL15645) (SEQ ID NO: 206)
*Cuphea hookeriana* fatty acyl-ACP thioesterase (GenBank #Q39513)
*Gossypium hirsutum* fatty acyl-ACP thioesterase (GenBank #AAD01982) (SEQ ID NO: 214)
*Vitis vinifera* fatty acyl-ACP thioesterase (GenBank #CAN81819) (SEQ ID NO: 215)
*Garcinia mangostana* fatty acyl-ACP thioesterase (GenBank #AAB51525)
*Brassica juncea* fatty acyl-ACP thioesterase (GenBank #ABI18986) (SEQ ID NO: 216)
*Madhuca longifolia* fatty acyl-ACP thioesterase (GenBank #AAX51637) (SEQ ID NO: 217)
*Brassica napus* fatty acyl-ACP thioesterase (GenBank #ABH11710)
*Oryza sativa* (*indica* cultivar-group) fatty acyl-ACP thioesterase (GenBank #EAY86877) (SEQ ID NO: 218)
*Oryza sativa* (*japonica* cultivar-group) fatty acyl-ACP thioesterase (GenBank #NP_001068400) (SEQ ID NO: 219)
*Oryza sativa* (*indica* cultivar-group) fatty acyl-ACP thioesterase (GenBank #EAY99617) (SEQ ID NO: 220)
*Cuphea hookeriana* fatty acyl-ACP thioesterase (GenBank #AAC49269)
*Ulmus Americana* fatty acyl-ACP thioesterase (GenBank #AAB71731)
*Cuphea lanceolata* fatty acyl-ACP thioesterase (GenBank #CAB60830) (SEQ ID NO: 221)
*Cuphea palustris* fatty acyl-ACP thioesterase (GenBank #AAC49180)
*Iris germanica* fatty acyl-ACP thioesterase (GenBank #AAG43858)
*Iris germanica* fatty acyl-ACP thioesterase (GenBank #AAG43858.1)
*Cuphea palustris* fatty acyl-ACP thioesterase (GenBank #AAC49179)
*Myristica fragrans* fatty acyl-ACP thioesterase (GenBank# AAB71729)
*Myristica fragrans* fatty acyl-ACP thioesterase (GenBank# AAB717291.1)
*Cuphea hookeriana* fatty acyl-ACP thioesterase (GenBank #U39834) (SEQ ID NO: 197)
*Umbelluaria californica* fatty acyl-ACP thioesterase (GenBank # M94159) (SEQ ID NO: 285)
*Cinnamomum camphora* fatty acyl-ACP thioesterase (GenBank #U31813) (SEQ ID NO: 223)
*Cuphea wrightii* fatty acyl-ACOP thioesterase (GenBank #U56103) (SEQ ID NO: 183)
*Ricinus communis* fatty acyl-ACP thioesterase (GenBank #ABS30422) (SEQ ID NO: 198)

The Examples below describe the successful targeting and expression of heterologous fatty acyl-ACP thioesterases from *Cuphea hookeriana*, *Umbellularia californica*, *Cinnamomun camphora*, *Cuphea palustris*, *Cuphea lanceolata*, *Iris germanica*, *Myristica fragrans* and *Ulmus americana* in *Prototheca* species. Additionally, alterations in fatty acid profiles were confirmed in the host cells expression these heterologous fatty acyl-ACP thioesterases. These results were quite unexpected given the lack of sequence identity between algal and higher plant thioesterases in general, and between *Prototheca moriformis* fatty acyl-ACP thioesterase and the above listed heterologous fatty acyl-ACP thioesterases. As shown in the Examples, the expression of these heterologous thioesterases in *Prototheca* generates a transgenic microalgae that is able to produce oil/lipids with truly unique fatty acid profiles that are currently not available from commercial seed crops, even through the blending of several seed crop oils. Table 5 shows the fatty acid profiles of common commercial seed oils. All commercial seed oil data below were compiled from the US Pharmacopeias Food and Chemicals Codes, 7$^{th}$ Ed. 2010-2011. Tallow data is from the National Research Council: Fat Content and Composition of Animal Products (1976).

ratios between different fatty acid chain lengths is something has not been available commercially in oils that have not been through further costly chemical processes (such as esterification, distillation, fractionation, and re-esterification). As another example, palm oil is the highest C16:0 fatty acid (32-47%) containing oils, but palm oil has very little C14:0 fatty acids. *Prototheca* containing the *U. americana* thioesterase achieved about 33-38% C16:0 fatty acids and about a 10-16% C14:0 fatty acids (about a 2:1 C16:0 to C14:0 ratio). This fatty acid profile is unachievable through blending of existing oils at a commercial level because the seed oils that are high in 16:0 fatty acids usually do not contain much 14:0 fatty acids.

The Examples below also describe, for the first time, the successful targeting and expression of at least two fatty acyl-ACP thioesterases in one clone. The alterations in the fatty acid profiles were confirmed in these clones and depending on which two thioesterases were co-expressed in one clone, the fatty acid profiles were impacted in different ways. As an example, from Table 5 above, both coconut oil and palm kernel oil have C12:C14 ratios of roughly 3:1. As described in the Examples below, a *Prototheca* transformant containing two heterologous thioesterase genes was able to

TABLE 5

Lipid profiles of commercial seed oils (in percentages).

| | C8:0 | C10:0 | C12:0 | C14:0 | C16:0 | C18:0 | C18:1 | C18:0-diOH | C18:1-OH | C18:2 | C18:3 α |
|---|---|---|---|---|---|---|---|---|---|---|---|
| *R. communis* (Castor oil) | 0 | 0 | 0 | 0 | 0.9-1.6 | 1.0-1.8 | 3.7-6.7 | 0.4-1.3 | 83.6-89.0 | 0 | 0.2-0.6 |
| *C. nucifera* (Coconut oil) | 5.0-9.0 | 4.0-8.0 | 44-52 | 15-21 | 8.0-11.0 | 1.0-4.0 | 5.0-8.0 | 0 | 0 | 0-2.5 | 0 |
| *Z. mays* (Corn oil) | 0 | 0 | 0 | <1.0 | 8.0-19.0 | 0.5-4.0 | 19-50 | 0 | 0 | 38-65 | <2.0 |
| *G. barbadense* (Cottonseed oil) | 0 | 0 | <0.1 | 0.5-2.0 | 17-29 | 1.0-4.0 | 13-44 | 0 | 0 | 40-63 | 0.1-2.1 |
| *B. rapa*, *B. napus*, *B. juncea* (Canola) | 0 | 0 | <0.1 | <0.2 | <6.0 | <2.5 | >50 | 0 | 0 | <40 | <14 |
| *O. europea* (Olive) | 0 | 0 | 0 | <0.1 | 6.5-20.0 | 0.5-5.0 | 56-85 | 0 | 0 | 3.5-20.0 | <1.2 |
| *A. hypogaea* (Peanut) | 0 | 0 | <0.1 | <0.2 | 7.0-16.0 | 1.3-6.5 | 35-72 | 0 | 0 | 13.0-43 | <0.6 |
| *E. guineensis* (Palm kernel) | 3.0-5.0 | 2.5-6.0 | 40-52 | 14.0-18.0 | 7.0-10.0 | 1.0-3.0 | 11.0-19.0 | 0 | 0 | 0.5-4.0 | 0 |
| *E. guineensis* (Palm) | 0 | 0 | 0 | 0.5-5.9 | 32.0-47.0 | 2.0-8.0 | 34-44 | 0 | 0 | 7.2-12.0 | 0 |
| *C. tinctorus* (Safflower) | 0 | 0 | <0.1 | <0.1 | 2.0-10.0 | 1.0-10.0 | 7.0-16.0 | 0 | 0 | 72-81 | <1.5 |
| *H. annus* (Sunflower) | 0 | 0 | <0.1 | <0.5 | 3.0-10.0 | 1.0-10.0 | 14-65 | 0 | 0 | 20-75 | <0.5 |
| *G. max* (Soybean) | 0 | 0 | <0.1 | <0.5 | 7.0-12.0 | 2.0-5.5 | 19-30 | 0 | 0 | 48-65 | 5.0-10.0 |
| *L. usitatissimum* (Solin-Flax) | 0 | 0 | <0.1 | <0.5 | 2.0-9.0 | 2.0-5.0 | 8.0-60 | 0 | 0 | 40-80 | <5.0 |
| *B. parkii* (Sheanut) | 0 | 0 | 0 | 0 | 3.8-4.1 | 41.2-56.8 | 34.0-46.9 | 0 | 0 | 3.7-6.5 | 0 |
| Cocoa Butter | | 0-1 | 0-1 | 0-4 | 22-30 | 24-37 | 29-38 | | | 0-3 | |
| Tallow | | | | 3-4 | 23-28 | 14-23 | 36-43 | | | 1-4 | <1 |
| Lard | | | | 1-2 | 22-26 | 13-18 | 39-45 | | | 8-15 | 0.5-1.5 |

As an example, none of these common seed oils contain high amounts of C8 or C10 fatty acids, with coconut oil and palm kernel oil being the largest sources, but both a ratio of 1:1 (C8:C10 fatty acids). As shown in the Examples, *Prototheca* transformed with *Cuphea palustris* C:8 preferring thioesterase was able to achieve not only a C8 fatty acid levels of over 12%, but also, the ratio of C8:C10 fatty acids were about a 5:1. Changes in fatty acid levels are useful for producing oils containing a tailored fatty acid profile for a variety of commercial applications. Additionally, changes of produce C12:C14 fatty acid levels at a ratio of roughly 5:1. This kind of ratio of C12:C14 fatty acids has been, up to now, unachievable at commercial levels (i.e., through blending of seed oils).

Another novel aspect of the oils produced by transgenic microalgae is the degree of saturation of the fatty acids. Palm oil is currently the largest source of saturated oil, with a total saturates to unsaturates of 52% to 48%. As shown in the Examples below, *Prototheca* with heterologous thioesterases from *U. americana* and *C. camphora* achieved total saturates levels of over 60% in the oil that it produced. Also shown in the Examples below, *Prototheca* with heterologous thioesterase from *U. americana* achieved total saturates level of over 86% in the oil that it produced.

Fatty acyl-CoA/aldehyde reductases suitable for use with the microbes and methods of the invention include, without limitation, those listed in Table 6.

TABLE 6

Fatty acyl-CoA/aldehyde reductases listed by GenBank accession numbers.

AAC45217, YP_047869, BAB85476, YP_001086217, YP_580344, YP_001280274, YP_264583, YP_436109, YP_959769, ZP_01736962, ZP_01900335, ZP_01892096, ZP_01103974, ZP_01915077, YP_924106, YP_130411, ZP_01222731, YP_550815, YP_983712, YP_001019688, YP_524762, YP_856798, ZP_01115500, YP_001141848, NP_336047, NP_216059, YP_882409, YP_706156, YP_001136150, YP_952365, ZP_01221833, YP_130076, NP_567936, AAR88762, ABK28586, NP_197634, CAD30694, NP_001063962, BAD46254, NP_001030809, EAZ10132, EAZ43639, EAZ07989, NP_001062488, CAB88537, NP_001052541, CAH66597, CAE02214, CAH66590, CAB88538, EAZ39844, AAZ06658, CAA68190, CAA52019, and BAC84377

Fatty acyl-CoA reductases suitable for use with the microbes and methods of the invention include, without limitation, those listed in Table 7.

TABLE 7

Fatty acyl-CoA reductases listed by GenBank accession numbers.

NP_187805, ABO14927, NP_001049083, CAN83375, NP_191229, EAZ42242, EAZ06453, CAD30696, BAD31814, NP_190040, AAD38039, CAD30692, CAN81280, NP_197642, NP_190041, AAL15288, and NP_190042

Fatty aldehyde decarbonylases suitable for use with the microbes and methods of the invention include, without limitation, those listed in Table 8.

TABLE 8

Fatty aldehyde decarbonylases listed by GenBank accession numbers.

NP_850932, ABN07985, CAN60676, AAC23640, CAA65199, AAC24373, CAE03390, ABD28319, NP_181306, EAZ31322, CAN63491, EAY94825, EAY86731, CAL55686, XP_001420263, EAZ23849, NP_200588, NP_001063227, CAN83072, AAR90847, and AAR97643

Combinations of naturally co-expressed fatty acyl-ACP thioesterases and acyl carrier proteins are suitable for use with the microbes and methods of the invention.

Additional examples of hydrocarbon or lipid modification enzymes include amino acid sequences contained in, referenced in, or encoded by nucleic acid sequences contained or referenced in, any of the following U.S. Pat. Nos. 6,610,527; 6,451,576; 6,429,014; 6,342,380; 6,265,639; 6,194,185; 6,114,160; 6,083,731; 6,043,072; 5,994,114; 5,891,697; 5,871,988; 6,265,639, and further described in GenBank Accession numbers: AAO18435; ZP_00513891; Q38710; AAK60613; AAK60610; AAK60611; NP_113747; CAB75874; AAK60612; AAF20201; BAA11024; AF205791; and CAA03710.

Other enzymes in the lipid biosynthetic pathways are also suitable for use with microbes and methods of the invention. For example, keto acyl-ACP synthase (Kas) enzymes work in conjunction with some of the above listed enzymes in the lipid biosynthetic pathway. There different classes of Kas enzymes: Kas I participates in successive condensation steps between the ever-growing acyl ACP chains and malonyl-ACP. Kas II typically participates in the final condensation step leading from C16:0-ACP to C18:0-ACP incorporating malonyl-ACP. As such, in higher plants and some microalgae species/strains that synthesize predominantly C16-C18:0 fatty acids (and their unsaturated derivatives), Kas II enzymes interact with products of FatA genes (acyl-ACP thioesterases).

Acyl-ACP thioesterases are the terminators of higher plant (and some microalgal species) fatty acid biosynthesis, and in most plant species, this is carried out by members of the FatA gene family, whose role is to terminate elongation at the C16:0 to C18:0 stage. In species that synthesize shorter chain fatty acids (such as *Cuphea*, *Elaeis*, *Myristica*, or *Umbellularia*), a different group of acyl-ACP thioesterases encoded by FatB genes carry out this termination step (see e.g., the codon optimized coding region of *Cocos nucifera* FatB3-B, SEQ ID NO: 189). The interaction between Kas II enzymes and acyl-Acp thioesterases is important for the correct termination of fatty acid chain elongation. As a consequence, in higher plant species (and microalgal species) that have evolved FatB genes capable of shorter chain lipid biosynthesis, there has been a corresponding co-evolution of an additional class of Kas genes, termed Kas IV genes. Kas IV genes are responsible for chain length elongation of a specific size range of fatty acids, 4-14 carbons in length.

Other suitable enzymes for use with the microbes and the methods of the invention include those that have at least 70% amino acid identity with one of the proteins listed in Tables 4, 6-8, and that exhibit the corresponding desired enzymatic activity (e.g., cleavage of a fatty acid from an acyl carrier protein, reduction of an acyl-CoA to an aldehyde or an alcohol, or conversion of an aldehyde to an alkane). In additional embodiments, the enzymatic activity is present in a sequence that has at least about 75%, at least about 80%, at least about 85%, at least about 90%, at least about 95%, or at least about 99% identity with one of the above described sequences, all of which are hereby incorporated by reference as if fully set forth.

By selecting the desired combination of exogenous genes to be expressed, one can tailor the product generated by the microbe, which may then be extracted from the aqueous biomass. For example, the microbe can contain: (i) an exogenous gene encoding a fatty acyl-ACP thioesterase; and, optionally, (ii) a naturally co-expressed acyl carrier protein or an acyl carrier protein otherwise having affinity for the fatty acyl-ACP thioesterase (or conversely); and, optionally, (iii) an exogenous gene encoding a fatty acyl-CoA/aldehyde reductase or a fatty acyl-CoA reductase; and, optionally, (iv) an exogenous gene encoding a fatty aldehyde reductase or a fatty aldehyde decarbonylase. The microbe, under culture conditions described herein, synthesizes a fatty acid linked to an ACP and the fatty acyl-ACP thioesterase catalyzes the cleavage of the fatty acid from the ACP to yield, through further enzymatic processing, a fatty acyl-CoA molecule. When present, the fatty acyl-CoA/ aldehyde reductase catalyzes the reduction of the acyl-CoA to an alcohol. Similarly, the fatty acyl-CoA reductase, when present, catalyzes the reduction of the acyl-CoA to an aldehyde. In those embodiments in which an exogenous gene encoding a fatty acyl-CoA reductase is present and expressed to yield an aldehyde product, a fatty aldehyde reductase, encoded by the third exogenous gene, catalyzes the reduction of the aldehyde to an alcohol. Similarly, a fatty aldehyde decarbonylase catalyzes the conversion of the aldehyde to an alkane or an alkene, when present.

In another embodiment, the microbe can contain: (i) an exogenous gene encoding a fatty acyl-ACP thioesterase; (ii) optionally, a naturally co-expressed acyl carrier protein or an acyl carrier protein having affinity for the fatty acid acyl-ACP thioesterase; (iii) a mutated endogenous desaturase gene, wherein the mutation renders the desaturase gene or desaturase protein inactive, such as a desaturase knockout; (iv) overexpression of an endogenous stearoyl acyl carrier protein desaturase or the expression of a heterologous SAD; and (v) any combination of the foregoing.

Genes encoding such enzymes, such as fatty acyl ACP thioesterases, can be obtained from cells already known to exhibit significant lipid production such as *Chlorella protothecoides*. Genes already known to have a role in lipid production, e.g., a gene encoding an enzyme that saturates double bonds, can be transformed individually into recipient cells. However, to practice the invention it is not necessary to make a priori assumptions as to which genes are required. Methods for identifying genes that can alter (improve) lipid production in microalgae are described in PCT Pub. No. 2008/151149.

Thus, the present invention provides a microorganism (e.g., a *Prototheca* cell) that has been genetically engineered to express a lipid pathway enzyme at an altered level compared to a wild-type cell of the same species. In some cases, the cell produces more lipid compared to the wild-type cell when both cells are grown under the same conditions. In some cases, the cell has been genetically engineered and/or selected to express a lipid pathway enzyme at a higher level than the wild-type cell. In some cases, the lipid pathway enzyme is selected from the group consisting of pyruvate dehydrogenase, acetyl-CoA carboxylase, acyl carrier protein, and glycerol-3 phosphate acyltransferase. In some cases, the cell has been genetically engineered and/or selected to express a lipid pathway enzyme at a lower level than the wild-type cell. In at least one embodiment in which the cell expresses the lipid pathway enzyme at a lower level, the lipid pathway enzyme comprises citrate synthase.

In some embodiments, the cell has been genetically engineered and/or selected to express a global regulator of fatty acid synthesis at an altered level compared to the wild-type cell, whereby the expression levels of a plurality of fatty acid synthetic genes are altered compared to the wild-type cell. In some cases, the lipid pathway enzyme comprises an enzyme that modifies a fatty acid. In some cases, the lipid pathway enzyme is selected from a stearoyl-ACP desaturase and a glycerolipid desaturase. In some cases, the cell has been genetically engineered and/or selected to express a lower level of a lipid pathway enzyme, or not to express a specific lipid pathway enzyme at all (i.e., wherein a lipid pathway enzyme has been knockout, or replaced with an exogenous gene).

Some microalgae produce significant quantities of non-lipid metabolites, such as, for example, polysaccharides. Because polysaccharide biosynthesis can use a significant proportion of the total metabolic energy available to cells, mutagenesis of lipid-producing cells followed by screening for reduced or eliminated polysaccharide production generates novel strains that are capable of producing higher yields of lipids.

In other embodiments, the present invention is directed to an oil-producing microbe containing one or more exogenous genes, wherein the exogenous genes encode protein(s) selected from the group consisting of a fatty acyl-ACP thioesterase, a fatty acyl-CoA reductase, a fatty aldehyde reductase, a fatty acyl-CoA/aldehyde reductase, a fatty aldehyde decarbonylase, a desaturase, and an acyl carrier protein. In another embodiment, an endogenous desaturase gene is overexpressed in a micro containing one or more of the above exogenous genes. In one embodiment, the exogenous gene is in operable linkage with a promoter, which is inducible or repressible in response to a stimulus. In some cases, the stimulus is selected from the group consisting of an exogenously provided small molecule, heat, cold, and limited or no nitrogen in the culture media. In some cases, the exogenous gene is expressed in a cellular compartment. In some embodiments, the cellular compartment is selected from the group consisting of a chloroplast, a plastid and a mitochondrion. In some embodiments the microbe is *Prototheca moriformis, Prototheca krugani, Prototheca stagnora* or *Prototheca zopfii*.

In one embodiment, the exogenous gene encodes a fatty acid acyl-ACP thioesterase. In some cases, the thioesterase encoded by the exogenous gene catalyzes the cleavage of an 8 to 18-carbon fatty acid from an acyl carrier protein (ACP). In some cases, the thioesterase encoded by the exogenous gene catalyzes the cleavage of a 10 to 14-carbon fatty acid from an ACP. In one embodiment, the thioesterase encoded by the exogenous gene catalyzes the cleavage of a 12-carbon fatty acid from an ACP.

In one embodiment, the exogenous gene encodes a fatty acyl-CoA/aldehyde reductase. In some cases, the reductase encoded by the exogenous gene catalyzes the reduction of an 8 to 18-carbon fatty acyl-CoA to a corresponding primary alcohol. In some cases, the reductase encoded by the exogenous gene catalyzes the reduction of a 10 to 14-carbon fatty acyl-CoA to a corresponding primary alcohol. In one embodiment, the reductase encoded by the exogenous gene catalyzes the reduction of a 12-carbon fatty acyl-CoA to dodecanol.

The present invention also provides a recombinant *Prototheca* cell containing two exogenous genes, wherein a first exogenous gene encodes a fatty acyl-ACP thioesterase and a second exogenous gene encodes a protein selected from the group consisting of a fatty acyl-CoA reductase, a fatty acyl-CoA/aldehyde reductase, and an acyl carrier protein. In some cases, the two exogenous genes are each in operable linkage with a promoter, which is inducible in response to a stimulus. In some cases, each promoter is inducible in response to an identical stimulus, such as limited or no nitrogen in the culture media. Limitation or complete lack of nitrogen in the culture media stimulates oil production in some microorganisms such as *Prototheca* species, and can be used as a trigger to induce oil production to high levels. When used in combination with the genetic engineering methods disclosed herein, the lipid as a percentage of dry cell weight can be pushed to high levels such as at least 30%, at least 40%, at least 50%, at least 60%, at least 70% and at least 75%; methods disclosed herein provide for cells with these levels of lipid, wherein the lipid is at least 1%-5%, preferably at least 4%, C8-C14, at least 0.25%-1%, preferably at least 0.3%, C8, at least 1%-5%, preferably at least 2%, C10, at least 1%-5%, preferably at least 2%, C12, and at least 1%-5%, preferably at least 2%, C14. In some embodiments the cells are over 10%, over 15%, over 20%, or over 25% lipid by dry cell weight and contain lipid that is at least 5%, at least 10% or at least 15% C8-C14, at least 10%, at least 15%, at least 20%, at least 25% or at least 30% C8-C14, at least 20%, at least 25%, at least 30%, at least 35% or at least 40%, C8-C14, 5%-40%, preferably 10-30%, C8-C14 and 10%-40%, preferably 20-30%, C8-C14.

The novel oils disclosed herein are distinct from other naturally occurring oils that are high in mid-chain fatty acids, such as palm oil, palm kernel oil, and coconut oil. For example, levels of contaminants such as carotenoids are far higher in palm oil and palm kernel oil than in the oils of the invention. Palm and palm kernel oils in particular contain alpha and beta carotenes and lycopene in much higher amounts than is in the oils of the invention. In addition, over 20 different carotenoids are found in palm and palm kernel oil, whereas the Examples demonstrate that the oils of the invention contain very few carotenoids species and very low levels. In addition, the levels of vitamin E compounds such as tocotrienols are far higher in palm, palm kernel, and coconut oil than in the oils of the invention.

In one embodiment, the thioesterase encoded by the first exogenous gene catalyzes the cleavage of an 8 to 18-carbon fatty acid from an ACP. In some embodiments, the second exogenous gene encodes a fatty acyl-CoA/aldehyde reductase which catalyzes the reduction of an 8 to 18-carbon fatty acyl-CoA to a corresponding primary alcohol. In some cases, the thioesterase encoded by the first exogenous gene catalyzes the cleavage of a 10 to 14-carbon fatty acid from an ACP, and the reductase encoded by the second exogenous gene catalyzes the reduction of a 10 to 14-carbon fatty acyl-CoA to the corresponding primary alcohol, wherein the thioesterase and the reductase act on the same carbon chain length. In one embodiment, the thioesterase encoded by the first exogenous gene catalyzes the cleavage of a 12-carbon fatty acid from an ACP, and the reductase encoded by the second exogenous gene catalyzes the reduction of a 12-carbon fatty acyl-CoA to dodecanol. In some embodiments, the second exogenous gene encodes a fatty acyl-CoA reductase which catalyzes the reduction of an 8 to 18-carbon fatty acyl-CoA to a corresponding aldehyde. In some embodiments, the second exogenous gene encodes an acyl carrier protein that is naturally co-expressed with the fatty acyl-ACP thioesterase.

In some embodiments, the second exogenous gene encodes a fatty acyl-CoA reductase, and the microbe further contains a third exogenous gene encoding a fatty aldehyde decarbonylase. In some cases, the thioesterase encoded by the first exogenous gene catalyzes the cleavage of an 8 to 18-carbon fatty acid from an ACP, the reductase encoded by the second exogenous gene catalyzes the reduction of an 8 to 18-carbon fatty acyl-CoA to a corresponding fatty aldehyde, and the decarbonylase encoded by the third exogenous gene catalyzes the conversion of an 8 to 18-carbon fatty aldehyde to a corresponding alkane, wherein the thioesterase, the reductase, and the decarbonylase act on the same carbon chain length.

In some embodiments, the second exogenous gene encodes an acyl carrier protein, and the microbe further contains a third exogenous gene encoding a protein selected from the group consisting of a fatty acyl-CoA reductase and a fatty acyl-CoA/aldehyde reductase. In some cases, the third exogenous gene encodes a fatty acyl-CoA reductase, and the microbe further contains a fourth exogenous gene encoding a fatty aldehyde decarbonylase.

The present invention also provides methods for producing an alcohol comprising culturing a population of recombinant microorganisms (e.g., *Prototheca* cells) in a culture medium, wherein the cells contain (i) a first exogenous gene encoding a fatty acyl-ACP thioesterase, and (ii) a second exogenous gene encoding a fatty acyl-CoA/aldehyde reductase, and the cells synthesize a fatty acid linked to an acyl carrier protein (ACP), the fatty acyl-ACP thioesterase catalyzes the cleavage of the fatty acid from the ACP to yield, through further processing, a fatty acyl-CoA, and the fatty acyl-CoA/aldehyde reductase catalyzes the reduction of the acyl-CoA to an alcohol.

The present invention also provides methods of producing a lipid molecule in a microorganism (e.g., a *Prototheca* cell). In one embodiment, the method comprises culturing a population of *Prototheca* cells in a culture medium, wherein the cells contain (i) a first exogenous gene encoding a fatty acyl-ACP thioesterase, and (ii) a second exogenous gene encoding a fatty acyl-CoA reductase, and wherein the microbes synthesize a fatty acid linked to an acyl carrier protein (ACP), the fatty acyl-ACP thioesterase catalyzes the cleavage of the fatty acid from the ACP to yield, through further processing, a fatty acyl-CoA, and the fatty acyl-CoA reductase catalyzes the reduction of the acyl-CoA to an aldehyde.

The present invention also provides methods of producing a fatty acid molecule having a specified carbon chain length in a microorganism (e.g., a *Prototheca* cell). In one embodiment, the method comprises culturing a population of lipid-producing *Prototheca* cells in a culture medium, wherein the microbes contain an exogenous gene encoding a fatty acyl-ACP thioesterase having an activity specific or preferential to a certain carbon chain length, such as 8, 10, 12 or 14 carbon atoms, and wherein the microbes synthesize a fatty acid linked to an acyl carrier protein (ACP) and the thioesterase catalyzes the cleavage of the fatty acid from the ACP when the fatty acid has been synthesized to the specific carbon chain length.

In the various embodiments described above, the microorganism (e.g., a *Prototheca* cell) can contain at least one exogenous gene encoding a lipid pathway enzyme. In some cases, the lipid pathway enzyme is selected from the group consisting of a stearoyl-ACP desaturase, a glycerolipid desaturase, a pyruvate dehydrogenase, an acetyl-CoA carboxylase, an acyl carrier protein, and a glycerol-3 phosphate acyltransferase. In other cases, the microorganism (e.g., *Prototheca* cell) contains a lipid modification enzyme selected from the group consisting of a fatty acyl-ACP thioesterase, a fatty acyl-CoA/aldehyde reductase, a fatty acyl-CoA reductase, a fatty aldehyde reductase, a fatty aldehyde decarbonylase, and/or an acyl carrier protein.

A number of exemplary transformation cassettes or constructs used to express a variety of the lipid pathway enzymes and lipid modification enzymes discussed herein are presented in the Examples. Other useful constructs, without limitation, are listed in Table 37, below.

TABLE 37

Exemplary transformation constructs, codon-optimized coding regions, and enzymes.

| Transformation Construct/Coding region/Enzyme | SEQ ID NO |
|---|---|
| *C. hookeriana* C10:0 specific thioesterase construct | 243 |
| coding region for *C. hookeriana* C10:0 specific thioesterase (codon-optimized) | 244 |

TABLE 37-continued

Exemplary transformation constructs, codon-optimized coding regions, and enzymes.

| Transformation Construct/Coding region/Enzyme | SEQ ID NO |
|---|---|
| C. hookeriana KAS IV enzyme construct | 245 |
| coding region for C. hookeriana KAS IV enzyme (codon-optimized) | 246 |
| C. hookeriana KAS IV enzyme | 247 |
| C. hookeriana C10:0 specific thioesterase plus C. hookeriana KAS IV enzyme construct | 248 |
| coding region for C. lanceolata C10:0 specific thioesterase with UTEX 1435 Δ12 fatty acid desaturase | 249 |
| U. californica C12:0 specific thioesterase construct | 250 |
| coding region for U. californica C12:0 specific thioesterase (codon-optimized) | 251 |
| G. mangostana C16:0 thioesterase construct | 252 |
| coding region for G. mangostana C16:0 thioesterase (codon-optimized) | 253 |
| B. napus C18:0 thioesterase construct | 254 |
| coding region for B. napus C18:0 thioesterase (codon-optimized) | 255 |
| O. europaea stearoyl-ACP desaturase construct | 256 |
| coding region for O. europaea stearoyl-ACP desaturase (codon-optimized) | 257 |
| C. hookeriana C16:0 thioesterase construct | 258 |
| coding region for C. hookeriana C16:0 thioesterase (codon-optimized) | 259 |
| E. guineensis C16:0 thioesterase construct | 260 |
| coding region for E. guineensis C16:0 thioesterase (codon-optimized) | 261 |
| C. tinctorius ACP-thioesterase at Δ12 fatty acid desaturase locus construct | 262 |
| coding region for C. tinctorius ACP-thioesterase (codon-optimized) | 263 |
| M. fragrans C14:0-C18:0 broad specificity thioesterase construct | 264 |
| coding region for M. fragrans C14:0-C18:0 broad specificity thioesterase (codon-optimized) | 265 |
| coding region for M. fragrans C:14:0 specific thioesterase | 266 |
| M. fragrans C14:0 specfic thioesterase with Δ12 FAD transit peptide | 267 |
| Ricinus communis ACP-thioesterase construct | 268 |
| coding region for Ricinus communis ACP-thioesterase (codon-optimized) | 269 |
| C. camphora C14:0 thioesterase construct | 270 |
| coding region for C. camphora C14:0 thioesterase (codon-optimized) | 271 |
| C. camphora C14:0 specific thioesterase construct | 272 |
| C. camphora C14:0 specific thioesterase construct | 273 |
| U. Americana C10:0-C16:0 specific thioesterase in a SAD locus | 274 |
| coding region for U. Americana C10:0-C16:0 specific thioesterase (codon-optimized) | 275 |
| C. wrightii KASA1 + C. wrightii FatB2 thioesterase + suc2 construct | 276 |
| coding region for C. wrightii KASA1 (codon-optimized) | 277 |
| coding region for C. wrightii FatB2 thioesterase (codon-optimized) | 278 |

VI. FUELS AND CHEMICALS PRODUCTION

For the production of fuel in accordance with the methods of the invention lipids produced by cells of the invention are harvested, or otherwise collected, by any convenient means. Lipids can be isolated by whole cell extraction. The cells are first disrupted, and then intracellular and cell membrane/cell wall-associated lipids as well as extracellular hydrocarbons can be separated from the cell mass, such as by use of centrifugation as described above. Intracellular lipids produced in microorganisms are, in some embodiments, extracted after lysing the cells of the microorganism. Once extracted, the lipids are further refined to produce oils, fuels, or oleochemicals.

After completion of culturing, the microorganisms can be separated from the fermentation broth. Optionally, the separation is effected by centrifugation to generate a concentrated paste. Centrifugation does not remove significant amounts of intracellular water from the microorganisms and is not a drying step. The biomass can then optionally be washed with a washing solution (e.g., DI water) to get rid of the fermentation broth and debris. Optionally, the washed microbial biomass may also be dried (oven dried, lyophilized, etc.) prior to cell disruption. Alternatively, cells can be lysed without separation from some or all of the fermentation broth when the fermentation is complete. For example, the cells can be at a ratio of less than 1:1 v:v cells to extracellular liquid when the cells are lysed.

Microorganisms containing a lipid can be lysed to produce a lysate. As detailed herein, the step of lysing a microorganism (also referred to as cell lysis) can be achieved by any convenient means, including heat-induced lysis, adding a base, adding an acid, using enzymes such as proteases and polysaccharide degradation enzymes such as amylases, using ultrasound, mechanical lysis, using osmotic shock, infection with a lytic virus, and/or expression of one or more lytic genes. Lysis is performed to release intracellular molecules which have been produced by the microorganism. Each of these methods for lysing a microorganism can be used as a single method or in combination simultaneously or sequentially. The extent of cell disruption can be observed by microscopic analysis. Using one or more of the methods described herein, typically more than 70% cell breakage is observed. Preferably, cell breakage is more than 80%, more preferably more than 90% and most preferred about 100%.

In particular embodiments, the microorganism is lysed after growth, for example to increase the exposure of cellular lipid and/or hydrocarbon for extraction or further processing. The timing of lipase expression (e.g., via an inducible promoter) or cell lysis can be adjusted to optimize the yield of lipids and/or hydrocarbons. Below are described a number of lysis techniques. These techniques can be used individually or in combination.

In one embodiment of the present invention, the step of lysing a microorganism comprises heating of a cellular suspension containing the microorganism. In this embodiment, the fermentation broth containing the microorganisms (or a suspension of microorganisms isolated from the fermentation broth) is heated until the microorganisms, i.e., the cell walls and membranes of microorganisms degrade or breakdown. Typically, temperatures applied are at least 50° C. Higher temperatures, such as, at least 30° C. at least 60° C., at least 70° C., at least 80° C., at least 90° C., at least 100° C., at least 110° C., at least 120° C., at least 130° C. or higher are used for more efficient cell lysis. Lysing cells by heat treatment can be performed by boiling the microorganism. Alternatively, heat treatment (without boiling) can be performed in an autoclave. The heat treated lysate may be cooled for further treatment. Cell disruption can also be performed by steam treatment, i.e., through addition of pressurized steam. Steam treatment of microalgae for cell disruption is described, for example, in U.S. Pat. No. 6,750,048. In some embodiments, steam treatment may be achieved by sparging steam into the fermentor and maintaining the broth at a desired temperature for less than about 90 minutes, preferably less than about 60 minutes, and more preferably less than about 30 minutes.

In another embodiment of the present invention, the step of lysing a microorganism comprises adding a base to a cellular suspension containing the microorganism. The base should be strong enough to hydrolyze at least a portion of the proteinaceous compounds of the microorganisms used. Bases which are useful for solubilizing proteins are known in the art of chemistry. Exemplary bases which are useful in the methods of the present invention include, but are not limited to, hydroxides, carbonates and bicarbonates of lithium, sodium, potassium, calcium, and mixtures thereof. A preferred base is KOH. Base treatment of microalgae for cell disruption is described, for example, in U.S. Pat. No. 6,750,048.

In another embodiment of the present invention, the step of lysing a microorganism comprises adding an acid to a cellular suspension containing the microorganism. Acid lysis can be effected using an acid at a concentration of 10-500 mN or preferably 40-160 nM. Acid lysis is preferably performed at above room temperature (e.g., at 40-160°, and preferably a temperature of 50-130°. For moderate temperatures (e.g., room temperature to 100° C. and particularly room temperature to 65°, acid treatment can usefully be combined with sonication or other cell disruption methods.

In another embodiment of the present invention, the step of lysing a microorganism comprises lysing the microorganism by using an enzyme. Preferred enzymes for lysing a microorganism are proteases and polysaccharide-degrading enzymes such as hemicellulase (e.g., hemicellulase from *Aspergillus niger*; Sigma Aldrich, St. Louis, Mo.; #H2125), pectinase (e.g., pectinase from *Rhizopus* sp.; Sigma Aldrich, St. Louis, Mo.; #P2401), Mannaway 4.0 L (Novozymes), cellulase (e.g., cellulose from *Trichoderma viride*; Sigma Aldrich, St. Louis, Mo.; #C9422), and driselase (e.g., driselase from *Basidiomycetes* sp.; Sigma Aldrich, St. Louis, Mo.; #D9515.

In other embodiments of the present invention, lysis is accomplished using an enzyme such as, for example, a cellulase such as a polysaccharide-degrading enzyme, optionally from *Chlorella* or a *Chlorella* virus, or a proteases, such as *Streptomyces griseus* protease, chymotrypsin, proteinase K, proteases listed in Degradation of Polylactide by Commercial Proteases, Oda Y et. al., Journal of Polymers and the Environment, Volume 8, Number 1, January 2000, pp. 29-32(4), Alcalase 2.4 FG (Novozymes), and Flavourzyme 100 L (Novozymes). Any combination of a protease and a polysaccharide-degrading enzyme can also be used, including any combination of the preceding proteases and polysaccharide-degrading enzymes.

In another embodiment, lysis can be performed using an expeller press. In this process, biomass is forced through a screw-type device at high pressure, lysing the cells and causing the intracellular lipid to be released and separated from the protein and fiber (and other components) in the cell.

In another embodiment of the present invention, the step of lysing a microorganism is performed by using ultrasound, i.e., sonication. Thus, cells can also by lysed with high frequency sound. The sound can be produced electronically and transported through a metallic tip to an appropriately concentrated cellular suspension. This sonication (or ultrasonication) disrupts cellular integrity based on the creation of cavities in cell suspension.

In another embodiment of the present invention, the step of lysing a microorganism is performed by mechanical lysis. Cells can be lysed mechanically and optionally homogenized to facilitate hydrocarbon (e.g., lipid) collection. For example, a pressure disrupter can be used to pump a cell containing slurry through a restricted orifice valve. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method releases intracellular molecules. Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. Cells can also be disrupted by shear forces, such as with the use of blending (such as with a high speed or Waring blender as examples), the french press, or even centrifugation in case of weak cell walls, to disrupt cells.

In another embodiment of the present invention, the step of lysing a microorganism is performed by applying an osmotic shock.

In another embodiment of the present invention, the step of lysing a microorganism comprises infection of the microorganism with a lytic virus. A wide variety of viruses are known to lyse microorganisms suitable for use in the present invention, and the selection and use of a particular lytic virus for a particular microorganism is within the level of skill in the art. For example, *paramecium bursaria chlorella* virus (PBCV-1) is the prototype of a group (family Phycodnaviridae, genus Chlorovirus) of large, icosahedral, plaque-forming, double-stranded DNA viruses that replicate in, and lyse, certain unicellular, eukaryotic *chlorella*-like green algae. Accordingly, any susceptible microalgae can be lysed by infecting the culture with a suitable *chlorella* virus. Methods of infecting species of *Chlorella* with a *chlorella* virus are known. See for example *Adv. Virus Res.* 2006; 66:293-336; *Virology*, 1999 Apr. 25; 257(1):15-23; *Virology*, 2004 Jan. 5; 318(1):214-23; *Nucleic Acids Symp. Ser.* 2000; (44):161-2; *J. Virol.* 2006 March; 80(5):2437-44; and *Annu. Rev. Microbiol.* 1999; 53:447-94.

In another embodiment of the present invention, the step of lysing a microorganism comprises autolysis. In this embodiment, a microorganism according to the invention is genetically engineered to produce a lytic protein that will lyse the microorganism. This lytic gene can be expressed using an inducible promoter so that the cells can first be grown to a desirable density in a fermentor, followed by induction of the promoter to express the lytic gene to lyse the cells. In one embodiment, the lytic gene encodes a polysaccharide-degrading enzyme. In certain other embodiments, the lytic gene is a gene from a lytic virus. Thus, for example, a lytic gene from a *Chlorella* virus can be expressed in an algal cell; see *Virology* 260, 308-315 (1999); *FEMS Microbiology Letters* 180 (1999) 45-53; *Virology* 263, 376-387 (1999); and *Virology* 230, 361-368 (1997). Expression of lytic genes is preferably done using an inducible promoter, such as a promoter active in microalgae that is induced by a stimulus such as the presence of a small molecule, light, heat, and other stimuli.

Various methods are available for separating lipids from cellular lysates produced by the above methods. For example, lipids and lipid derivatives such as fatty aldehydes, fatty alcohols, and hydrocarbons such as alkanes can be extracted with a hydrophobic solvent such as hexane (see Frenz et al. 1989, Enzyme Microb. Technol., 11:717). Lipids and lipid derivatives can also be extracted using liquefaction (see for example Sawayama et al. 1999, Biomass and Bioenergy 17:33-39 and Inoue et al. 1993, Biomass Bioenergy 6(4):269-274); oil liquefaction (see for example Minowa et al. 1995, Fuel 74(12):1735-1738); and supercritical $CO_2$ extraction (see for example Mendes et al. 2003, Inorganica Chimica Acta 356:328-334). Miao and Wu describe a protocol of the recovery of microalgal lipid from a culture of *Chlorella prototheocoides* in which the cells were harvested by centrifugation, washed with distilled water and dried by freeze drying. The resulting cell powder was pulverized in a mortar and then extracted with n-hexane. Miao and Wu, Biosource Technology (2006) 97:841-846.

Thus, lipids, lipid derivatives and hydrocarbons generated by the microorganisms of the present invention can be recovered by extraction with an organic solvent. In some cases, the preferred organic solvent is hexane. Typically, the organic solvent is added directly to the lysate without prior separation of the lysate components. In one embodiment, the lysate generated by one or more of the methods described above is contacted with an organic solvent for a period of time sufficient to allow the lipid and/or hydrocarbon components to form a solution with the organic solvent. In some cases, the solution can then be further refined to recover specific desired lipid or hydrocarbon components. Hexane extraction methods are well known in the art.

Lipids and lipid derivatives such as fatty aldehydes, fatty alcohols, and hydrocarbons such as alkanes produced by cells as described herein can be modified by the use of one or more enzymes, including a lipase, as described above. When the hydrocarbons are in the extracellular environment of the cells, the one or more enzymes can be added to that environment under conditions in which the enzyme modifies the hydrocarbon or completes its synthesis from a hydrocarbon precursor. Alternatively, the hydrocarbons can be partially, or completely, isolated from the cellular material before addition of one or more catalysts such as enzymes. Such catalysts are exogenously added, and their activity occurs outside the cell or in vitro.

Thus, lipids and hydrocarbons produced by cells in vivo, or enzymatically modified in vitro, as described herein can be optionally further processed by conventional means. The processing can include "cracking" to reduce the size, and thus increase the hydrogen:carbon ratio, of hydrocarbon molecules. Catalytic and thermal cracking methods are routinely used in hydrocarbon and triglyceride oil processing. Catalytic methods involve the use of a catalyst, such as a solid acid catalyst. The catalyst can be silica-alumina or a zeolite, which result in the heterolytic, or asymmetric, breakage of a carbon-carbon bond to result in a carbocation and a hydride anion. These reactive intermediates then undergo either rearrangement or hydride transfer with another hydrocarbon. The reactions can thus regenerate the intermediates to result in a self-propagating chain mechanism. Hydrocarbons can also be processed to reduce, optionally to zero, the number of carbon-carbon double, or triple, bonds therein. Hydrocarbons can also be processed to remove or eliminate a ring or cyclic structure therein. Hydrocarbons can also be processed to increase the hydrogen:carbon ratio. This can include the addition of hydrogen ("hydrogenation") and/or the "cracking" of hydrocarbons into smaller hydrocarbons.

Thermal methods involve the use of elevated temperature and pressure to reduce hydrocarbon size. An elevated temperature of about 800° C. and pressure of about 700 kPa can be used. These conditions generate "light," a term that is sometimes used to refer to hydrogen-rich hydrocarbon molecules (as distinguished from photon flux), while also generating, by condensation, heavier hydrocarbon molecules which are relatively depleted of hydrogen. The methodology provides homolytic, or symmetrical, breakage and produces alkenes, which may be optionally enzymatically saturated as described above.

Catalytic and thermal methods are standard in plants for hydrocarbon processing and oil refining. Thus hydrocarbons produced by cells as described herein can be collected and processed or refined via conventional means. See Hillen et al. (Biotechnology and Bioengineering, Vol. XXIV:193-205 (1982)) for a report on hydrocracking of microalgae-produced hydrocarbons. In alternative embodiments, the fraction is treated with another catalyst, such as an organic compound, heat, and/or an inorganic compound. For processing of lipids into biodiesel, a transesterification process is used as described below in this Section.

Hydrocarbons produced via methods of the present invention are useful in a variety of industrial applications. For example, the production of linear alkylbenzene sulfonate (LAS), an anionic surfactant used in nearly all types of detergents and cleaning preparations, utilizes hydrocarbons generally comprising a chain of 10-14 carbon atoms. See, for example, U.S. Pat. Nos. 6,946,430; 5,506,201; 6,692,730; 6,268,517; 6,020,509; 6,140,302; 5,080,848; and 5,567,359. Surfactants, such as LAS, can be used in the manufacture of personal care compositions and detergents, such as those described in U.S. Pat. Nos. 5,942,479; 6,086,903; 5,833,999; 6,468,955; and 6,407,044.

Increasing interest is directed to the use of hydrocarbon components of biological origin in fuels, such as biodiesel, renewable diesel, and jet fuel, since renewable biological starting materials that may replace starting materials derived from fossil fuels are available, and the use thereof is desirable. There is an urgent need for methods for producing hydrocarbon components from biological materials. The present invention fulfills this need by providing methods for production of biodiesel, renewable diesel, and jet fuel using the lipids generated by the methods described herein as a biological material to produce biodiesel, renewable diesel, and jet fuel.

Traditional diesel fuels are petroleum distillates rich in paraffinic hydrocarbons. They have boiling ranges as broad as 370° to 780° F., which are suitable for combustion in a compression ignition engine, such as a diesel engine vehicle.

The American Society of Testing and Materials (ASTM) establishes the grade of diesel according to the boiling range, along with allowable ranges of other fuel properties, such as cetane number, cloud point, flash point, viscosity, aniline point, sulfur content, water content, ash content, copper strip corrosion, and carbon residue. Technically, any hydrocarbon distillate material derived from biomass or otherwise that meets the appropriate ASTM specification can be defined as diesel fuel (ASTM D975), jet fuel (ASTM D1655), or as biodiesel if it is a fatty acid methyl ester (ASTM D6751).

After extraction, lipid and/or hydrocarbon components recovered from the microbial biomass described herein can be subjected to chemical treatment to manufacture a fuel for use in diesel vehicles and jet engines.

Biodiesel is a liquid which varies in color—between golden and dark brown—depending on the production feedstock. It is practically immiscible with water, has a high boiling point and low vapor pressure. Biodiesel refers to a diesel-equivalent processed fuel for use in diesel-engine vehicles. Biodiesel is biodegradable and non-toxic. An additional benefit of biodiesel over conventional diesel fuel is lower engine wear. Typically, biodiesel comprises C14-C18 alkyl esters. Various processes convert biomass or a lipid produced and isolated as described herein to diesel fuels. A preferred method to produce biodiesel is by transesterification of a lipid as described herein. A preferred alkyl ester for use as biodiesel is a methyl ester or ethyl ester.

Biodiesel produced by a method described herein can be used alone or blended with conventional diesel fuel at any concentration in most modern diesel-engine vehicles. When blended with conventional diesel fuel (petroleum diesel), biodiesel may be present from about 0.1% to about 99.9%. Much of the world uses a system known as the "B" factor to state the amount of biodiesel in any fuel mix. For example, fuel containing 20% biodiesel is labeled B20. Pure biodiesel is referred to as B100.

Biodiesel can also be used as a heating fuel in domestic and commercial boilers. Existing oil boilers may contain rubber parts and may require conversion to run on biodiesel. The conversion process is usually relatively simple, involving the exchange of rubber parts for synthetic parts due to biodiesel being a strong solvent. Due to its strong solvent power, burning biodiesel will increase the efficiency of boilers. Biodiesel can be used as an additive in formulations of diesel to increase the lubricity of pure Ultra-Low Sulfur Diesel (ULSD) fuel, which is advantageous because it has virtually no sulfur content. Biodiesel is a better solvent than petrodiesel and can be used to break down deposits of residues in the fuel lines of vehicles that have previously been run on petrodiesel.

Biodiesel can be produced by transesterification of triglycerides contained in oil-rich biomass. Thus, in another aspect of the present invention a method for producing biodiesel is provided. In a preferred embodiment, the method for producing biodiesel comprises the steps of (a) cultivating a lipid-containing microorganism using methods disclosed herein (b) lysing a lipid-containing microorganism to produce a lysate, (c) isolating lipid from the lysed microorganism, and (d) transesterifying the lipid composition, whereby biodiesel is produced. Methods for growth of a microorganism, lysing a microorganism to produce a lysate, treating the lysate in a medium comprising an organic solvent to form a heterogeneous mixture and separating the treated lysate into a lipid composition have been described above and can also be used in the method of producing biodiesel.

The lipid profile of the biodiesel is usually highly similar to the lipid profile of the feedstock oil. Other oils provided by the methods and compositions of the invention can be subjected to transesterification to yield biodiesel with lipid profiles including (a) at least 1%-5%, preferably at least 4%, C8-C14; (b) at least 0.25%-1%, preferably at least 0.3%, C8; (c) at least 1%-5%, preferably at least 2%, C10; (d) at least 1%-5%, preferably at least 2%, C12; and (3) at least 20%-40%, preferably at least 30%, C8-C14.

Lipid compositions can be subjected to transesterification to yield long-chain fatty acid esters useful as biodiesel. Preferred transesterification reactions are outlined below and include base catalyzed transesterification and transesterification using recombinant lipases. In a base-catalyzed transesterification process, the triacylglycerides are reacted with an alcohol, such as methanol or ethanol, in the presence of an alkaline catalyst, typically potassium hydroxide. This reaction forms methyl or ethyl esters and glycerin (glycerol) as a byproduct.

Animal and plant oils are typically made of triglycerides which are esters of free fatty acids with the trihydric alcohol, glycerol. In transesterification, the glycerol in a triacylglyceride (TAG) is replaced with a short-chain alcohol such as methanol or ethanol. A typical reaction scheme is as follows:

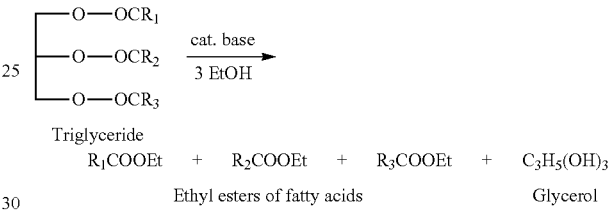

Triglyceride

R$_1$COOEt + R$_2$COOEt + R$_3$COOEt + C$_3$H$_5$(OH)$_3$

Ethyl esters of fatty acids      Glycerol

In this reaction, the alcohol is deprotonated with a base to make it a stronger nucleophile. Commonly, ethanol or methanol is used in vast excess (up to 50-fold). Normally, this reaction will proceed either exceedingly slowly or not at all. Heat, as well as an acid or base can be used to help the reaction proceed more quickly. The acid or base are not consumed by the transesterification reaction, thus they are not reactants but catalysts. Almost all biodiesel has been produced using the base-catalyzed technique as it requires only low temperatures and pressures and produces over 98% conversion yield (provided the starting oil is low in moisture and free fatty acids).

Transesterification has also been carried out, as discussed above, using an enzyme, such as a lipase instead of a base. Lipase-catalyzed transesterification can be carried out, for example, at a temperature between the room temperature and 80° C., and a mole ratio of the TAG to the lower alcohol of greater than 1:1, preferably about 3:1. Lipases suitable for use in transesterification include, but are not limited to, those listed in Table 9. Other examples of lipases useful for transesterification are found in, e.g. U.S. Pat. Nos. 4,798, 793; 4,940,845 5,156,963; 5,342,768; 5,776,741 and WO89/01032. Such lipases include, but are not limited to, lipases produced by microorganisms of *Rhizopus, Aspergillus, Candida, Mucor, Pseudomonas, Rhizomucor, Candida,* and *Humicola* and pancreas lipase.

TABLE 9

Lipases suitable for use in transesterification.

*Aspergillus niger* lipase ABG73614, *Candida antarctica* lipase B (novozym-435) CAA83122, *Candida cylindracea* lipase AAR24090, *Candida lipolytica* lipase (Lipase L; Amano Pharmaceutical Co., Ltd.), *Candida rugosa* lipase (e.g., Lipase-OF; Meito Sangyo Co., Ltd.), *Mucor miehei* lipase (Lipozyme IM 20), *Pseudomonas fluorescens* lipase AAA25882, *Rhizopus japonicas* lipase (Lilipase A-10FG) Q7M4U7_1, *Rhizomucor miehei* lipase B34959, *Rhizopus*

TABLE 9-continued

Lipases suitable for use in transesterification.

oryzae lipase (Lipase F) AAF32408, *Serratia marcescens* lipase (SM Enzyme) ABI13521, *Thermomyces lanuginosa* lipase CAB58509, Lipase P (Nagase ChemteX Corporation), and Lipase QLM (Meito Sangyo Co., Ltd., Nagoya, Japan)

One challenge to using a lipase for the production of fatty acid esters suitable for biodiesel is that the price of lipase is much higher than the price of sodium hydroxide (NaOH) used by the strong base process. This challenge has been addressed by using an immobilized lipase, which can be recycled. However, the activity of the immobilized lipase must be maintained after being recycled for a minimum number of cycles to allow a lipase-based process to compete with the strong base process in terms of the production cost Immobilized lipases are subject to poisoning by the lower alcohols typically used in transesterification. U.S. Pat. No. 6,398,707 (issued Jun. 4, 2002 to Wu et al.) describes methods for enhancing the activity of immobilized lipases and regenerating immobilized lipases having reduced activity. Some suitable methods include immersing an immobilized lipase in an alcohol having a carbon atom number not less than 3 for a period of time, preferably from 0.5-48 hours, and more preferably from 0.5-1.5 hours. Some suitable methods also include washing a deactivated immobilized lipase with an alcohol having a carbon atom number not less than 3 and then immersing the deactivated immobilized lipase in a vegetable oil for 0.5-48 hours.

In particular embodiments, a recombinant lipase is expressed in the same microorganisms that produce the lipid on which the lipase acts. Suitable recombinant lipases include those listed above in Table 9 and/or having GenBank Accession numbers listed above in Table 9, or a polypeptide that has at least 70% amino acid identity with one of the lipases listed above in Table 9 and that exhibits lipase activity. In additional embodiments, the enzymatic activity is present in a sequence that has at least about 75%, at least about 80%, at least about 85%, at least about 90%, at least about 95%, or at least about 99% identity with one of the above described sequences, all of which are hereby incorporated by reference as if fully set forth. DNA encoding the lipase and selectable marker is preferably codon-optimized cDNA. Methods of recoding genes for expression in microalgae are described in U.S. Pat. No. 7,135,290.

The common international standard for biodiesel is EN 14214. ASTM D6751 is the most common biodiesel standard referenced in the United States and Canada. Germany uses DIN EN 14214 and the UK requires compliance with BS EN 14214. Basic industrial tests to determine whether the products conform to these standards typically include gas chromatography, HPLC, and others. Biodiesel meeting the quality standards is very non-toxic, with a toxicity rating ($LD_{50}$) of greater than 50 mL/kg.

Although biodiesel that meets the ASTM standards has to be non-toxic, there can be contaminants which tend to crystallize and/or precipitate and fall out of solution as sediment. Sediment formation is particularly a problem when biodiesel is used at lower temperatures. The sediment or precipitates may cause problems such as decreasing fuel flow, clogging fuel lines, clogging filters, etc. Processes are well-known in the art that specifically deal with the removal of these contaminants and sediments in biodiesel in order to produce a higher quality product. Examples for such processes include, but are not limited to, pretreatment of the oil to remove contaminants such as phospholipids and free fatty acids (e.g., degumming, caustic refining and silica adsorbant filtration) and cold filtration. Cold filtration is a process that was developed specifically to remove any particulates and sediments that are present in the biodiesel after production. This process cools the biodiesel and filters out any sediments or precipitates that might form when the fuel is used at a lower temperature. Such a process is well known in the art and is described in US Patent Application Publication No. 2007-0175091. Suitable methods may include cooling the biodiesel to a temperature of less than about 38° C. so that the impurities and contaminants precipitate out as particulates in the biodiesel liquid. Diatomaceous earth or other filtering material may then added to the cooled biodiesel to form a slurry, which may then filtered through a pressure leaf or other type of filter to remove the particulates. The filtered biodiesel may then be run through a polish filter to remove any remaining sediments and diatomaceous earth, so as to produce the final biodiesel product.

Example 13 describes the production of biodiesel using triglyceride oil from *Prototheca moriformis*. The Cold Soak Filterability by the ASTM D6751 A1 method of the biodiesel produced in Example 13 was 120 seconds for a volume of 300 ml. This test involves filtration of 300 ml of B100, chilled to 40° F. for 16 hours, allowed to warm to room temp, and filtered under vacuum using 0.7 micron glass fiber filter with stainless steel support. Oils of the invention can be transesterified to generate biodiesel with a cold soak time of less than 120 seconds, less than 100 seconds, and less than 90 seconds.

Subsequent processes may also be used if the biodiesel will be used in particularly cold temperatures. Such processes include winterization and fractionation. Both processes are designed to improve the cold flow and winter performance of the fuel by lowering the cloud point (the temperature at which the biodiesel starts to crystallize). There are several approaches to winterizing biodiesel. One approach is to blend the biodiesel with petroleum diesel. Another approach is to use additives that can lower the cloud point of biodiesel. Another approach is to remove saturated methyl esters indiscriminately by mixing in additives and allowing for the crystallization of saturates and then filtering out the crystals. Fractionation selectively separates methyl esters into individual components or fractions, allowing for the removal or inclusion of specific methyl esters. Fractionation methods include urea fractionation, solvent fractionation and thermal distillation.

Another valuable fuel provided by the methods of the present invention is renewable diesel, which comprises alkanes, such as C10:0, C12:0, C14:0, C16:0 and C18:0 and thus, are distinguishable from biodiesel. High quality renewable diesel conforms to the ASTM D975 standard. The lipids produced by the methods of the present invention can serve as feedstock to produce renewable diesel. Thus, in another aspect of the present invention, a method for producing renewable diesel is provided. Renewable diesel can be produced by at least three processes: hydrothermal processing (hydrotreating); hydroprocessing; and indirect liquefaction. These processes yield non-ester distillates. During these processes, triacylglycerides produced and isolated as described herein, are converted to alkanes.

In one embodiment, the method for producing renewable diesel comprises (a) cultivating a lipid-containing microorganism using methods disclosed herein (b) lysing the microorganism to produce a lysate, (c) isolating lipid from the lysed microorganism, and (d) deoxygenating and hydrotreating the lipid to produce an alkane, whereby renewable diesel is produced. Lipids suitable for manufacturing renewable diesel can be obtained via extraction from microbial biomass using an organic solvent such as hexane, or via other methods, such as those described in U.S. Pat. No. 5,928,696. Some suitable methods may include mechanical pressing and centrifuging.

In some methods, the microbial lipid is first cracked in conjunction with hydrotreating to reduce carbon chain length and saturate double bonds, respectively. The material is then isomerized, also in conjunction with hydrotreating. The naptha fraction can then be removed through distillation, followed by additional distillation to vaporize and distill components desired in the diesel fuel to meet an ASTM D975 standard while leaving components that are heavier than desired for meeting the D975 standard. Hydrotreating, hydrocracking, deoxygenation and isomerization methods of chemically modifying oils, including triglyceride oils, are well known in the art. See for example European patent applications EP1741768 (A1); EP1741767 (A1); EP1682466 (A1); EP1640437 (A1); EP1681337 (A1); EP1795576 (A1); and U.S. Pat. Nos. 7,238,277; 6,630,066; 6,596,155; 6,977,322; 7,041,866; 6,217,746; 5,885,440; 6,881,873.

In one embodiment of the method for producing renewable diesel, treating the lipid to produce an alkane is performed by hydrotreating of the lipid composition. In hydrothermal processing, typically, biomass is reacted in water at an elevated temperature and pressure to form oils and residual solids. Conversion temperatures are typically 300° to 660° F., with pressure sufficient to keep the water primarily as a liquid, 100 to 170 standard atmosphere (atm). Reaction times are on the order of 15 to 30 minutes. After the reaction is completed, the organics are separated from the water. Thereby a distillate suitable for diesel is produced.

In some methods of making renewable diesel, the first step of treating a triglyceride is hydroprocessing to saturate double bonds, followed by deoxygenation at elevated temperature in the presence of hydrogen and a catalyst. In some methods, hydrogenation and deoxygenation occur in the same reaction. In other methods deoxygenation occurs before hydrogenation. Isomerization is then optionally performed, also in the presence of hydrogen and a catalyst. Naphtha components are preferably removed through distillation. For examples, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

One suitable method for the hydrogenation of triglycerides includes preparing an aqueous solution of copper, zinc, magnesium and lanthanum salts and another solution of alkali metal or preferably, ammonium carbonate. The two solutions may be heated to a temperature of about 20° C. to about 85° C. and metered together into a precipitation container at rates such that the pH in the precipitation container is maintained between 5.5 and 7.5 in order to form a catalyst. Additional water may be used either initially in the precipitation container or added concurrently with the salt solution and precipitation solution. The resulting precipitate may then be thoroughly washed, dried, calcined at about 300° C. and activated in hydrogen at temperatures ranging from about 100° C. to about 400° C. One or more triglycerides may then be contacted and reacted with hydrogen in the presence of the above-described catalyst in a reactor. The reactor may be a trickle bed reactor, fixed bed gas-solid reactor, packed bubble column reactor, continuously stirred tank reactor, a slurry phase reactor, or any other suitable reactor type known in the art. The process may be carried out either batchwise or in continuous fashion. Reaction temperatures are typically in the range of from about 170° C. to about 250° C. while reaction pressures are typically in the range of from about 300 psig to about 2000 psig. Moreover, the molar ratio of hydrogen to triglyceride in the process of the present invention is typically in the range of from about 20:1 to about 700:1. The process is typically carried out at a weight hourly space velocity (WHSV) in the range of from about 0.1 hr$^{-1}$ to about 5 hr$^{-1}$. One skilled in the art will recognize that the time period required for reaction will vary according to the temperature used, the molar ratio of hydrogen to triglyceride, and the partial pressure of hydrogen. The products produced by the such hydrogenation processes include fatty alcohols, glycerol, traces of paraffins and unreacted triglycerides. These products are typically separated by conventional means such as, for example, distillation, extraction, filtration, crystallization, and the like.

Petroleum refiners use hydroprocessing to remove impurities by treating feeds with hydrogen. Hydroprocessing conversion temperatures are typically 300° to 700° F. Pressures are typically 40 to 100 atm. The reaction times are typically on the order of 10 to 60 minutes. Solid catalysts are employed to increase certain reaction rates, improve selectivity for certain products, and optimize hydrogen consumption.

Suitable methods for the deoxygenation of an oil includes heating an oil to a temperature in the range of from about 350° F. to about 550° F. and continuously contacting the heated oil with nitrogen under at least pressure ranging from about atmospheric to above for at least about 5 minutes.

Suitable methods for isomerization include using alkali isomerization and other oil isomerization known in the art.

Hydrotreating and hydroprocessing ultimately lead to a reduction in the molecular weight of the triglyceride feed. The triglyceride molecule is reduced to four hydrocarbon molecules under hydroprocessing conditions: a propane molecule and three heavier hydrocarbon molecules, typically in the C8 to C18 range.

Thus, in one embodiment, the product of one or more chemical reaction(s) performed on lipid compositions of the invention is an alkane mixture that comprises ASTM D975 renewable diesel. Production of hydrocarbons by microorganisms is reviewed by Metzger et al. Appl Microbiol Biotechnol (2005) 66: 486-496 and A Look Back at the U.S. Department of Energy's Aquatic Species Program: Biodiesel from Algae, NREL/TP-580-24190, John Sheehan, Terri Dunahay, John Benemann and Paul Roessler (1998).

The distillation properties of a diesel fuel is described in terms of T10-T90 (temperature at 10% and 90%, respectively, volume distilled). Renewable diesel was produced from *Prototheca moriformis* triglyceride oil and is described in Example 13. The T10-T90 of the material produced in Example 13 was 57.9° C. Methods of hydrotreating, isomerization, and other covalent modification of oils disclosed herein, as well as methods of distillation and fractionation (such as cold filtration) disclosed herein, can be employed to generate renewable diesel compositions with other T10-T90 ranges, such as 20, 25, 30, 35, 40, 45, 50, 60 and 65° C. using triglyceride oils produced according to the methods disclosed herein.

The T10 of the material produced in Example 13 was 242.1° C. Methods of hydrotreating, isomerization, and other covalent modification of oils disclosed herein, as well as methods of distillation and fractionation (such as cold filtration) disclosed herein, can be employed to generate renewable diesel compositions with other T10 values, such as T10 between 180 and 295, between 190 and 270, between 210 and 250, between 225 and 245, and at least 290.

The T90 of the material produced in Example 13 was 300° C. Methods of hydrotreating, isomerization, and other covalent modification of oils disclosed herein, as well as methods of distillation and fractionation (such as cold filtration) disclosed herein can be employed to generate renewable diesel compositions with other T90 values, such as T90 between 280 and 380, between 290 and 360, between 300 and 350, between 310 and 340, and at least 290.

The FBP of the material produced in Example 13 was 300° C. Methods of hydrotreating, isomerization, and other covalent modification of oils disclosed herein, as well as methods of distillation and fractionation (such as cold filtration) disclosed herein, can be employed to generate renewable diesel compositions with other FBP values, such as FBP between 290 and 400, between 300 and 385, between 310 and 370, between 315 and 360, and at least 300.

Other oils provided by the methods and compositions of the invention can be subjected to combinations of hydrotreating, isomerization, and other covalent modification including oils with lipid profiles including (a) at least 1%-5%, preferably at least 4%, C8-C14; (b) at least 0.25%-1%, preferably at least 0.3%, C8; (c) at least 1%-5%, preferably at least 2%, C10; (d) at least 1%-5%, preferably at least 2%, C12; and (3) at least 20%-40%, preferably at least 30% C8-C14.

A traditional ultra-low sulfur diesel can be produced from any form of biomass by a two-step process. First, the biomass is converted to a syngas, a gaseous mixture rich in hydrogen and carbon monoxide. Then, the syngas is catalytically converted to liquids. Typically, the production of liquids is accomplished using Fischer-Tropsch (FT) synthesis. This technology applies to coal, natural gas, and heavy oils. Thus, in yet another preferred embodiment of the method for producing renewable diesel, treating the lipid composition to produce an alkane is performed by indirect liquefaction of the lipid composition.

The present invention also provides methods to produce jet fuel. Jet fuel is clear to straw colored. The most common fuel is an unleaded/paraffin oil-based fuel classified as Aeroplane A-1, which is produced to an internationally standardized set of specifications. Jet fuel is a mixture of a large number of different hydrocarbons, possibly as many as a thousand or more. The range of their sizes (molecular weights or carbon numbers) is restricted by the requirements for the product, for example, freezing point or smoke point. Kerosene-type Aeroplane fuel (including Jet A and Jet A-1) has a carbon number distribution between about 8 and 16 carbon numbers. Wide-cut or naphta-type Aeroplane fuel (including Jet B) typically has a carbon number distribution between about 5 and 15 carbons.

Both Aeroplanes (Jet A and Jet B) may contain a number of additives. Useful additives include, but are not limited to, antioxidants, antistatic agents, corrosion inhibitors, and fuel system icing inhibitor (FSII) agents. Antioxidants prevent gumming and usually, are based on alkylated phenols, for example, AO-30, AO-31, or AO-37. Antistatic agents dissipate static electricity and prevent sparking. Stadis 450 with dinonylnaphthylsulfonic acid (DINNSA) as the active ingredient, is an example. Corrosion inhibitors, e.g., DCI-4A is used for civilian and military fuels and DCI-6A is used for military fuels. FSII agents, include, e.g., Di-EGME.

In one embodiment of the invention, a jet fuel is produced by blending algal fuels with existing jet fuel. The lipids produced by the methods of the present invention can serve as feedstock to produce jet fuel. Thus, in another aspect of the present invention, a method for producing jet fuel is provided. Herewith two methods for producing jet fuel from the lipids produced by the methods of the present invention are provided: fluid catalytic cracking (FCC); and hydrodeoxygenation (HDO).

Fluid Catalytic Cracking (FCC) is one method which is used to produce olefins, especially propylene from heavy crude fractions. The lipids produced by the method of the present invention can be converted to olefins. The process involves flowing the lipids produced through an FCC zone and collecting a product stream comprised of olefins, which is useful as a jet fuel. The lipids produced are contacted with a cracking catalyst at cracking conditions to provide a product stream comprising olefins and hydrocarbons useful as jet fuel.

In one embodiment, the method for producing jet fuel comprises (a) cultivating a lipid-containing microorganism using methods disclosed herein, (b) lysing the lipid-containing microorganism to produce a lysate, (c) isolating lipid from the lysate, and (d) treating the lipid composition, whereby jet fuel is produced. In one embodiment of the method for producing a jet fuel, the lipid composition can be flowed through a fluid catalytic cracking zone, which, in one embodiment, may comprise contacting the lipid composition with a cracking catalyst at cracking conditions to provide a product stream comprising $C_2$-$C_5$ olefins.

In certain embodiments of this method, it may be desirable to remove any contaminants that may be present in the lipid composition. Thus, prior to flowing the lipid composition through a fluid catalytic cracking zone, the lipid composition is pretreated. Pretreatment may involve contacting the lipid composition with an ion-exchange resin. The ion exchange resin is an acidic ion exchange resin, such as Amberlyst™-15 and can be used as a bed in a reactor through which the lipid composition is flowed, either upflow or downflow. Other pretreatments may include mild acid washes by contacting the lipid composition with an acid, such as sulfuric, acetic, nitric, or hydrochloric acid. Contacting is done with a dilute acid solution usually at ambient temperature and atmospheric pressure.

The lipid composition, optionally pretreated, is flowed to an FCC zone where the hydrocarbonaceous components are cracked to olefins. Catalytic cracking is accomplished by contacting the lipid composition in a reaction zone with a catalyst composed of finely divided particulate material. The reaction is catalytic cracking, as opposed to hydrocracking, and is carried out in the absence of added hydrogen or the consumption of hydrogen. As the cracking reaction proceeds, substantial amounts of coke are deposited on the catalyst. The catalyst is regenerated at high temperatures by burning coke from the catalyst in a regeneration zone. Coke-containing catalyst, referred to herein as "coked catalyst", is continually transported from the reaction zone to the regeneration zone to be regenerated and replaced by essentially coke-free regenerated catalyst from the regeneration zone. Fluidization of the catalyst particles by various gaseous streams allows the transport of catalyst between the reaction zone and regeneration zone. Methods for cracking hydrocarbons, such as those of the lipid composition described herein, in a fluidized stream of catalyst, transporting catalyst between reaction and regeneration zones, and combusting coke in the regenerator are well known by those skilled in the art of FCC processes. Exemplary FCC applications and catalysts useful for cracking the lipid composition to produce $C_2$-$C_5$ olefins are described in U.S. Pat. Nos. 6,538,169, 7,288,685, which are incorporated in their entirety by reference.

Suitable FCC catalysts generally comprise at least two components that may or may not be on the same matrix. In some embodiments, both two components may be circulated throughout the entire reaction vessel. The first component generally includes any of the well-known catalysts that are used in the art of fluidized catalytic cracking, such as an active amorphous clay-type catalyst and/or a high activity, crystalline molecular sieve. Molecular sieve catalysts may be preferred over amorphous catalysts because of their much-improved selectivity to desired products. IN some preferred embodiments, zeolites may be used as the molecular sieve in the FCC processes. Preferably, the first catalyst component comprises a large pore zeolite, such as an Y-type zeolite, an active alumina material, a binder material, comprising either silica or alumina and an inert filler such as kaolin.

In one embodiment, cracking the lipid composition of the present invention, takes place in the riser section or, alternatively, the lift section, of the FCC zone. The lipid composition is introduced into the riser by a nozzle resulting in the rapid vaporization of the lipid composition. Before contacting the catalyst, the lipid composition will ordinarily have a temperature of about 149° C. to about 316° C. (300° F. to 600° F.). The catalyst is flowed from a blending vessel to the riser where it contacts the lipid composition for a time of abort 2 seconds or less.

The blended catalyst and reacted lipid composition vapors are then discharged from the top of the riser through an outlet and separated into a cracked product vapor stream including olefins and a collection of catalyst particles covered with substantial quantities of coke and generally referred to as "coked catalyst." In an effort to minimize the contact time of the lipid composition and the catalyst which may promote further conversion of desired products to undesirable other products, any arrangement of separators such as a swirl arm arrangement can be used to remove coked catalyst from the product stream quickly. The separator, e.g. swirl arm separator, is located in an upper portion of a chamber with a stripping zone situated in the lower portion of the chamber. Catalyst separated by the swirl arm arrangement drops down into the stripping zone. The cracked product vapor stream comprising cracked hydrocarbons including light olefins and some catalyst exit the chamber via a conduit which is in communication with cyclones. The cyclones remove remaining catalyst particles from the product vapor stream to reduce particle concentrations to very low levels. The product vapor stream then exits the top of the separating vessel. Catalyst separated by the cyclones is returned to the separating vessel and then to the stripping zone. The stripping zone removes adsorbed hydrocarbons from the surface of the catalyst by counter-current contact with steam.

Low hydrocarbon partial pressure operates to favor the production of light olefins. Accordingly, the riser pressure is set at about 172 to 241 kPa (25 to 35 psia) with a hydrocarbon partial pressure of about 35 to 172 kPa (5 to 25 psia), with a preferred hydrocarbon partial pressure of about 69 to 138 kPa (10 to 20 psia). This relatively low partial pressure for hydrocarbon is achieved by using steam as a diluent to the extent that the diluent is 10 to 55 wt-% of lipid composition and preferably about 15 wt-% of lipid composition. Other diluents such as dry gas can be used to reach equivalent hydrocarbon partial pressures.

The temperature of the cracked stream at the riser outlet will be about 510° C. to 621° C. (950° F. to 1150° F.). However, riser outlet temperatures above 566° C. (1050° F.) make more dry gas and more olefins. Whereas, riser outlet temperatures below 566° C. (1050° F.) make less ethylene and propylene. Accordingly, it is preferred to run the FCC process at a preferred temperature of about 566° C. to about 630° C., preferred pressure of about 138 kPa to about 240 kPa (20 to 35 psia). Another condition for the process is the catalyst to lipid composition ratio which can vary from about 5 to about 20 and preferably from about 10 to about 15.

In one embodiment of the method for producing a jet fuel, the lipid composition is introduced into the lift section of an FCC reactor. The temperature in the lift section will be very hot and range from about 700° C. (1292° F.) to about 760° C. (1400° F.) with a catalyst to lipid composition ratio of about 100 to about 150. It is anticipated that introducing the lipid composition into the lift section will produce considerable amounts of propylene and ethylene.

In another embodiment of the method for producing a jet fuel using the lipid composition or the lipids produced as described herein, the structure of the lipid composition or the lipids is broken by a process referred to as hydrodeoxygenation (HDO). HDO means removal of oxygen by means of hydrogen, that is, oxygen is removed while breaking the structure of the material. Olefinic double bonds are hydrogenated and any sulphur and nitrogen compounds are removed. Sulphur removal is called hydrodesulphurization (HDS). Pretreatment and purity of the raw materials (lipid composition or the lipids) contribute to the service life of the catalyst.

Generally in the HDO/HDS step, hydrogen is mixed with the feed stock (lipid composition or the lipids) and then the mixture is passed through a catalyst bed as a co-current flow, either as a single phase or a two phase feed stock. After the HDO/MDS step, the product fraction is separated and passed to a separate isomerzation reactor. An isomerization reactor for biological starting material is described in the literature (FI 100 248) as a co-current reactor.

The process for producing a fuel by hydrogenating a hydrocarbon feed, e.g., the lipid composition or the lipids herein, can also be performed by passing the lipid composition or the lipids as a co-current flow with hydrogen gas through a first hydrogenation zone, and thereafter the hydrocarbon effluent is further hydrogenated in a second hydrogenation zone by passing hydrogen gas to the second hydrogenation zone as a counter-current flow relative to the hydrocarbon effluent. Exemplary HDO applications and catalysts useful for cracking the lipid composition to produce $C_2$-$C_5$ olefins are described in U.S. Pat. No. 7,232,935, which is incorporated in its entirety by reference.

Typically, in the hydrodeoxygenation step, the structure of the biological component, such as the lipid composition or lipids herein, is decomposed, oxygen, nitrogen, phosphorus and sulphur compounds, and light hydrocarbons as gas are removed, and the olefinic bonds are hydrogenated. In the second step of the process, i.e. in the so-called isomerization step, isomerzation is carried out for branching the hydrocarbon chain and improving the performance of the paraffin at low temperatures.

In the first step, i.e. HDO step, of the cracking process, hydrogen gas and the lipid composition or lipids herein which are to be hydrogenated are passed to a HDO catalyst bed system either as co-current or counter-current flows, said catalyst bed system comprising one or more catalyst bed(s), preferably 1-3 catalyst beds. The HDO step is typically operated in a co-current manner. In case of a HDO catalyst bed system comprising two or more catalyst beds, one or more of the beds may be operated using the counter-current flow principle. In the HDO step, the pressure varies between 20 and 150 bar, preferably between 50 and 100 bar, and the temperature varies between 200 and 500° C., preferably in the range of 300-400° C. In the HDO step, known hydrogenation catalysts containing metals from Group VII and/or VIB of the Periodic System may be used. Preferably, the hydrogenation catalysts are supported Pd, Pt, Ni, NiMo or a CoMo catalysts, the support being alumina and/or silica. Typically, $NiMo/Al_2O_3$ and $CoMo/Al_2O_3$ catalysts are used.

Prior to the HDO step, the lipid composition or lipids herein may optionally be treated by prehydrogenation under milder conditions thus avoiding side reactions of the double bonds. Such prehydrogenation is carried out in the presence of a prehydrogenation catalyst at temperatures of 50-400° C. and at hydrogen pressures of 1-200 bar, preferably at a temperature between 150 and 250° C. and at a hydrogen pressure between 10 and 100 bar. The catalyst may contain metals from Group VIII and/or VIB of the Periodic System. Preferably, the prehydrogenation catalyst is a supported Pd, Pt, Ni, NiMo or a CoMo catalyst, the support being alumina and/or silica.

A gaseous stream from the HDO step containing hydrogen is cooled and then carbon monoxide, carbon dioxide, nitrogen, phosphorus and sulphur compounds, gaseous light hydrocarbons and other impurities are removed therefrom. After compressing, the purified hydrogen or recycled hydrogen is returned back to the first catalyst bed and/or between the catalyst beds to make up for the withdrawn gas stream. Water is removed from the condensed liquid. The liquid is passed to the first catalyst bed or between the catalyst beds.

After the HDO step, the product is subjected to an isomerization step. It is substantial for the process that the impurities are removed as completely as possible before the hydrocarbons are contacted with the isomerization catalyst. The isomerization step comprises an optional stripping step, wherein the reaction product from the HDO step may be purified by stripping with water vapour or a suitable gas such as light hydrocarbon, nitrogen or hydrogen. The optional stripping step is carried out in counter-current manner in a unit upstream of the isomerization catalyst, wherein the gas and liquid are contacted with each other, or before the actual isomerization reactor in a separate stripping unit utilizing counter-current principle.

After the stripping step the hydrogen gas and the hydrogenated lipid composition or lipids herein, and optionally an n-paraffin mixture, are passed to a reactive isomerization unit comprising one or several catalyst bed(s). The catalyst beds of the isomerization step may operate either in co-current or counter-current manner.

It is important for the process that the counter-current flow principle is applied in the isomerization step. In the isomerization step this is done by carrying out either the optional stripping step or the isomerization reaction step or both in counter-current manner. In the isomerzation step, the pressure varies in the range of 20-150 bar, preferably in the range of 20-100 bar, the temperature being between 200 and 500° C., preferably between 300 and 400° C. In the isomerization step, isomerization catalysts known in the art may be used. Suitable isomerization catalysts contain molecular sieve and/or a metal from Group VII and/or a carrier. Preferably, the isomerization catalyst contains SAPO-11 or SAPO41 or ZSM-22 or ZSM-23 or ferrierite and Pt, Pd or Ni and $Al_2O_3$ or $SiO_2$. Typical isomerization catalysts are, for example, $Pt/SAPO-11/Al_2O_3$, $Pt/ZSM-22/Al_2O_3$, $Pt/ZSM-23/Al_2O_3$ and $Pt/SAPO-11/SiO_2$. The isomerization step and the HDO step may be carried out in the same pressure vessel or in separate pressure vessels. Optional prehydrogenation may be carried out in a separate pressure vessel or in the same pressure vessel as the HDO and isomerization steps.

Thus, in one embodiment, the product of one or more chemical reactions is an alkane mixture that comprises HRJ-5. In another embodiment, the product of the one or more chemical reactions is an alkane mixture that comprises ASTM D1655 jet fuel. In some embodiments, the composition conforming to the specification of ASTM 1655 jet fuel has a sulfur content that is less than 10 ppm. In other embodiments, the composition conforming to the specification of ASTM 1655 jet fuel has a T10 value of the distillation curve of less than 205° C. In another embodiment, the composition conforming to the specification of ASTM 1655 jet fuel has a final boiling point (FBP) of less than 300° C. In another embodiment, the composition conforming to the specification of ASTM 1655 jet fuel has a flash point of at least 38° C. In another embodiment, the composition conforming to the specification of ASTM 1655 jet fuel has a density between $775K/M^3$ and $840K/M^3$. In yet another embodiment, the composition conforming to the specification of ASTM 1655 jet fuel has a freezing point that is below −47° C. In another embodiment, the composition conforming to the specification of ASTM 1655 jet fuel has a net Heat of Combustion that is at least 42.8 MJ/K. In another embodiment, the composition conforming to the specification of ASTM 1655 jet fuel has a hydrogen content that is at least 13.4 mass %. In another embodiment, the composition conforming to the specification of ASTM 1655 jet fuel has a thermal stability, as tested by quantitative gravimetric JFTOT at 260° C., that is below 3 mm of Hg. In another embodiment, the composition conforming to the specification of ASTM 1655 jet fuel has an existent gum that is below 7 mg/dl.

Thus, the present invention discloses a variety of methods in which chemical modification of microalgal lipid is undertaken to yield products useful in a variety of industrial and other applications. Examples of processes for modifying oil produced by the methods disclosed herein include, but are not limited to, hydrolysis of the oil, hydroprocessing of the oil, and esterification of the oil. Other chemical modification of microalgal lipid include, without limitation, epoxidation, oxidation, hydrolysis, sulfations, sulfonation, ethoxylation, propoxylation, amidation, and saponification. The modification of the microalgal oil produces basic oleochemicals that can be further modified into selected derivative oleochemicals for a desired function. In a manner similar to that described above with reference to fuel producing processes, these chemical modifications can also be performed on oils generated from the microbial cultures described herein. Examples of basic oleochemicals include, but are not limited to, soaps, fatty acids, fatty esters, fatty alcohols, fatty nitrogen compounds, fatty acid methyl esters, and glycerol. Examples of derivative oleochemicals include, but are not limited to, fatty nitriles, esters, dimer acids, quats, surfactants, fatty alkanolamides, fatty alcohol sulfates, resins, emulsifiers, fatty alcohols, olefins, drilling muds, polyols, polyurethanes, polyacrylates, rubber, candles, cosmetics, metallic soaps, soaps, alpha-sulphonated methyl esters, fatty alcohol sulfates, fatty alcohol ethoxylates, fatty alcohol ether sulfates, imidazolines, surfactants, detergents, esters, quats, ozonolysis products, fatty amines, fatty alkanolamides, ethoxy sulfates, monoglycerides, diglycerides, triglycerides (including medium chain triglycerides), lubricants, hydraulic fluids, greases, dielectric fluids, mold release agents, metal working fluids, heat transfer fluids, other functional fluids, industrial chemicals (e.g., cleaners, textile processing aids, plasticizers, stabilizers, additives), surface coatings, paints and lacquers, electrical wiring insulation, and higher alkanes.

Hydrolysis of the fatty acid constituents from the glycerolipids produced by the methods of the invention yields free fatty acids that can be derivatized to produce other useful chemicals. Hydrolysis occurs in the presence of water and a catalyst which may be either an acid or a base. The liberated free fatty acids can be derivatized to yield a variety of products, as reported in the following: U.S. Pat. No. 5,304,664 (Highly sulfated fatty acids); U.S. Pat. No. 7,262,158 (Cleansing compositions); U.S. Pat. No. 7,115,173 (Fabric softener compositions); U.S. Pat. No. 6,342,208 (Emulsions for treating skin); U.S. Pat. No. 7,264,886 (Water repellant compositions); U.S. Pat. No. 6,924,333 (Paint additives); U.S. Pat. No. 6,596,768 (Lipid-enriched ruminant feedstock); and U.S. Pat. No. 6,380,410 (Surfactants for detergents and cleaners).

With regard to hydrolysis, in one embodiment of the invention, a triglyceride oil is optionally first hydrolyzed in a liquid medium such as water or sodium hydroxide so as to obtain glycerol and soaps. There are various suitable triglyceride hydrolysis methods, including, but not limited to, saponification, acid hydrolysis, alkaline hydrolysis, enzymatic hydrolysis (referred herein as splitting), and hydrolysis using hot-compressed water. One skilled in the art will recognize that a triglyceride oil need not be hydrolyzed in order to produce an oleochemical; rather, the oil may be converted directly to the desired oleochemical by other known process. For example, the triglyceride oil may be directly converted to a methyl ester fatty acid through esterification.

In some embodiments, catalytic hydrolysis of the oil produced by methods disclosed herein occurs by splitting the oil into glycerol and fatty acids. As discussed above, the fatty acids may then be further processed through several other modifications to obtained derivative oleochemicals. For example, in one embodiment the fatty acids may undergo an amination reaction to produce fatty nitrogen compounds. In another embodiment, the fatty acids may undergo ozonolysis to produce mono- and dibasic-acids.

In other embodiments hydrolysis may occur via the, splitting of oils produced herein to create oleochemicals. In some preferred embodiments of the invention, a triglyceride oil may be split before other processes is performed. One skilled in the art will recognize that there are many suitable triglyceride splitting methods, including, but not limited to, enzymatic splitting and pressure splitting.

Generally, enzymatic oil splitting methods use enzymes, lipases, as biocatalysts acting on a water/oil mixture. Enzymatic splitting then splits the oil or fat, respectively, is into glycerol and free fatty acids. The glycerol may then migrates into the water phase whereas the organic phase enriches with free fatty acids.

The enzymatic splitting reactions generally take place at the phase boundary between organic and aqueous phase, where the enzyme is present only at the phase boundary. Triglycerides that meet the phase boundary then contribute to or participate in the splitting reaction. As the reaction proceeds, the occupation density or concentration of fatty acids still chemically bonded as glycerides, in comparison to free fatty acids, decreases at the phase boundary so that the reaction is slowed down. In certain embodiments, enzymatic splitting may occur at room temperature. One of ordinary skill in the art would know the suitable conditions for splitting oil into the desired fatty acids.

By way of example, the reaction speed can be accelerated by increasing the interface boundary surface. Once the reaction is complete, free fatty acids are then separated from the organic phase freed from enzyme, and the residue which still contains fatty acids chemically bonded as glycerides is fed back or recycled and mixed with fresh oil or fat to be subjected to splitting. In this manner, recycled glycerides are then subjected to a further enzymatic splitting process. In some embodiments, the free fatty acids are extracted from an oil or fat partially split in such a manner. In that way, if the chemically bound fatty acids (triglycerides) are returned or fed back into the splitting process, the enzyme consumption can be drastically reduced.

The splitting degree is determined as the ratio of the measured acid value divided by the theoretically possible acid value which can be computed for a given oil or fat. Preferably, the acid value is measured by means of titration according to standard common methods. Alternatively, the density of the aqueous glycerol phase can be taken as a measure for the splitting degree.

In one embodiment, the slitting process as described herein is also suitable for splitting the mono-, di- and triglyceride that are contained in the so-called soap-stock from the alkali refining processes of the produced oils. In this manner, the soap-stock can be quantitatively converted without prior saponification of the neutral oils into the fatty acids. For this purpose, the fatty acids being chemically bonded in the soaps are released, preferably before splitting, through an addition of acid. In certain embodiments, a buffer solution is used in addition to water and enzyme for the splitting process.

In one embodiment, oils produced in accordance with the methods of the invention can also be subjected to saponification as a method of hydrolysis Animal and plant oils are typically made of triacylglycerols (TAGs), which are esters of fatty acids with the trihydric alcohol, glycerol. In an alkaline hydrolysis reaction, the glycerol in a TAG is removed, leaving three carboxylic acid anions that can associate with alkali metal cations such as sodium or potassium to produce fatty acid salts. In this scheme, the carboxylic acid constituents are cleaved from the glycerol moiety and replaced with hydroxyl groups. The quantity of base (e.g., KOH) that is used in the reaction is determined by the desired degree of saponification. If the objective is, for example, to produce a soap product that comprises some of the oils originally present in the TAG composition, an amount of base insufficient to convert all of the TAGs to fatty acid salts is introduced into the reaction mixture. Normally, this reaction is performed in an aqueous solution and proceeds slowly, but may be expedited by the addition of heat. Precipitation of the fatty acid salts can be facilitated by addition of salts, such as water-soluble alkali metal halides (e.g., NaCl or KCl), to the reaction mixture. Preferably, the base is an alkali metal hydroxide, such as NaOH or KOH. Alternatively, other bases, such as alkanolamines, including for example triethanolamine and aminomethylpropanol, can be used in the reaction scheme. In some cases, these alternatives may be preferred to produce a clear soap product. In one embodiment the lipid composition subjected to saponification is a tallow mimetic (i.e., lipid composition similar to that of tallow) produced as described herein, or a blend of a tallow mimetic with another triglyceride oil.

In some methods, the first step of chemical modification may be hydroprocessing to saturate double bonds, followed by deoxygenation at elevated temperature in the presence of hydrogen and a catalyst. In other methods, hydrogenation and deoxygenation may occur in the same reaction. In still other methods deoxygenation occurs before hydrogenation. Isomerization may then be optionally performed, also in the presence of hydrogen and a catalyst. Finally, gases and naphtha components can be removed if desired. For example, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

In some embodiments of the invention, the triglyceride oils are partially or completely deoxygenated. The deoxygenation reactions form desired products, including, but not limited to, fatty acids, fatty alcohols, polyols, ketones, and aldehydes. In general, without being limited by any particular theory, the deoxygenation reactions involve a combination of various different reaction pathways, including without limitation: hydrogenolysis, hydrogenation, consecutive hydrogenation-hydrogenolysis, consecutive hydrogenolysis-hydrogenation, and combined hydrogenation-hydrogenolysis reactions, resulting in at least the partial removal of oxygen from the fatty acid or fatty acid ester to produce reaction products, such as fatty alcohols, that can be easily converted to the desired chemicals by further processing. For example, in one embodiment, a fatty alcohol may be converted to olefins through FCC reaction or to higher alkanes through a condensation reaction.

One such chemical modification is hydrogenation, which is the addition of hydrogen to double bonds in the fatty acid constituents of glycerolipids or of free fatty acids. The hydrogenation process permits the transformation of liquid oils into semi-solid or solid fats, which may be more suitable for specific applications.

Hydrogenation of oil produced by the methods described herein can be performed in conjunction with one or more of the methods and/or materials provided herein, as reported in the following: U.S. Pat. No. 7,288,278 (Food additives or medicaments); U.S. Pat. No. 5,346,724 (Lubrication products); U.S. Pat. No. 5,475,160 (Fatty alcohols); U.S. Pat. No. 5,091,116 (Edible oils); U.S. Pat. No. 6,808,737 (Structural fats for margarine and spreads); U.S. Pat. No. 5,298,637 (Reduced-calorie fat substitutes); U.S. Pat. No. 6,391,815 (Hydrogenation catalyst and sulfur adsorbent); U.S. Pat. No. 5,233,099 and U.S. Pat. No. 5,233,100 (Fatty alcohols); U.S. Pat. No. 4,584,139 (Hydrogenation catalysts); U.S. Pat. No. 6,057,375 (Foam suppressing agents); and U.S. Pat. No. 7,118,773 (Edible emulsion spreads).

One skilled in the art will recognize that various processes may be used to hydrogenate carbohydrates. One suitable method includes contacting the carbohydrate with hydrogen or hydrogen mixed with a suitable gas and a catalyst under conditions sufficient in a hydrogenation reactor to form a hydrogenated product. The hydrogenation catalyst generally can include Cu, Re, Ni, Fe, Co, Ru, Pd, Rh, Pt, Os, Ir, and alloys or any combination thereof, either alone or with promoters such as W, Mo, Au, Ag, Cr, Zn, Mn, Sn, B, P, Bi, and alloys or any combination thereof. Other effective hydrogenation catalyst materials include either supported nickel or ruthenium modified with rhenium. In an embodiment, the hydrogenation catalyst also includes any one of the supports, depending on the desired functionality of the catalyst. The hydrogenation catalysts may be prepared by methods known to those of ordinary skill in the art.

In some embodiments the hydrogenation catalyst includes a supported Group VIII metal catalyst and a metal sponge material (e.g., a sponge nickel catalyst). Raney nickel provides an example of an activated sponge nickel catalyst suitable for use in this invention. In other embodiment, the hydrogenation reaction in the invention is performed using a catalyst comprising a nickel-rhenium catalyst or a tungsten-modified nickel catalyst. One example of a suitable catalyst for the hydrogenation reaction of the invention is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 weight % of sodium hydroxide. The aluminum is selectively dissolved by the aqueous alkali solution resulting in a sponge shaped material comprising mostly nickel with minor amounts of aluminum. The initial alloy includes promoter metals (i.e., molybdenum or chromium) in the amount such that about 1 to 2 weight % remains in the formed sponge nickel catalyst. In another embodiment, the hydrogenation catalyst is prepared using a solution of ruthenium(III) nitrosylnitrate, ruthenium (III) chloride in water to impregnate a suitable support material. The solution is then dried to form a solid having a water content of less than about 1% by weight. The solid may then be reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the catalyst described includes a catalyst support. The catalyst support stabilizes and supports the catalyst. The type of catalyst support used depends on the chosen catalyst and the reaction conditions. Suitable supports for the invention include, but are not limited to, carbon, silica, silica-alumina, zirconia, titania, ceria, vanadia, nitride, boron nitride, heteropolyacids, hydroxyapatite, zinc oxide, chromia, zeolites, carbon nanotubes, carbon fullerene and any combination thereof.

The catalysts used in this invention can be prepared using conventional methods known to those in the art. Suitable methods may include, but are not limited to, incipient wetting, evaporative impregnation, chemical vapor deposition, wash-coating, magnetron sputtering techniques, and the like.

The conditions for which to carry out the hydrogenation reaction will vary based on the type of starting material and the desired products. One of ordinary skill in the art, with the benefit of this disclosure, will recognize the appropriate reaction conditions. In general, the hydrogenation reaction is conducted at temperatures of 80° C. to 250° C., and preferably at 90° C. to 200° C., and most preferably at 100° C. to 150° C. In some embodiments, the hydrogenation reaction is conducted at pressures from 500 KPa to 14000 KPa.

The hydrogen used in the hydrogenolysis reaction of the current invention may include external hydrogen, recycled hydrogen, in situ generated hydrogen, and any combination thereof. As used herein, the term "external hydrogen" refers to hydrogen that does not originate from the biomass reaction itself, but rather is added to the system from another source.

In some embodiments of the invention, it is desirable to convert the starting carbohydrate to a smaller molecule that will be more readily converted to desired higher hydrocarbons. One suitable method for this conversion is through a hydrogenolysis reaction. Various processes are known for performing hydrogenolysis of carbohydrates. One suitable method includes contacting a carbohydrate with hydrogen or hydrogen mixed with a suitable gas and a hydrogenolysis catalyst in a hydrogenolysis reactor under conditions sufficient to form a reaction product comprising smaller molecules or polyols. As used herein, the term "smaller molecules or polyols" includes any molecule that has a smaller molecular weight, which can include a smaller number of carbon atoms or oxygen atoms than the starting carbohydrate. In an embodiment, the reaction products include smaller molecules that include polyols and alcohols. Someone of ordinary skill in the art would be able to choose the appropriate method by which to carry out the hydrogenolysis reaction.

In some embodiments, a 5 and/or 6 carbon sugar or sugar alcohol may be converted to propylene glycol, ethylene glycol, and glycerol using a hydrogenolysis catalyst. The hydrogenolysis catalyst may include Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. The hydrogenolysis catalyst may also include a carbonaceous pyropolymer catalyst containing transition metals (e.g., chromium, molybdemum, tungsten, rhenium, manganese, copper, cadmium) or Group VIII metals (e.g., iron, cobalt, nickel, platinum, palladium, rhodium, ruthenium, iridium, and osmium). In certain embodiments, the hydrogenolysis catalyst may include any of the above metals combined with an alkaline earth metal oxide or adhered to a catalytically active support. In certain embodiments, the catalyst described in the hydrogenolysis reaction may include a catalyst support as described above for the hydrogenation reaction.

The conditions for which to carry out the hydrogenolysis reaction will vary based on the type of starting material and the desired products. One of ordinary skill in the art, with the benefit of this disclosure, will recognize the appropriate conditions to use to carry out the reaction. In general, they hydrogenolysis reaction is conducted at temperatures of 110° C. to 300° C., and preferably at 170° C. to 220° C., and most preferably at 200° C. to 225° C. In some embodiments, the hydrogenolysis reaction is conducted under basic conditions, preferably at a pH of 8 to 13, and even more preferably at a pH of 10 to 12. In some embodiments, the hydrogenolysis reaction is conducted at pressures in a range between 60 KPa and 16500 KPa, and preferably in a range between 1700 KPa and 14000 KPa, and even more preferably between 4800 KPa and 11000 KPa.

The hydrogen used in the hydrogenolysis reaction of the current invention can include external hydrogen, recycled hydrogen, in situ generated hydrogen, and any combination thereof.

In some embodiments, the reaction products discussed above may be converted into higher hydrocarbons through a condensation reaction in a condensation reactor. In such embodiments, condensation of the reaction products occurs in the presence of a catalyst capable of forming higher hydrocarbons. While not intending to be limited by theory, it is believed that the production of higher hydrocarbons proceeds through a stepwise addition reaction including the formation of carbon-carbon, or carbon-oxygen bond. The resulting reaction products include any number of compounds containing these moieties, as described in more detail below.

In certain embodiments, suitable condensation catalysts include an acid catalyst, a base catalyst, or an acid/base catalyst. As used herein, the term "acid/base catalyst" refers to a catalyst that has both an acid and a base functionality. In some embodiments the condensation catalyst can include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the condensation catalyst can also include a modifier. Suitable modifiers include La, Y, Sc, P, B, Bi, Li, Na, K, Rb, Cs, Mg, Ca, Sr, Ba, and any combination thereof. In some embodiments, the condensation catalyst can also include a metal. Suitable metals include Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof.

In certain embodiments, the catalyst described in the condensation reaction may include a catalyst support as described above for the hydrogenation reaction. In certain embodiments, the condensation catalyst is self-supporting. As used herein, the term "self-supporting" means that the catalyst does not need another material to serve as support. In other embodiments, the condensation catalyst in used in conjunction with a separate support suitable for suspending the catalyst. In an embodiment, the condensation catalyst support is silica.

The conditions under which the condensation reaction occurs will vary based on the type of starting material and the desired products. One of ordinary skill in the art, with the benefit of this disclosure, will recognize the appropriate conditions to use to carry out the reaction. In some embodiments, the condensation reaction is carried out at a temperature at which the thermodynamics for the proposed reaction are favorable. The temperature for the condensation reaction will vary depending on the specific starting polyol or alcohol. In some embodiments, the temperature for the condensation reaction is in a range from 80° C. to 500° C., and preferably from 125° C. to 450° C., and most preferably from 125° C. to 250° C. In some embodiments, the condensation reaction is conducted at pressures in a range between 0 Kpa to 9000 KPa, and preferably in a range between 0 KPa and 7000 KPa, and even more preferably between 0 KPa and 5000 KPa.

The higher alkanes formed by the invention include, but are not limited to, branched or straight chain alkanes that have from 4 to 30 carbon atoms, branched or straight chain alkenes that have from 4 to 30 carbon atoms, cycloalkanes that have from 5 to 30 carbon atoms, cycloalkenes that have from 5 to 30 carbon atoms, aryls, fused aryls, alcohols, and ketones. Suitable alkanes include, but are not limited to, butane, pentane, pentene, 2-methylbutane, hexane, hexene, 2-methylpentane, 3-methylpentane, 2,2,-dimethylbutane, 2,3-dimethylbutane, heptane, heptene, octane, octene, 2,2,4-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, nonyldecane, nonyldecene, eicosane, eicosene, uneicosane, uneicosene, doeicosane, doeicosene, trieicosane, trieicosene, tetraeicosane, tetraeicosene, and isomers thereof. Some of these products may be suitable for use as fuels.

In some embodiments, the cycloalkanes and the cycloalkenes are unsubstituted. In other embodiments, the cycloalkanes and cycloalkenes are mono-substituted. In still other embodiments, the cycloalkanes and cycloalkenes are multi-substituted. In the embodiments comprising the substituted cycloalkanes and cycloalkenes, the substituted group includes, without limitation, a branched or straight chain alkyl having 1 to 12 carbon atoms, a branched or straight chain alkylene having 1 to 12 carbon atoms, a phenyl, and any combination thereof. Suitable cycloalkanes and cycloalkenes include, but are not limited to, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, isomers and any combination thereof.

In some embodiments, the aryls formed are unsubstituted. In another embodiment, the aryls formed are mono-substituted. In the embodiments comprising the substituted aryls, the substituted group includes, without limitation, a branched or straight chain alkyl having 1 to 12 carbon atoms, a branched or straight chain alkylene having 1 to 12 carbon atoms, a phenyl, and any combination thereof. Suitable aryls for the invention include, but are not limited to, benzene, toluene, xylene, ethyl benzene, para xylene, meta xylene, and any combination thereof.

The alcohols produced in the invention have from 4 to 30 carbon atoms. In some embodiments, the alcohols are cyclic. In other embodiments, the alcohols are branched. In another embodiment, the alcohols are straight chained. Suitable alcohols for the invention include, but are not limited to, butanol, pentanol, hexanol, heptanol, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, and isomers thereof.

The ketones produced in the invention have from 4 to 30 carbon atoms. In an embodiment, the ketones are cyclic. In another embodiment, the ketones are branched. In another embodiment, the ketones are straight chained. Suitable ketones for the invention include, but are not limited to, butanone, pentanone, hexanone, heptanone, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, and isomers thereof.

Another such chemical modification is interesterification. Naturally produced glycerolipids do not have a uniform distribution of fatty acid constituents. In the context of oils, interesterification refers to the exchange of acyl radicals between two esters of different glycerolipids. The interesterification process provides a mechanism by which the fatty acid constituents of a mixture of glycerolipids can be rearranged to modify the distribution pattern. Interesterification is a well-known chemical process, and generally comprises heating (to about 200° C.) a mixture of oils for a period (e.g, 30 minutes) in the presence of a catalyst, such as an alkali metal or alkali metal alkylate (e.g., sodium methoxide). This process can be used to randomize the distribution pattern of the fatty acid constituents of an oil mixture, or can be directed to produce a desired distribution pattern. This method of chemical modification of lipids can be performed on materials provided herein, such as microbial biomass with a percentage of dry cell weight as lipid at least 20%.

Directed interesterification, in which a specific distribution pattern of fatty acids is sought, can be performed by maintaining the oil mixture at a temperature below the melting point of some TAGs which might occur. This results in selective crystallization of these TAGs, which effectively removes them from the reaction mixture as they crystallize. The process can be continued until most of the fatty acids in the oil have precipitated, for example. A directed interesterification process can be used, for example, to produce a product with a lower calorie content via the substitution of longer-chain fatty acids with shorter-chain counterparts. Directed interesterification can also be used to produce a product with a mixture of fats that can provide desired melting characteristics and structural features sought in food additives or products (e.g., margarine) without resorting to hydrogenation, which can produce unwanted trans isomers.

Interesterification of oils produced by the methods described herein can be performed in conjunction with one or more of the methods and/or materials, or to produce products, as reported in the following: U.S. Pat. No. 6,080,853 (Nondigestible fat substitutes); U.S. Pat. No. 4,288,378 (Peanut butter stabilizer); U.S. Pat. No. 5,391,383 (Edible spray oil); U.S. Pat. No. 6,022,577 (Edible fats for food products); U.S. Pat. No. 5,434,278 (Edible fats for food products); U.S. Pat. No. 5,268,192 (Low calorie nut products); U.S. Pat. No. 5,258,197 (Reduce calorie edible compositions); U.S. Pat. No. 4,335,156 (Edible fat product); U.S. Pat. No. 7,288,278 (Food additives or medicaments); U.S. Pat. No. 7,115,760 (Fractionation process); U.S. Pat. No. 6,808,737 (Structural fats); U.S. Pat. No. 5,888,947 (Engine lubricants); U.S. Pat. No. 5,686,131 (Edible oil mixtures); and U.S. Pat. No. 4,603,188 (Curable urethane compositions).

In one embodiment in accordance with the invention, transesterification of the oil, as described above, is followed by reaction of the transesterified product with polyol, as reported in U.S. Pat. No. 6,465,642, to produce polyol fatty acid polyesters. Such an esterification and separation process may comprise the steps as follows: reacting a lower alkyl ester with polyol in the presence of soap; removing residual soap from the product mixture; water-washing and drying the product mixture to remove impurities; bleaching the product mixture for refinement; separating at least a portion of the unreacted lower alkyl ester from the polyol fatty acid polyester in the product mixture; and recycling the separated unreacted lower alkyl ester.

Transesterification can also be performed on microbial biomass with short chain fatty acid esters, as reported in U.S. Pat. No. 6,278,006. In general, transesterification may be performed by adding a short chain fatty acid ester to an oil in the presence of a suitable catalyst and heating the mixture. In some embodiments, the oil comprises about 5% to about 90% of the reaction mixture by weight. In some embodiments, the short chain fatty acid esters can be about 10% to about 50% of the reaction mixture by weight. Non-limiting examples of catalysts include base catalysts, sodium methoxide, acid catalysts including inorganic acids such as sulfuric acid and acidified clays, organic acids such as methane sulfonic acid, benzenesulfonic acid, and toluenesulfonic acid, and acidic resins such as Amberlyst 15. Metals such as sodium and magnesium, and metal hydrides also are useful catalysts.

Another such chemical modification is hydroxylation, which involves the addition of water to a double bond resulting in saturation and the incorporation of a hydroxyl moiety. The hydroxylation process provides a mechanism for converting one or more fatty acid constituents of a glycerolipid to a hydroxy fatty acid. Hydroxylation can be performed, for example, via the method reported in U.S. Pat. No. 5,576,027. Hydroxylated fatty acids, including castor oil and its derivatives, are useful as components in several industrial applications, including food additives, surfactants, pigment wetting agents, defoaming agents, water proofing additives, plasticizing agents, cosmetic emulsifying and/or deodorant agents, as well as in electronics, pharmaceuticals, paints, inks, adhesives, and lubricants. One example of how the hydroxylation of a glyceride may be performed is as follows: fat may be heated, preferably to about 30-50° C.

combined with heptane and maintained at temperature for thirty minutes or more; acetic acid may then be added to the mixture followed by an aqueous solution of sulfuric acid followed by an aqueous hydrogen peroxide solution which is added in small increments to the mixture over one hour; after the aqueous hydrogen peroxide, the temperature may then be increased to at least about 60° C. and stirred for at least six hours; after the stirring, the mixture is allowed to settle and a lower aqueous layer formed by the reaction may be removed while the upper heptane layer formed by the reaction may be washed with hot water having a temperature of about 60° C.; the washed heptane layer may then be neutralized with an aqueous potassium hydroxide solution to a pH of about 5 to 7 and then removed by distillation under vacuum; the reaction product may then be dried under vacuum at 100° C. and the dried product steam-deodorized under vacuum conditions and filtered at about 50° to 60° C. using diatomaceous earth.

Hydroxylation of microbial oils produced by the methods described herein can be performed in conjunction with one or more of the methods and/or materials, or to produce products, as reported in the following: U.S. Pat. No. 6,590,113 (Oil-based coatings and ink); U.S. Pat. No. 4,049,724 (Hydroxylation process); U.S. Pat. No. 6,113,971 (Olive oil butter); U.S. Pat. No. 4,992,189 (Lubricants and lube additives); U.S. Pat. No. 5,576,027 (Hydroxylated milk); and U.S. Pat. No. 6,869,597 (Cosmetics).

Hydroxylated glycerolipids can be converted to estolides. Estolides consist of a glycerolipid in which a hydroxylated fatty acid constituent has been esterified to another fatty acid molecule. Conversion of hydroxylated glycerolipids to estolides can be carried out by warming a mixture of glycerolipids and fatty acids and contacting the mixture with a mineral acid, as described by Isbell et al., JAOCS 71(2): 169-174 (1994). Estolides are useful in a variety of applications, including without limitation those reported in the following: U.S. Pat. No. 7,196,124 (Elastomeric materials and floor coverings); U.S. Pat. No. 5,458,795 (Thickened oils for high-temperature applications); U.S. Pat. No. 5,451,332 (Fluids for industrial applications); U.S. Pat. No. 5,427,704 (Fuel additives); and U.S. Pat. No. 5,380,894 (Lubricants, greases, plasticizers, and printing inks).

Another such chemical modification is olefin metathesis. In olefin metathesis, a catalyst severs the alkylidene carbons in an alkene (olefin) and forms new alkenes by pairing each of them with different alkylidine carbons. The olefin metathesis reaction provides a mechanism for processes such as truncating unsaturated fatty acid alkyl chains at alkenes by ethenolysis, cross-linking fatty acids through alkene linkages by self-metathesis, and incorporating new functional groups on fatty acids by cross-metathesis with derivatized alkenes.

In conjunction with other reactions, such as transesterification and hydrogenation, olefin metathesis can transform unsaturated glycerolipids into diverse end products. These products include glycerolipid oligomers for waxes; short-chain glycerolipids for lubricants; homo- and hetero-bifunctional alkyl chains for chemicals and polymers; short-chain esters for biofuel; and short-chain hydrocarbons for jet fuel. Olefin metathesis can be performed on triacylglycerols and fatty acid derivatives, for example, using the catalysts and methods reported in U.S. Pat. No. 7,119,216, US Patent Pub. No. 2010/0160506, and U.S. Pat. Pub. No. 2010/0145086.

Olefin metathesis of bio-oils generally comprises adding a solution of Ru catalyst at a loading of about 10 to 250 ppm under inert conditions to unsaturated fatty acid esters in the presence (cross-metathesis) or absence (self-metathesis) of other alkenes. The reactions are typically allowed to proceed from hours to days and ultimately yield a distribution of alkene products. One example of how olefin metathesis may be performed on a fatty acid derivative is as follows: A solution of the first generation Grubbs Catalyst (dichloro[2 (1-methylethoxy-α-O)phenyl]methylene-α-C] (tricyclohexyl-phosphine) in toluene at a catalyst loading of 222 ppm may be added to a vessel containing degassed and dried methyl oleate. Then the vessel may be pressurized with about 60 psig of ethylene gas and maintained at or below about 30° C. for 3 hours, whereby approximately a 50% yield of methyl 9-decenoate may be produced.

Olefin metathesis of oils produced by the methods described herein can be performed in conjunction with one or more of the methods and/or materials, or to produce products, as reported in the following: Patent App. PCT/US07/081427 (α-olefin fatty acids) and U.S. patent application Ser. No. 12/281,938 (petroleum creams), Ser. No. 12/281,931 (paintball gun capsules), Ser. No. 12/653,742 (plasticizers and lubricants), Ser. No. 12/422,096 (bifunctional organic compounds), and Ser. No. 11/795,052 (candle wax).

Other chemical reactions that can be performed on microbial oils include reacting triacylglycerols with a cyclopropanating agent to enhance fluidity and/or oxidative stability, as reported in U.S. Pat. No. 6,051,539; manufacturing of waxes from triacylglycerols, as reported in U.S. Pat. No. 6,770,104; and epoxidation of triacylglycerols, as reported in "The effect of fatty acid composition on the acrylation kinetics of epoxidized triacylglycerols", Journal of the American Oil Chemists' Society, 79:1, 59-63, (2001) and Free Radical Biology and Medicine, 37:1, 104-114 (2004).

The generation of oil-bearing microbial biomass for fuel and chemical products as described above results in the production of delipidated biomass meal. Delipidated meal is a byproduct of preparing algal oil and is useful as animal feed for farm animals, e.g., ruminants, poultry, swine and aquaculture. The resulting meal, although of reduced oil content, still contains high quality proteins, carbohydrates, fiber, ash, residual oil and other nutrients appropriate for an animal feed. Because the cells are predominantly lysed by the oil separation process, the delipidated meal is easily digestible by such animals. Delipidated meal can optionally be combined with other ingredients, such as grain, in an animal feed. Because delipidated meal has a powdery consistency, it can be pressed into pellets using an extruder or expander or another type of machine, which are commercially available.

The invention, having been described in detail above, is exemplified in the following examples, which are offered to illustrate, but not to limit, the claimed invention.

VII. METHODS FOR PREPARING RECOMBINANT MICROALGAL BIOMASS

The present invention provides recombinant microbial, preferably algal, biomass suitable for human consumption that is rich in nutrients, including lipid and/or protein constituents, methods of combining the same with ingredients, including edible ingredients and other ingredients and food compositions containing the same. Although much of the following discussion is directed to algal biomass or algal oil, it is intended to apply equally to microbial biomass or microbial oil generally. The invention arose in part from the discoveries that recombinant algal biomass can be prepared with a high oil content and/or with excellent functionality, and the resulting biomass incorporated into food products in which the oil and/or protein content of the biomass can substitute in whole or in part for oils and/or fats and/or proteins present in conventional food products. Algal oil, which can comprise predominantly monosaturated oil, provides health benefits compared with saturated, hydrogenated (trans fats) and polyunsaturated fats often found in conventional food products. Algal oil also can be used as a healthy stable cooking oil free of trans fats. The remainder of the algal biomass can encapsulate the oil at least until a food product is cooked, thereby increasing shelf-life of the oil. In uncooked products, in which cells remain intact, the biomass, along with natural antioxidants found in the oil, also protects the oil from oxidation, which would otherwise create unpleasant odors, tastes, and textures. The biomass also provides several beneficial micro-nutrients in addition to the oil and/or protein, such as algal-derived dietary fibers (both soluble and insoluble carbohydrates), phospholipids, glycoprotein, phytosterols, tocopherols, tocotrieneols, and selenium.

1. Microalgae for Use in the Methods of the Invention

A variety species of microalgae that produce suitable oils and/or lipids and/or protein can be used in accordance with the methods of the present invention, although microalgae that naturally produce high levels of suitable oils and/or lipids and/or protein are preferred. Considerations affecting the selection of microalgae for use in the invention include, in addition to production of suitable oils, lipids, or protein for production of food products: (1) high lipid (or protein) content as a percentage of cell weight; (2) ease of growth; (3) ease of propagation; (4) ease of biomass processing; (5) glycerolipid profile; and (6) absence of algal toxins (Example 5 below demonstrates dried recombinant microalgal biomass and oils or lipids extracted from the biomass lacks algal toxins).

In some embodiments, the cell wall of the microalgae must be disrupted during food processing (e.g., cooking) to release the active components or for digestion, and, in these embodiments, strains of microalgae with cell walls susceptible to digestion in the gastrointestinal tract of an animal, e.g., a human or other monogastrics, are preferred, especially if the algal biomass is to be used in uncooked food products. Digestibility is generally decreased for recombinant microalgal strains which have a high content of cellulose/hemicellulose in the cell walls. Digestibility can be evaluated using a standard pepsin digestibility assay.

2. Methods of Generating a Microalgae Strain Lacking or that has Significantly Reduced Pigmentation Microalgae, such as *Chlorella*, can be capable of either photosynthetic or heterotrophic growth. *Prototheca* is an obligate heterotroph. When grown in heterotrophic conditions where the carbon source is a fixed carbon source and in the absence of light, the normally green colored microalgae has a yellow color, lacking or is significantly reduced in green pigmentation. Microalgae of reduced (or lacking in) green pigmentation can be advantageous as a food ingredient. One advantage of microalgae of reduced (or is lacking) in green pigmentation is that the microalgae has a reduced chlorophyll flavor. Another advantage of microalgae of reduced (or is lacking in) green pigmentation is that as a food ingredient, the addition of the microalgae to foodstuffs will not impart a green color that can be unappealing to the consumer. The reduced green pigmentation of microalgae grown under heterotrophic conditions is transient. When switched back to phototrophic growth, microalgae capable of both phototrophic and heterotrophic growth will regain the green pigmentation. Additionally, even with reduced green pigments, heterotrophically grown microalgae is a yellow color and this may be unsuitable for some food applications where the consumer expects the color of the foodstuff to be white or light in color. Thus, it is advantageous to generate a microalgae strain that is capable of heterotrophic growth (so it is reduced or lacking in green pigmentation) and is also reduced in yellow pigmentation (so that it is a neutral color for food applications).

One method for generating such microalgae strain lacking in or has significantly reduced pigmentation is through mutagenesis and then screening for the desired phenotype. Several methods of mutagenesis are known and practiced in the art. For example, Urano et al., (Urano et al., *J Bioscience Bioengineering* (2000) v. 90(5): pp. 567-569) describes yellow and white color mutants of *Chlorella ellipsoidea* generated using UV irradiation. Kamiya (Kamiya, *Plant Cell Physiol*. (1989) v. 30(4): 513-521) describes a colorless strain of *Chlorella vulgaris*, 11 h (M125).

In addition to mutagenesis by UV irradiation, chemical mutagenesis can also be employed in order to generate microalgae with reduced (or lacking in) pigmentation. Chemical mutagens such as ethyl methanesulfonate (EMS) or N-methyl-N'nitro-N-nitroguanidine (NTG) have been shown to be effective chemical mutagens on a variety of microbes including yeast, fungi, *mycobacterium* and microalgae. Mutagenesis can also be carried out in several rounds, where the microalgae is exposed to the mutagen (either UV or chemical or both) and then screened for the desired reduced pigmentation phenotype. Colonies with the desired phenotype are then streaked out on plates and reisolated to ensure that the mutation is stable from one generation to the next and that the colony is pure and not of a mixed population.

In a particular example, *Chlorella protothecoides* was used to generate strains lacking in or with reduced pigmentation using a combination of UV and chemical mutagenesis. *Chlorella protothecoides* was exposed to a round of chemical mutagenesis with NTG and colonies were screened for color mutants. Colonies not exhibiting color mutations were then subjected to a round of UV irradiation and were again screened for color mutants. In one embodiment, a *Chlorella protothecoides* strain lacking in pigmentation was isolated and is *Chlorella protothecoides* 33-55, deposited on Oct. 13, 2009 at the American Type Culture Collection at 10801 University Boulevard, Manassas, Va. 20110-2209, in accordance with the Budapest Treaty, with a Patent Deposit Designation of PTA-10397. In another embodiment, a *Chlorella protothecoides* strain with reduced pigmentation was isolated and is *Chlorella protothecoides* 25-32, deposited on Oct. 13, 2009 at the American Type Culture Collection at 10801 University Boulevard, Manassas, Va. 20110-2209, in accordance with the Budapest Treaty, with a Patent Deposit Designation of PTA-10396.

High lipid biomass from microalgae is an advantageous material for inclusion in food products compared to low lipid biomass, because it allows for the addition of less recombinant microalgal biomass to incorporate the same amount of lipid into a food composition. This is advantageous, because healthy oils from high lipid microalgae can be added to food products without altering other attributes such as texture and taste compared with low lipid biomass. The lipid-rich biomass provided by the methods of the invention typically has at least 25% lipid by dry cell weight. Process conditions can be adjusted to increase the percentage weight of cells that is lipid. For example, in certain embodiments, a microalgae is cultured in the presence of a limiting concentration of one or more nutrients, such as, for example, nitrogen, phosphorous, or sulfur, while providing an excess of a fixed carbon source, such as glucose. Nitrogen limitation tends to increase microbial lipid yield over microbial lipid yield in a culture in which nitrogen is provided in excess. In particular embodiments, the increase in lipid yield is at least about 10%, 50%, 100%, 200%, or 500%. The microbe can be cultured in the presence of a limiting amount of a nutrient for a portion of the total culture period or for the entire period. In some embodiments, the nutrient concentration is cycled between a limiting concentration and a non-limiting concentration at least twice during the total culture period.

High protein biomass from algae is another advantageous material for inclusion in food products. The methods of the invention can also provide biomass that has at least 20%, 30%, 40% or 50% of its dry cell weight as protein. Growth conditions can be adjusted to increase the percentage weight of cells that is protein. In a preferred embodiment, a microalgae is cultured in a nitrogen rich environment and an excess of fixed carbon energy such as glucose or any of the other carbon sources discussed above. Conditions in which nitrogen is in excess tends to increase microbial protein yield over microbial protein yield in a culture in which nitrogen is not provided in excess. For maximal protein production, the microbe is preferably cultured in the presence of excess nitrogen for the total culture period. Suitable nitrogen sources for microalgae may come from organic nitrogen sources and/or inorganic nitrogen sources.

Recombinant microalgal cultures generated according to the methods described herein yield recombinant microalgal biomass in fermentation media. To prepare the biomass for use as a food composition, the biomass is concentrated, or harvested, from the fermentation medium. At the point of harvesting the recombinant microalgal biomass from the fermentation medium, the biomass comprises predominantly intact cells suspended in an aqueous culture medium. To concentrate the biomass, a dewatering step is performed. Dewatering or concentrating refers to the separation of the biomass from fermentation broth or other liquid medium and so is solid-liquid separation. Thus, during dewatering, the culture medium is removed from the biomass (for example, by draining the fermentation broth through a filter that retains the biomass), or the biomass is otherwise removed from the culture medium. Common processes for dewatering include centrifugation, filtration, and the use of mechanical pressure. These processes can be used individually or in any combination.

After concentration, recombinant microalgal biomass can be processed, as described herein, to produce vacuum-packed cake, algal flakes, algal homogenate, algal powder, algal flour, or algal oil.

3. Chemical Composition of Recombinant Microalgal Biomass

The recombinant microalgal biomass generated by the culture methods described herein comprises recombinant microalgal oil and/or protein as well as other constituents generated by the microorganisms or incorporated by the microorganisms from the culture medium during fermentation.

Heterotrophic growth results in relatively low chlorophyll content (as compared to phototrophic systems such as open ponds or closed photobioreactor systems). Reduced chlorophyll content generally improves organoleptic properties of microalgae and therefore allows more algal biomass (or oil prepared therefrom) to be incorporated into a food product. The reduced chlorophyll content found in heterotrophically grown microalgae (e.g., *Chlorella*) also reduces the green color in the biomass as compared to phototrophically grown microalgae. Thus, the reduced chlorophyll content avoids an often undesired green coloring associated with food products containing phototrophically grown microalgae and allows for the incorporation or an increased incorporation of algal biomass into a food product. In at least one embodiment, the food product contains heterotrophically grown microalgae of reduced chlorophyll content compared to phototrophically grown microalgae.

The recombinant microalgal oil of the biomass described herein (or extracted from the biomass) can comprise glycerolipids with one or more distinct fatty acid ester side chains. Glycerolipids are comprised of a glycerol molecule esterified to one, two, or three fatty acid molecules, which can be of varying lengths and have varying degrees of saturation. Specific blends of algal oil can be prepared either within a single species of algae, or by mixing together the biomass (or algal oil) from two or more species of microalgae.

Thus, the oil composition, i.e., the properties and proportions of the fatty acid constituents of the glycerolipids, can also be manipulated by combining biomass (or oil) from at least two distinct species of microalgae. In some embodiments, at least two of the distinct species of microalgae have different glycerolipid profiles. The distinct species of microalgae can be cultured together or separately as described herein, preferably under heterotrophic conditions, to generate the respective oils. Different species of microalgae can contain different percentages of distinct fatty acid constituents in the cell's glycerolipids.

In some embodiments, the recombinant microalgal oil is primarily comprised of monounsaturated oil. In some cases, the algal oil is at least 20% monounsaturated oil by weight. In various embodiments, the algal oil is at least 25%, 50%, 75% or more monounsaturated oil by weight or by volume. In some embodiments, the monounsaturated oil is 18:1, 16:1, 14:1 or 12:1. In some embodiments, the recombinant microalgal oil comprises at least 10%, 20%, 25%, or 50% or more esterified oleic acid or esterified alpha-linolenic acid by weight of by volume. In at least one embodiment, the algal oil comprises less than 10%, less than 5%, less than 3%, less than 2%, or less than 1% by weight or by volume, or is substantially free of, esterified docosahexanoic acid (DHA (22:6)). For examples of production of high DHA-containing microalgae, such as in *Crypthecodinium cohnii*, see U.S. Pat. Nos. 7,252,979, 6,812,009 and 6,372,460.

High protein recombinant microalgal biomass has been generated using different methods of culture. Recombinant microalgal biomass with a higher percentage of protein content is useful in accordance with the present invention. For example, the protein content of various species of microalgae has been reported (see Table 1 of Becker, *Biotechnology Advances* (2007) 25:207-210). Controlling the renewal rate in a semi-continuos photoautotrophic culture of *Tetraselmis suecica* has been reported to affect the protein content per cell, the highest being approximately 22.8% protein (Fabregas, et al., *Marine Biotechnology* (2001) 3:256-263).

Recombinant microalgal biomass generated by culture methods described herein and useful in accordance to those embodiments of the present invention relating to high protein typically comprises at least 30% protein by dry cell weight. In some embodiments, the recombinant microalgal biomass comprises at least 40%, 50%, 75% or more protein by dry cell weight. In some embodiments, the recombinant microalgal biomass comprises from 30-75% protein by dry cell weight or from 40-60% protein by dry cell weight. In some embodiments, the protein in the recombinant microalgal biomass comprises at least 40% digestible crude protein. In other embodiments, the protein in the recombinant microalgal biomass comprises at least 50%, 60%, 70%, 80%, or at least 90% digestible crude protein. In some embodiments, the protein in the recombinant microalgal biomass comprises from 40-90% digestible crude protein, from 50-80% digestible crude protein, or from 60-75% digestible crude protein.

Recombinant microalgal biomass (and oil extracted therefrom), can also include other constituents produced by the microalgae, or incorporated into the biomass from the culture medium. These other constituents can be present in varying amounts depending on the culture conditions used and the species of microalgae (and, if applicable, the extraction method used to recover recombinant microalgal oil from the biomass). The other constituents can include, without limitation, phospholipids (e.g., algal lecithin), carbohydrates, soluble and insoluble fiber, glycoproteins, phytosterols (e.g., β-sitosterol, campesterol, stigmasterol, ergosterol, and brassicasterol), tocopherols, tocotrienols, carotenoids (e.g., α-carotene, β-carotene, and lycopene), xanthophylls (e.g., lutein, zeaxanthin, α-cryptoxanthin, and β-cryptoxanthin), proteins, polysaccharides (e.g., arabinose, mannose, galactose, 6-methyl galactose and glucose) and various organic or inorganic compounds (e.g., selenium).

In some cases, the recombinant microalgal biomass comprises at least 10% soluble fiber. In other embodiments, the recombinant microalgal biomass comprises at least 20% to 25% soluble fiber. In some embodiments, the recombinant microalgal biomass comprises at least 30% insoluble fiber. In other embodiments, the recombinant microalgal biomass comprises at least 50% to at least 70% insoluble fiber. Total dietary fiber is the sum of soluble fiber and insoluble fiber. In some embodiments, the recombinant microalgal biomass comprises at least 40% total dietary fiber. In other embodiments, the recombinant microalgal biomass comprises at least 50%, 55%, 60%, 75%, 80%, 90%, to 95% total dietary fiber.

VIII. PROCESSING RECOMBINANT MICROALGAL BIOMASS INTO FINISHED FOOD INGREDIENTS

The concentrated recombinant microalgal biomass produced in accordance with the methods of the invention is itself a finished food ingredient and may be used in foodstuffs without further, or with only minimal, modification. For example, the cake can be vacuum-packed or frozen. Alternatively, the biomass may be dried via lyophilization, a "freeze-drying" process, in which the biomass is frozen in a freeze-drying chamber to which a vacuum is applied. The application of a vacuum to the freeze-drying chamber results in sublimation (primary drying) and desorption (secondary drying) of the water from the biomass. However, the present invention provides a variety of recombinant microalgal derived finished food ingredients with enhanced properties resulting from processing methods of the invention that can be applied to the concentrated recombinant microalgal biomass.

Drying the recombinant microalgal biomass, either predominantly intact or in homogenate form, is advantageous to facilitate further processing or for use of the biomass in the methods and compositions described herein. Drying refers to the removal of free or surface moisture/water from predominantly intact biomass or the removal of surface water from a slurry of homogenized (e.g., by micronization) biomass. Different textures and flavors can be conferred on food products depending on whether the algal biomass is dried, and if so, the drying method. Drying the biomass generated from the cultured microalgae described herein removes water that may be an undesirable component of finished food products or food ingredients. In some cases, drying the biomass may facilitate a more efficient recombinant microalgal oil extraction process.

In one embodiment, the concentrated recombinant microalgal biomass is drum dried to a flake form to produce algal flake, as described in part A of this section. In another embodiment, the concentrated micralgal biomass is spray or flash dried (i.e., subjected to a pneumatic drying process) to form a powder containing predominantly intact cells to produce algal powder, as described in part B of this section. In another embodiment, the concentrated recombinant microalgal biomass is micronized (homogenized) to form a homogenate of predominantly lysed cells that is then spray or flash dried to produce algal flour, as described in part C of this section. In another embodiment, oil is extracted from the concentrated recombinant microalgal biomass to form algal oil, as described in part D of this section.

1. Algal Flake

Algal flake of the invention is prepared from concentrated recombinant microalgal biomass that is applied as a film to the surface of a rolling, heated drum. The dried solids are then scraped off with a knife or blade, resulting in a small flakes. U.S. Pat. No. 6,607,900 describes drying recombinant microalgal biomass using a drum dryer without a prior centrifugation (concentration) step, and such a process may be used in accordance with the methods of the invention.

Because the biomass may be exposed to high heat during the drying process, it may be advantageous to add an antioxidant to the biomass prior to drying. The addition of an antioxidant will not only protect the biomass during drying, but also extend the shelf-life of the dried recombinant microalgal biomass when stored. In a preferred embodiment, an antioxidant is added to the recombinant microalgal biomass prior to subsequent processing such as drying or homogenization. Antioxidants that are suitable for use are discussed in detail below.

Additionally, if there is significant time between the production of the dewatered recombinant microalgal biomass and subsequent processing steps, it may be advantageous to pasteurize the biomass prior to drying. Free fatty acids from lipases may form if there is significant time between producing and drying the biomass. Pasteurization of the biomass inactivates these lipases and prevents the formation of a "soapy" flavor in the resulting dried biomass product. Thus, in one embodiment, the invention provides pasteurized recombinant microalgal biomass. In another embodiment, the pasteurized recombinant microalgal biomass is an algal flake.

2. Algal Powder

Algal powder of the invention is prepared from concentrated recombinant microalgal biomass using a pneumatic or spray dryer (see for example U.S. Pat. No. 6,372,460). In a spray dryer, material in a liquid suspension is sprayed in a fine droplet dispersion into a current of heated air. The entrained material is rapidly dried and forms a dry powder. In some cases, a pulse combustion dryer can also be used to achieve a powdery texture in the final dried material. In other cases, a combination of spray drying followed by the use of a fluid bed dryer is used to achieve the optimal conditions for dried microbial biomass (see, for example, U.S. Pat. No. 6,255,505). As an alternative, pneumatic dryers can also be used in the production of algal powder. Pneumatic dryers draw or entrain the material that is to be dried in a stream of hot air. While the material is entrained in the hot air, the moisture is rapidly removed. The dried material is then separated from the moist air and the moist air is then recirculated for further drying.

3. Algal Flour

Algal flour of the invention is prepared from concentrated recombinant microalgal biomass that has been mechanically lysed and homogenized and the homogenate spray or flash dried (or dried using another pneumatic drying system). The production of algal flour requires that cells be lysed to release their oil and that cell wall and intracellular components be micronized or reduced in particle size to an average size of no more than 20 μm, preferably 10 μm. The lysed microbial cells can agglomerate to form bigger particles of up to 1,000 μm. The resulting oil, water, and micronized particles are emulsified such that the oil does not separate from the dispersion prior to drying. For example, a pressure disrupter can be used to pump a cell containing slurry through a restricted orifice valve to lyse the cells. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method releases intracellular molecules. A Niro (Niro Soavi GEA) homogenizer (or any other high pressure homogenizer) can be used to process cells to particles predominantly 0.2 to 5 microns in length. Processing of algal biomass under high pressure (approximately 1000 bar) typically lyses over 90% of the cells and reduces particle size to less than 5 microns.

Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. In one embodiment, algal biomass is disrupted and formed into a stable emulsion using a Dyno-mill ECM Ultra (CB Mills) ball mill Cells can also be disrupted by shear forces, such as with the use of blending (such as with a high speed or Waring blender as examples), the french press, or even centrifugation in case of weak cell walls, to disrupt cells. A suitable ball mill including specifics of ball size and blade is described in U.S. Pat. No. 5,330,913.

The immediate product of homogenization is a slurry of particles smaller in size than the original cells that is suspended in oil and water. The particles represent cellular debris. The oil and water are released by the cells. Additional water may be contributed by aqueous media containing the cells before homogenization. The particles are preferably in the form of a micronized homogenate. If left to stand, some of the smaller particles may coalesce. However, an even dispersion of small particles can be preserved by seeding with a microcrystalline stabilizer, such as microcrystalline cellulose.

To form the algal flour, the slurry is spray or flash dried, removing water and leaving a dry power containing cellular debris and oil. Although the oil content of the powder can be at least 10, 25 or 50% by weight of the dry powder, the powder can have a dry rather than greasy feel and appearance (e.g., lacking visible oil) and can also flow freely when shaken. Various flow agents (including silica-derived products) can also be added. After drying, the water or moisture content of the powder is typically less than 10%, 5%, 3% or 1% by weight. Other dryers such as pneumatic dryers or pulse combustion dryers can also be used to produce algal flour.

The oil content of algal flour can vary depending on the percent oil of the algal biomass. Algal flour can be produced from algal biomass of varying oil content. In certain embodiments, the algal flour is produced from algal biomass of the same oil content. In other embodiments, the algal flour is produced from algal biomass of different oil content. In the latter case, algal biomass of varying oil content can be combined and then the homogenization step performed. In other embodiments, algal flour of varying oil content is produced first and then blended together in various proportions in order to achieve an algal flour product that contains the final desired oil content. In a further embodiment, algal biomass of different lipid profiles can be combined together and then homogenized to produce algal flour. In another embodiment, algal flour of different lipid profiles is produced first and then blended together in various proportions in order to achieve an algal flour product that contains the final desired lipid profile.

The algal flour of the invention is useful for a wide range of food preparations. Because of the oil content, fiber content and the micronized particles, algal flour is a multifunctional food ingredient. Algal flour can be used in baked goods, quick breads, yeast dough products, egg products, dressing, sauces, nutritional beverages, algal milk, pasta and gluten free products. Additional details of formulating these food products and more with algal flour is described in the Examples below.

Algal flour can be used in baked goods in place of convention fat sources (e.g., oil, butter or margarine) and eggs. Baked goods and gluten free products have superior moisture content and a cumb structure that is indistinguishable from conventional baked goods made with butter and eggs. Because of the superior moisture content, these baked goods have a longer shelf life and retain their original texture longer than conventional baked goods that are produced without algal flour.

Algal flour can also act as a fat extender with used in smoothies, sauces, or dressings. The composition of algal flour is unique in its ability to convey organoleptic qualities and mouth-feel comparable to a food product with a higher fat content. Dressings, sauces and beverages made with algal flour have a rheology and opacity that is close to conventional higher fat recipes although these food products contains about half the fat/oil levels. Algal flour is also a superior emulsifier and is suitable in use in food preparation that requires thickness, opacity and viscosity, such as, sauces, dressings and soups. Additionally the lipid profile found in algal flour of the inventions described herein does not contain trans-fat and have a higher level of healthy, unsaturated fats as compared to butter or margarine (or other animal fats). Thus, products made with algal flour can have a lower fat content (with healthier fats) without sacrificing the mouthfeel and organoleptic qualities of the same food product that is made using a conventional recipe using a conventional fat source.

Algal flour can also be added to powdered or liquid eggs, which are typically served in a food service setting. The addition of algal flour improves the appearance, texture and mouthfeel of powdered and liquid eggs and also extends improved appearance, texture and mouthfeel over time, even when the prepared eggs are held on a steam table. Specific formulations and sensory panel results are described below in the Examples.

4. Algal Oil

In one aspect, the present invention is directed to a method of preparing algal oil by harvesting algal oil from an algal biomass comprising at least 15% oil by dry weight under GMP conditions, in which the algal oil is greater than 50% 18:1 lipid. In some cases, the algal biomass comprises a mixture of at least two distinct species of microalgae. In some cases, at least two of the distinct species of microalgae have been separately cultured. In at least one embodiment, at least two of the distinct species of microalgae have different glycerolipid profiles. In some cases, the algal biomass is derived from algae grown heterotrophically. In some cases, all of the at least two distinct species of microalgae contain at least 15% oil by dry weight.

In one aspect, the present invention is directed to a method of making a food composition comprising combining algal oil obtained from algal cells containing at least 10%, or at least 15% oil by dry weight with one or more other edible ingredients to form the food composition. In some cases, the method further comprises preparing the algal oil under GMP conditions.

Algal oil can be separated from lysed biomass for use in food product (among other applications). The algal biomass remaining after oil extraction is referred to as delipidated meal. Delipidated meal contains less oil by dry weight or volume than the microalgae contained before extraction. Typically 50-90% of oil is extracted so that delipidated meal contains, for example, 10-50% of the oil content of biomass before extraction. However, the biomass still has a high nutrient value in content of protein and other constituents discussed above. Thus, the delipidated meal can be used in animal feed or in human food applications.

In some embodiments of the method, the algal oil is at least 50% w/w oleic acid and contains less than 5% DHA. In some embodiments of the method, the algal oil is at least 50% w/w oleic acid and contains less than 0.5% DHA. In some embodiments of the method, the algal oil is at least 50% w/w oleic acid and contains less than 5% glycerolipid containing carbon chain length greater than 18. In some cases, the algal cells from which the algal oil is obtained comprise a mixture of cells from at least two distinct species of microalgae. In some cases, at least two of the distinct species of microalgae have been separately cultured. In at least one embodiment, at least two of the distinct species of microalgae have different glycerolipid profiles. In some cases, the algal cells are cultured under heterotrophic conditions. In some cases, all of the at least two distinct species of microalgae contain at least 10%, or at least 15% oil by dry weight.

In one aspect, the present invention is directed to algal oil containing at least 50% monounsaturated oil and containing less than 1% DHA prepared under GMP conditions. In some cases, the monounsaturated oil is 18:1 lipid. In some cases, the algal oil is packaged in a capsule for delivery of a unit dose of oil. In some cases, the algal oil is derived from a mixture of at least two distinct species of microalgae. In some cases, at least two of the distinct species of microalgae have been separately cultured. In at least one embodiment, at least two of the distinct species of microalgae have different glycerolipid profiles. In some cases, the algal oil is derived from algal cells cultured under heterotrophic conditions.

In one aspect, the present invention is directed to oil comprising greater than 60% 18:1, and at least 0.20 mg/g tocotrienol.

In one aspect, the present invention is directed to a fatty acid alkyl ester composition comprising greater than 60% 18:1 ester, and at least 0.20 mg/g tocotrienol.

Algal oil of the invention is prepared from concentrated, washed recombinant microalgal biomass by extraction. The cells in the biomass are lysed prior to extraction. Optionally, the microbial biomass may also be dried (oven dried, lyophilized, etc.) prior to lysis (cell disruption). Alternatively, cells can be lysed without separation from some or all of the fermentation broth when the fermentation is complete. For example, the cells can be at a ratio of less than 1:1 v:v cells to extracellular liquid when the cells are lysed.

Microalgae containing lipids can be lysed to produce a lysate. As detailed herein, the step of lysing a microorganism (also referred to as cell lysis) can be achieved by any convenient means, including heat-induced lysis, adding a base, adding an acid, using enzymes such as proteases and polysaccharide degradation enzymes such as amylases, using ultrasound, mechanical pressure-based lysis, and lysis using osmotic shock. Each of these methods for lysing a microorganism can be used as a single method or in combination simultaneously or sequentially. The extent of cell disruption can be observed by microscopic analysis. Using one or more of the methods above, typically more than 70% cell breakage is observed. Preferably, cell breakage is more than 80%, more preferably more than 90% and most preferred about 100%.

Lipids and oils generated by the microalgae in accordance with the present invention can be recovered by extraction. In some cases, extraction can be performed using an organic solvent or an oil, or can be performed using a solventless-extraction procedure.

For organic solvent extraction of the recombinant microalgal oil, the preferred organic solvent is hexane. Typically, the organic solvent is added directly to the lysate without prior separation of the lysate components. In one embodiment, the lysate generated by one or more of the methods described above is contacted with an organic solvent for a period of time sufficient to allow the lipid components to form a solution with the organic solvent. In some cases, the solution can then be further refined to recover specific desired lipid components. The mixture can then be filtered and the hexane removed by, for example, rotoevaporation. Hexane extraction methods are well known in the art. See, e.g., Frenz et al., *Enzyme Microb. Technol.,* 11:717 (1989).

Miao and Wu describe a protocol of the recovery of recombinant microalgal lipid from a culture of *Chlorella protothecoides* in which the cells were harvested by centrifugation, washed with distilled water and dried by freeze drying. The resulting cell powder was pulverized in a mortar and then extracted with n-hexane. Miao and Wu, *Biosource Technology* 97:841-846 (2006).

In some cases, recombinant microalgal oils can be extracted using liquefaction (see for example Sawayama et al., *Biomass and Bioenergy* 17:33-39 (1999) and Inoue et al., *Biomass Bioenergy* 6(4):269-274 (1993)); oil liquefaction (see for example Minowa et al., *Fuel* 74(12):1735-1738 (1995)); or supercritical $CO_2$ extraction (see for example Mendes et al., *Inorganica Chimica Acta* 356:328-334 (2003)).

Oil extraction includes the addition of an oil directly to a lysate without prior separation of the lysate components. After addition of the oil, the lysate separates either of its own accord or as a result of centrifugation or the like into different layers. The layers can include in order of decreasing density: a pellet of heavy solids, an aqueous phase, an emulsion phase, and an oil phase. The emulsion phase is an emulsion of lipids and aqueous phase. Depending on the percentage of oil added with respect to the lysate (w/w or v/v), the force of centrifugation if any, volume of aqueous media and other factors, either or both of the emulsion and oil phases can be present. Incubation or treatment of the cell lysate or the emulsion phase with the oil is performed for a time sufficient to allow the lipid produced by the microorganism to become solubilized in the oil to form a heterogeneous mixture.

In various embodiments, the oil used in the extraction process is selected from the group consisting of oil from soy, rapeseed, canola, palm, palm kernel, coconut, corn, waste vegetable oil, Chinese tallow, olive, sunflower, cotton seed, chicken fat, beef tallow, porcine tallow, microalgae, macroalgae, *Cuphea*, flax, peanut, choice white grease (lard), *Camelina sativa* mustard seedcashew nut, oats, lupine, kenaf, *calendula*, hemp, coffee, linseed, hazelnut, *euphorbia*, pumpkin seed, coriander, *camellia*, sesame, safflower, rice, tung oil tree, cocoa, copra, pium poppy, castor beans, pecan, jojoba, *jatropha, macadamia*, Brazil nuts, and avocado. The amount of oil added to the lysate is typically greater than 5% (measured by v/v and/or w/w) of the lysate with which the oil is being combined. Thus, a preferred v/v or w/w of the oil is greater than 5%, 10%, 20%, 25%, 50%, 70%, 90%, or at least 95% of the cell lysate.

Lipids can also be extracted from a lysate via a solventless extraction procedure without substantial or any use of organic solvents or oils by cooling the lysate. Sonication can also be used, particularly if the temperature is between room temperature and 65° C. Such a lysate on centrifugation or settling can be separated into layers, one of which is an aqueous:lipid layer. Other layers can include a solid pellet, an aqueous layer, and a lipid layer. Lipid can be extracted from the emulsion layer by freeze thawing or otherwise cooling the emulsion. In such methods, it is not necessary to add any organic solvent or oil. If any solvent or oil is added, it can be below 5% v/v or w/w of the lysate.

IX. COMBINING RECOMBINANT MICROALGAL BIOMASS OR MATERIALS DERIVED THEREFROM WITH OTHER FOOD INGREDIENTS

In one aspect, the present invention is directed to a food composition comprising at least 0.1% w/w algal biomass and one or more other edible ingredients, wherein the algal biomass comprises at least 10% triglyceride by dry weight, optionally wherein at least 90% of the oil is glycerolipid. The algal cells are cultivated heterotrophically and optionally in the absence of light. In some embodiments, the algal biomass contains at least 25%, 40%, 50% or 60% oil by dry weight. In some cases, the algal biomass contains 10-90%, 25-75%, 40-75% or 50-70% oil by dry weight, optionally wherein at least 90% of the oil is glycerolipid. In at least one embodiment, at least 50% by weight of the oil is monounsaturated glycerolipid oil. In some cases, at least 50%, 60%, 70% 80% or 90% by weight of the oil is a C18:1 lipid. In some embodiments, the lipid profile of the algal triglyceride oil is similar to a naturally occurring oil. Some of the naturally occurring oils are provided in table 5. In one embodiment, the algal triglycerides produced by the invention are similar to cocoa butter, coconut oil, palm oil, beef tallow or lard. In some cases, less than 5% by weight of the oil is docosahexanoic acid (DHA) (22:6). In at least one embodiment, less than 1% by weight of the oil is DHA. An algal lipid content with low levels of polyunsaturated fatty acids (PUFA) is preferred to ensure chemical stability of the biomass. In preferred embodiments, the algal biomass is grown under heterotrophic conditions and has reduced green pigmentation. In other embodiments, the microalgae is a color mutant that lacks or is reduced in pigmentation.

This invention also provide a food composition comprising at least 0.1% w/w algal triglyceride oil isolated from recombinant algal cells cultivated under heterotrophic conditions and one or more other ingredients. The recombinant algal cells can be optionally cultivated in the dark. In some embodiments, the triglyceride profile of the algal triglycerol oil is similar to the triglyceride profile of a naturally occurring oil. Some of the naturally occurring oils are provided in table 5. In an embodiment of the invention, the algal triglycerides produced by the invention are similar to cocoa butter, coconut oil, palm oil, beef tallow or lard. In at least one embodiment, at least 50% by weight of the oil is monounsaturated glycerolipid oil. In some cases, at least 50%, 60%, 70% 80% or 90% by weight of the oil is a C18:1 lipid.

In another aspect, the present invention is directed to a food composition comprising at least 0.1% w/w algal biomass and one or more other edible ingredients, wherein the algal biomass comprises at least 30% protein by dry weight, at least 40% protein by dry weight, at least 45% protein by dry weight, at least 50% protein by dry weight, at least 55% protein by dry weight, at least 60% protein by dry weight or at least 75% protein by dry weight. In some cases, the algal biomass contains 30-75% or 40-60% protein by dry weight. In some embodiments, at least 40% of the crude protein is digestible, at least 50% of the crude protein is digestible, at least 60% of the crude protein is digestible, at least 70% of the crude protein is digestible, at least 80% of the crude protein is digestible, or at least 90% of the crude protein is digestible. In some cases, the algal biomass is grown under heterotrophic conditions. In at least one embodiment, the algal biomass is grown under nitrogen-replete conditions. In other embodiments, the microalgae is a color mutant that lacks or is reduced in pigmentation.

In some cases, the algal biomass comprises predominantly intact cells. In some embodiments, the food composition comprises oil which is predominantly or completely encapsulated inside cells of the biomass. In some cases, the food composition comprises predominantly intact recombinant microalgal cells. In some cases, the algal oil is predominantly encapsulated in cells of the biomass. In other cases, the biomass comprises predominantly lysed cells (e.g., a homogenate). As discussed above, such a homogenate can be provided as a slurry, flake, powder, or flour.

In some embodiments of the food composition, the algal biomass further comprises at least 10 ppm selenium. In some cases, the biomass further comprises at least 15% w/w algal polysaccharide. In some cases, the biomass further comprises at least 5% w/w algal glycoprotein. In some cases, the biomass comprises between 0 and 115 mcg/g total carotenoids. In some cases, the biomass comprises at least 0.5% w/w algal phospholipids. In all cases, as just noted, these components are true cellular components and not extracellular.

In some cases, the algal biomass of the food composition contains components that have antioxidant qualities. The strong antioxidant qualities can be attributed to the multiple antioxidants present in the algal biomass, which include, but are not limited to carotenoids, essential minerals such as zinc, copper, magnesium, calcium, and manganese. Algal biomass has also been shown to contain other antioxidants such as tocotrienols and tocopherols. These members of the vitamin E family are important antioxidants and have other health benefits such as protective effects against stroke-induced injuries, reversal of arterial blockage, growth inhibition of breast and prostate cancer cells, reduction in cholesterol levels, a reduced-risk of type II diabetes and protective effects against glaucomatous damage. Natural sources of tocotrienols and tocopherols can be found in oils produced from palm, sunflower, corn, soybean and olive oil, however compositions provided herein have significantly greater levels of tocotrienols than heretofore known materials.

In some cases, food compositions of the present invention contain algal oil comprising at least 0.05 mg/g, at least 0.07 mg/g or at least 0.08 mg/g total tocopherol. In some cases, food compositions of the present invention contain algal oil comprising at least 0.15 mg/g, at least 0.20 mg/g or at least 0.25 mg/g total tocotrienol.

In particular embodiments of the compositions and/or methods described above, the microalgae can produce carotenoids. In some embodiments, the carotenoids produced by the microalgae can be co-extracted with the lipids or oil produced by the microalgae (i.e., the oil or lipid will contain the carotenoids). In some embodiments, the carotenoids produced by the microalgae are xanthophylls. In some embodiments, the carotenoids produced by the microalgae are carotenes. In some embodiments, the carotenoids produced by the microalgae are a mixture of carotenes and xanthophylls. In various embodiments, the carotenoids produced by the microalgae comprise at least one carotenoid selected from the group consisting of astaxanthin, lutein, zeaxanthin, alpha-carotene, trans-beta carotene, cis-beta carotene, lycopene and any combination thereof.

In some embodiments of the food composition, the algal biomass is derived from algae cultured and dried under good manufacturing practice (GMP) conditions. In some cases, the algal biomass is combined with one or more other edible ingredients, including without limitation, grain, fruit, vegetable, protein, lipid, herb and/or spice ingredients. In some cases, the food composition is a salad dressing, egg product, baked good, bread, bar, pasta, sauce, soup drink, beverage, frozen dessert, butter or spread. In particular embodiments, the food composition is not a pill or powder. In some cases, the food composition in accordance with the present invention weighs at least 50 g, or at least 100 g.

Biomass can be combined with one or more other edible ingredients to make a food product. The biomass can be from a single algal source (e.g., strain) or algal biomass from multiple sources (e.g., different strains). The biomass can also be from a single algal species, but with different composition profile. For example, a manufacturer can blend microalgae that is high in oil content with microalgae that is high in protein content to the exact oil and protein content that is desired in the finished food product. The combination can be performed by a food manufacturer to make a finished product for retail sale or food service use. Alternatively, a manufacturer can sell algal biomass as a product, and a consumer can incorporate the algal biomass into a food product, for example, by modification of a conventional recipe. In either case, the algal biomass is typically used to replace all or part of the oil, fat, eggs, or the like used in many conventional food products.

In one aspect, the present invention is directed to a food composition comprising at least 0.1% w/w algal biomass and one or more other edible ingredients, wherein the algal biomass is formulated through blending of algal biomass that contains at least 40% protein by dry weight with algal biomass that contains 40% lipid by dry weight to obtain a blend of a desired percent protein and lipid by dry weight. In some embodiments, the biomass is from the same strain of algae. Alternatively, algal biomass that contains at least 40% lipid by dry weight containing less than 1% of its lipid as DHA is blended with algal biomass that contains at least 20% lipid by dry weight containing at least 5% of its lipid as DHA to obtain a blend of dry biomass that contains in the aggregate at least 10% lipid and 1% DHA by dry weight.

In one aspect, the present invention is directed to a method of preparing algal biomass by drying an algal culture to provide algal biomass comprising at least 15% oil by dry weight under GMP conditions, in which the algal oil is greater than 50% monounsaturated lipid.

In one aspect, the present invention is directed to algal biomass containing at least 15% oil by dry weight manufactured under GMP conditions, in which the algal oil is greater than 50%, 60%, 70%, 80% or 90% C18:1 lipid. In one aspect, the present invention is directed to algal biomass containing at least 40% oil by dry weight manufactured under GMP conditions. In one aspect, the present invention is directed to algal biomass containing at least 55% oil by dry weight manufactured under GMP conditions. In some cases, the algal biomass is packaged as a tablet for delivery of a unit dose of biomass. In some cases, the algal biomass is packaged with or otherwise bears a label providing directions for combining the algal biomass with other edible ingredients.

In one aspect, the present invention is directed to methods of combining recombinant microalgal biomass and/or materials derived therefrom, as described above, with at least one other finished food ingredient, as described below, to form a food composition or foodstuff. In various embodiments, the food composition formed by the methods of the invention comprises an egg product (powdered or liquid), a pasta product, a dressing product, a mayonnaise product, a cake product, a bread product, an energy bar, a milk product, a juice product, a spread, or a smoothie. In some cases, the food composition is not a pill or powder. In various embodiments, the food composition weighs at least 10 g, at least 25 g, at least 50 g, at least 100 g, at least 250 g, or at least 500 g or more. In some embodiments, the food composition formed by the combination of recombinant microalgal biomass and/or product derived therefrom is an uncooked product. In other cases, the food composition is a cooked product.

In other cases, the food composition is a cooked product. In some cases, the food composition contains less than 25% oil or fat by weight excluding oil contributed by the algal biomass. Fat, in the form of saturated triglycerides (TAGs or trans fats), is made when hydrogenating vegetable oils, as is practiced when making spreads such as margarines. The fat contained in algal biomass has no trans fats present. In some cases, the food composition contains less than 10% oil or fat by weight excluding oil contributed by the biomass. In at least one embodiment, the food composition is free of oil or fat excluding oil contributed by the biomass. In some cases, the food composition is free of oil other than oil contributed by the biomass. In some cases, the food composition is free of egg or egg products.

In one aspect, the present invention is directed to a method of making a food composition in which the fat or oil in a conventional food product is fully or partially substituted with algal biomass containing at least 10% by weight oil. In one embodiment, the method comprises determining an amount of the algal biomass for substitution using the proportion of algal oil in the biomass and the amount of oil or fat in the conventional food product, and combining the algal biomass with at least one other edible ingredient and less than the amount of oil or fat contained in the conventional food product to form a food composition. In some cases, the amount of algal biomass combined with the at least one other ingredient is 1-4 times the mass or volume of oil and/or fat in the conventional food product.

In some embodiments, the method described above further includes providing a recipe for a conventional food product containing the at least one other edible ingredient combined with an oil or fat, and combining 1-4 times the mass or volume of the algal biomass with the at least one other edible ingredient as the mass or volume of fat or oil in the conventional food product. In some cases, the method further includes preparing the algal biomass under GMP conditions.

In some cases, the food composition formed by the combination of recombinant microalgal biomass and/or product derived therefrom comprises at least 0.1%, at least 0.5%, at least 1%, at least 5%, at least 10%, at least 25%, or at least 50% w/w or v/v recombinant microalgal biomass or recombinant microalgal oil. In some embodiments, food compositions formed as described herein comprise at least 2%, at least 5%, at least 10%, at least 25%, at least 50%, at least 75%, at least 90%, or at least 95% w/w recombinant microalgal biomass or product derived therefrom. In some cases, the food composition comprises 5-50%, 10-40%, or 15-35% algal biomass or product derived therefrom by weight or by volume.

As described above, recombinant microalgal biomass can be substituted for other components that would otherwise be conventionally included in a food product. In some embodiments, the food composition contains less than 50%, less than 40%, or less than 30% oil or fat by weight excluding recombinant microalgal oil contributed by the biomass or from recombinant microalgal sources. In some cases, the food composition contains less than 25%, less than 20%, less than 15%, less than 10%, or less than 5% oil or fat by weight excluding recombinant microalgal oil contributed by the biomass or from recombinant microalgal sources. In at least one embodiment, the food composition is free of oil or fat excluding recombinant microalgal oil contributed by the biomass or from recombinant microalgal sources. In some cases, the food composition is free of eggs, butter, or other fats/oils or at least one other ingredient that would ordinarily be included in a comparable conventional food product. Some food products are free of dairy products (e.g., butter, cream and/or cheese).

The amount of algal biomass used to prepare a food composition depends on the amount of non-algal oil, fat, eggs, or the like to be replaced in a conventional food product and the percentage of oil in the algal biomass. Thus, in at least one embodiment, the methods of the invention include determining an amount of the algal biomass to combine with at least one other edible ingredient from a proportion of oil in the biomass and a proportion of oil and/or fat that is ordinarily combined with the at least one other edible ingredient in a conventional food product. For example, if the algal biomass is 50% w/w recombinant microalgal oil, and complete replacement of oil or fat in a conventional recipe is desired, then the oil can for example be replaced in a 2:1 ratio. The ratio can be measured by mass, but for practical purposes, it is often easier to measure volume using a measuring cup or spoon, and the replacement can be by volume. In a general case, the volume or mass of oil or fat to be replaced is replaced by (100/100-X) volume or mass of algal biomass, where X is the percentage of recombinant microalgal oil in the biomass. In general, oil and fats to be replaced in conventional recipes can be replaced in total by algal biomass, although total replacement is not necessary and any desired proportion of oil and/or fats can be retained and the remainder replaced according to taste and nutritional needs. Because the algal biomass contains proteins and phospholipids, which function as emulsifiers, items such as eggs can be replaced in total or in part with algal biomass. If an egg is replaced in total with biomass, it is sometimes desirable or necessary to augment the emulsifying properties in the food composition with an additional emulsifying agent(s) and/or add additional water or other liquid(s) to compensate for the loss of these components that would otherwise be provided by the egg. Because an egg is not all fat, the amount of biomass used to replace an egg may be less than that used to replace pure oil or fat. An average egg weighs about 58 g and comprises about 11.2% fat. Thus, about 13 g of algal biomass comprising 50% recombinant microalgal oil by weight can be used to replace the total fat portion of an egg in total. Replacing all or part of the eggs in a food product has the additional benefit of reducing cholesterol.

For simplicity, substitution ratios can also be provided in terms of mass or volume of oil, fat and/or eggs replaced with mass or volume of biomass. In some methods, the mass or volume of oil, fat and/or eggs in a conventional recipe is replaced with 5-150%, 25-100% or 25-75% of the mass or volume of oil, fat and/or eggs. The replacement ratio depends on factors such as the food product, desired nutritional profile of the food product, overall texture and appearance of the food product, and oil content of the biomass.

In cooked foods, the determination of percentages (i.e., weight or volume) can be made before or after cooking. The percentage of algal biomass can increase during the cooking process because of loss of liquids. Because some algal biomass cells may lyse in the course of the cooking process, it can be difficult to measure the content of algal biomass directly in a cooked product. However, the content can be determined indirectly from the mass or volume of biomass that went into the raw product as a percentage of the weight or volume of the finished product (on a biomass dry solids basis), as well as by methods of analyzing components that are unique to the algal biomass such as genomic sequences or compounds that are delivered solely by the algal biomass, such as certain carotenoids.

In some cases, it may be desirable to combine algal biomass with the at least one other edible ingredient in an amount that exceeds the proportional amount of oil, fat, eggs, or the like that is present in a conventional food product. For example, one may replace the mass or volume of oil and/or fat in a conventional food product with 1, 2, 3, 4, or more times that amount of algal biomass. Some embodiments of the methods of the invention include providing a recipe for a conventional food product containing the at least one other edible ingredient combined with an oil or fat, and combining 1-4 times the mass or volume of algal biomass with the at least one other edible ingredient as the mass or volume of fat or oil in the conventional food product.

Algal biomass (predominantly intact or homogenized or micronized) and/or algal oil are combined with at least one other edible ingredient to form a food product. In some food products, the algal biomass and/or algal oil is combined with 1-20, 2-10, or 4-8 other edible ingredients. The edible ingredients can be selected from all the major food groups, including without limitation, fruits, vegetables, legumes, meats, fish, grains (e.g., wheat, rice, oats, cornmeal, barley), herbs, spices, water, vegetable broth, juice, wine, and vinegar. In some food compositions, at least 2, 3, 4, or 5 food groups are represented as well as the algal biomass or algal oil.

Oils, fats, eggs and the like can also be combined into food compositions, but, as has been discussed above, are usually present in reduced amounts (e.g., less than 50%, 25%, or 10% of the mass or volume of oil, fat or eggs compared with conventional food products. Some food products of the invention are free of oil other than that provided by algal biomass and/or algal oil. Some food products are free of oil other than that provided by algal biomass. Some food products are free of fats other than that provided by algal biomass or algal oil. Some food products are free of fats other than that provided by algal biomass. Some food products are free of both oil and fats other than that provided by algal biomass or algal oil. Some food products are free of both oil and fats other than that provided by algal biomass. Some food products are free of eggs. In some embodiments, the oils produced by the microalgae can be tailored by culture conditions or strain selection to comprise a particular fatty acid component(s) or levels.

In some cases, the algal biomass used in making the food composition comprises a mixture of at least two distinct species of microalgae. In some cases, at least two of the distinct species of microalgae have been separately cultured. In at least one embodiment, at least two of the distinct species of microalgae have different glycerolipid profiles. In some cases, the method described above further comprises culturing algae under heterotrophic conditions and preparing the biomass from the algae. In some cases, all of the at least two distinct species of microalgae contain at least 10%, or at least 15% oil by dry weight. In some cases, a food composition contains a blend of two distinct preparations of biomass of the same species, wherein one of the preparations contains at least 30% oil by dry weight and the second contains less than 15% oil by dry weight. In some cases, a food composition contains a blend of two distinct preparations of biomass of the same species, wherein one of the preparations contains at least 50% oil by dry weight and the second contains less than 15% oil by dry weight, and further wherein the species is *Chlorella protothecoides.*

As well as using algal biomass as an oil, fat or egg replacement in otherwise conventional foods, algal biomass can be used as a supplement in foods that do not normally contain oil, such as a smoothie. The combination of oil with products that are mainly carbohydrate can have benefits associated with the oil, and from the combination of oil and carbohydrate by reducing the glycemic index of the carbohydrate. The provision of oil encapsulated in biomass is advantageous in protecting the oil from oxidation and can also improve the taste and texture of the smoothie.

Oil extracted from algal biomass can be used in the same way as the biomass itself, that is, as a replacement for oil, fat, eggs, or the like in conventional recipes. The oil can be used to replace conventional oil and/or fat on about a 1:1 weight/ weight or volume/volume basis. The oil can be used to replace eggs by substitution of about 1 teaspoon of algal oil per egg optionally in combination with additional water and/or an emulsifier (an average 58 g egg is about 11.2% fat, algal oil has a density of about 0.915 g/ml, and a teaspoon has a volume of about 5 ml=1.2 teaspoons of algal oil/egg). The oil can also be incorporated into dressings, sauces, soups, margarines, creamers, shortenings and the like. The oil is particularly useful for food products in which combination of the oil with other food ingredients is needed to give a desired taste, texture and/or appearance. The content of oil by weight or volume in food products can be at least 5, 10, 25, 40 or 50%.

In at least one embodiment, oil extracted from algal biomass can also be used as a cooking oil by food manufacturers, restaurants and/or consumers. In such cases, algal oil can replace conventional cooking oils such as safflower oil, canola oil, olive oil, grape seed oil, corn oil, sunflower oil, coconut oil, palm oil, or any other conventionally used cooking oil. The oil obtained from algal biomass as with other types of oil can be subjected to further refinement to increase its suitability for cooking (e.g., increased smoke point). Oil can be neutralized with caustic soda to remove free fatty acids. The free fatty acids form a removable soap stock. The color of oil can be removed by bleaching with chemicals such as carbon black and bleaching earth. The bleaching earth and chemicals can be separated from the oil by filtration. Oil can also be deodorized by treating with steam.

Predominantly intact biomass, homogenized or micronized biomass (as a slurry, flake, powder or flour) and purified algal oil can all be combined with other food ingredients to form food products. All are a source of oil with a favorable nutritional profile (relatively high monounsaturated content). Predominantly intact, homogenized, and micronized biomass also supply high quality protein (balanced amino acid composition), carbohydrates, fiber and other nutrients as discussed above. Foods incorporating any of these products can be made in vegan or vegetarian form. Another advantage in using recombinant microalgal biomass (either predominantly intact or homogenized (or micronized) or both) as a protein source is that it is a vegan/vegetarian protein source that is not from a major allergen source, such as soy, eggs or dairy.

Other edible ingredients with which algal biomass and/or algal oil can be combined in accordance with the present invention include, without limitation, grains, fruits, vegetables, proteins, meats, herbs, spices, carbohydrates, and fats. The other edible ingredients with which the algal biomass and/or algal oil is combined to form food compositions depend on the food product to be produced and the desired taste, texture and other properties of the food product.

Although in general any of these sources of algal oil can be used in any food product, the preferred source depends in part whether the oil is primarily present for nutritional or caloric purposes rather than for texture, appearance or taste of food, or alternatively whether the oil in combination with other food ingredients is intended to contribute a desired taste, texture or appearance of the food as well as or instead of improving its nutritional or caloric profile.

The food products can be cooked by conventional procedures as desired. Depending on the length and temperature, the cooking process may break down some cell walls, releasing oil such that it combines with other ingredients in the mixture. However, at least some algal cells often survive cooking intact. Alternatively, food products can be used without cooking. In this case, the algal wall remains intact, protecting the oil from oxidation.

The algal biomass, if provided in a form with cells predominantly intact, or as a homogenate powder, differs from oil, fat or eggs in that it can be provided as a dry ingredient, facilitating mixing with other dry ingredients, such as flour. In one embodiment the algal biomass is provided as a dry homogenate that contains between 25 and 40% oil by dry weight. A biomass homogenate can also be provided as slurry. After mixing of dry ingredients (and biomass homogenate slurry, if used), liquids such as water can be added. In some food products, the amount of liquid required is somewhat higher than in a conventional food product because of the non-oil component of the biomass and/or because water is not being supplied by other ingredients, such as eggs. However, the amount of water can readily be determined as in conventional cooking.

In one aspect, the present invention is directed to a food ingredient composition comprising at least 0.5% w/w algal biomass containing at least 10% algal oil by dry weight and at least one other edible ingredient, in which the food ingredient can be converted into a reconstituted food product by addition of a liquid to the food ingredient composition. In one embodiment, the liquid is water.

Homogenized or micronized high-oil biomass is particularly advantageous in liquid, and/or emulsified food products (water in oil and oil in water emulsions), such as sauces, soups, drinks, salad dressings, butters, spreads and the like in which oil contributed by the biomass forms an emulsion with other liquids. Products that benefit from improved rheology, such as dressings, sauces and spreads are described below in the Examples. Using homogenized biomass an emulsion with desired texture (e.g., mouth-feel), taste and appearance (e.g., opacity) can form at a lower oil content (by weight or volume of overall product) than is the case with conventional products employing conventional oils, thus can be used as a fat extender. Such is useful for low-calorie (i.e., diet) products. Purified algal oil is also advantageous for such liquid and/or emulsified products. Both homogenized or micronized high-oil biomass and purified algal oil combine well with other edible ingredients in baked goods achieving similar or better taste, appearance and texture to otherwise similar products made with conventional oils, fats and/or eggs but with improved nutritional profile (e.g., higher content of monosaturated oil, and/or higher content or quality of protein, and/or higher content of fiber and/or other nutrients).

Predominantly intact biomass is particularly useful in situations in which it is desired to change or increase the nutritional profile of a food (e.g., higher oil content, different oil content (e.g., more monounsaturated oil), higher protein content, higher calorie content, higher content of other nutrients). Such foods can be useful for example, for athletes or patients suffering from wasting disorders. Predominantly intact biomass can be used as a bulking agent. Bulking agents can be used, for example, to augment the amount of a more expensive food (e.g., meat helper and the like) or in simulated or imitation foods, such as vegetarian meat substitutes. Simulated or imitation foods differ from natural foods in that the flavor and bulk are usually provided by different sources. For example, flavors of natural foods, such as meat, can be imparted into a bulking agent holding the flavor. Predominantly intact biomass can be used as a bulking agent in such foods. Predominantly intact biomass is also particularly useful in dried food, such as pasta because it has good water binding properties, and can thus facilitate rehydration of such foods. Predominantly intact biomass is also useful as a preservative, for example, in baked goods. The predominantly intact biomass can improve water retention and thus shelf-life.

Algal biomass that has been disrupted or micronized can also improve water retention and thus shelf-life. Increased moisture retention is especially desirable in gluten-free products, such as gluten-free baked goods. A detailed description of formulation of a gluten-free cookie using disrupted algal biomass and subsequent shelf-life study is described in the Examples below.

In some cases, the algal biomass can be used in egg preparations. In some embodiments, algal biomass (e.g., algal flour) added to a conventional dry powder egg preparation to create scrambled eggs that are creamier, have more moisture and a better texture than dry powdered eggs prepared without the algal biomass. In other embodiments, algal biomass is added to whole liquid eggs in order to improve the overall texture and moisture of eggs that are prepared and then held on a steam table. Specific examples of the foregoing preparations are described in the Examples below.

Algal biomass (predominantly intact and/or homogenized or micronized) and/or algal oil can be incorporated into virtually any food composition. Some examples include baked goods, such as cakes, brownies, yellow cake, bread including brioche, cookies including sugar cookies, biscuits, and pies. Other examples include products often provided in dried form, such as pastas or powdered dressing, dried creamers, commuted meats and meat substitutes. Incorporation of predominantly intact biomass into such products as a binding and/or bulking agent can improve hydration and increase yield due to the water binding capacity of predominantly intact biomass. Re-hydrated foods, such as scrambled eggs made from dried powdered eggs, may also have improved texture and nutritional profile. Other examples include liquid food products, such as sauces, soups, dressings (ready to eat), creamers, milk drinks, juice drinks, smoothies, creamers. Other liquid food products include nutritional beverages that serve as a meal replacement or algal milk. Other food products include butters or cheeses and the like including shortening, margarine/spreads, nut butters, and cheese products, such as nacho sauce. Other food products include energy bars, chocolate confections-lecithin replacement, meal replacement bars, granola bar-type products. Another type of food product is batters and coatings. By providing a layer of oil surrounding a food, predominantly intact biomass or a homogenate repel additional oil from a cooking medium from penetrating a food. Thus, the food can retain the benefits of high monounsaturated oil content of coating without picking up less desirable oils (e.g., trans fats, saturated fats, and by products from the cooking oil). The coating of biomass can also provide a desirable (e.g., crunchy) texture to the food and a cleaner flavor due to less absorption of cooking oil and its byproducts.

In uncooked foods, most algal cells in the biomass remain intact. This has the advantage of protecting the algal oil from oxidation, which confers a long shelf-life and minimizes adverse interaction with other ingredients. Depending on the nature of the food products, the protection conferred by the cells may reduce or avoid the need for refrigeration, vacuum packaging or the like. Retaining cells intact also prevents direct contact between the oil and the mouth of a consumer, which reduces the oily or fatty sensation that may be undesirable. In food products in which oil is used more as nutritional supplement, such can be an advantage in improving the organoleptic properties of the product. Thus, predominantly intact biomass is suitable for use in such products. However, in uncooked products, such as a salad dressing, in which oil imparts a desired mouth feeling (e.g., as an emulsion with an aqueous solution such as vinegar), use of purified algal oil or micronized biomass is preferred. In cooked foods, some algal cells of original intact biomass may be lysed but other algal cells may remain intact. The ratio of lysed to intact cells depends on the temperature and duration of the cooking process. In cooked foods in which dispersion of oil in a uniform way with other ingredients is desired for taste, texture and/or appearance (e.g., baked goods), use of micronized biomass or purified algal oil is preferred. In cooked foods, in which algal biomass is used to supply oil and/or protein and other nutrients, primarily for their nutritional or caloric value rather than texture.

Algal biomass can also be useful in increasing the satiety index of a food product (e.g., a meal-replacement drink or smoothie) relative to an otherwise similar conventional product made without the algal biomass. The satiety index is a measure of the extent to which the same number of calories of different foods satisfy appetite. Such an index can be measured by feeding a food being tested and measuring appetite for other foods at a fixed interval thereafter. The less appetite for other foods thereafter, the higher the satiety index. Values of satiety index can be expressed on a scale in which white bread is assigned a value of 100. Foods with a higher satiety index are useful for dieting. Although not dependent on an understanding of mechanism, algal biomass is believed to increase the satiety index of a food by increasing the protein and/or fiber content of the food for a given amount of calories.

Algal biomass (predominantly intact and homogenized or micronized) and/or algal oil can also be manufactured into nutritional or dietary supplements. For example, algal oil can be encapsulated into digestible capsules in a manner similar to fish oil. Such capsules can be packaged in a bottle and taken on a daily basis (e.g., 1-4 capsules or tablets per day). A capsule can contain a unit dose of algal biomass or algal oil. Likewise, biomass can be optionally compressed with pharmaceutical or other excipients into tablets. The tablets can be packaged, for example, in a bottle or blister pack, and taken daily at a dose of, e.g., 1-4 tablets per day. In some cases, the tablet or other dosage formulation comprises a unit dose of biomass or algal oil. Manufacturing of capsule and tablet products and other supplements is preferably performed under GMP conditions appropriate for nutritional supplements as codified at 21 C.F.R. 111, or comparable regulations established by foreign jurisdictions. The algal biomass can be mixed with other powders and be presented in sachets as a ready-to-mix material (e.g., with water, juice, milk or other liquids). The algal biomass can also be mixed into products such as yogurts.

Although algal biomass and/or algal oil can be incorporated into nutritional supplements, the functional food products discussed above have distinctions from typical nutritional supplements, which are in the form of pills, capsules, or powders. The serving size of such food products is typically much larger than a nutritional supplement both in terms of weight and in terms of calories supplied. For example, food products often have a weight of over 100 g and/or supply at least 100 calories when packaged or consumed at one time. Typically food products contain at least one ingredient that is either a protein, a carbohydrate or a liquid and often contain two or three such other ingredients. The protein or carbohydrate in a food product often supplies at least 30%, 50%, or 60% of the calories of the food product.

As discussed above, algal biomass can be made by a manufacturer and sold to a consumer, such as a restaurant or individual, for use in a commercial setting or in the home. Such algal biomass is preferably manufactured and packaged under Good Manufacturing Practice (GMP) conditions for food products. The algal biomass in predominantly intact form or homogenized or micronized form as a powder is often packaged dry in an airtight container, such as a sealed bag. Homogenized or micronized biomass in slurry form can be conveniently packaged in a tub among other containers. Optionally, the algal biomass can be packaged under vacuum to enhance shelf life. Refrigeration of packaged algal biomass is not required. The packaged algal biomass can contain instructions for use including directions for how much of the algal biomass to use to replace a given amount of oil, fat or eggs in a conventional recipe, as discussed above. For simplicity, the directions can state that oil or fat are to be replaced on a 2:1 ratio by mass or volume of biomass, and eggs on a ratio of 11 g biomass or 1 teaspoon of algal oil per egg. As discussed above, other ratios are possible, for example, using a ratio of 10-175% mass or volume of biomass to mass or volume of oil and/or fat and/or eggs in a conventional recipe. Upon opening a sealed package, the instructions may direct the user to keep the algal biomass in an airtight container, such as those widely commercially available (e.g., Glad), optionally with refrigeration.

Algal biomass (predominantly intact or homogenized or micronized powder) can also be packaged in a form combined with other dry ingredients (e.g., sugar, flour, dry fruits, flavorings) and portioned packed to ensure uniformity in the final product. The mixture can then be converted into a food product by a consumer or food service company simply by adding a liquid, such as water or milk, and optionally mixing, and/or cooking without adding oils or fats. In some cases, the liquid is added to reconstitute a dried algal biomass composition. Cooking can optionally be performed using a microwave oven, convection oven, conventional oven, or on a cooktop. Such mixtures can be used for making cakes, breads, pancakes, waffles, drinks, sauces and the like. Such mixtures have advantages of convenience for the consumer as well as long shelf life without refrigeration. Such mixtures are typically packaged in a sealed container bearing instructions for adding liquid to convert the mixture into a food product.

Algal oil for use as a food ingredient is likewise preferably manufactured and packaged under GMP conditions for a food. The algal oil is typically packaged in a bottle or other container in a similar fashion to conventionally used oils. The container can include an affixed label with directions for using the oil in replacement of conventional oils, fats or eggs in food products, and as a cooking oil. When packaged in a sealed container, the oil has a long shelf-life (at least one year) without substantial deterioration. After opening, algal oil comprised primarily of monounsaturated oils is not acutely sensitive to oxidation. However, unused portions of the oil can be kept longer and with less oxidation if kept cold and/or out of direct sunlight (e.g., within an enclosed space, such as a cupboard). The directions included with the oil can contain such preferred storage information.

Optionally, the algal biomass and/or the algal oil may contain a food approved preservative/antioxidant to maximize shelf-life, including but not limited to, carotenoids (e.g., astaxanthin, lutein, zeaxanthin, alpha-carotene, beta-carotene and lycopene), phospholipids (e.g., N-acylphosphatidylethanolamine, phosphatidic acid, phosphatidylethanolamine, phosphatidylcholine, phosphatidylinositol and lysophosphatidylcholine), tocopherols (e.g., alpha tocopherol, beta tocopherol, gamma tocopherol and delta tocopherol), tocotrienols (e.g., alpha tocotrienol, beta tocotrienol, gamma tocotrienol and delta tocotrienol), Butylated hydroxytoluene, Butylated hydroxyanisole, polyphenols, rosmarinic acid, propyl gallate, ascorbic acid, sodium ascorbate, sorbic acid, benzoic acid, methyl parabens, levulinic acid, anisic acid, acetic acid, citric acid, and bioflavonoids.

The description of incorporation of predominantly intact biomass, homogenized, or micronized biomass (slurry, flake, powder, or flour) or algal oil into food for human nutrition is in general also applicable to food products for non-human animals.

The biomass imparts high quality oil or proteins or both in such foods. The content of algal oil is preferably at least 10 or 20% by weight as is the content of algal protein. Obtaining at least some of the algal oil and/or protein from predominantly intact biomass is sometimes advantageous for food for high performance animals, such as sport dogs or horses. Predominantly intact biomass is also useful as a preservative. Algal biomass or oil is combined with other ingredients typically found in animal foods (e.g., a meat, meat flavor, fatty acid, vegetable, fruit, starch, vitamin, mineral, antioxidant, probiotic) and any combination thereof. Such foods are also suitable for companion animals, particularly those having an active life style. Inclusion of taurine is recommended for cat foods. As with conventional animal foods, the food can be provided in bite-size particles appropriate for the intended animal.

Delipidated meal is useful as animal feed for farm animals, e.g., ruminants, poultry, swine, and aquaculture. Delipidated meal is a byproduct of preparing purified algal oil either for food or other purposes. The resulting meal although of reduced oil content still contains high quality proteins, carbohydrates, fiber, ash and other nutrients appropriate for an animal feed. Because the cells are predominantly lysed, delipidated meal is easily digestible by such animals. Delipidated meal can optionally be combined with other ingredients, such as grain, in an animal feed. Because delipidated meal has a powdery consistency, it can be pressed into pellets using an extruder or expanders, which are commercially available.

The tailored oils of the present invention can be used in place of conventional oils such as palm oil, palm kernel oil, coconut oil, cocoa butter, tallow, or lard.

Palm Oil:

Palm oil is used around the world in such foods as margarine, shortening, baked goods, and confections. Palm oil is comprised of approximately 50% saturated fat and 50% unsaturated fat, and can therefore be separated into (solid) palm stearin containing C18:0 and lower chain saturated fatty acids and (liquid) palm olein containing C18:1 and higher chain unsaturated fatty acids. Palm stearin can be used to form solid trans-free fats. A microbial triglyceride composition of the present invention in which the oil comprises higher amounts of C18:1 is an excellent healthier substitute for partially hydrogenated vegetable oils that are high in trans-fats that are commonly used today. Foods containing trans-fats, including hydrogenated vegetable oils, are widely believed to be an unhealthy food. The invention provides a tailored oil, higher in C18:1, that is healthier than the partially hydrogenated vegetable oils. Thus, the present invention provides a healthier oil and meets the demands placed by the public on the food industry to supply healthier choices. The tailored oils of the present invention can be used as a replacement of the unhealthy partially hydrogenated vegetable oils.

In addition to food products, palm oil, with its moderate linoleic acid content and high level of natural antioxidants, is suitable for direct use in most cooking ad frying applications. The use of palm oil as a frying oil is a major use of palm oil worldwide. Potato chips, French fries, doughnuts, ramen noodles, nuts, etc. are typically fried in palm oil.

For the large scale frying of potato chips, palm olein or a blend of palm olein with soya or rapeseed oil is preferred. This is because the surface appearance of the finished product is improved. French fries are often purchased as part fried and deep frozen products.

In addition to its use in baking and frying, palm oil is also extensively used as an ingredient in numerous types of foods, including biscuits, crackers, bread, cereals, chips, chocolate, ice cream, soup, sauces, mayonnaise and many others.

The palm oil mimetic of the present invention are a healthy replacement of palm oil in the human food supply.

Palm Kernel Oil & Coconut Oil:

Whole palm kernel oil and whole coconut oil as well as fractionated parts are used alone or in blends with other oils for the manufacture of cocoa butter substitutes and other confectionary fats (toffees and caramels), biscuit dough and filling creams, cake icings, ice cream, imitation whipping cream, non-dairy creamers (coffee whiteners), filled milk and table margarines and spreads. These oils are also used widely in making bar and liquid soap. Palm kernel oil and coconut oil are high in C12:0 and C14:0. Table 5 discloses that the total amount of C12:0 and C14:0 of coconut oil is approximately 50%-75%. Similarly, the total amount of C12:0 and C14:0 of palm kernel oil is approximately 50%-70%. The present invention provides a palm oil mimetic, a microbial oil comprising about 50%-75% C12:0 and C14:0.

Cocoa Butter:

Cocoa butter, is a pale-yellow, pure edible vegetable fat extracted from the cocoa bean. It is used to make chocolate, biscuits, baked goods, pharmaceuticals, ointments and toiletries. Cocoa butter historically has served as a major ingredient in the commercial production of both white chocolate and milk chocolate.

Additionally, pharmaceutical companies have made use of cocoa butter's specific physical properties. As an edible oil, solid at room temperature, but melts at body temperature, it is considered an ideal base for delivering medicinal ingredients, for example as a suppository.

Cocoa butter is also one of the most stable fats known, a quality that coupled with natural antioxidant that prevents rancidity, grants it a storage life of two to five years. The velvety texture, pleasant fragrance and emollient properties of cocoa butter have made it a popular ingredient in products for the skin, such as cosmetics, soaps and lotions.

The moisturizing abilities of cocoa butter are frequently recommended for prevention of stretch marks in pregnant women, treatment of chapped skin and lips, and as a daily moisturizer to prevent dry, itchy skin.

Example 14 provides a microbial triglyceride composition that is very similar to cocoa butter. The cocoa butter mimetic of the invention is useful in all applications that use cocoa butter.

Tallow:

The USA is by far the biggest producer and exporter of beef tallow, with production accounting for approx. 25 to 30% of global oil and fat production. In the past, beef tallow was used in early cultures for lighting (woodchips soaked in beef tallow) and used for making soaps and ointments. Today, beef tallow is a major raw material used in the production of chemical intermediate products, such as fatty acids and fat alcohols. In addition to its principal uses in edible fats and oils, beef tallow is also used as baking and cooking fat, as well as in margarine production. With its similar fatty acid spectrum, beef tallow was formerly used to stretch cocoa butter.

In food and cooking, tallow may be used as oil for frying and as ingredient for making pemmican, a Native American dish. Tallow may also be used as shortening for breads and pastries and as part of the ingredients for margarine. Aside from beef fat, tallow may also be sourced from horses, sheep, and pigs. People who don't eat meat and are vegetarians have also their own version of tallow using wax isolated from the seeds of the tallow tree, *Triadica*

*sebiferum.* Tallow is also used as part of the ingredients of various animal feeds like those for chickens and pigs.

The tallow mimetic as described herein is useful as a replacement of tallow.

Lard:

Lard is isolated from pigs and is one of the few edible oils with a relatively high smoke point, attributable to its high saturated fatty acids content. Pure lard is especially useful for cooking since it produces little smoke when heated and has a distinct taste when combined with other foods. Many chefs and bakers deem lard a superior cooking fat over shortening because of lard's range of applications and taste.

Because of the relatively large fat crystals found in lard, it is extremely effective as a shortening in baking. Pie crusts made with lard tend to be more flaky than those made with butter. Many cooks employ both types of fat in their pastries to combine the shortening properties of lard with the flavor of butter.

Example 14 provides a microbial triglyceride composition that is similar lard. The lard mimetic of the invention is useful in all applications that use lard.

X. EXAMPLES

Example 1: Methods for Culturing *Prototheca*

*Prototheca* strains were cultivated to achieve a high percentage of oil by dry cell weight. Cryopreserved cells were thawed at room temperature and 500 ul of cells were added to 4.5 ml of medium (4.2 g/L $K_2HPO_4$, 3.1 g/L $NaH_2PO_4$, 0.24 g/L $MgSO_4.7H_2O$, 0.25 g/L Citric Acid monohydrate, 0.025 g/L $CaCl_2\ 2H_2O$, 2 g/L yeast extract) plus 2% glucose and grown for 7 days at 28° C. with agitation (200 rpm) in a 6-well plate. Dry cell weights were determined by centrifuging 1 ml of culture at 14,000 rpm for 5 min in a pre-weighed Eppendorf tube. The culture supernatant was discarded and the resulting cell pellet washed with 1 ml of deionized water. The culture was again centrifuged, the supernatant discarded, and the cell pellets placed at −80° C. until frozen. Samples were then lyophilized for 24 hrs and dry cell weights calculated. For determination of total lipid in cultures, 3 ml of culture was removed and subjected to analysis using an Ankom system (Ankom Inc., Macedon, N.Y.) according to the manufacturer's protocol. Samples were subjected to solvent extraction with an Amkom XT10 extractor according to the manufacturer's protocol. Total lipid was determined as the difference in mass between acid hydrolyzed dried samples and solvent extracted, dried samples. Percent oil dry cell weight measurements are shown in Table 10.

TABLE 10

| Percent oil by dry cell weight | | |
|---|---|---|
| Species | Strain | % Oil |
| Prototheca stagnora | UTEX 327 | 13.14 |
| Prototheca moriformis | UTEX 1441 | 18.02 |
| Prototheca moriformis | UTEX 1435 | 27.17 |

Microalgae samples from multiple strains from the genus *Prototheca* were genotyped. Genomic DNA was isolated from algal biomass as follows. Cells (approximately 200 mg) were centrifuged from liquid cultures 5 minutes at 14,000×g. Cells were then resuspended in sterile distilled water, centrifuged 5 minutes at 14,000×g and the supernatant discarded. A single glass bead ~2 mm in diameter was added to the biomass and tubes were placed at −80° C. for at least 15 minutes. Samples were removed and 150 µl of grinding buffer (1% Sarkosyl, 0.25 M Sucrose, 50 mM NaCl, 20 mM EDTA, 100 mM Tris-HCl, pH 8.0, RNase A 0.5 ug/ul) was added. Pellets were resuspended by vortexing briefly, followed by the addition of 40 ul of 5M NaCl. Samples were vortexed briefly, followed by the addition of 66 µl of 5% CTAB (Cetyl trimethylammonium bromide) and a final brief vortex. Samples were next incubated at 65° C. for 10 minutes after which they were centrifuged at 14,000×g for 10 minutes. The supernatant was transferred to a fresh tube and extracted once with 300 µl of Phenol:Chloroform:Isoamyl alcohol 12:12:1, followed by centrifugation for 5 minutes at 14,000×g. The resulting aqueous phase was transferred to a fresh tube containing 0.7 vol of isopropanol (~190 µl), mixed by inversion and incubated at room temperature for 30 minutes or overnight at 4° C. DNA was recovered via centrifugation at 14,000×g for 10 minutes. The resulting pellet was then washed twice with 70% ethanol, followed by a final wash with 100% ethanol. Pellets were air dried for 20-30 minutes at room temperature followed by resuspension in 50 µl of 10 mM TrisCl, 1 mM EDTA (pH 8.0).

Five µl of total algal DNA, prepared as described above, was diluted 1:50 in 10 mM Tris, pH 8.0. PCR reactions, final volume 20 µl, were set up as follows. Ten µl of 2×iProof HF master mix (BIO-RAD) was added to 0.4 µl primer SZ02613 (5'-TGTTGAAGAATGAGCCGGCGAC-3' (SEQ ID NO:9) at 10 mM stock concentration). This primer sequence runs from position 567-588 in Gen Bank accession no. L43357 and is highly conserved in higher plants and algal plastid genomes. This was followed by the addition of 0.4 µl primer SZ02615 (5'-CAGTGAGCTATTACGCACTC-3' (SEQ ID NO:10) at 10 mM stock concentration). This primer sequence is complementary to position 1112-1093 in Gen Bank accession no. L43357 and is highly conserved in higher plants and algal plastid genomes. Next, 5 µl of diluted total DNA and 3.2 µl dH₂O were added. PCR reactions were run as follows: 98° C., 45"; 98° C., 8"; 53° C., 12"; 72° C., 20" for 35 cycles followed by 72° C. for 1 min and holding at 25° C. For purification of PCR products, 20 µl of 10 mM Tris, pH 8.0, was added to each reaction, followed by extraction with 40 µl of Phenol:Chloroform:isoamyl alcohol 12:12:1, vortexing and centrifuging at 14,000×g for 5 minutes. PCR reactions were applied to S-400 columns (GE Healthcare) and centrifuged for 2 minutes at 3,000×g. Purified PCR products were subsequently TOPO cloned into PCR8/GW/TOPO and positive clones selected for on LB/Spec plates. Purified plasmid DNA was sequenced in both directions using M13 forward and reverse primers. In total, twelve *Prototheca* strains were selected to have their 23S rRNA DNA sequenced and the sequences are listed in the Sequence Listing. A summary of the strains and Sequence Listing Numbers is included below. The sequences were analyzed for overall divergence from the UTEX 1435 (SEQ ID NO: 15) sequence. Two pairs emerged (UTEX 329/UTEX 1533 and UTEX 329/UTEX 1440) as the most divergent. In both cases, pairwise alignment resulted in 75.0% pairwise sequence identity. The percent sequence identity to UTEX 1435 is also included below:

| Species | Strain | % nt identity | SEQ ID NO. |
|---|---|---|---|
| Prototheca kruegani | UTEX 329 | 75.2 | SEQ ID NO: 11 |
| Prototheca wickerhamii | UTEX 1440 | 99 | SEQ ID NO: 12 |
| Prototheca stagnora | UTEX 1442 | 75.7 | SEQ ID NO: 13 |
| Prototheca moriformis | UTEX 288 | 75.4 | SEQ ID NO: 14 |

-continued

| Species | Strain | % nt identity | SEQ ID NO. |
|---|---|---|---|
| Prototheca moriformis | UTEX 1439; 1441; 1435; 1437 | 100 | SEQ ID NO: 15 |
| Prototheca wikerhamii | UTEX 1533 | 99.8 | SEQ ID NO: 16 |
| Prototheca moriformis | UTEX 1434 | 75.9 | SEQ ID NO: 17 |
| Prototheca zopfii | UTEX 1438 | 75.7 | SEQ ID NO: 18 |
| Prototheca moriformis | UTEX 1436 | 88.9 | SEQ ID NO: 19 |

Lipid samples from a subset of the above-listed strains were analyzed for lipid profile using HPLC. Results are shown below in Table 11.

TABLE 11

Diversity of lipid chains in *Prototheca* species

| Strain | C14:0 | C16:0 | C16:1 | C18:0 | C18:1 | C18:2 | C18:3 | C20:0 | C20:1 |
|---|---|---|---|---|---|---|---|---|---|
| UTEX 327 | 0 | 12.01 | 0 | 0 | 50.33 | 17.14 | 0 | 0 | 0 |
| UTEX 1441 | 1.41 | 29.44 | 0.70 | 3.05 | 57.72 | 12.37 | 0.97 | 0.33 | 0 |
| UTEX 1435 | 1.09 | 25.77 | 0 | 2.75 | 54.01 | 11.90 | 2.44 | 0 | 0 |

Oil extracted from *Prototheca moriformis* UTEX 1435 (via solvent extraction or using an expeller press was analyzed for carotenoids, chlorophyll, tocopherols, other sterols and tocotrienols. The results are summarized below in Table 12.

TABLE 12

Carotenoid, chlorophyll, tocopherol/sterols and tocotrienol analysis in oil extracted from *Prototheca moriformis* (UTEX 1435).

| | Pressed oil (mcg/ml) | Solvent extracted oil (mcg/ml) |
|---|---|---|
| cis-Lutein | 0.041 | 0.042 |
| trans-Lutein | 0.140 | 0.112 |
| trans-Zeaxanthin | 0.045 | 0.039 |
| cis-Zeaxanthin | 0.007 | 0.013 |
| t-alpha-Crytoxanthin | 0.007 | 0.010 |
| t-beta-Crytoxanthin | 0.009 | 0.010 |
| t-alpha-Carotene | 0.003 | 0.001 |
| c-alpha-Carotene | none detected | none detected |
| t-beta-Carotene | 0.010 | 0.009 |
| 9-cis-beta-Carotene | 0.004 | 0.002 |
| Lycopene | none detected | none detected |
| Total Carotenoids | 0.267 | 0.238 |
| Chlorophyll | <0.01 mg/kg | <0.01 mg/kg |

| Tocopherols and Sterols | | |
|---|---|---|
| | Pressed oil (mg/100 g) | Solvent extracted oil (mg/100 g) |
| gamma Tocopherol | 0.49 | 0.49 |
| Campesterol | 6.09 | 6.05 |
| Stigmasterol | 47.6 | 47.8 |
| Beta-sitosterol | 11.6 | 11.5 |
| Other sterols | 445 | 446 |

| Tocotrienols | | |
|---|---|---|
| | Pressed oil (mg/g) | Solvent extracted oil (mg/g) |
| alpha Tocotrienol | 0.26 | 0.26 |
| beta Tocotrienol | <0.01 | <0.01 |

TABLE 12-continued

Carotenoid, chlorophyll, tocopherol/sterols and tocotrienol analysis in oil extracted from *Prototheca moriformis* (UTEX 1435).

| gamma Tocotrienol | 0.10 | 0.10 |
|---|---|---|
| delta Tocotrienol | <0.01 | <0.01 |
| Total Tocotrienols | 0.36 | 0.36 |

Oil extracted from *Prototheca moriformis*, from four separate lots, were refined and bleached using standard vegetable oil processing methods. Briefly, crude oil extracted from *Prototheca moriformis* was clarified in a horizontal decanter, where the solids were separated from the oil. The clarified oil was then transferred to a tank with citric acid and water and left to settle for approximately 24 hours. After 24 hours, the mixture in the tank formed 2 separate layers. The bottom layer was composed of water and gums that were then removed by decantation prior to transferring the degummed oil into a bleaching tank. The oil was then heated along with another dose of citric acid. Bleaching clay was then added to the bleaching tank and the mixture was further heated under vacuum in order to evaporate off any water that was present. The mixture was then pumped through a leaf filter in order to remove the bleaching clay. The filtered oil was then passed through a final 5 μm polishing filter and then collected for storage until use. The refined and bleached (RB) oil was then analyzed for carotenoids, chlorophyll, sterols, tocotrienols and tocopherols. The results of these analyses are summarized in Table 13 below. "Nd" denotes none detected and the sensitivity of detection is listed below:

Sensitivity of Detection
Carotenoids (mcg/g) nd=<0.003 mcg/g
Chlorophyll (mcg/g) nd=<0.03 mcg/g
Sterols (%) nd=0.25%
Tocopherols (mcg/g); nd=3 mcg/g

TABLE 13

Carotenoid, chlorophyll, sterols, tocotrienols and tocopherol analysis from refined and bleached *Prototheca moriformis* oil.

| | Lot A | Lot B | Lot C | Lot D |
|---|---|---|---|---|
| Carotenoids (mcg/g) | | | | |
| Lutein | 0.025 | 0.003 | nd | 0.039 |
| Zeaxanthin | nd | nd | nd | nd |
| cis-Lutein/Zeaxanthin | nd | nd | nd | nd |
| trans-alpha-Cryptoxanthin | nd | nd | nd | nd |
| trans-beta-Cryptoxanthin | nd | nd | nd | nd |
| trans-alpha-Carotene | nd | nd | nd | nd |
| cis-alpha-Carotene | nd | nd | nd | nd |
| trans-beta-Carotene | nd | nd | nd | nd |
| cis-beta-Carotene | nd | nd | nd | nd |

TABLE 13-continued

Carotenoid, chlorophyll, sterols, tocotrienols and tocopherol analysis from refined and bleached *Protohteca moriformis* oil.

|  | Lot A | Lot B | Lot C | Lot D |
|---|---|---|---|---|
| Lycopene | nd | nd | nd | nd |
| Unidentified | 0.219 | 0.066 | 0.050 | 0.026 |
| Total Carotenoids | 0.244 | 0.069 | 0.050 | 0.065 |
| Chlorophyll (mcg/g) | | | | |
| Chlorophyll A | 0.268 | 0.136 | 0.045 | 0.166 |
| Chlorophyll B | nd | nd | nd | nd |
| Total Chlorophyll | 0.268 | 0.136 | 0.045 | 0.166 |
| Sterols (%) | | | | |
| Brassicasterol | nd | nd | nd | nd |
| Campesterol | nd | nd | nd | nd |
| Stigmasterol | nd | nd | nd | nd |
| beta-Sitosterol | nd | nd | nd | nd |
| Total Sterols | nd | nd | nd | nd |
| Tocopherols (mcg/g) | | | | |
| alpha-Tocopherol | 23.9 | 22.8 | 12.5 | 8.2 |
| beta-Tocopherol | 3.72 | nd | nd | nd |
| gamma-Tocopherol | 164 | 85.3 | 43.1 | 38.3 |
| delta-Tocopherol | 70.1 | 31.1 | 18.1 | 14.3 |
| Total Tocopherols | 262 | 139.2 | 73.7 | 60.8 |
| Tocotrienols (mcg/g) | | | | |
| alpha-Tocotrienol | 190 | 225 | 253 | 239 |
| beta-Tocotrienol | nd | nd | nd | nd |
| gamma-Tocotrienol | 47.3 | 60.4 | 54.8 | 60.9 |
| delta-Tocotrienol | 12.3 | 16.1 | 17.5 | 15.2 |
| Total Tocotrienols | 250 | 302 | 325 | 315 |

The same four lots of *Prototheca moriformis* oil was also analyzed for trace elements and the results are summarized below in Table 14.

TABLE 14

Elemental analysis of refined and bleached *Prototheca moriformis* oil.

|  | Lot A | Lot B | Lot C | Lot D |
|---|---|---|---|---|
| Elemental Analysis (ppm) | | | | |
| Calcium | 0.08 | 0.07 | <0.04 | 0.07 |
| Phosphorous | <0.2 | 0.38 | <0.2 | 0.33 |
| Sodium | <0.5 | 0.55 | <0.5 | <0.5 |
| Potassium | 1.02 | 1.68 | <0.5 | 0.94 |
| Magnesium | <0.04 | <0.04 | <0.04 | 0.07 |
| Manganese | <0.05 | <0.05 | <0.05 | <0.05 |
| Iron | <0.02 | <0.02 | <0.02 | <0.02 |
| Zinc | <0.02 | <0.02 | <0.02 | <0.02 |
| Copper | <0.05 | <0.05 | <0.05 | <0.05 |
| Sulfur | 2.55 | 4.45 | 2.36 | 4.55 |
| Lead | <0.2 | <0.2 | <0.2 | <0.2 |
| Silicon | 0.37 | 0.41 | 0.26 | 0.26 |
| Nickel | <0.2 | <0.2 | <0.2 | <0.2 |
| Organic chloride | <1.0 | <1.0 | <1.0 | 2.2 |
| Inorganic chloride | <1.0 | <1.0 | <1.0 | <1.0 |
| Nitrogen | 4.4 | 7.8 | 4.2 | 6.9 |
| Lithium | <0.02 | <0.02 | <0.02 | <0.02 |
| Boron | 0.07 | 0.36 | 0.09 | 0.38 |
| Aluminum | — | <0.2 | <0.2 | <0.2 |
| Vanadium | <0.05 | <0.05 | <0.05 | <0.05 |
| Lovibond Color (°L) | | | | |
| Red | 5.0 | 4.3 | 3.2 | 5.0 |
| Yellow | 70.0 | 70.0 | 50.0 | 70.0 |

TABLE 14-continued

Elemental analysis of refined and bleached *Prototheca moriformis* oil.

|  | Lot A | Lot B | Lot C | Lot D |
|---|---|---|---|---|
| Mono & Diglycerides by HPLC (%) | | | | |
| Diglycerides | 1.68 | 2.23 | 1.25 | 1.61 |
| Monoglycerides | 0.03 | 0.04 | 0.02 | 0.03 |
| Free fatty acids (FFA) | 1.02 | 1.72 | 0.86 | 0.83 |
| Soaps | 0 | 0 | 0 | |
| Oxidized and Polymerized Triglycerides | | | | |
| Oxidized Triglycerides (%) | 3.41 | 2.41 | 4.11 | 1.00 |
| Polymerized Triglycerides (%) | 1.19 | 0.45 | 0.66 | 0.31 |
| Peroxide Value (meg/kg) | 0.75 | 0.80 | 0.60 | 1.20 |
| p-Anisidine value (dimensionless) | 5.03 | 9.03 | 5.44 | 20.1 |
| Water and Other Impurities (%) | | | | |
| Karl Fisher Moisture | 0.8 | 0.12 | 0.07 | 0.18 |
| Total polar compounds | 5.02 | 6.28 | 4.54 | 5.23 |
| Unsaponificable matter | 0.92 | 1.07 | 0.72 | 1.04 |
| Insoluble impurities | <0.01 | <0.01 | 0.01 | <0.01 |
| Total oil (%) | | | | |
| Neutral oil | 98.8 | 98.2 | 99.0 | 98.9 |

Example 2: General Methods for Biolistic Transformation of *Prototheca*

Seashell Gold Microcarriers 550 nanometers were prepared according to the protocol from manufacturer. Plasmid (20 μg) was mixed with 50 μl of binding buffer and 60 μl (30 mg) of S550d gold carriers and incubated in ice for 1 min Precipitation buffer (100 μl) was added, and the mixture was incubated in ice for another 1 min After vortexing, DNA-coated particles were pelleted by spinning at 10,000 rpm in an Eppendorf 5415C microfuge for 10 seconds. The gold pellet was washed once with 500 μl of cold 100% ethanol, pelleted by brief spinning in the microfuge, and resuspended with 50 μl of ice-cold ethanol. After a brief (1-2 sec) sonication, 10 μl of DNA-coated particles were immediately transferred to the carrier membrane.

*Prototheca* strains were grown in proteose medium (2 g/L yeast extract, 2.94 mM NaNO3, 0.17 mM CaCl2.2H2O, 0.3 mM MgSO4.7H2O, 0.4 mM K2HPO4, 1.28 mM KH2PO4, 0.43 mM NaCl) with 2% glucose on a gyratory shaker until it reaches a cell density of $2\times10^6$ cells/ml. The cells were harvested, washed once with sterile distilled water, and resuspended in 50 μl of medium. $1\times10^7$ cells were spread in the center third of a non-selective proteose media plate. The cells were bombarded with the PDS-1000/He Biolistic Particle Delivery system (Bio-Rad). Rupture disks (1350 psi) were used, and the plates are placed 6 cm below the screen/macrocarrier assembly. The cells were allowed to recover at 25° C. for 12-24 h. Upon recovery, the cells were scraped from the plates with a rubber spatula, mixed with 100 μl of medium and spread on plates containing the appropriate antibiotic selection. After 7-10 days of incubation at 25° C., colonies representing transformed cells were visible on the plates. Colonies were picked and spotted on selective (either antibiotic or carbon source) agar plates for a second round of selection.

Example 3: Transformation of *Chlorella*

Vector Construction

A BamHI-SacII fragment containing the CMV promoter, a hygromycin resistance cDNA, and a CMV 3' UTR (SEQ ID NO: 152, a subsequence of the pCAMBIA1380 vector, Cambia, Canberra, Australia) was cloned into the BamHI and SacII sites of pBluescript and is referred to herein as pHyg.

Biolistic Transformation of *Chlorella*

S550d gold carriers from Seashell Technology were prepared according to the protocol from manufacturer. Linearized pHyg plasmid (20 µg) was mixed with 50 µl of binding buffer and 60 µl (30 mg) of S550d gold carriers and incubated in ice for 1 min Precipitation buffer (100 µl) was added, and the mixture was incubated in ice for another 1 min After vortexing, DNA-coated particles were pelleted by spinning at 10,000 rpm in an Eppendorf 5415C microfuge for 10 seconds. The gold pellet was washed once with 500 µl of cold 100% ethanol, pelleted by brief spinning in the microfuge, and resuspended with 50 µl of ice-cold ethanol. After a brief (1-2 sec) sonication, 10 µl of DNA-coated particles were immediately transferred to the carrier membrane.

*Chlorella protothecoides* culture (Univeristy of Texas Culture Collection 250) was grown in proteose medium (2 g/L yeast extract, 2.94 mM NaNO3, 0.17 mM CaCl2.2H2O, 0.3 mM MgSO4.7H2O, 0.4 mM K2HPO4, 1.28 mM KH2PO4, 0.43 mM NaCl) on a gyratory shaker under continuous light at 75 µmol photons $m^{-2}$ $sec^{-1}$ until it reached a cell density of $2\times10^6$ cells/ml. The cells were harvested, washed once with sterile distilled water, and resuspended in 50 µl of medium. $1\times10^7$ cells were spread in the center third of a non-selective proteose media plate. The cells were bombarded with the PDS-1000/He Biolistic Particle Delivery system (Bio-Rad). Rupture disks (1100 and 1350 psi) were used, and the plates were placed 9 and 12 cm below the screen/macrocarrier assembly. The cells were allowed to recover at 25° C. for 12-24 h. Upon recovery, the cells were scraped from the plates with a rubber spatula, mixed with 100 µl of medium and spread on hygromycin contained plates (200 µg/ml). After 7-10 days of incubation at 25° C., colonies representing transformed cells were visible on the plates from 1100 and 1350 psi rupture discs and from 9 and 12 cm distances. Colonies were picked and spotted on selective agar plates for a second round of selection.

Transformation of *Chlorella* by Electroporation

*Chlorella protothecoides* culture was grown in proteose medium on a gyratory shaker under continuous light at 75 µmol photons $m^{-2}$ $sec^{-1}$ until it reached a cell density of $2\times10^6$ cells/ml. The cells were harvested, washed once with sterile distilled water, and resuspended in a tris-phosphate buffer (20 mM Tris-HCl, pH 7.0; 1 mM potassium phosphate) containing 50 mM sucrose to a density of $4\times10^8$ cells/ml. About 250 µl cell suspension ($1\times10^8$ cells) was placed in a disposable electroporation cuvette of 4 mm gap. To the cell suspension, 5 µg of linearized pHyg plasmid DNA and 200 µg of carrier DNA (sheared salmon sperm DNA) was added. The electroporation cuvette was then incubated in a water bath at 16° C. for 10 minutes. An electrical pulse (1100 V/cm) was then applied to the cuvette at a capacitance of 25 µF (no shunt resistor was used for the electroporation) using a Gene Pulser II (Bio-Rad Labs, Hercules, Calif.) electroporation apparatus. The cuvette was then incubated at room temperature for 5 minutes, following which the cell suspension was transferred to 50 ml of proteose media, and shaken on a gyratory shaker for 2 days. Following recovery, the cells were harvested by centrifugation at low speed, resuspended in proteose media, and plated at low density on plates supplemented with 200 µg/ml hygromycin. The plates were incubated under continuous light at 75 µmol photons $m^{-2}$ $sec^{-1}$. Transformants appeared as colonies in 1-2 weeks. Colonies were picked and spotted on selective agar plates for a second round of selection.

Genotyping

A subset of colonies that survived a second round of selection were cultured in small volume and harvested. Pellets of approximately 5-10 uL volume were resuspended in 50 uL of 10 mM NaEDTA by vortexing and then incubated at 100° C. for 10. The tubes were then vortexed briefly and sonicated for 10 seconds, then centrifuged at 12,000×g for 1 minute. 2 uL of supernatant as template was used in a 50 uL PCR reaction. Primers used for genotyping were SEQ ID NO: 153 and SEQ ID NO: 154. PCR conditions were as follows: 95° C. 5 min×1 cycle; 95° C. 30 sec–58° C. 30 sec–72° C. 1 min 30 sec×35 cycles; 72° C. 10 min×1 cycle. The expected 992 bp fragment was found in 6 of 10 colonies from the biolistic method and from a single electroporation colony. A lower sized, nonspecific band was present in all lanes. To confirm the identity of the amplified 992 bp fragment, two biolistic bands and the electroporation band were excised from the gel and individually sequenced. The sequence of all three bands corresponded to the expected 992 bp fragment. (DNA ladder: Bionexus® All Purpose Hi-Lo® DNA ladder catalog # BN2050).

Example 4: Algal-Derived Promoters and Genes for Use in Microalgae

A. 5'UTR and Promoter Sequences from *Chlorella protothecoides*

A cDNA library was generated from mixotrophically grown *Chlorella protothecoides* (UTEX 250) using standard techniques. Based upon the cDNA sequences, primers were designed in certain known housekeeping genes to "walk" upstream of the coding regions using Seegene's DNA Walking kit (Rockville, Md.). Sequences isolated include an actin (SEQ ID NO: 155) and elongation factor-1a (EF1a) (SEQ ID NO: 156) promoter/UTR, both of which contain introns (as shown in the lower case) and exons (upper case italicized) and the predicted start site (in bold) and two beta-tubulin promoter/UTR elements: Isoform A (SEQ ID NO: 157) and Isoform B (SEQ ID NO: 158).

B. Lipid Biosynthesis Enzyme and Plastid Targeting Sequences from *C. protothecoides*

From the cDNA library described above, three cDNAs encoding proteins functional in lipid metabolism in *Chlorella protothecoides* (UTEX 250) were cloned using the same methods as described above. The nucleotide and amino acid sequences for an acyl ACP desaturase (SEQ ID NOs: 159 and 160) and two geranyl geranyl diphosphate synthases (SEQ ID NOs: 161-164) are included in the Sequence Listing below. Additionally, three cDNAs with putative signal sequences targeting to the plastid were also cloned. The nucleotide and amino acid sequences for a glyceraldehyde-3-phosphate dehydrogenase (SEQ ID NOs: 165 and 166), an oxygen evolving complex protein OEE33 (SEQ ID NOs: 167 and 168) and a Clp protease (SEQ ID NOs: 169 and 170) are included in the Sequence Listing below. The putative plastid targeting sequence has been underlined in both the nucleotide and amino acid sequence. The plastid targeting sequences can be used to target the product of transgenes to the plastid of microbes, such as lipid modification enzymes.

Example 5: Genetic Engineering of *Chlorella protothecoides* to Express an Exogenous Sucrose Invertase Strains and Media:

*Chlorella protothecoides* (UTEX 250) was obtained from the Culture Collection of Alga at the University of Texas (Austin, Tex., USA). The stock cultures were maintained on modified Proteose medium. Modified Proteose medium consists of 0.25 g NaNO$_3$, 0.09 g K$_2$HPO$_4$, 0.175 g KH$_2$PO$_4$ 0.025 g, 0.025 g CaCl$_2$.2H$_2$O, 0.075 g MgSO$_4$.7H$_2$O, and 2 g yeast extract per liter (g/L).

Plasmid Construction:

To express the secreted form of invertase in *Chlorella protothecoides*, a *Saccharomyces cerevisiae* SUC2 gene was placed under the control of three different promoters: Cauliflower mosaic virus 35S promoter (CMV), *Chlorella* virus promoter (NC-1A), and *Chlorella* HUP1 promoter. A yeast SUC2 gene was synthesized to accommodate codon usage optimized for *C. protothecoides* and includes a signal sequence required for directing extracellular secretion of invertase. Each construct was built in pBluescript KS+, and EcoRI/AscI, AscI/XhoI, and XhoI/BamHI sites were introduced to each promoter, invertase gene, and CMV 3'UTR, respectively, by PCR ampilication using specific primers. Purified PCR products were cloned sequentially.

Transformation of *Chlorella protothecoides*:

A *Chlorella protothecoides* culture was grown in modified Proteose medium on a gyratory shaker under continuous light at 75 µmol photons m$^{-2}$ sec$^{-1}$ till it reached a cell density of 6×10$^6$ cells/ml.

For biolistic transformation, S550d gold carriers from Seashell Technology were prepared according to the protocol from the manufacturer. Briefly, a linearized construct (20 µg) by BsaI was mixed with 50 µl of binding buffer and 60 µl (3 mg) of S550d gold carriers and incubated in ice for 1 min Precipitation buffer (100 µl) was added, and the mixture was incubated in ice for another 1 min After mild vortexing, DNA-coated particles were pelleted by spinning at 10,000 rpm in an Eppendorf microfuge for 10 seconds. The gold pellet was washed once with 500 µl of cold 100% ethanol, pelleted by brief spinning in the microfuge, and resuspended with 50 µl of ice-cold ethanol. After a brief (1-2 sec) sonication, 10 µl of DNA-coated particles were immediately transferred to the carrier membrane. The cells were harvested, washed once with sterile distilled water, resuspended in 50 µl of medium (1×10$^7$ cells), and were spread in the center third of a non-selective Proteous plate. The cells were bombarded with the PDS-1000/He Biolistic Particle Delivery system (Bio-Rad). Rupture disks (1100 and 1350 psi) were used, and the plates were placed 9-12 cm below the screen/macrocarrier assembly. The cells were allowed to recover at 25° C. for 12-24 hours. Upon recovery, the cells were scraped from the plates with a rubber spatula, mixed with 100 µl of medium and spread on modified Proteose plates with 1% sucrose. After 7-10 days of incubation at 25° C. in the dark, colonies representing transformed cells were visible on the plates.

For transformation with electroporation, cells were harvested, washed once with sterile distilled water, and resuspended in a Tris-phosphate buffer (20 mM Tris-HCl, pH 7.0; 1 min potassium phosphate) containing 50 min sucrose to a density of 4×10$^8$ cells/ml. About 250 µl cell suspension (1×10$^8$ cells) was placed in a disposable electroporation cuvette of 4 mm gap. To the cell suspension, 5 µg of linearized plasmid DNA and 200 µg of carrier DNA (sheared salmon sperm DNA) were added. The electroporation cuvette was then incubated in an ice water bath at 16° C. for 10 min. An electrical pulse (1100 V/cm) was then applied to the cuvette at a capacitance of 25 µF (no shunt resistor was used for the electroporation) using a Gene Pulser II (Bio-Rad Labs, Hercules, Calif.) electroporation apparatus. The cuvette was then incubated at room temperature for 5 minutes, following which the cell suspension was transferred to 50 ml of modified Proteose media, and shaken on a gyratory shaker for 2 days. Following recovery, the cells were harvested at low speed (4000 rpm), resuspended in modified Proteose media, and plated out at low density on modified Proteose plates with 1% sucrose. After 7-10 days of incubation at 25° C. in the dark, colonies representing transformed cells were visible on the plates.

Screening Transformants and Genotyping:

The colonies were picked from dark grown-modified Proteose plates with 1% sucrose, and approximately the same amount of cells were transferred to 24 well-plates containing 1 ml of modified Proteose liquid media with 1% sucrose. The cultures were kept in dark and agitated by orbital shaker from Labnet (Berkshire, UK) at 430 rpm for 5 days.

To verify the presence of the invertase gene introduced in *Chlorella* transformants, DNA of each transformant was isolated and amplified with a set of gene-specific primers (CMV construct: forward primer (CAACCACGTCT-TCAAAGCAA) (SEQ ID NO: 153)/reverse primer (TCCG-GTGTGTTGTAAGTCCA) (SEQ ID NO: 171), CV constructs: forward primer (TTGTCGGAATGTCATATCAA) (SEQ ID NO: 172)/reverse primer (TCCGGTGTGTTG-TAAGTCCA) (SEQ ID NO: 171), and HUP1 construct: forward primer (AACGCCTTTGTACAACTGCA) (SEQ ID NO: 173)/reverse primer (TCCGGTGTGTTG-TAAGTCCA) (SEQ ID NO: 171)). For quick DNA isolation, a volume of cells (approximately 5-10 uL in size) were resuspended in 50 uL of 10 min Na-EDTA. The cell suspension was incubated at 100° C. for 10 min and sonicated for 10 sec. After centrifugation at 12000 g for 1 min, 3 uL of supernatant was used for the PCR reaction. PCR amplification was performed in the DNA thermal cycler (Perkin-Elmer GeneAmp 9600). The reaction mixture (50 uL) contained 3 uL extracted DNA, 100 pmol each of the respective primers described above, 200 uM dNTP, 0.5 units of Taq DNA polymerase (NEB), and Taq DNA polymerase buffer according to the manufacturer's instructions. Denaturation of DNA was carried out at 95° C. for 5 min for the first cycle, and then for 30 sec. Primer annealing and extension reactions were carried out at 58° C. for 30 sec and 72° C. for 1 min respectively. The PCR products were then visualized on 1% agarose gels stained with ethidium bromide.

Growth in Liquid Culture:

After five days growth in darkness, the genotype-positive transformants showed growth on minimal liquid Proteose media +1% sucrose in darkness, while wild-type cells showed no growth in the same media in darkness.

Example 6: Transformation of Algal Strains with a Secreted Invertase Derived from *S. cerevisiae*

Secreted Invertase:

A gene encoding a secreted sucrose invertase (Gen Bank Accession no. NP_012104 from *Saccharomyces cerevisiae*) was synthesized de-novo as a 1599 bp Asc I-Xho fragment that was subsequently sub-cloned into a pUC19 derivative possessing the Cauliflower Mosaic Virus 35s promoter and 3' UTR as EcoR I/Asc I and Xho/Sac I cassettes, respectively.

Growth of Algal Cells:

Media used in these experiments was liquid base media (2 g/L yeast extract, 2.94 min NaNO$_3$, 0.17 min CaCl$_2$.2H$_2$O, 0.3 min MgSO$_4$.7H$_2$O, 0.4 min K$_2$HPO$_4$, 1.28 min KH$_2$PO$_4$, 0.43 min NaCl) and solid base media (+1.5% agarose) containing fixed carbon in the form of sucrose or glucose (as designated) at 1% final concentration. The strains used in this experiment did not grow in the dark on base media in the absence of an additional fixed carbon source. Species were struck out on plates, and grown in the dark at 28° C. Single colonies were picked and used to inoculate 500 mL of liquid base media containing 1% glucose and allowed to grow in the dark until mid-log phase, measuring cell counts each day. Each of the following strains had been previously tested for growth on sucrose in the dark as a sole carbon source and exhibited no growth, and were thus chosen for transformation with a secreted invertase: (1) *Chlorella protothecoides* (UTEX 31); (2) *Chlorella minutissima* (UTEX 2341); and (3) *Chlorella emersonii* (CCAP 211/15).

Transformation of Algal Cells Via Particle Bombardment:

Sufficient culture was centrifuged to give approximately $1-5 \times 10^8$ total cells. The resulting pellet was washed with base media with no added fixed carbon source. Cells were centrifuged again and the pellet was resuspended in a volume of base media sufficient to give $5 \times 10^7$ to $2 \times 10^8$ cells/ml. 250-1000 µl of cells were then plated on solid base media supplemented with 1% sucrose and allowed to dry onto the plate in a sterile hood. Plasmid DNA was precipitated onto gold particles according to the manufacturer's recommendations (Seashell Technology, La Jolla, Calif.). Transformations were carried out using a BioRad PDS He-1000 particle delivery system using 1350 psi rupture disks with the macrocarrier assembly set at 9 cm from the rupture disk holder. Following transformations, plates were incubated in the dark at 28° C. All strains generated multiple transformant colonies. Control plates transformed with no invertase insert, but otherwise prepared in an identical fashion, contained no colonies.

Analysis of *Chlorella protothecoides* Transformants:

Genomic DNA was extracted from *Chlorella protothecoides* wild type cells and transformant colonies as follows: Cells were resuspended in 100 ul extraction buffer (87.5 min Tris Cl, pH 8.0, 50 min NaCl, 5 min EDTA, pH 8.0, 0.25% SDS) and incubated at 60° C., with occasional mixing via inversion, for 30 minutes. For PCR, samples were diluted 1:100 in 20 min Tris Cl, pH 8.0.

Genotyping was done on genomic DNA extracted from WT, the transformants and plasmid DNA. The samples were genotyped for the marker gene. Primers 2383 (5' CTGACCCGACCTATGGGAGCGCTCTTGGC 3') (SEQ ID NO: 174) and 2279 (5' CTTGACTTCCCTCACCTGGAATTTGTCG 3') (SEQ ID NO: 175) were used in this genotyping PCR. The PCR profile used was as follows: 94° C. denaturation for 5 min; 35 cycles of 94° C.—30 sec, 60° C.—30 sec, 72° C.—3 min; 72° C.—5 min A band of identical size was amplified from the positive controls (plasmid) and two transformants of *Chlorella protothecoides* (UTEX 31).

Analysis of *Chlorella minutissima* and *Chlorella emersonii* transformants: Genomic DNA was extracted from *Chlorella* WT and the transformants as follows: Cells were resuspended in 100 ul extraction buffer (87.5 min Tris Cl, pH 8.0, 50 min NaCl, 5 min EDTA, pH 8.0, 0.25% SDS) and incubated at 60° C., with occasional mixing via inversion, for 30 minutes. For PCR, samples were diluted 1:100 in 20 min Tris Cl, pH 8.0. Genotyping was done on genomic DNA extracted from WT, the transformants and plasmid DNA. The samples were genotyped for the marker gene. Primers 2336 (5' GTGGCCATATGGACTTACAA 3') (SEQ ID NO: 176) and 2279 (5' CTTGACTTCCCTCACCTGGAATTTGTCG 3') (SEQ ID NO: 175) were designated primer set 2 (1215 bp expected product), while primers 2465 (5' CAAGGGCTGGATGAATGACCCCAATGGACTGTGG-TACGACG 3') (SEQ ID NO: 177) and 2470 (5' CAC-CCGTCGTCATGTTCACGGAGCCCAGTGCG 3') (SEQ ID NO: 178) were designated primer set 4 (1442 bp expected product). The PCR profile used was as follows: 94° C. denaturation for 2 min; 29 cycles of 94° C.—30 sec, 60° C.—30 sec, 72° C.—1 min, 30 sec; 72° C.—5 min A plasmid control containing the secreted invertase was used as a PCR control.

The sequence of the invertase construct corresponds to SEQ ID NO: 8.

Example 7: Homologous Recombination in *Prototheca* Species

Homologous recombination of transgenes has several advantages. First, the introduction of transgenes without homologous recombination can be unpredictable because there is no control over the number of copies of the plasmid that gets introduced into the cell. Also, the introduction of transgenes without homologous recombination can be unstable because the plasmid may remain episomal and is lost over subsequent cell divisions. Another advantage of homologous recombination is the ability to "knock-out" gene targets, introduce epitope tags, switch promoters of endogenous genes and otherwise alter gene targets (e.g., the introduction of point mutations).

Two vectors were constructed using a specific region of the *Prototheca moriformis* (UTEX 1435) genome, designated KE858. KE858 is a 1.3 kb, genomic fragment that encompasses part of the coding region for a protein that shares homology with the transfer RNA (tRNA) family of proteins. Southern blots have shown that the KE858 sequence is present in a single copy in the *Prototheca moriformis* (UTEX 1435) genome. The first type of vector that was constructed, designated SZ725 (SEQ ID NO: 179), consisted of the entire 1.3 kb KE858 fragment cloned into a pUC19 vector backbone that also contains the optimized yeast invertase (suc2) gene. The KE858 fragment contains a unique SnaB1 site that does not occur anywhere else in the targeting construct. The second type of vector that was constructed, designated SZ726 (SEQ ID NO: 180), consisted of the KE858 sequence that had been disrupted by the insertion of the yeast invertase gene (suc2) at the SnaB1 site within the KE858 genomic sequence. The entire DNA fragment containing the KE858 sequences flanking the yeast invertase gene can be excised from the vector backbone by digestion with EcoRI, which cuts at either end of the KE858 region.

Both vectors were used to direct homologous recombination of the yeast invertase gene (suc2) into the corresponding KE858 region of the *Prototheca moriformis* (UTEX 1435) genome. The linear DNA ends homologous to the genomic region that was being targeted for homologous recombination were exposed by digesting the vector construct SZ725 with SnaB1 and vector construct SZ726 with EcoRI. The digested vector constructs were then introduced into *Prototheca moriformis* cultures using methods described above. Transformants from each vector construct were then selected using sucrose plates. Ten independent, clonally pure transformants from each vector transformation were analyzed for successful recombination of the yeast invertase gene into the desired genomic location (using Southern blots) and for transgene stability.

Southern blot analysis of the SZ725 transformants showed that 4 out of the 10 transformants picked for analysis contained the predicted recombinant bands, indicating that a single crossover event had occurred between the KE858 sequences on the vector and the KE858 sequences in the genome. In contrast, all ten of the SZ726 transformants contained the predicted recombinant bands, indicating that double crossover events had occurred between the EcoRI fragment of pSZ726 carrying KE858 sequence flanking the yeast invertase transgene and the corresponding KE858 region of the genome.

Sucrose invertase expression and transgene stability were assessed by growing the transformants for over 15 generations in the absence of selection. The four SZ725 transformants and the ten SZ276 transformants that were positive for the transgene by Southern blotting were selected and 48 single colonies from each of the transformants were grown serially: first without selection in glucose containing media and then with selection in media containing sucrose as the sole carbon source. All ten SZ276 transformants (100%) retained their ability to grow on sucrose after 15 generations, whereas about 97% of the SZ725 transformants retained their ability to grow on sucrose after 15 generations. Transgenes introduced by a double crossover event (SZ726 vector) have extremely high stability over generation doublings. In contrast, transgenes introduced by a single cross over event (SZ725 vector) can result in some instability over generation doublings because is tandem copies of the transgenes were introduced, the repeated homologous regions flanking the transgenes may recombine and excise the transgenic DNA located between them.

These experiments demonstrate the successful use of homologous recombination to generate Prototheca transformants containing a heterologous sucrose invertase gene that is stably integrated into the nuclear chromosomes of the organism. The success of the homologous recombination enables other genomic alterations in Prototheca, including gene deletions, point mutations and epitope tagging a desired gene product. These experiments also demonstrate the first documented system for homologous recombination in the nuclear genome of a eukaryotic microalgae.

Use of Homologous Recombination to Knock-Out an Endogenous Prototheca moriformis Gene:

In a Prototheca moriformis cDNA/genomic screen, like that described above in Example 4, an endogenous stearoyl ACP desaturase (SAPD) cDNA was identified. Stearoyl ACP desaturase enzymes are part of the lipid synthesis pathway and they function to introduce double bonds into the fatty acyl chains. In some cases, it may be advantages to knock-out or reduce the expression of lipid pathway enzymes in order to alter a fatty acid profile. A homologous recombination construct was created to assess whether the expression of an endogenous stearoyl ACP desaturase enzyme can be reduced (or knocked out) and if a corresponding reduction in unsaturated fatty acids can be observed in the lipid profile of the host cell. An approximately 1.5 kb coding sequence of a stearoyl ACP desaturase gene from Prototheca moriformis (UTEX 1435) was identified and cloned (SEQ ID NO: 181). The homologous recombination construct was constructed using 0.5 kb of the SAPD coding sequence at the 5' end (5' targeting site), followed by the Chlamydomonas reinhardtii β-tublin promoter driving a codon-optimized yeast sucrose invertase suc2 gene with the Chlorella vulgaris 3'UTR. The rest (~1 kb) of the Prototheca moriformis SAPD coding sequence was then inserted after the C. vulgaris 3'UTR to make up the 3' targeting site. The sequence for this homologous recombination cassette is listed in SEQ ID NO: 182. As shown above, the success-rate for integration of the homologous recombination cassette into the nuclear genome can be increased by linearizing the cassette before transforming the microalgae, leaving exposed ends. The homologous recombination cassette targeting an endogenous SAPD enzyme in Prototheca moriformis is linearized and then transformed into the host cell (Prototheca moriformis, UTEX 1435). A successful integration will eliminate the endogenous SAPD enzyme coding region from the host genome via a double reciprocal recombination event, while expression of the newly inserted suc2 gene will be regulated by the C. reinhardtii β-tubulin promoter. The resulting clones can be screened using plates/media containing sucrose as the sole carbon source. Clones containing a successful integration of the homologous recombination cassette will have the ability to grow on sucrose as the sole carbon source and changes in overall saturation of the fatty acids in the lipid profile will serve as a secondary confirmation factor. Additionally, Southern blotting assays using a probe specific for the yeast sucrose invertase suc2 gene and RT-PCR can also confirm the presence and expression of the invertase gene in positive clones. As an alternative, the same construct without the β-tubulin promoter can be used to excise the endogenous SAPD enzyme coding region. In this case, the newly inserted yeast sucrose invertase suc2 gene will be regulated by the endogenous SAPD promoter/5'UTR.

Example 8: Expression of Various Thioesterases in Prototheca

Methods and effects of expressing a heterologous thioesterase gene in Prototheca species have been previously described in PCT Application No. PCT/US2009/66142, hereby incorporated by reference. The effect of other thioesterase genes/gene products from higher plants species was further investigated. These thioesterases include thioesterases from the following higher plants:

| Species | GenBank Accession No. | Specificity | SEQ ID NO: |
| --- | --- | --- | --- |
| Cinnamomum camphora | Q39473 | C14 | SEQ ID NOs: 30-31 |
| Umbellularia californica | Q41635 | C10-C12 | SEQ ID NOs: 34-35 |
| Cuphea hookeriana | AAC49269 | C8-C10 | SEQ ID NOs: 32-33 |
| Cuphea palustris | AAC49179 | C8 | SEQ ID NOs: 36-37 |
| Cuphea lanceolata | CAB60830 | C10 | SEQ ID NOs: 38-39 |
| Iris germanica | AAG43858.1 | C14 | SEQ ID NOs: 40-41 |
| Myristica fragrans | AAB717291.1 | C14 | SEQ ID NOs: 42-43 |
| Cuphea palustris | AAC49180 | C14 | SEQ ID NOs: 44-45 |
| Ulmus americana | AAB71731 | broad | SEQ ID NOs: 46-47 |

In all cases, each of the above thioesterase constructs was transformed in to Prototheca moriformis (UTEX 1435) using biolistic particle bombardment. Other transformation methods including homologous recombination as disclosed in PCT Application No. PCT/US2009/66142, would also be suitable for heterologous expression of genes of interest. Transformation of Prototheca moriformis (UTEX 1435) with each of the above thioesterase constructs was performed using the methods described in Example 2. Each of the constructs contained a NeoR gene and selection for positive clones was carried out using 100 μg/ml G418. All coding regions were codon optimized to reflect the codon bias inherent in Prototheca moriformis UTEX 1435 (see Table 2) nuclear genes. Both amino acid sequences and the cDNA sequences for the construct used are listed in the sequence identity listing. The transit peptide for each of the higher plant thioesterase was replaced with an algal codon optimized transit peptide from Prototheca moriformis delta 12 fatty acid desaturase (SEQ ID NO: 48)) or from Chlorella protothecoides stearoyl ACP desaturase (SEQ ID NO: 49). All thioesterase constructs were driven by the Chlamydomonas reinhardtii beta-tubulin promoter/5'UTR. Growth and lipid production of selected positive clones were compared to wildtype (untransformed) Prototheca moriformis (UTEX 1435). Wildtype and selected positive clones were grown on 2% glucose G418 plates. Lipid profiles analysis on selected positive clones for each construct is summarized below (expressed in Area %) in Table 15.

TABLE 15

Lipid profiles of *Protheca moriformis* expressing various heterologous thioesterases.

| | | | | | Thioesterase | | | | |
|---|---|---|---|---|---|---|---|---|---|
| Fatty Acid | UTEX 1435 wt | U. californica | C. camphora | I. germanica | M. fragrans | C. palustris C8:0 | C. hookeriana | C. lanceolata | C. palustris C14:0 | U. americana |
| C8:0 | 0 | 0 | 0 | 0 | | 3.1 | 1.8 | 0 | 0 | .09 |
| C10:0 | 0.02 | .07 | .02 | .01 | .09 | .56 | 6.85 | 1.91 | .01 | 2.85 |
| C12:0 | 0.05 | 14 | 1.82 | .09 | .05 | .25 | .2 | .29 | .06 | .74 |
| C14:0 | 1.65 | 3 | 17.3 | 2.59 | 5.31 | 1.45 | 1.8 | 1.83 | 2.87 | 10.45 |
| C16:0 | 28.0 | 21.4 | 24.3 | 26.52 | 31.08 | 22.84 | 23.9 | 25.55 | 27.23 | 33.3 |
| C18:0 | 2.9 | 2.9 | 2.7 | 3.11 | 2.71 | 3.24 | 2.8 | 3.26 | 3.62 | 3.47 |
| C18:1 | 53.8 | 45.2 | 41.3 | 49.96 | 39.77 | 56.62 | 49.8 | 55.43 | 51.04 | 38.71 |
| C18:2 | 10.95 | 10 | 9.7 | 11.86 | 14.17 | 8.24 | 9.7 | 8.17 | 10.81 | 7.38 |
| C18:3 α | 0.8 | .86 | .8 | .40 | .64 | .61 | .9 | .58 | .97 | .52 |
| Total saturates (area %) | 32.62 | 44.97 | 46.14 | 32.32 | 39.24 | 31.44 | 37.35 | 32.84 | 33.79 | 50.9 |

The results show that all of the thioesterases expressed impacted fatty acid profiles to some level. Looking at the "Total saturates" row, the degree of saturation was profoundly impacted by the expression of several of the thioesterases, including those from *U. californica*, *C. camphora*, and most notably, *U. americana*. These changes in the percentage of total saturates were unexpected in that the heterologous expression of thioesterases from higher plants can apparently impact more than just lipid chain lengths; it can also impact other attributes of lipid profiles produced by microalgae, namely the degree of saturation of the fatty acids.

Selected clones transformed with *C. palustris* C8 thioesterase, *C. hookeriana* thioesterase, *U. californica* and *C. camphora* thioesterase were further grown in varying amounts of G418 (from 25 mg/L to 50 mg/L) and at varying temperatures (from 22° C. to 25° C.) and the lipid profile was determined for these clones. Table 16 summarizes the lipid profile (in Area %) of representative clones containing each thioesterase. A second construct containing the *U. americana* thioesterase was constructed and transformed into *Prototheca moriformis* (UTEX 1435) using the biolistic methods described above. This second construct was introduced into the cell via homologous recombination. Methods of homologous recombination in *Prototheca* species were described previously in PCT Application No. PCT/US2009/66142. The homologous DNA that was used was from genomic DNA sequence of 6S rRNA from *Prototheca moriformis* UTEX 1435. The selection agent was the ability to grow on sucrose, using a codon optimized suc2 gene from *S. cerevisiae* driven by the *C. reinhardtii* beta tubulin promoter. The native *U. americana* transit peptide was replaced by the *Chlorella prototheocoides* (UTEX 250) stearoyl ACP desaturase transit peptide. The cDNA of this construct is listed in the Sequence Listing as SEQ ID NO: 50. Selection of positive clones was performed on 2% sucrose plates and the resulting cultures for lipid profile determination was also grown on 2% sucrose containing medium. A representative lipid profile for this *Prototheca moriformis* strain containing a homologously recombined heterologous *U. americana* thioesterase is summarized in Table 16.

TABLE 16

Lipid profiles of *Prototheca moriformis* strains containing heterologous thioesterase genes.

| | C. palustris C8 | C. hookeriana | C. camphora | U. americana 2 |
|---|---|---|---|---|
| C8:0 | 12.28 | 2.37 | 0 | 0 |
| C10:0 | 2.17 | 12.09 | 0.02 | 4.69 |
| C12:0 | 0.34 | 0.33 | 3.81 | 1.02 |
| C14:0 | 1.59 | 2.08 | 32.73 | 16.21 |
| C16:0 | 15.91 | 20.07 | 24.03 | 38.39 |
| C18:0 | 1.59 | 1.57 | 1.21 | 2.83 |
| C18:1 | 50.64 | 41.80 | 18.64 | 27.22 |
| C18:2 | 13.02 | 16.37 | 16.57 | 7.65 |
| C18:3 α | 1.52 | 1.75 | 1.66 | 0.74 |
| Total saturates | 33.88 | 38.51 | 61.80 | 63.14 |

As with the clones described above, all transformants containing a heterologous thioesterase gene showed impacted fatty acid profiles to some level, and the total percent of saturated fatty acids were also changed, as compared to wildtype (untransformed) *Prototheca moriformis*. The *Prototheca moriformis* containing the *U. americana* thioesterase introduced by homologous recombination had the greatest increase in total saturates.

Additionally, transgenic clones containing the exogenous *C. hookeriana*, *C. camphora*, *U. californica* or *U. americana* thioesterase were assessed for novel lipid profiles. The *C. hookeriana* thioesterase containing clone achieved the following lipid profile when grown in 2% glucose, 25 mg/ml G418 at 22° C.: 5.10% C8:0; 18.28% C10:0; 0.41% C12:0; 1.76% C14:0; 16.31% C16:0; 1.40% C18:0; 40.49% C18:1; and 13.16% C18:2. The *C. camphora* thioesterase-containing clone (also containing an exogenous sucrose invertase) achieved the following lipid profile when grown in 2% sucrose at 25° C.: 0.04% C10:0; 6.01% C12:0; 35.98% C14:0; 19.42 C16:0; 1.48% C18:0; 25.44% C18:1; and 9.34% C18:2. The *U. californica* thioesterase containing clone achieved the following lipid profile when grown in 2% glucose, 25-100 mg/ml G418 at 22° C.: 0% C8:0; 0.11% C10:0; 34.01% C12:0; 5.75% C14:0; 14.02% C16:0; 1.10% C18:0; 28.93% C18:1; and 13.01% C18:2. The *U. americana* thioesterase containing clone achieved the following lipid profile when grown in 2% glucose at 28° C.: 1.54% C10:0; 0.43% C12:0; 7.56% C14:0; 39.45% C16:0; 2.49% C18:0; 38.49% C18:1; and 7.88% C18:2.

Example 9: Transformation of Prototheca with Multiple Exogenous Heterologous Thioesterase Genes Microalgae strain *Prototheca moriformis* (UTEX 1435) was transformed using the above disclosed methods to express multiple thioesterases in a single clone. The expression of multiple thioesterases in a single clone allows the microalgae to produce oils with fatty acid profiles completely different from those elaborated when any single thioesterase is expressed alone (as demonstrated in the preceding Examples). *Prototheca moriformis* (UTEX 1435) was first transformed with the *Cinnamomum camphora* thioesterase (a C14 preferring thioesterase) along with a sucrose invertase gene, the suc2 from *S. cerevisiae* (selection was the ability to grow on sucrose) using homologous recombination. The DNA used for this homologous recombination construct is from the KE858 region of *Prototheca moriformis* genomic DNA as described in the Section III above. The relevant portion of this construct is listed in the Sequence Listing as SEQ ID NO: 51. Positive clones were screened on sucrose-containing plates. A positive clone was then re-transformed with one of three cassettes, each encoding resistance to the antibiotic G418 as well as an additional thioesterase: (1) thioesterase gene from *Cuphea hookeriana* (C8-10 preferring), SEQ ID NO: 52; (2) thioesterase gene from *Umbellularia californica* (C12 preferring), SEQ ID NO: 53; or thioesterase from *Ulmus americana* (broad; C10-C16 preferring), SEQ ID NO: 54. Included in the Sequence Listing is the sequence of the relevant portion of each construct. Clones expressing both thioesterase genes were screened on sucrose containing medium with 50 µg/ml G418. Positive clones were selected and growth and lipid profile were assayed. Table 17 summarizes the lipid profile of representative positive clones (expressed in Area %).

thioesterase were produced. A positive representative clone had a fatty acid profile of: 0% C8:0; 0.06% C10:0; 5.91% C12:0; 43.27% C14:0; 19.63% C16:0; 0.87% C18:0; 13.96% C18:1; and 13.78% C18:2, with a total saturates at 69.74%. This clone had a C12-C14 level at over 49%, which is over 37 times the C12-C14 level in wildtype cells.

The above data shows that multiple thioesterases can be successfully co-expressed in microalgae. The co-expression of multiple thioesterases results in altered fatty acid profiles that differ significantly not only from the wild type strain, but also from the fatty acid profile obtained by the expression of any one of the individual thioesterases. The expression of multiple thioesterases with overlapping chain length specificity can result in cumulative increases in those specific fatty acids.

The expression of heterologous thioesterases (either alone or in combination) in *Prototheca moriformis* not only alters the fatty acid/lipid profiles in the host strain, but when compared to oils currently available from a variety of seed crops (Table 5), these profiles are of truly unique oils found in no other currently available system. Not only do the transgenic strains show significant differences from the untransformed wildtype strain, they have remarkably different profiles from any of the commercial oils that are shown in Table 5. As an example, both coconut and palm kernel oils have levels of C8-C10 fatty acids ranging from 5.5-17%. Transgenic strain expressing the *C. palustris* C8-preferring thioesterase or the *C. hookeriana* C10-preferring thioesterase accumulates anywhere from 3.66 to 8.65%, respectively. These C8-C10 fatty acid levels are similar to coconut oil and palm kernel, however, the transgenic algal strains lack the significantly higher C12:0 fatty acids, and they have extremely high C16:0 (23% in transgenics versus 11-16% in

TABLE 17

Lipid profiles of *Prototheca moriformis* transformed with multiple thioesterases.

| Fatty Acid | UTEX 1435 | UTEX 1435 + C. camphora TE | UTEX 1435 + C. camphora TE genetic background | | |
|---|---|---|---|---|---|
| | | | +C. hookeriana TE | +U. californica TE | +U. americana TE |
| C8:0 | 0 | 0 | 0.19 | 0 | 0.06 |
| C10:0 | 0.02 | 0.02 | 2.16 | 0.07 | 1.87 |
| C12:0 | 0.05 | 0.66 | 0.53 | 13.55 | 1.61 |
| C14:0 | 1.65 | 10.52 | 7.64 | 8.0 | 14.58 |
| C16:0 | 28.0 | 22.56 | 22.31 | 19.98 | 29.53 |
| C18:0 | 2.9 | 6.67 | 3.23 | 2.24 | 2.93 |
| C18:1 | 53.8 | 47.78 | 48.54 | 42.55 | 37.3 |
| C18:2 | 10.95 | 12.3 | 11.76 | 10.13 | 8.9 |
| C18:3 α | 0.8 | 0.93 | 0.91 | 0.91 | 0.76 |
| Total saturates (Area %) | 32.62 | 40.43 | 36.06 | 43.84 | 50.58 |

Additionally, a double thioesterase clone with *C. camphora* and *U. californica* thioesterases was grown in 2% sucrose containing medium with 50 mg/L G418 at 22° C. The fatty acid profile obtained from this strain under these growth conditions was: C8:0 (0); C10:0 (0.10); C12:0 (31.03); C14:0 (7.47); C16:0 (15.20); C18:0 (0.90); C18:1 (30.60); C18:2 (12.44); and C18:3a (1.38), with a total saturates of 54.7.

Double thioesterase clones with two homologous recombination constructs (one targeting the 6S region and the other targeting the KE858 region) containing the *C. camphora* coconut or palm kernel oil, respectively and/or 18:1 (50-57% in transgenics versus 8-19% in coconut or palm kernel oil, respectively.

Example 10: Identification of Endogenous Nitrogen-Dependent Prototheca Promoters A. Identification and Characterization of Endogenous Nitrogen-Dependent Promoters.

A cDNA library was generated from *Prototheca moriformis* (UTEX 1435) using standard techniques. The *Prototh*- eca moriformis cells were grown for 48 hours under nitrogen replete conditions. Then a 5% inoculum (v/v) was then transferred to low nitrogen and the cells were harvested every 24 hours for seven days. After about 24 hours in culture, the nitrogen supply in the media was completely depleted. The collected samples were immediately frozen using dry ice and isopropanol. Total RNA was subsequently isolated from the frozen cell pellet samples and a portion from each sample was held in reserve for RT-PCR studies. The rest of the total RNA harvested from the samples was subjected to polyA selection. Equimolar amounts of polyA selected RNA from each condition was then pooled and used to generate a cDNA library in vector pcDNA 3.0 (Invitrogen). Roughly 1200 clones were randomly picked from the resulting pooled cDNA library and subjected to sequencing on both strands. Approximately 68 different cDNAs were selected from among these 1200 sequences and used to design cDNA-specific primers for use in real-time RT-PCR studies.

RNA isolated from the cell pellet samples that were held in reserve was used as substrate in the real time RT-PCR studies using the cDNA-specific primer sets generated above. This reserved RNA was converted into cDNA and used as substrate for RT-PCR for each of the 68 gene specific primer sets. Threshold cycle or $C_T$ numbers were used to indicate relative transcript abundance for each of the 68 cDNAs within each RNA sample collected throughout the time course. cDNAs showing significant increase (greater than three fold) between nitrogen replete and nitrogen-depleted conditions were flagged as potential genes whose expression was up-regulated by nitrogen depletion. As discussed in the specification, nitrogen depletion/limitation is a known inducer of lipogenesis in oleaginous microorganisms.

In order to identify putative promoters/5'UTR sequences from the cDNAs whose expression was upregulated during nitrogen depletion/limitation, total DNA was isolated from *Prototheca moriformis* (UTEX 1435) grown under nitrogen replete conditions and were then subjected to sequencing using 454 sequencing technology (Roche). cDNAs flagged as being up-regulated by the RT-PCR results above were compared using BLAST against assembled contigs arising from the 454 genomic sequencing reads. The 5' ends of cDNAs were mapped to specific contigs, and where possible, greater than 500 bp of 5' flanking DNA was used to putatively identify promoters/UTRs. The presence of promoters/5'UTR were subsequently confirmed and cloned using PCR amplification of genomic DNA. Individual cDNA 5' ends were used to design 3' primers and 5' end of the 454 contig assemblies were used to design 5' gene-specific primers.

As a first screen, one of the putative promoters, the 5'UTR/promoter isolated from Aat2 (Ammonium transporter, SEQ ID NO: 63), was cloned into the *Cinnamomum camphora* C14 thioesterase construct with the *Chlorella prototheocoides* stearoyl ACP desaturase transit peptide, replacing the *C. sorokinana* glutamate dehydrogenase promoter. This construct is listed as SEQ ID NO: 81. To test the putative promoter, the thioesterase construct is transformed into *Prototheca moriformis* cells to confirm actual promoter activity by screening for an increase in C14/C12 fatty acids under low/no nitrogen conditions, using the methods described above. Similar testing of the putative nitrogen-regulated promoters isolated from the cDNA/genomic screen can be done using the same methods.

Other putative nitrogen-regulated promoters/5'UTRs that were isolated from the cDNA/genomic screen were:

| Promoter/5'UTR | SEQ ID NO. | Fold increased |
|---|---|---|
| FatB/A promoter/5'UTR | SEQ ID NO: 55 | n/a |
| NRAMP metal transporter promoter/5'UTR | SEQ ID NO: 56 | 9.65 |
| Flap Flagellar-associated protein promoter/5'UTR | SEQ ID NO: 57 | 4.92 |
| SulfRed Sulfite reductase promoter/5'UTR | SEQ ID NO: 58 | 10.91 |
| SugT Sugar transporter promoter/5'UTR | SEQ ID NO: 59 | 17.35 |
| Amt03-Ammonium transporter 03 promoter/5'UTR | SEQ ID NO: 60 | 10.1 |
| Amt02-Ammonium transporter 02 promoter/5'UTR | SEQ ID NO: 61 | 10.76 |
| Aat01-Amino acid transporter 01 promoter/5'UTR | SEQ ID NO: 62 | 6.21 |
| Aat02-Amino acid transporter 02 promoter/5'UTR | SEQ ID NO: 63 | 6.5 |
| Aat03-Amino acid transporter 03 promoter/5'UTR | SEQ ID NO: 64 | 7.87 |
| Aat04-Amino acid transporter 04 promoter/5'UTR | SEQ ID NO: 65 | 10.95 |
| Aat05-Amino acid transporter 05 promoter/5'UTR | SEQ ID NO: 66 | 6.71 |

Fold increase refers to the fold increase in cDNA abundance after 24 hours of culture in low nitrogen medium.

To gain further insight into potential regulation of these putative promoter/5'UTRs, eight of the sequences were selected for further testing: (1) FatB/A; (2) SulfRed Sulfite reductase; (3) SugT Sugar transporter; (4) Amt02-Ammonium transporter 02; (5) Aat01-Amino acid transporter 01; (6) Aat03-Amino acid transporter 03; (7) Aat04-Amino acid transporter 04; and (8) Aat05-Amino acid transporter 05. Higher resolution transcriptome analysis utilizing Illumina sequencing reads were carried out on RNA isolated from *Prototheca moriformis* cells various time points: T0 (seed); 20 hours; 32 hours; 48 hours; 62 hours; and 114 hours post inoculation from seed. The medium at T0 (seed) was nitrogen replete, while at the time points 20 hours and longer, the medium contained little to no nitrogen. Assembled transcript contigs generated from RNA isolated from each of the time points were then blasted independently with each of the eight previously identified transcripts. The results are summarized in Table 18 below.

TABLE 18

Transcriptome expression profiles for eight putative promoters/5'UTRs.

| cDNA | | TS | T20 | T32 | T48 | T62 | T114 |
|---|---|---|---|---|---|---|---|
| aa trans_01 | absolute | 98 | 96 | 321 | 745 | 927 | 1300 |
| | relative | 1 | 0.98 | 3.28 | 7.61 | 9.47 | 13.28 |
| aa trans_03 | absolute | 7 | 21 | 51 | 137 | 102 | 109 |
| | relative | 1 | 2.95 | 7.2 | 19.42 | 14.47 | 15.45 |
| aa trans_04 | absolute | 1 | 6 | 25 | 90 | 131 | 160 |
| | relative | 1 | 5.16 | 21.29 | 74.97 | 109.35 | 133.31 |

TABLE 18-continued

Transcriptome expression profiles for eight putative promoters/5'UTRs.

| cDNA | | TS | T20 | T32 | T48 | T62 | T114 |
|---|---|---|---|---|---|---|---|
| aa trans_05 | absolute | 109 | 88 | 123 | 210 | 214 | 273 |
| | relative | 1 | 0.81 | 1.13 | 1.93 | 1.97 | 2.51 |
| ammon trans_02 | absolute | 683 | 173 | 402 | 991 | 1413 | 1397 |
| | relative | 1 | 0.25 | 0.59 | 1.45 | 2.07 | 2.04 |
| fatA/B-1_cDNA | absolute | 13 | 36 | 654 | 617 | 544 | 749 |
| | relative | 1 | 2.8 | 51.57 | 48.65 | 42.9 | 59.1 |
| sug trans_01 | absolute | 25 | 25 | 106 | 261 | 266 | 251 |
| | relative | 1 | 1 | 4.22 | 10.4 | 10.63 | 10 |
| sulfite reductase_01 | absolute | 634 | 238 | 138 | 145 | 163 | 155 |
| | relative | 1 | 0.38 | 0.22 | 0.22 | 0.26 | 0.24 |

From the above-summarized results, several of the transcripts show increased accumulation over time, although interestingly, the sulfite reductase mRNA shows a distinct decrease in mRNA accumulation over time.

These eight putative promoter/5'UTR regions were cloned upstream of the *C. camphora* thioesterase coding region with its native transit peptide taken out and substituted with the transit peptide from *Chlorella protothecoides* (UTEX 250) stearoyl ACP desaturase. Each putative promoter/5'UTR region construct was introduced into *Prototheca moriformis* UTEX 1435 via homologous recombination using DNA from the genomic sequence of 6S rRNA. Also contained within the construct is a suc2 sucrose invertase gene from *S. cerevisiae* for selection of positive clones on sucrose containing media/plates. The cDNA sequence for the relevant portions of the construct for Aat01 is listed in the Sequence Listing as SEQ ID NO: 67. For the other constructs, the same backbone was use, the only variable was the putative promoter/5'UTR sequence. An additional control transgenic strain was generated in which the *C. reinhardtii* beta tubulin promoter was used to drive expression of the *C. camphora* thioesterase gene. This promoter have shown to drive constitutive expression of the gene of interest, and thus provides a useful control against which to measure expression of the same thioesterase message when driven by the various putative N-regulated promoters/5'UTRs tested.

Once the transgenic clones were generated, three separate experiments were carried out. The first two experiments assess the potential nitrogen regulatability of all eight putative promoters by measuring steady state thioesterase mRNA levels via RT-PCR, fatty acid profiles and ammonia levels in the culture supernatants. Clones were initially grown at 28° C. with agitation (200 rpm) in nitrogen rich seed medium (1 g/L ammonium nitrate-15 min nitrogen as ammonia, 4 g/L yeast extract) for 24 to 48 hours, at which point 20 OD units ($A_{750}$) were used to inoculate 50 ml of low nitrogen media (0.2 g/L ammonium sulfate-3 min nitrogen as ammonia, 0.2 g/L yeast extract). Cells were sampled every 24 hours for 6 days and a sample was also collected right before switching to low nitrogen conditions. A portion of the cells from each sample was then used for total RNA extraction using Trizol reagent (according to manufacturer's suggested methods) Ammonia assays revealed that ammonia levels in the supernatants fell below the limits of detection (~100 µM) after 24 hours in low nitrogen medium.

For real-time RT-PCR, all RNA levels were normalized to levels of an internal control RNA expressed in *Prototheca moriformis* (UTEX 1435) for each time point. The internal control RNA, termed cd189, is a product of the ARG9 gene which encodes N-acetyl ornithine aminotransferase. Primers sets used for real-time RT-PCR in these experiments were:

| Gene specific to | Primer sequence 5'-3' | SEQ ID NO: |
|---|---|---|
| *C. camphora* TE forward | TACCCCGCCTGGGGCGACAC | SEQ ID NO: 68 |
| *C. camphora* TE reverse | CTTGCTCAGGCGGCGGGTGC | SEQ ID NO: 69 |
| cd189 forward | CCGGATCTCGGCCAGGGCTA | SEQ ID NO: 70 |
| cd189 reverse | TCGATGTCGTGCACCGTCGC | SEQ ID NO: 71 |

Lipid profiles from each of the transformants from each time point were also generated and compared to the RT-PCR results. Based on the ammonia levels, RT-PCR results and changes in C12-C14 fatty acid levels, it was concluded that the Amino acid transporter 01 (Aat-01), Amino acid transporter 04 (Aat-04), and Ammonium transporter 02 (Amt-02) sequences do contain a functional nitrogen-regulatable promoter/5'UTR.

From the RT-PCR results, Aat-01 demonstrated the ability to drive steady state *C. camphora* thioesterase mRNA levels up to four times higher than control (*C. reinhardtii* beta tubulin promoter). The mRNA levels also correlated with nitrogen limitation and a marked increase in C12-C14 fatty acid levels. These results demonstrate that the 5'UTR associated with the Aat-01 promoter is likely more efficient at driving protein synthesis under lipid biosynthesis than the control *C. reinhardtii* promoter. Like the Aat-01 promoter, the Aat-04 promoter was able to drive mRNA accumulation up to five times higher than that of the *C. reinhardtii* control promoter. However, the Aat-04 promoter construct only produced a modest ability to impact C12-C14 fatty acid levels. These data demonstrate that the Aat-04 promoter is clearly regulatable by nitrogen depletion, but the UTR associated with the promoter likely functions poorly as a translational enhancer. Finally, the Amt-02 promoter was similar to the Aat-01 promoter, in that it was able to drive mRNA accumulation up to three times higher than that of the control promoter. The mRNA levels also correlated with nitrogen limitation and a marked increase in C12-C14 fatty acid levels. Taken together, all three of these promoters were demonstrated to be nitrogen-regulated.

B. Further Characterization of the Ammonium Transporter 3 (Amt03) Promoter and Expression of Various Thioesterases.

As described above, partial cDNAs termed ammonium transporter 02 and 03 (amt02 and amt03) were identified. Along with these two partial cDNAs, a third partial cDNA termed ammonium transporter 01 (amt01) was also identified. Alignment of the partial cDNA and the putative translated amino acid sequences were compared. Results show amt01 to be more distantly related of the three sequences, while amt02 and amt03 differ by only a single amino acid.

Promoters/5'UTRs were generated initially in silico by blasting the partial cDNA sequences against Roche 454 genomic DNA assemblies and Illumina transcriptome assemblies as described above. Transcript contigs showing identity to the cDNA encoding amt01, amt02, and amt03 were identified, however, the transcript contigs could not differentiate between the three mRNAs as the contigs contained sequences shared by all three. Roche 454 genomic DNA assemblies gave hits to amt02 and amt03 cDNA sequences and contained N-terminal protein sequences. PCR was carried out to clone the 5' flanking regions. The PCR primers used to validate the clone amt02 and amt03 promoter/UTR were:

```
Amt03 forward:
                                    (SEQ ID NO: 85)
5'-GGAGGAATTCGGCCGACAGGACGCGCGTCA-3'

Amt03 reverse:
                                    (SEQ ID NO: 86)
5'-GGAGACTAGTGGCTGCGACCGGCCTGTG-3'

Amt02 forward:
                                    (SEQ ID NO: 87)
5'-GGAGGAATTCTCACCAGCGGACAAAGCACCG-3'

Amt02 reverse:
                                    (SEQ ID NO: 88)
5'-GGAGACTAGTGGCTGCGACCGGCCTCTGG-3'
```

In both cases, the 5' and 3' primers contained useful restriction sites for the anticipated cloning into expression vectors to validate the functionality of these promoter/5'UTR regions.

Pair wise alignments between the DNAs cloned through this combined in silico and PCR-based method and the original cDNA encoding amt02 (SEQ ID NO: 61) and amt03 (SEQ ID NO: 60) were performed. Results of these alignments showed significant differences between the original cDNAs and the cloned genomic sequences, indicating that ammonium transporters likely represent a diverse gene family. Additionally, the promoter/5'UTR clone based on the combined method for amt03 was different than the original amt03 sequence, whereas the amt02 sequences were identical. Further experiments to characterize the amt03 promoter/UTR sequence (SEQ ID NO: 89) was carried out and described below.

The above identified amt03 promoter/UTR sequence (SEQ ID NO: 89) was tested by cloning this putative promoter/UTR sequence to drive the expression of four different thioesterases. The expression cassette contained upstream and downstream homologous recombination sequences to the 6S locus of the genome (SEQ ID NOs: 82 and 84, respectively). The cassette also contains a *S. cerevisiae* SUC2 sucrose invertase cDNA to enable the selection for positive clones on sucrose containing medium. The sucrose invertase expression was driven by the *C. reinhardtii* beta tubulin promoter and also contained a *C. vulgaris* nitrate reductase 3'UTR. The amt03 promoter/UTR sequence was then cloned downstream of the sucrose invertase cassette followed by in-frame thioesterase cDNA sequence from one of four thioesterase genes: (1) C14 thioesterase from *C. camphora*; (2) C12 thioesterase from *U. californica*; (3) C10-C16 thioesterase from *U. americana*; or (4) C10 thioesterase from *C. hookeriana* and also contained a *C. vulgaris* nitrate reductase 3'UTR. The C14 *C. camphora* thioesterase, C12 *U. californica* thioesterase, and the C10-C16 *U. americana* all contained the transit peptide from a *Chlorella protothecoides* stearoyl ACP desaturase. The C10 *C. hookeriana* thioesterase contained the transit peptide from a *Prototheca moriformis* delta 12 fatty acid desaturase (FAD). In all cases, the sequences were codon optimized for expression in *Prototheca moriformis*. The sequences to the foregoing thioesterase constructs are described in the Sequence Listing:

| amt03 promoter/UTR::*C. camphora* thioesterase construct | SEQ ID NO: 90 |
|---|---|
| *C. camphora* thioesterase construct | SEQ ID NO: 91 |
| *U. californica* thioesterase construct | SEQ ID NO: 92 |
| *U. americana* thioesterase construct | SEQ ID NO: 93 |
| *C. hookeriana* thioesterase construct | SEQ ID NO: 94 |

Transgenic lines were generated via biolistic transformation methods as described above in Example 2 into wild type *Prototheca moriformis* cells and selection was carried out on sucrose containing plates/medium. Positive lines were then screened for the degree to which their fatty acid profiles were altered. Four lines, one resulting from the transformation with each of the four above-described constructs, were then subjected to additional analysis. Line 76 expressed the *C. camphora* C14 thioesterase, line 37 expressed the *U. californica* C12 thioesterase, line 60 expressed the *U. americana* C10-C16 thioesterase, and line 56 expressed the *C. hookeriana* C10 thioesterase. Each line was grown for 48 hours in medium containing sucrose as the sole carbon source and samples of cells were removed at 14, 24, 36 and 48 hours (seed culture) for determination of fatty acid profile via direct transesterification to fatty acid methyl esters and subsequent analysis by GC-FID (described above) and for isolation of total RNA. At the end of 48 hours, these cells were used to inoculate cultures with no or low levels of nitrogen (containing sucrose as the sole carbon source) maintained at either pH 5.0 (citrate buffered, 0.05M final concentration) or pH 7.0 (HEPES buffered, 0.1M final concentration). Culture samples were removed at 12, 24, 72 and 108 hours (lipid production) for fatty acid profiling and isolation of total RNA. Ammonia assays of these cultures revealed that ammonia levels fell below the limits of detection (ca. 100 µM) after 24 hours in low nitrogen medium.

Real-time RT-PCR assays on the mRNA levels of the thioesterases were performed on total RNA from each of the time points collected above and all mRNA levels were normalized to the levels of an internal control RNA (cd189). Primer sets used in real-time PCR are shown in Table 19 below:

TABLE 19

Primer sets for real-time PCR.

| Gene specific to | Primer sequence 5'-3' | SEQ ID NO: |
|---|---|---|
| *C. camphora* TE forward | TACCCCGCCTGGGGCGACAC | SEQ ID NO: 68 |
| *C. camphora* TE reverse | CTTGCTCAGGCGGCGGGTGC | SEQ ID NO: 69 |
| *U. californica* TE forward | CTGGGCGACGGCTTCGGCAC | SEQ ID NO: 95 |
| *U. californica* TE reverse | AAGTCGCGGCGCATGCCGTT | SEQ ID NO: 96 |
| *U. americana* TE forward | CCCAGCTGCTCACCTGCACC | SEQ ID NO: 97 |
| *U. americana* TE reverse | CACCCAAGGCCAACGGCAGCGCCGTG | SEQ ID NO: 98 |

TABLE 19-continued

Primer sets for real-time PCR.

| Gene specific to | Primer sequence 5'-3' | SEQ ID NO: |
|---|---|---|
| C. hookeriana TE forward | TACCCCGCCTGGGGCGACAC | SEQ ID NO: 99 |
| C. hookeriana TE reverse | AGCTTGGACAGGCGGCGGGT | SEQ ID NO: 100 |
| cd189 reverse | TCGATGTCGTGCACCGTCGC | SEQ ID NO: 71 |
| cd189 forward | CCGGATCTCGGCCAGGGCTA | SEQ ID NO: 70 |

The results from the fatty acid profiles at each of the time points in the seed culture phase showed very little impact from the thioesterases. With the commencement of the lipid production phase, the fatty acid profiles were significantly impacted, with the increases that are far more dramatic for the cultures maintained at pH 7.0 as compared to the cultures at pH 5.0. While the magnitude of the difference between pH 7.0 and 5.0 target fatty acid accumulation varied with each thioesterase tested, the overall effect was the same: that the cells grown at pH 5.0 showed significantly lower levels of the target fatty acids accumulated, but more than compared to control wild type cells.

Analysis of the RNA isolated from these same samples correlated very will with the fatty acid profile data, in that there was a clear impact of culture pH on the steady state mRNA levels for each of the thioesterases. Taking the fatty acid accumulation data and the mRNA data together, the pH regulation of thioesterase gene expression driven by the amt03 promoter/UTR was clearly mediated either at the level of transcription, mRNA stability or both. Additionally, it was observed that the steady state levels of *U. californica* mRNA were four logs lower as compared to the steady state levels of *C. hookeriana* mRNA. This observation is consistent with the hypothesis that the individual mRNA sequences may play a role in controlling expression. These data imply that ammonium uptake in *Prototheca moriformis* by the amt03 family of transporters is coupled directly to pH.

Additional fatty acid profile analysis was performed on twelve lines generated from the transformation of *Prototheca moriformis* cells with the construct amt03 promoter/UTR driving the expression of the *U. americana* C10-C16 thioesterase. Line 60, described above, was a part of the following analysis. Table 20 below shows the lipid profiles of three of the twelve lines that were analyzed along with the wild type control.

saturates from the twelve lines analyzed ranged from about 63% to over 86%). Additionally, the *U. americana* thioesterase, when expressed at these levels, dramatically reduces the level of unsaturates, especially C18:1 and C18:2 (see lines 40 and 44), where in line 44, C18:1 levels are reduced by over 8 fold compared to the wild type. Also, the *U. americana* thioesterase (driven by the amt03 promoter) greatly increases the levels of mid-chain fatty acids. Line 44 shows C10:0-C14:0 levels at greater than 56%, approximately 42 fold higher than the levels seen in the wildtype strain and C8:0-C14:0 levels at greater than 57%. Additional strains transformed with a construct of the Amt03 promoter driving the expression of the *U. americana* thioesterase had representative lipid profile of: 0.23% C8:0; 9.64% C10:0; 2.62% C12:0; 31.52% C14:0; 37.63% C16:0; 5.34% C18:0; 7.05% C18:1; and 5.03% C18:2, with a total saturates percentage at 86.98%.

Additional lipid profiles generated from the transformation of *Prototheca moriformis* cells with the construct amt03 promoter/UTR (SEQ ID NO: 89) driving the expression of the *C. hookeriana* C10 thioesterase (SEQ ID NO: 94). Positive clones expressing this construct were selected and grown at pH 7.0 conditions. Representative lipid profile from a positive clone was: 9.87% C8:0; 23.97% C10:0; 0.46% C12:0; 1.24% C14:0; 10.24% C16:0; 2.45% C18:0; 42.81% C18:1; and 7.32% C18:2. This clone had a C8-C10 percentage of 33.84

Taken together, the data suggest that the amt03 promoter/UTR, and other promoters like it, can be used as a tightly regulated promoter, which may be particularly useful for expressing a potentially toxic compound and strict enforcement of gene expression is required. The ability of *Prototheca moriformis* to grow under a wide range (at least pH 5.0 to 7.0) of pH regimes makes this organism particularly useful in combination with regulatory elements such as the amt03 promoter/UTR. Additionally, the lipid profile data above demonstrates the impressive ability of the amt03 promoter/UTR to drive gene expression.

Example 11: Altering the Levels of Saturated Fatty Acids in the Microalgae *Prototheca moriformis*

As part of a genomics screen using a bioinformatics based approach based on cDNAs, Illumia transcriptome and Roche 454 sequencing of genomic DNA from *Prototheca moriformis* (UTEX 1435), two specific groups of genes involved in fatty acid desaturation were identified: stearoyl ACP desaturases (SAD) and delta 12 fatty acid desaturases (Δ12 FAD). Stearoyl ACP desaturase enzymes are part of the lipid synthesis pathway and they function to introduce double

TABLE 20

Fatty acid profiles of transformants containing the
U. americana TE driven by the amt03 promoter/UTR.

| Area % | C8:0 | C10:0 | C12:0 | C14:0 | C16:0 | C18:0 | C18:1 | C18:2 | Total Saturates |
|---|---|---|---|---|---|---|---|---|---|
| wild type | 0.00 | 0.01 | 0.04 | 1.27 | 27.20 | 3.85 | 58.70 | 7.18 | 32.36 |
| Line 40 | 2.38 | 20.61 | 3.41 | 28.41 | 29.92 | 1.91 | 8.57 | 3.74 | 86.64 |
| Line 44 | 1.50 | 20.16 | 4.44 | 31.88 | 26.66 | 1.88 | 6.95 | 5.42 | 86.50 |
| Line 60 | 0.98 | 14.56 | 3.15 | 27.49 | 31.76 | 2.14 | 12.23 | 6.36 | 80.06 |

As shown in the table above, the levels of total saturates was increased dramatically over that of wild type with over 2.6 fold in the case of line 40 compared to wildtype (total bonds into the fatty acyl chains, for example, the synthesis of C18:1 fatty acids from C18:0 fatty acids. Delta 12 fatty acid desaturases are also part of the lipid synthesis pathway and they function to introduce double bonds into already unsaturated fatty acids, for example, the synthesis of C18:2 fatty acids from C18:1 fatty acids. Southern blot analysis using probes based on the two classes of fatty acid desaturase genes identified during the bioinformatics efforts indicated that each class of desaturase genes was likely comprised of multiple family members. Additionally the genes encoding stearoyl ACP desaturases fell into two distinct families Based on these results, three gene disruption constructs were designed to potentially disrupt multiple gene family members by targeting more highly conserved coding regions within each family of desaturase enzymes.

Three homologous recombination targeting constructs were designed using: (1) highly conserved portions of the coding sequence of delta 12 fatty acid desaturase (d12FAD) family members and (2) two constructs targeting each of the two distinct families of SAD, each with conserved regions of the coding sequences from each family. This strategy would embed a selectable marker gene (the suc2 sucrose invertase cassette from S. cerevisiae conferring the ability to hydrolyze sucrose) into these highly conserved coding regions (targeting multiple family members) rather than a classic gene replacement strategy where the homologous recombination would target flanking regions of the targeted gene.

All constructs were introduced into the cells by biolistic transformation using the methods described above and constructs were linearized before being shot into the cells. Transformants were selected on sucrose containing plates/media and changes in lipid profile were assayed using the above-described method. Relevant sequences from each of the three targeting constructs are listed below.

| Description | SEQ ID NO: |
|---|---|
| 5' sequence from coding region of d12FAD from targeting construct | SEQ ID NO: 72 |
| 3' sequence from coding region of d12FAD from targeting construct | SEQ ID NO: 73 |
| d12FAD targeting construct cDNA sequence | SEQ ID NO: 74 |
| 5' sequence from coding region of SAD2A | SEQ ID NO: 75 |
| 3' sequence from coding region of SAD2A | SEQ ID NO: 76 |
| SAD2A targeting construct cDNA sequence | SEQ ID NO: 77 |
| 5' sequence from coding region os SAD2B | SEQ ID NO: 78 |
| 3' sequence from coding region of SAD2B | SEQ ID NO: 79 |
| SAD2B targeting construct cDNA sequence | SEQ ID NO: 80 |

Representative positive clones from transformations with each of the constructs were picked and the lipid profiles for these clones were determined (expressed in Area %) and summarized in Table 21 below.

TABLE 21

Lipid profiles for desaturase knockouts.

| Fatty Acid | d12FAD KO | SAD2A KO | SAD2B KO | wt UTEX 1435 |
|---|---|---|---|---|
| C8:0 | 0 | 0 | 0 | 0 |
| C10:0 | 0.01 | 0.01 | 0.01 | 0.01 |
| C12:0 | 0.03 | 0.03 | 0.03 | 0.03 |
| C14:0 | 1.08 | 0.985 | 0.795 | 1.46 |
| C16:0 | 24.42 | 25.335 | 23.66 | 29.87 |
| C18:0 | 6.85 | 12.89 | 19.555 | 3.345 |
| C18:1 | 58.35 | 47.865 | 43.115 | 54.09 |
| C18:2 | 7.33 | 10.27 | 9.83 | 9.1 |
| C18:3 alpha | 0.83 | 0.86 | 1 | 0.89 |
| C20:0 | 0.48 | 0.86 | 1.175 | 0.325 |

Each of the construct had a measurable impact on the desired class of fatty acid and in all three cases C18:0 levels increased markedly, particularly with the two SAD knockouts. Further comparison of multiple clones from the SAD knockouts indicated that the SAD2B knockout lines had significantly greater reductions in C18:1 fatty acids than the C18:1 fatty acid levels observed with the SAD2A knockout lines.

Additional Δ12 fatty acid desaturase (FAD) knockouts were generated in a Prototheca moriformis background using the methods described above. In order to identify potential homologous of Δ12FADs, the following primers were used in order to amplify a genomic region encoding a putative FAD:

SEQ ID NO: 101
Primer 1 5'-TCACTTCATGCCGGCGGTCC-3'

SEQ ID NO: 102
Primer 2 5'- GCGCTCCTGCTTGGCTCGAA-3'

The sequences resulting from the genomic amplification of Prototheca moriformis genomic DNA using the above primers were highly similar, but indicated that multiple genes or alleles of Δ12FADs exist in Prototheca.

Based on this result, two gene disruption constructs were designed that sought to inactivate one or more Δ12FAD genes. The strategy would to embed a sucrose invertase (suc2 from S. cerevisiae) cassette, thus conferring the ability to hydrolyze sucrose as a selectable marker, into highly conserved coding regions rather than use a classic gene replacement strategy. The first construct, termed pSZ1124, contained 5' and 3' genomic targeting sequences flanking a C. reinhardtii β-tubulin promoter driving the expression of the S. cerevisiae suc2 gene and a Chlorella vulgaris nitrate reductase 3'UTR (S. cerevisiae suc2 cassette). The second construct, termed pSZ1125, contained 5' and 3' genomic targeting sequences flanking a C. reinhardtii β-tubulin promoter driving the expression of the S. cerevisiae suc2 gene and a Chlorella vulgaris nitrate reductase 3'UTR. The relevant sequences of the constructs are listed in the Sequence Listing:

| pSZ1124 (FAD2B) 5' genomic targeting sequence | SEQ ID NO: 103 |
|---|---|
| pSZ1124 (FAD2B) 3' genomic targeting sequence | SEQ ID NO: 104 |
| S. cerevisiae suc2 cassette | SEQ ID NO: 105 |
| pSZ1125 (FAD2C) 5' genomic targeting sequence | SEQ ID NO: 106 |
| pSZ1125 (FAD2C) 3' genomic targeting sequence | SEQ ID NO: 107 | pSZ1124 and pSZ1125 were each introduced into a Prototheca moriformis background and positive clones were selected based on the ability to hydrolyze sucrose. Table 22 summarizes the lipid profiles (in Area %, generated using methods described above) obtained in two transgenic lines in which pSZ1124 and pSZ1125 targeting vectors were utilized.

TABLE 22

Lipid profiles of Δ12 FAD knockouts

|        | C10:0 | C12:0 | C14:0 | C16:0 | C16:1 | C18:0 | C18:1 | C18:2 | C18:3α |
|--------|-------|-------|-------|-------|-------|-------|-------|-------|--------|
| parent | 0.01  | 0.03  | 1.15  | 26.13 | 1.32  | 4.39  | 57.20 | 8.13  | 0.61   |
| FAD2B  | 0.02  | 0.03  | 0.80  | 12.84 | 1.92  | 0.86  | 74.74 | 7.08  | 0.33   |
| FAD2C  | 0.02  | 0.04  | 1.42  | 25.85 | 1.65  | 2.44  | 66.11 | 1.39  | 0.22   |

The transgenic containing the FAD2B (pSZ1124) construct gave a very interesting and unexpected result in lipid profile, in that the C18:2 levels, which would be expected to decrease, only decreased by about one area %. However, the C18:1 fatty acid levels increased significantly, almost exclusively at the expense of the C16:0 levels, which decreased significantly. The transgenic containing the FAD2C (pSZ1125) construct also gave a change in lipid profile: the levels of C18:2 are reduced significantly along with a corresponding increase in C18:1 levels.

Beef Tallow Mimetic

One positive clone generated from the above SAD2B knockout experiment as described above was selected to be used as the background for the further introduction of a C14-preferring fatty acyl-ACP thioesterase gene. The construct introducing the *C. camphora* C14-preferring thioesterase contained targeting sequence to the 6S rRNA genomic region (allowing for targeted integration of the transforming DNA via homologous recombination) and the expression construct contained the *C. reinhardtii* β-tubulin promoter driving the expression of the neoR gene with the *Chlorella vulgaris* nitrate reductase 3'UTR, followed by a second *C. reinhardtii* β-tubulin promoter driving the expression of a codon-optimized *C. camphora* thioesterase with a *Chlorella protothecoides* stearoyl ACP desaturase transit peptide with a second *Chlorella vulgaris* nitrate reductase 3'UTR. The 5' 6S rRNA genomic donor sequence is listed in SEQ ID NO: 82; the 3' 6S rRNA genomic donor sequence is listed in SEQ ID NO: 84; and the relevant expression construct for the *C. camphora* thioesterase is listed in SEQ ID NO: 83.

Transformation was carried out using biolistic methods as described above and the cells were allowed to recover for 24 hours on plates containing 2% sucrose. After this time, the cells were re-suspended and re-plated on plates containing 2% sucrose and 50 μg/ml G418 for selection. Nine clones out of the positive clones generated were selected for lipid production and lipid profile. The nine transgenic clones (with the SAD2B KO and expressing *C. camphora* C14-preferring thioesterase) were cultured as described above and analyzed for lipid profile. The results are summarized below in Table 23. The lipid profile for tallow is also included in Table 23 below (National Research Council 1976: Fat Content and Composition of Animal Product).

TABLE 23

Lipid profile of thioesterase transformed clones.

|                                    | C10:0 | C12:0 | C14:0 | C16:0 | C16:1 | C18:0 | C18:1 | C18:2 | C18:3 | C20  |
|------------------------------------|-------|-------|-------|-------|-------|-------|-------|-------|-------|------|
| SAD2BKO C. camphora TE clone 1     | 0.01  | 0.33  | 6.13  | 24.24 | 0.19  | 11.08 | 42.03 | 13.45 | 0.98  | 0.73 |
| SAD2BKO C. camphora TE clone 2     | 0.01  | 0.16  | 3.42  | 23.80 | 0.40  | 9.40  | 50.62 | 10.2  | 0.62  | 0.70 |
| SAD2BKO C. camphora TE clone 3     | 0.01  | 0.20  | 4.21  | 25.69 | 0.40  | 7.79  | 50.51 | 9.37  | 0.66  | 0.63 |
| SAD2BKO C. camphora TE clone 4     | 0.01  | 0.21  | 4.29  | 23.57 | 0.31  | 9.44  | 50.07 | 10.07 | 0.70  | 0.70 |
| SAD2BKO C. camphora TE clone 5     | 0.01  | 0.18  | 3.87  | 24.42 | 0.32  | 9.24  | 49.75 | 10.17 | 0.71  | 0.71 |
| SAD2BKO C. camphora TE clone 6     | 0.01  | 0.28  | 5.34  | 23.78 | 0.33  | 9.12  | 49.12 | 10.00 | 0.68  | 0.70 |
| SAD2BKO C. camphora TE clone 7     | 0.01  | 0.15  | 3.09  | 23.07 | 0.32  | 10.08 | 51.21 | 10.00 | 0.66  | 0.74 |
| SAD2BKO C. camphora TE clone 8     | 0.01  | 0.29  | 5.33  | 24.62 | 0.37  | 7.02  | 49.67 | 10.74 | 0.69  | 0.70 |
| SAD2BKO C. camphora TE clone 9     | 0.01  | 0.12  | 2.74  | 25.13 | 0.30  | 10.17 | 50.18 | 9.42  | 0.71  | 0.71 |
| wt UTEX 1435                       | 0.01  | 0.02  | 0.96  | 23.06 | 0.79  | 3.14  | 61.82 | 9.06  | 0.46  | 0.27 |
| SAD2BKO                            | 0.01  | 0.03  | 0.80  | 23.66 | 0.13  | 19.56 | 43.12 | 9.83  | 1.00  | 1.18 |
| Tallow                             | 0.00  | 0.00  | 4.00  | 26.00 | 3.00  | 14.00 | 41.00 | 3.00  | 1.00  | 0.00 |

As can be seen in Table 23, the lipid profiles of the transgenic lines are quite similar to the lipid profile of tallow. Taken collectively, the data demonstrate the utility of combining specific transgenic backgrounds, in this case, a SAD2B knockout with a C14-preferring thioesterase (from *C. camphora*), to generate an transgenic algal strain that produce oil similar to the lipid profile of tallow.

Construct Used to Down Regulate the Expression of β-Ketoacyl Synthase II (KASII) by Targeted Knock-Out Approach Vector down-regulating KASII gene expression by targeted knock-out approach was introduced into a classically mutagenized derivative of UTEX 1435, S1331. The *Saccharomyces cerevisiae* invertase gene was utilized as a selectable marker, conferring the ability to grow on sucrose. The invertase expression cassette under control of *C. reinhardtii* B-tubulin promoter was inserted in the middle of the 315 bp long KASII genomic region to permit targeted integration (pSZ1503).

Relevant restriction sites in pSZ1503 are indicated in lowercase, bold and underlining and are 5'-3' BspQ 1, Kpn I, AscI, Xho I, Sac I, BspQ I, respectively. BspQ I sites delimit the 5' and 3' ends of the transforming DNA. Bold, lowercase sequences represent genomic DNA from S1331 that permit targeted integration at KASII locus via homologous recombination. Proceeding in the 5' to 3' direction, the *C. reinhardtii* B-tubulin promoter driving the expression of the yeast sucrose invertase gene (conferring the ability of S1331 to metabolize sucrose) is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text.

Nucleotide sequence of transforming DNA contained in pSZ1503_[KASII_btub-y.inv-nr_KASII]:

(SEQ ID NO: 149)

gctcttcccgcaccggctggctccaccccaacttgaacctcgagaacccgcgcctggcgtcgacccgtcgtgctcgtggggccgcgga aggagcgcgccgaagacctggacgtcgtcctctccaactcctttggctttggcgggcacaattcgtgcgtcggtacc ctttcttgcgctatga cacttccagcaaaaggtagggcgggctgcgagacggcttcccggcgctgcatgcaacaccgatgatgcttcgaccccccgaagctccttcggg gctgcatgggcgctccgatgccgctccagggcgagcgctgtttaaatagccaggcccccgattgcaaagacattatagcgagctaccaaagcca tattcaaacacctagatcactaccacttctacacaggccactcgagcttgcgatcgcactccgctaagggggcgcctcttcctcttcgtttcagtcac aacccgcaaac ggcgcgccATGctgctgcaggccttcctgttcctgctggccggcttcgccgccaagatcagcgcctccatgacgaacga

*gacgtccgaccgcccctggtgcacttcaccccaacaagggctggatgaacgaccccaacggcctgtggtacgacgagaaggacgcca*

*agtggcacctgtacttccagtacaacccgaacgacaccgtctgggggacgcccttgttctggggccacgccacgtccgacgacctgaccaa*

*ctgggaggaccagcccatcgccatcgcccgaagcgcaacgactccggcgccttctccggctccatggtggtggactacaacaacacctcc*

*ggcttcttcaacgacaccatcgacccgcgccagcgctgcgtggccatctggacctacaacacccggagtccgaggagcagtacatctcct*

*acagcctggacggcggctacaccttcaccgagtaccagaagaacccgtgctggccgccaactccacccagttccgcgacccgaaggtctt*

*ctggtacgagccctccagaagtggatcatgaccgcggccaagtcccaggactacaagatcgagatctactcctccgacgacctgaagtcc*

*tggaagctggagtccgcgttcgccaacgagggcttcctcggctaccagtacgagtgccccggcctgatcgaggtccccaccgagcaggacc*

*ccagcaagtcctactgggtgatgttcatctccatcaaccccggcgccccggccggcggctccttcaaccagtacttcgtcggcagcttcaacg*

*gcacccacttcgaggccttcgacaaccagtcccgcgtggtggacttcggcaaggactactacgccctgcagaccttcttcaacaccgacccg*

*acctacgggagcgccctgggcatcgcgtgggcctccaactggagtactccgccttcgtgccaccaaccctggcgctcctccatgtccctc*

*gtgcgcaagttctccctcaacaccgagtaccaggccaaccgagacggagctgatcaacctgaaggccgagccgatcctgaacatcagc*

*aacgccggcccctggagccggttcgccaccaacaccacgttgacgaaggccaacagctacaacgtcgacctgtccaacagcaccggcac*

*cctggagttcgagctggtgtacgccgtcaacaccacccagacgatctccaagtccgtgttcgcggacctctccctctggttcaagggcctgga*

*ggaccccgaggagtacctccgcatgggcttcgaggtgtccgcgtcctccttcttcctggaccgcgggaacagcaaggtgaagttcgtgaagg*

*agaaccctacttcaccaaccgcatgagcgtgaacaaccagcccttcaagagcgagaacgacctgtcctactacaaggtgtacggcttgct*

*ggaccagaacatcctggagctgtacttcaacgacggcgacgtcgtgtccaccaacacctacttcatgaccaccgggaacgccctgggctcc*

*gtgaacatgacgacgggggtggacaacctgttctacatcgacaagttccaggtgcgcgaggtcaaag*TGAcaattggcagcagcagctcg gatagtatcgacacactctggacgctggtcgtgtgatggactgttgccgccacacttgctgccttgacctgtgaatatcctgccgcttttatcaaaca gcctcagtgtgtttgatcttgtgtgtacgcgcttttgcgagttgctagctgcttgtgctatttgcgaataccaccccagcatcccttccctcgtttcata tcgcttgcatcccaaccgcaacttatctacgctgtcctgctatccctcagcgctgctcctgctcctgctcactgccctcgcacagccttggtttgggc

```
tccgcctgtattctcctggtactgcaacctgtaaaccagcactgcaatgctgatgcacgggaagtagtgggatgggaacacaaatggaggatcgt agagctcatcttccgaaagtacgacgagtgagcgagctgattctctttgagcggggtcgggtggttcggggagagtgcgcggaaaggcg cagagacgtgcggccggccgtgtccctccgtcttccctggttggtgctatagtaacctgcctgtgtcgcgtgcgcgtcgggaagagc
```

The cDNAs of the KAS II allele 1 and allele 2 are identified in SEQ ID NOs: 279 and 280, respectively. The amino acid sequences of alleles 1 and 2 are identified in SEQ ID NOs: 281 and 282, respectively.

To determine the impact of KASII inactivation on lipid composition, pSZ1503 vector DNA was transformed into S1331 to generate a targeted KASII knock-out phenotype. Initial single clones were isolated and grown under standard lipid production conditions at pH5.0. The resulting profiles of the best representative clone and the wild-type cells are shown below in Table 31

TABLE 31

Fatty acid profiles in S1331 and a derivative transgenic line transformed with pSZ1503 DNA.

| Sample ID | C10:0 | C12:0 | C14:0 | C16:0 | C16:1 | C18:0 | C18:1 | C18:2 | C18:3 α |
|---|---|---|---|---|---|---|---|---|---|
| 1331-5 | 0.01 | 0.03 | 0.96 | 24.28 | 0.64 | 3.94 | 62.69 | 6.21 | 0.49 |
| D698-2 | 0.01 | 0.01 | 0.83 | 38.36 | 1.38 | 2.21 | 48.31 | 7.60 | 0.55 |

Example 12: Engineering *Prototheca* with Alternative Selectable Markers

A. Expression of a Secretable α-Galactosidase in *Prototheca moriformis*

Methods and effects of expressing a heterologous sucrose invertase gene in *Prototheca* species have been previously described in PCT Application No. PCT/US2009/66142, hereby incorporated by reference. The expression of other heterologous polysaccharide degrading enzymes was examined in this Example. The ability to grow on melibiose (α-D-gal-glu) by *Prototheca moriformis* UTEX 1435 with one of the following exogenous gene encoding a α-galactosidase was tested: MEL1 gene from *Saccharomyces carlbergensis* (amino acid sequence corresponding to NCBI accession number P04824 (SEQ ID NO: 108)), AglC gene from *Aspergillus niger* (amino acid sequence corresponding to NCBI accession number Q9UUZ4 (SEQ ID NO: 116)), and the α-galactosidase from the higher plant *Cyamopsis tetragobobola* (Guar bean) (amino acid sequence corresponding to NCBI accession number P14749 (SEQ ID NO: 120). The above accession numbers and corresponding amino acid sequences are hereby incorporated by reference. In all cases, genes were optimized according to the preferred codon usage in *Prototheca moriformis*. The relevant portions of the expression cassette are listed below along with the Sequence Listing numbers. All expression cassettes used the 5' and 3' Clp homologous recombination targeting sequences for stable genomic integration, the *Chlamydomonas reinhardtii* TUB2 promoter/5'UTR, and the *Chlorella vulgaris* nitrate reductase 3'UTR.

| | |
|---|---|
| *S. carlbergensis* MEL1 amino acid sequence | SEQ ID NO: 108 |
| *S. carlbergensis* MEL1 amino acid sequence signal peptide | SEQ ID NO: 109 |
| *S. carlbergensis* MEL1 transformation cassette | SEQ ID NO: 110 |
| *S. carlbergensis* MEL1 sequence (codon optimized) | SEQ ID NO: 111 |
| 5' Clp homologous recombination targeting sequence | SEQ ID NO: 112 |
| 3' Clp homologous recombination targeting sequence | SEQ ID NO: 113 |
| *Chlamydomonas reinhardtii* TUB2 promoter/5'UTR | SEQ ID NO: 114 |
| *Chlorella vulgaris* nitrate reductase 3'UTR | SEQ ID NO: 115 |
| *A. niger* AlgC amino acid sequence | SEQ ID NO: 116 |
| *A. niger* AlgC amino acid sequence signal peptide | SEQ ID NO: 117 |
| *A. niger* AlgC sequence (codon optimized) | SEQ ID NO: 118 |
| *A. niger* AlgC transformation cassette | SEQ ID NO: 119 |
| *C. tetragonobola* α-galactosidase amino acid sequence | SEQ ID NO: 120 |
| *C. tetragonobola* α-galactosidase sequence (codon optimized) | SEQ ID NO: 121 |
| *C. tetragonobola* α-galactosidase transformation cassette | SEQ ID NO: 122 |

*Prototheca moriformis* cells were transformed with each of the three expression cassettes containing *S. carlbergensis* MEL1, *A. niger* AlgC, or *C. tetragonobola* α-galactosidase gene using the biolistic transformation methods as described in Example 2 above. Positive clones were screened using plates containing 2% melibiose as the sole carbon source. No colonies appeared on the plates for the *C. tetragonobola* expression cassette transformants. Positive clones were picked from the plates containing the *S. carlbergensis* MEL1 transformants and the *A. niger* AlgC transformants. Integration of the transforming DNA was confirmed using PCR with primers targeting a portion of the *C. vulgaris* 3'UTR and the 3' Clp homologous recombination targeting sequence.

```
5' primer C. vulgaris 3'UTR: downstream Clp
sequence
                               (SEQ ID NO: 123)
ACTGCAATGCTGATGCACGGGA 3' primer C. vulgaris 3'UTR: downstream Clp
sequence
                               (SEQ ID NO: 124)
TCCAGGTCCTTTTCGCACT
```

As a negative control, genomic DNA from untransformed *Prototheca moriformis* cells were also amplified with the primer set. No products were amplified from genomic DNA from the wild type cells.

Several positive clones from each of the *S. carlbergensis* MEL1 transformants and the *A. niger* AlgC transformants (as confirmed by PCR) were tested for their ability to grow on melibiose as the sole carbon source in liquid media. These selected clones were grown for 3 days in conditions and base medium described in Example 1 above with melibiose as the sole carbon source. All clones containing either α-galactosidase-encoding genes grew robustly during this time, while the untransformed wild type strain and *Prototheca moriformis* expressing a *Saccharomyces cerevisiae* SUC2 sucrose invertase both grew poorly on the melibiose media. These results suggest that the α-galactosidase encoding genes may be used as a selectable marker for transformation. Also, these data indicate that the native signal peptides present in the *S. carlbergensis* MEL1 (SEQ ID NO: 109) or *A. niger* AlgC (SEQ ID NO: 117) are useful for targeting proteins to the periplasm in *Prototheca moriformis* cells.

B. THIC Genes Complements Thiamine Auxotrophy in *Prototheca*

Thiamine prototrophy in *Prototheca moriformis* cells was examined using expression of exogenous THIC genes Thiamine biosynthesis in plants and algae is typically carried out in the plastid, hence most nuclear encoded proteins involved in its production will need to be efficiently targeted to the plastid. DNA sequencing and transcriptome sequencing of *Prototheca moriformis* cells revealed that all of the genes encoding the thiamine biosynthetic enzymes were present in the genome, with the exception of THIC. To dissect the lesion responsible for thiamine auxotrophy at the biochemical level, the growth of *Prototheca moriformis* cells under five different regimes were examined: (1) in the presence of 2 µM thiamine hydrochloride; (2) without thiamine; (3) without thiamine, but with 2 µM hydroxyethyl thiazole (THZ); (4) without thiamine, but with 2 µM 2-methyl-4-amino-5-(aminomethyl)pyrimidine (PYR); and (5) without thiamine, but with 2 µM THZ and 2 µM PYR. Results from the growth experiments under these 5 different conditions indicated that *Prototheca moriformis* cells are capable of de novo synthesis, but can only produce thiamine pyrophosphate (TPP) if the PYR precursor is provided. This result is consistent with the hypothesis that the thiamine auxotrophy of *Prototheca moriformis* is due to the inability to synthesize hydroxymethylpyrimidine phosphate (HMP-P) from aminoimidazole ribonucleotide, which is the conversion catalyze by THIC enzyme.

*Prototheca moriformis* cells were transformed using the biolistic transformation methods described above in Example 2, expressing the *Coccomyxa* C-169 THIC (amino acid sequence corresponding to JGI Protein ID 30481, and hereby incorporated by reference) and a *S. cerevisiae* SUC2 sucrose invertase as the selective marker. This expression construct contained the native transit peptide sequence from *Coccomyxa* C-169 THIC, upstream and downstream homologous recombination targeting sequences to the 6S region of genomic DNA, a *C. reinhardtii* TUB2 promoter/5'UTR region (SEQ ID NO: 104), and a *Chlorella vulgaris* nitrate reductase 3'UTR (SEQ ID NO: 115). The *S. cerevisiae* SUC2 expression was also driven by a *C. reinhardtii* TUB2 promoter/5'UTR region (SEQ ID NO: 114) and contained a *Chlorella vulgaris* nitrate reductase 3'UTR (SEQ ID NO: 115). Genes were optimized according to the preferred codon usage in *Prototheca moriformis*. The relevant expression cassette sequences are listed in the Sequence Listing and detailed below:

| | |
|---|---|
| *Coccomyxa* C-169 THIC amino acid sequence | SEQ ID NO: 125 |
| *Coccomyxa* C-169 THIC amino acid sequence native transit peptide | SEQ ID NO: 126 |
| *Coccomyxa* C-169 THIC transformation cassette | SEQ ID NO: 127 |
| *Coccomyxa* C-169 THIC sequence (codon optimized) | SEQ ID NO: 128 |
| *S. cerevisiae* SUC2 sequence (codon optimized) | SEQ ID NO: 129 |
| 5' 6S homologous recombination targeting sequence | SEQ ID NO: 82 |
| 3' 6S homologous recombination targeting sequence | SEQ ID NO: 84 |

Selection of positive clones were performed on plates without thiamine and containing sucrose as the sole carbon source. Positive clones were confirmed using PCR with a 5' primer that binds within the *Coccomyxa* C-169 THIC gene and a 3' primer that anneals downstream of the transforming DNA in the 6S locus. PCR confirmed positive clones were also confirmed using Southern blot assays.

To observe the thiamine auxotrophy of wildtype *Prototheca moriformis* cells, it was necessary to first deplete cells of internal thiamine reserves. To test growth in medium without thiamine, cells were first grown to stationary phase in medium containing 2 µM thiamine and then the cells were diluted to an optical density at 750 nm (OD750) of approximately 0.05 in medium without thiamine. The diluted cells were then grown once more to stationary phase in medium without thiamine (about 2-3 days). These thiamine-depleted cells were used to inoculate cultures for growth studies in medium without thiamine. Wildtype cells were grown in medium with glucose as the carbon source (with or without thiamine) and positive clones with the native transit peptide *Coccomyxa* C-169 THIC construct were grown in medium with sucrose as the sole carbon source. Growth was measured by monitoring the absorbance at 750 nm Results of the growth experiments showed substantial greater growth in thiamine-free medium of strains expressing the transgene compared to wildtype cells in thiamine-free medium. However, the transformants failed to achieve the growth rate and cell densities of wildtype cells in thiamine-containing media. There was also a strong correlation between the amount of growth in the transformant clones in thiamine-free medium and the copy number of the integrated *Coccomyxa* enzyme (i.e., the more copy numbers of the transgene, the better the growth of the cells in thiamine-free medium).

Additional transformants were generated using expression constructs containing the *Coccomyxa* THIC, the *Arabidopsis thaliana* THIC gene, and the *Synechocystis* sp. PCC 6803 thiC gene. In the case of the *Coccomyxa* and the *A. thaliana* THIC gene, the native transit peptide sequence was replaced with the transit peptide sequence from a *Chlorella protothecoides* stearoyl-ACP desaturase (SAD) gene. *Synechocystis* sp. is a *cyanobacterium* and the thiC protein does not contain a native transit peptide sequence. In the *Synechocystis* sp thiC construct, the transit peptide sequence from a *Chlorella protothecoides* SAD gene was fused to the N-terminus of the *Synechocystis* sp. thiC. In all cases, the sequences were codon optimized for expression in *Prototheca moriformis*. All three of the foregoing constructs contained a upstream and downstream homologous recombination targeting sequence to the 6S region of the genome (SEQ ID NOs: 82 and 84), a *Chlorella protothecoides* actin promoter/5' UTR, and a *Chlorella protothecoides* EF1A gene 3'UTR. All three constructs contained a neoR gene driven by the *C. reinhardtii* TUB2 promoter/5'UTR (SEQ ID NO: 114) and contained the *C. vulgaris* 3'UTR (SEQ ID NO: 115), conferring the selection by G418. The amino acid sequence of the *A. thaliana* THIC corresponded to NCBI accession number NP_180524 and the amino acid sequence of the *Synechocystis* sp. thiC corresponded to NCBI accession number NP_442586, both sequences hereby incorporated by reference. The relevant expression cassette sequences are listed in the Sequence Listing and detailed below:

| | |
|---|---|
| *Coccomyxa* THIC expression construct with *C. protothecoides* transit peptide | SEQ ID NO: 130 |
| *Coccomyxa* THIC with *C. protothecoides* transit peptide | SEQ ID NO: 131 |
| *C. protothecoides* actin promoter/5' UTR | SEQ ID NO: 132 |
| *C. protothecoides* EF1A 3'UTR | SEQ ID NO: 133 |
| *A. thaliana* THIC expression construct | SEQ ID NO: 134 |
| *A. thaliana* THIC with *C. protothecoides* transit peptide | SEQ ID NO: 135 |
| *A. thaliana* THIC amino acid sequence with native transit peptide | SEQ ID NO: 136 |
| *Synechocystis* sp. thiC expression construct | SEQ ID NO: 137 |
| *Synechocystis* sp. thiC with *C. protothecoides* transit peptide | SEQ ID NO: 138 |
| *Synechocystis* sp. thiC amino acid sequence | SEQ ID NO: 139 |
| neoR gene | SEQ ID NO: 140 |

Positive clones were screened on plates containing G418 and several clones from each transformation were picked for verification by PCR. Integration of the transforming DNA constructs containing the *Coccomyxa* C-169 (with *C. protothecoides* transit peptide), *A. thaliana* and *Synechocystis* sp. PCC 6803 THIC genes, respectively into the 6S locus of the genome was confirmed using PCR analysis with the following primers:

```
5' THIC Coccomyxa confirmation primer sequence
                                      (SEQ ID NO: 141)
ACGTCGCGACCCATGCTTCC 3' THIC confirmation primer sequence
                                      (SEQ ID NO: 142)
GGGTGATCGCCTACAAGA 5' THIC A. thaliana confirmation primer sequence
                                      (SEQ ID NO: 143)
GCGTCATCGCCTACAAGA 5' thiC Synechocystis sp. confirmation primer
sequence
                                      (SEQ ID NO: 144)
CGATGCTGTGCTACGTGA
```

Growth experiments on thiamine depleted cells (as described above) were performed using selected confirmed positive clones from transformants of each of the different constructs in medium containing G418. All transformants were able to grow (with varying degrees of robustness) in thiamine-free medium. Comparison of the growth of the transformants in thiamine-free medium to wild type cells on thiamine-containing medium showed the following ranking with respect to their ability to support growth in thiamine-free medium: (1) *A. thaliana* transformants; (2) *Coccomyxa* C-169 (with *C. protothecoides* transit peptide) transformants; and (3) *Synechocystis* sp. transformants. These results suggest that while a single copy of *A. thaliana* THIC was able to complement thiamine auxotrophy in *Prototheca moriformis* cells, multiple copies of *Coccomyxa* C-169 (with either the native transit peptide sequence or a transit peptide sequence from *C. protothecoides*) and *Synechocystis* sp. THIC was required to enable rapid growth in the absence of thiamine Given the variability in results of the different THIC from the different sources, the ability of any particular THIC gene to fully complement the lesion present in *Prototheca* species is not predictable.

An alignment of the three THIC amino acid sequences was performed. While there exist significant sequence conservation between thiC from *Synechocystis* sp. compared to the THICs from *Coccomyxa* and *A. thaliana* (41% identity at the amino acid level), the cyanobacterial protein is missing a domain at the N-terminus that is well-conserved in the algal and plant proteins. Despite the missing domain (and presumably resulting in structural differences), the construct expressing the *Synechocystis* sp. thiC was able to at least partially restore thiamine prototrophic in *Prototheca moriformis* cells.

Example 13: Fuel Production

A. Extraction of Oil from Microalgae Using an Expeller Press and a Press Aid

Microalgal biomass containing 38% oil by DCW was dried using a drum dryer resulting in resulting moisture content of 5-5.5%. The biomass was fed into a French L250 press. 30.4 kg (67 lbs.) of biomass was fed through the press and no oil was recovered. The same dried microbial biomass combined with varying percentage of switchgrass as a press aid was fed through the press. The combination of dried microbial biomass and 20% w/w switchgrass yielded the best overall percentage oil recovery. The pressed cakes were then subjected to hexane extraction and the final yield for the 20% switchgrass condition was 61.6% of the total available oil (calculated by weight). Biomass with above 50% oil dry cell weight did not require the use of a pressing aid such as switchgrass in order to liberate oil. Other methods of extraction of oil from microalgae using an expeller press are described in PCT Application No. PCT/US2010/31108 and is hereby incorporated by reference.

B. Production of Biodiesel from *Prototheca* Oil

Degummed oil from *Prototheca moriformis* UTEX 1435, produced according to the methods described above, was subjected to transesterification to produce fatty acid methyl esters. Results are shown in Table 24 below.

The lipid profile of the oil was:
C10:0 0.02
C12:0 0.06
C14:0 1.81
C14:1 0.07
C16:0 24.53
C16:1 1.22
C18:0 2.34
C18:1 59.21
C18:2 8.91
C18:3 0.28
C20:0 0.23
C20:1 0.10
C20:1 0.08
C21:0 0.02
C22:0 0.06
C24:0 0.10

TABLE 24

Biodiesel profile from *Prototheca moriformis* triglyceride oil.

| Method | Test | Result | Units |
|---|---|---|---|
| ASTM D6751 A1 | Cold Soak Filterability of Biodiesel Blend Fuels | Filtration Time | 120 | sec |
| | | Volume Filtered | 300 | ml |
| ASTM D93 | Pensky-Martens Closed Cup Flash Point | Procedure Used | A | |
| | | Corrected Flash Point | 165.0 | ° C. |
| ASTM D2709 | Water and Sediment in Middle Distillate Fuels (Centrifuge Method) | Sediment and Water | 0.000 | Vol % |
| EN 14538 | Determination of Ca and Mg Content by ICP OES | Sum of (Ca and Mg) | <1 | mg/kg |
| EN 14538 | Determination of Ca and Mg Content by ICP OES | Sum of (Na and K) | <1 | mg/kg |
| ASTM D445 | Kinematic/Dynamic Viscosity | Kinematic Viscosity @ 104° F./40° C. | 4.873 | mm$^2$/s |
| ASTM D874 | Sulfated Ash from Lubricating Oils and Additives | Sulfated Ash | <0.005 | Wt % |
| ASTM D5453 | Determination of Total Sulfur in Light Hydrocarbons, Spark Ignition Engine Fuel, Diesel Engine Fuel, and Engine Oil by Ultraviolet Fluorescence. | Sulfur, mg/kg | 1.7 | mg/kg |
| ASTM D130 | Corrosion - Copper Strip | Biodiesel-Cu Corrosion 50° C. (122° F.)/3 hr | 1a | |
| ASTM D2500 | Cloud Point | Cloud Point | 6 | ° C. |
| ASTM D4530 | Micro Carbon Residue | Average Micro Method Carbon Residue | <0.10 | Wt % |
| ASTM D664 | Acid Number of Petroleum Products by Potentiometric Titration | Procedure Used | A | |
| | | Acid Number | 0.20 | mg KOH/g |
| ASTM D6584 | Determination of Free and Total Glycerin in B-100 Biodiesel Methyl Esters By Gas Chromatography | Free Glycerin | <0.005 | Wt % |
| | | Total Glycerin | 0.123 | Wt % |
| ASTM D4951 | Additive Elements in Lubricating Oils by ICP-AES | Phosphorus | 0.000200 | Wt % |
| ASTM D1160 | Distillation of Petroleum Products at Reduced Pressure | IBP | 248 | ° C. |
| | | AET @ 5% Recovery | 336 | ° C. |
| | | AET @ 10% Recovery | 338 | ° C. |
| | | AET @ 20% Recovery | 339 | ° C. |
| | | AET @ 30% Recovery | 340 | ° C. |
| | | AET @ 40% Recovery | 342 | ° C. |
| | | AET @ 50% Recovery | 344 | ° C. |
| | | AET @ 60% Recovery | 345 | ° C. |
| | | AET @ 70% Recovery | 347 | ° C. |
| | | AET @ 80% Recovery | 349 | ° C. |
| | | AET @ 90% Recovery | 351 | ° C. |
| | | AET @ 95% Recovery | 353 | ° C. |
| | | FBP | 362 | ° C. |
| | | % Recovered | 98.5 | % |
| | | % Loss | 1.5 | % |
| | | % Residue | 0.0 | % |
| | | Cold Trap Volume | 0.0 | ml |
| | | IBP | 248 | ° C. |
| EN 14112 | Determination of Oxidation Stability (Accelerated Oxidation Test) | Oxidation Stability | >12 | hr |
| | | Operating Temp (usually 110 deg C.) | 110 | ° C. |
| ASTM D4052 | Density of Liquids by Digital Density Meter | API Gravity @ 60° F. | 29.5 | ° API |
| ASTM D 6890 | Determination of Ignition Delay (ID) and Derived Cetane Number (DCN) | Derived Cetane Number (DCN) | >61.0 | |

The lipid profile of the biodiesel was highly similar to the lipid profile of the feedstock oil. Other oils provided by the methods and compositions of the invention can be subjected to transesterification to yield biodiesel with lipid profiles including (a) at least 4% C8-C14; (b) at least 0.3% C8; (c) at least 2% C10; (d) at least 2% C12; and (3) at least 30% C8-C14.

The Cold Soak Filterability by the ASTM D6751 A1 method of the biodiesel produced was 120 seconds for a volume of 300 ml. This test involves filtration of 300 ml of B100, chilled to 40° F. for 16 hours, allowed to warm to room temp, and filtered under vacuum using 0.7 micron glass fiber filter with stainless steel support. Oils of the invention can be transesterified to generate biodiesel with a cold soak time of less than 120 seconds, less than 100 seconds, and less than 90 seconds.

C. Production of Renewable Diesel

Degummed oil from *Prototheca moriformis* UTEX 1435, produced according to the methods described above and having the same lipid profile as the oil used to make biodiesel in this Example, above, was subjected to transesterification to produce renewable diesel.

The oil was first hydrotreated to remove oxygen and the glycerol backbone, yielding n-paraffins. The n-parrafins were then subjected to cracking and isomerization. A chromatogram of the material is shown in FIG. 1. The material was then subjected to cold filtration, which removed about 5% of the C18 material. Following the cold filtration the total volume material was cut to flash point and evaluated for flash point, ASTM D-86 distillation distribution, cloud point and viscosity. Flash point was 63° C.; viscosity was 2.86 cSt (centistokes); cloud point was 4° C. ASTM D86 distillation values are shown in Table 25:

TABLE 25

ASTM D86 distillation values.
Readings in ° C.:

| Volume | Temperature |
|---|---|
| IBP | 173 |
| 5 | 217.4 |
| 10 | 242.1 |
| 15 | 255.8 |
| 20 | 265.6 |
| 30 | 277.3 |
| 40 | 283.5 |
| 50 | 286.6 |
| 60 | 289.4 |
| 70 | 290.9 |
| 80 | 294.3 |
| 90 | 300 |
| 95 | 307.7 |
| FBP | 331.5 |

The T10-T90 of the material produced was 57.9° C. Methods of hydrotreating, isomerization, and other covalent modification of oils disclosed herein, as well as methods of distillation and fractionation (such as cold filtration) disclosed herein, can be employed to generate renewable diesel compositions with other T10-T90 ranges, such as 20, 25, 30, 35, 40, 45, 50, 60 and 65° C. using triglyceride oils produced according to the methods disclosed herein.

The T10 of the material produced was 242.1° C. Methods of hydrotreating, isomerization, and other covalent modification of oils disclosed herein, as well as methods of distillation and fractionation (such as cold filtration) disclosed herein, can be employed to generate renewable diesel compositions with other T10 values, such as T10 between 180 and 295, between 190 and 270, between 210 and 250, between 225 and 245, and at least 290.

The T90 of the material produced was 300° C. Methods of hydrotreating, isomerization, and other covalent modification of oils disclosed herein, as well as methods of distillation and fractionation (such as cold filtration) disclosed herein can be employed to generate renewable diesel compositions with other T90 values, such as T90 between 280 and 380, between 290 and 360, between 300 and 350, between 310 and 340, and at least 290.

The FBP of the material produced was 300° C. Methods of hydrotreating, isomerization, and other covalent modification of oils disclosed herein, as well as methods of distillation and fractionation (such as cold filtration) disclosed herein, can be employed to generate renewable diesel compositions with other FBP values, such as FBP between 290 and 400, between 300 and 385, between 310 and 370, between 315 and 360, and at least 300.

Other oils provided by the methods and compositions of the invention can be subjected to combinations of hydrotreating, isomerization, and other covalent modification including oils with lipid profiles including (a) at least 4% C8-C14; (b) at least 0.3% C8; (c) at least 2% C10; (d) at least 2% C12; and (3) at least 30% C8-C14.

Example 14: Production of Tailored Oils

Using the methods and materials as disclosed herein, various tailored oils were produced. Table 32 shows the strain, the gene and the genebank accession numbers of the genes conferring the phenotype and the various fatty acid profiles produced by the indicated strain. Strains A and B are both *Prototheca moriformis* (UTEX 1435) strains, both of which were classically mutagenized by a fee-for-service laboratory to improve oil yield. Strains A and B were then genetically engineered as described herein with the appropriate DNA constructs to express the desired genes. The strains were also engineered to inactivate endogenous desaturases, as indicated. The nucleotide sequences of the thioesterases were codon optimized for expression and use in *Prototheca*.

The fatty acid profile of wild type, un-engineered *Prototheca* is shown in the first line of Table 32. As can be seen, the fatty acid profile has been dramatically altered in different ways in the different strains. For example, the percentage of C8:0 produced by non-genetically engineered *P. moriformis* cells is 0%. However, *P. moriformis* cells engineered to express a *C. hookeriana* thioesterase increased C8:0 production from 0% to 13.2% of the total triglycerides. As another example, the total combined amount of C8:0 and C10:0 in the engineered strains was about 39% of the total fatty acids. In contrast, the total combined amount of C8:0 and C10:0 in the wild type cells is 0.01%. In another example, the total amount of saturated fatty acids was increased from about 32% to about 90% by the expression of an *U. americana* thioesterase in cells in which expression of endogenous SAD2b was disrupted. This is an increase of almost 300%.

The various fatty acid profiles as disclosed below are useful in myriad applications involving triglyceride oils. For example, high levels of lower carbon chain length saturated fatty acids comprising triglyceride (C12:0, C14:0, C16:0) are particularly useful in renewable jet fuel production. For biodiesel production, high amounts of C18:1 are desirable. For bar soap production, controlling and achieving the appropriate balance between the levels of saturation and shorter chain fatty acids is desirable. As an example, high amounts of C12:0 are desirable for lathering properties while longer chain lengths provide more structure, while linoleic and linolenic containing triglycerides are less desirable as they contribute to oxidative instability. For liquid soaps, high amounts of C12:0 and C14:0 are desirable. Additionally, for both bar soap and liquid soap production, low amounts of C6:0, C8:0 and C10:0 are desirable as these lower chain triglycerides are skin irritants.

oil mimetic, a plasmid was constructed and used to transform Strain A and oil production was carried out. The construct, pSZ1413 (SEQ ID NO: 231), comprised codon optimized *Cuphea wrightii* FATB2 gene (SEQ ID NO: 284) (Gen bank accession no. U56106) and SAD2B (stearoyl ACP desaturase) gene disruption.

As shown in Table 33 below, the palm kernel oil mimetic was similar to palm kernel oil. The percentages of the three

TABLE 32

Genes and accession numbers conferring phenotypes of various triglyceride profiles.

| Trait | Gen Bank Accession and Description | Gene Conferring Phenotype | Construct* | Seq. Id. No. | Strain Genetic Background | C8:0 | C10:0 | C12:0 | C14:0 | C16:0 | C18:0 | C18:1 | C18:2 | Total Saturates |
|---|---|---|---|---|---|---|---|---|---|---|---|---|---|---|
| Wild Type | | | na | | UTEX 1435 | 0.00 | 0.01 | 0.04 | 1.27 | 27.20 | 3.85 | 58.70 | 7.18 | 32.36 |
| Highest C8 | U39834 | *C. hookeriana* TE | pSZ 1458 | | A | 13.20 | 25.84 | 0.51 | 1.41 | 10.22 | 1.39 | 38.21 | 7.42 | 52.57 |
| Highest C10 | U39834 | *C. hookeriana* TE | pSZ 1458 | | A | 13.20 | 25.84 | 0.51 | 1.41 | 10.22 | 1.39 | 38.21 | 7.42 | 52.57 |
| Highest C12 | U56104 and U67317 (SEQ ID NO: 185) | *C. wrightii* TE + *C. wrightii* KASA1 | pSZ 1491 (SEQ ID NO: 232) | | B | .02 | 13.63 | 50.59 | 6.49 | 6.64 | 0.87 | 13.74 | 6.83 | 78.00 |
| Highest C14 | U31813 | *Cinnamomum camphora* TE | pSZ 941 (SEQ ID NO: 236)/944 (SEQ ID NO: 228) | | UTEX 1435 | 0.00 | 0.06 | 5.91 | 43.27 | 19.63 | 0.87 | 13.96 | 13.78 | 69.74 |
| Highest C16 | Q39513.1 | *C. hookeriana* TE | pSZ 1417 (SEQ ID NO: 226) | | A | 0.00 | 0.02 | 0.11 | 10.62 | 69.92 | 2.18 | 12.95 | 5.15 | 80.35 |
| Highest C18 | U56104 as SAD2B gene disruption | *C. wrightii* TE | pSZ 1410 (SEQ ID NO: 230) | | A | 0.00 | 0.11 | 1.28 | 1.82 | 24.55 | 37.38 | 23.51 | 7.88 | 65.14 |
| Highest C8-C10 | U39834 | *C. hookeriana* TE | pSZ 1458 | | A | 13.20 | 25.84 | 0.51 | 1.41 | 10.22 | 1.39 | 38.21 | 7.42 | 52.57 |
| Highest C8-C14 | U56104 | *C. wrightii* TE | pSZ 1283 (SEQ ID NO: 229) | | A | .22 | 17.64 | 45.85 | 10.94 | 5.55 | 0.79 | 13.49 | 4.68 | 74.65 |
| Highest C10-C14 | U56104 | *C. wrightii* TE | pSZ 1283 (SEQ ID NO: 229) | | A | .22 | 17.64 | 45.85 | 10.94 | 5.55 | 0.79 | 13.49 | 4.68 | 74.65 |
| Highest C12-C14 | ABB71579.1 (SEQ ID NO: 286) | *C. callophylla* TE | pSZ 1570 (SEQ ID NO: 235) | | B | .01 | 0.88 | 28.04 | 34.08 | 19.82 | 1.00 | 10.52 | 4.42 | 83.83 |
| Lowest 18:1 | AAB71731 (SEQ ID NO: 287) as SAD2B gene disruption | *Ulmus americana* TE | pSZ 1321 (SEQ ID NO: 242) | | A | .12 | 10.39 | 3.55 | 35.21 | 33.54 | 4.90 | 5.15 | 5.69 | 87.71 |
| Highest 18:1 | FADc Disruption with *Carthamus tincorus* TE AAA33019.1 | *Carthamus tinctorus* TE | pSZ 1500 (SEQ ID NO: 233) | | A | 0 | 0 | 0 | 0 | 16.49 | 0 | 83.51 | 0.00 | 16.49 |
| Lowest 18:2 | FADc Disruption with *Carthamus tincorus* TE AAA33019.1 | *Carthamus tinctorus* TE | pSZ 1501 (SEQ ID NO: 234) | | A | 0 | 0 | .03 | 1.05 | 18.01 | 1.44 | 77.11 | 0.00 | 20.53 |
| Highest Saturates | AAB71731 as a SAD2B Disruption | *Ulmus americana* TE | pSZ 1321 (SEQ ID NO: 242) | | A | .30 | 13.07 | 3.57 | 33.58 | 33.52 | 5.16 | 5.36 | 4.50 | 89.20 |

Palm Kernel Oil

We produced a microbial palm kernel oil mimetic that was similar to palm kernel oil (PKO). To produce the palm kernel oil mimetic, a plasmid was constructed and used to transform Strain A and oil production was carried out. The most abundant fatty acids of the PKO mimetic (C12:0, C14:0 and C18:1) were identical to or within 10% of the palm kernel oil.

TABLE 33

| Triglyceride profile of palm kernel oil mimetic. | | | | | | | | |
|---|---|---|---|---|---|---|---|---|
| | C8:0 | C10:0 | C12:0 | C14:0 | C16:0 | C18:0 | C18:1 | C18:2 |
| E. guineensis (Palm kernel) | 3.0-5.0 | 2.5-6.0 | 40-52 | 14.0-18.0 | 7.0-10.0 | 1.0-3.0 | 11.0-19.0 | 0.5-4.0 |
| pSZ1413 | | 8.33 | 37.45 | 18.22 | 13.52 | 1.25 | 15.29 | 4.95 |

Palm Oil

We produced a microbial palm oil mimetic that was similar to palm oil. Several different plasmids were constructed and transformed individually into Strain A and oil production was carried out. The construct, pSZ1503 (SEQ ID NO: 283), was designed to disrupt an endogenous KASII gene. The construct, pSZ1439 (SEQ ID NO: 237), comprised a codon optimized Elaeis guiniensis TE gene (SEQ ID NO: 205) (Gen bank accession no. AAD42220.2). The construct, pSZ1420 (SEQ ID NO: 225), comprised a codon optimized Cuphea hookeriana TE gene (SEQ ID NO: 201) (Gen Bank Accession no. Q39513). The construct, pSZ1119 (SEQ ID NO: 227), comprised a codon optimized Cuphea hookeriana KAS IV gene (SEQ ID NO: 186) (Gen Bank Accession no. AF060519) as well as a Cuphea wrightii FATB2 gene (SEQ ID NO: 184) (Gen Bank Accession no. U56104).

As shown in Table 34 below, the palm oil mimetic was similar to palm oil. The percentages of the three most abundant fatty acids of the palm oil mimetic (C16:0, C18:1 and C18:2) were identical to or within 10% of palm oil.

TABLE 34

| Triglyceride profile of palm oil mimetic. | | | | | | | |
|---|---|---|---|---|---|---|---|
| | C10:0 | C12:0 | C14:0 | C16:0 | C18:0 | C18:1 | C18:2 |
| E. guineensis (Palm) | 0 | 0 | 0.5-5.9 | 32.0-47.0 | 2.0-8.0 | 34-44 | 7.2-12.0 |
| pSZ1503 | 0.01 | 0.01 | 0.83 | 38.36 | 2.21 | 48.31 | 7.60 |
| pSZ1439 | 0.01 | 0.04 | 1.88 | 43.50 | 3.32 | 39.95 | 9.16 |
| pSZ1420 | 0.02 | 0.04 | 2.44 | 48.04 | 2.76 | 35.62 | 8.91 |
| pSZ1119 | 1.77 | 0.40 | 7.85 | 35.45 | 2.47 | 42.85 | 8.15 |

Cocoa Butter

We produced a microbial cocoa butter mimetic that was similar to cocoa butter. The construct, pSZ1451, was constructed and transformed into Strain A and oil production was carried out. The construct, pSZ1451 (SEQ ID NO: 239), comprised codon optimized Carthamus tinctorus TE gene (SEQ ID NO: 187) (Gen Bank Accession no. AAA33019.1).

As shown in Table 35 below, the cocoa butter oil mimetic was similar to cocoa butter. The percentages of the three most abundant fatty acids of the cocoa butter mimetic (C16:0, C18:0 and C18:1) were identical to or within 10% of cocoa butter.

TABLE 35

| Triglyceride profile of cocoa butter mimetic. | | | | | | | | |
|---|---|---|---|---|---|---|---|---|
| | C8:0 | C10:0 | C12:0 | C14:0 | C16:0 | C18:0 | C18:1 | C18:2 |
| Cocoa Butter | 0 | 0-1 | 0-1 | 0-4 | 22-38 | 24-37 | 29-38 | 0-3 |
| pSZ1451 | | 0.05 | 0.14 | 0.99 | 28.34 | 27.39 | 29.40 | 10.26 |

Lard

We produced a microbial lard mimetic that was similar to lard. Several different plasmids were constructed and transformed individually into Strain A and oil production was carried out. The construct, pSZ1493 (SEQ ID NO: 241), was designed to disrupt the endogenous SAD 2B gene and simultaneously express a codon optimized Umbellularia californica TE gene (SEQ ID NO: 285) (Gen Bank Accession no. M94159). The construct, pSZ1452 (SEQ ID NO: 240), was designed to disrupt the endogenous SAD 2B gene and express a codon optimized Garcinia mangostana TE gene (SEQ ID NO: 196) (Gen Bank Accession no. AAB51525.1). The construct, pSZ1449 (SEQ ID NO: 238), was designed to express the codon optimized Brassica napus TE gene (SEQ ID NO: 195) (Gen Bank Accession no. CAA52070.1). The polynucleotide sequence of the construct pSZ1458 was identical to pSZ1449 except that a codon optimized polynucleotide sequence encoding a Cuphea hookeriana thioesterase (Gen Bank accession No. U39834) replaced the polynucleotide sequence encoding Brassica napus TE gene (SEQ ID NO: 195) (Gen Bank Accession no. CAA52070.1).

As shown in Table 36 below, the lard mimetic was similar to lard. The percentages of the three most abundant fatty acids of the lard mimetic (C16:0, C18:0 and C18:1) were identical to or within 10% of lard.

TABLE 36

| Triglyceride profile of lard mimetic. | | | | | |
|---|---|---|---|---|---|
| | C14:0 | C16:0 | C18:0 | C18:1 | C18:2 |
| Lard | 3-4 | 22-26 | 13-18 | 39-45 | 8-15 |
| pSZ1493 | 1.32 | 24.79 | 17.49 | 41.87 | 10.01 |

TABLE 36-continued

Triglyceride profile of lard mimetic.

|  | C14:0 | C16:0 | C18:0 | C18:1 | C18:2 |
|---|---|---|---|---|---|
| pSZ1452 | 1.16 | 24.49 | 17.94 | 45.49 | 8.05 |
| pSZ1449 | 1.16 | 23.98 | 15.79 | 47.88 | 8.29 |

Although this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

All references cited herein, including patents, patent applications, and publications, including Genbank Accession numbers, are hereby incorporated by reference in their entireties, whether previously specifically incorporated or not. The publications mentioned herein are cited for the purpose of describing and disclosing reagents, methodologies and concepts that may be used in connection with the present invention. Nothing herein is to be construed as an admission that these references are prior art in relation to the inventions described herein. In particular, the following patent applications are hereby incorporated by reference in their entireties for all purposes: PCT Application No. PCT/US2008/065563, filed Jun. 2, 2008, entitled "Production of Oil in Microorganisms", PCT Application No. PCT/US2010/31108, filed Apr. 14, 2010, entitled "Methods of Microbial Oil Extraction and Separation", and PCT Application No. PCT/US2009/066142, filed Nov. 30, 2009, entitled "Production of Tailored Oils in Heterotrophic Microorganisms".

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10006034B2). An electronic copy of the "Sequence Listing" will also be available from the USPTO upon request and payment of the fee set forth in 37 CFR 1.19(b)(3).

What is claimed is:

1. A process for producing a triglyceride oil from a microalgae, the process comprising:
   (i) cultivating a recombinant oleaginous microalgal cell comprising exogenous nucleic acids encoding a KAS (keto-acyl ACP synthase) or wherein nucleic acids encoding an endogenous KAS are disrupted by homologous recombination to produce said triglyceride oil; and
   (ii) isolating said triglyceride oil from said recombinant oleaginous microalgal cell,
   wherein said triglyceride oil has a fatty acid profile that is at least 40% saturated fatty acids, and said fatty acid profile of said triglyceride oil comprises at least: 10% C8:0, 20% C10:0, 50% C12:0, 40% C14:0, 60% C16:0, or 30% C18:0.

2. The process of claim 1, wherein said exogenous nucleic acids encoding said KAS encode a KAS I enzyme, a KAS II enzyme, or a KAS IV enzyme.

3. The process of claim 1, wherein said recombinant oleaginous microalgal cell further comprises nucleic acids encoding a FatB acyl-ACP thioesterase.

4. The process of claim 3, wherein said exogenous nucleic acids encoding said FatB acyl-ACP thioesterase are from a plant of the genus *Cuphea*, *Ulmus*, or *Cinnamomum*.

5. The process of claim 1, wherein nucleic acids encoding an endogenous desaturase of said recombinant oleaginous microalgal cell have been disrupted.

6. The process of claim 5, wherein exogenous nucleic acids encoding a FatB acyl-ACP thioesterase disrupt nucleic acids encoding an endogenous desaturase.

7. The process of claim 6, wherein said exogenous nucleic acids encoding said FatB acyl-ACP thioesterase are from a plant of the genus *Cuphea*.

8. The process of claim 1, wherein said triglyceride oil has a fatty acid profile that is at least 55% saturated fatty acids.

9. The process of claim 1, wherein said triglyceride oil has a fatty acid profile that is at least 65% saturated fatty acids.

10. The process of claim 1, wherein said triglyceride oil has a fatty acid profile that is at least 80% saturated fatty acids.

11. The process of claim 1, wherein said triglyceride oil is a cocoa butter mimetic having percentages of C16:0, C18:0 and C18:1 fatty acid constituents within 10% of the percentages, respectively, of cocoa butter.

12. The process of claim 1, wherein said recombinant oleaginous microalgal cell is of the genus *Prototheca*.

13. The process of claim 12, wherein said recombinant oleaginous microalgal cell is a species of *Prototheca* selected from *Prototheca moriformis*, *Prototheca krugani*, *Prototheca stagnora*, *Prototheca wickerhamii*, or *Prototheca zopfii*.

14. The process of claim 13, wherein said recombinant oleaginous microalgal cell is *Prototheca moriformis*.

15. The process of claim 1, wherein said recombinant oleaginous microalgal cell is of the genus *Chlorella*.

16. The process of claim 15, wherein said recombinant oleaginous microalgal cell is *Chlorella prothecoides*.

17. The process of claim 2, wherein said exogenous nucleic acids encoding said KAS encodes KAS II.

18. A process for producing a triglyceride oil from a microalgal cell of the genus *Prototheca*, the process comprising:
   (i) cultivating a recombinant oleaginous *Prototheca* cell comprising exogenous nucleic acids encoding a KAS (keto-acyl ACP synthase) or wherein nucleic acids encoding an endogenous KAS are disrupted by homologous recombination to produce said triglyceride oil; and (ii) isolating said triglyceride oil from said recombinant oleaginous *Prototheca* cell,
wherein said triglyceride oil has a fatty acid profile that is at least 40% saturated fatty acids, and said fatty acid profile of said triglyceride oil comprises at least: 10% C8:0, 20% C10:0, 50% C12:0, 40% C14:0, 60% C16:0, or 30% C18:0.

19. The process of claim 18, wherein said exogenous nucleic acids encoding said KAS encode a KAS I enzyme, a KAS II enzyme, or a KAS IV enzyme.

20. The process of claim 18, wherein nucleic acids encoding an endogenous desaturase of said recombinant oleaginous *Prototheca* cell have been disrupted.

21. The process of claim 18, wherein said triglyceride oil has a fatty acid profile that is at least 50% saturated fatty acids.

22. The process of claim 18, wherein said triglyceride oil is a cocoa butter mimetic having percentages of C16:0, C18:0 and C18:1 fatty acid constituents within 10% of the percentages, respectively, of cocoa butter.

23. The process of claim 18, wherein said recombinant oleaginous *Prototheca* cell is selected from *Prototheca moriformis*, *Prototheca krugani*, *Prototheca stagnora*, *Prototheca wickerhamii*, or *Prototheca zopfii*.

24. The process of claim 23, wherein said recombinant oleaginous *Prototheca* cell is *Prototheca moriformis*.

25. A process for producing a triglyceride oil from a *Prototheca moriformis* cell, the process comprising:
(i) cultivating a recombinant *Prototheca moriformis* cell comprising exogenous nucleic acids encoding a KAS (keto-acyl ACP synthase) or wherein nucleic acids encoding an endogenous KAS are disrupted by homologous recombination to produce said triglyceride oil; and (ii) isolating said triglyceride oil from said *Prototheca moriformis* cell, wherein said triglyceride oil has a fatty acid profile that is at least 40% saturated fatty acids, and said fatty acid profile of said triglyceride oil comprises at least: 10% C8:0, 20% C10:0, 50% C12:0, 40% C14:0, 60% C16:0, or 30% C18:0.

26. The process of claim 25, wherein said exogenous nucleic acids encoding said KAS encode a KAS I enzyme, a KAS II enzyme, or a KAS IV enzyme.

27. The process of claim 25, wherein nucleic acids encoding an endogenous desaturase of said *Prototheca moriformis* cell have been disrupted.

28. The process of claim 25, wherein said triglyceride oil has a fatty acid profile that is at least 50% saturated fatty acids.

29. The process of claim 25, wherein said triglyceride oil is a cocoa butter mimetic having percentages of C16:0, C18:0 and C18:1 fatty acid constituents within 10% of the percentages, respectively, of cocoa butter.

30. The process of claim 18, wherein said triglyceride oil has a fatty acid profile of at least 60% saturated fatty acids.

31. The process of claim 18, wherein said triglyceride oil has a fatty acid profile of at least 65% saturated fatty acids.

32. The process of claim 25, wherein said triglyceride oil has a fatty acid profile of at least 55% saturated fatty acids.

33. The process of claim 25, wherein said triglyceride oil has a fatty acid profile of at least 60% saturated fatty acids.

34. The process of claim 25, wherein said triglyceride oil has a fatty acid profile that is at least 65% saturated fatty acids.

\* \* \* \* \*

UNITED STATES PATENT AND TRADEMARK OFFICE
CERTIFICATE OF CORRECTION

PATENT NO. : 10,006,034 B2
APPLICATION NO. : 14/819117
DATED : June 26, 2018
INVENTOR(S) : Scott Franklin et al.

It is certified that error appears in the above-identified patent and that said Letters Patent is hereby corrected as shown below:

In the Claims

In Line 2 of Claim 16 (Column 174, Line 56) change "*prothecoides*" to --*protothecoides*--.

In Line 5 of Claim 18 (Column 174, Line 63) delete "a" before KAS.

Signed and Sealed this
Twenty-seventh Day of August, 2019

Andrei Iancu
*Director of the United States Patent and Trademark Office*